United States Patent [19]
Lang et al.

[11] Patent Number: 6,114,393
[45] Date of Patent: Sep. 5, 2000

[54] USE OF INHIBITORS OF THE SODIUM-HYDROGEN EXCHANGER FOR THE PRODUCTION OF A PHARMACEUTICAL FOR THE TREATMENT OF DISORDERS WHICH ARE CAUSED BY PROTOZOA

[75] Inventors: Hans Jochen Lang, Hofheim; Michael Lanzer, Kitzingen; Jochen Wiesner; Cecilia Sanchez, both of Wuerzburg; Stefan Wünsch, Gerbrunn, all of Germany

[73] Assignee: Hoechst Marion Roussel Deutschland GmbH, Frankfurt am Main, Germany

[21] Appl. No.: 09/140,544

[22] Filed: Aug. 26, 1998

[30] Foreign Application Priority Data

Aug. 28, 1997 [DE] Germany .......................... 197 37 463

[51] Int. Cl.$^7$ ...................... A61K 31/155; A61K 31/505; A61K 31/415; A61K 31/405; A61K 31/38
[52] U.S. Cl. .......................... 514/634; 514/256; 514/396; 514/406; 514/415; 514/438; 514/461; 514/895
[58] Field of Search ..................... 514/634, 895, 514/256, 396, 406, 415, 438, 461

[56] References Cited

U.S. PATENT DOCUMENTS

| | | | |
|---|---|---|---|
| 5,091,394 | 2/1992 | Englert et al. | 514/331 |
| 5,364,868 | 11/1994 | Englert et al. | 514/331 |
| 5,739,142 | 4/1998 | Gericke et al. | 514/275 |
| 5,849,775 | 12/1998 | Schwark et al. | 514/396 |
| 5,856,344 | 1/1999 | Kleemann et al. | 514/346 |
| 5,880,156 | 3/1999 | Lang et al. | 514/618 |

FOREIGN PATENT DOCUMENTS

| | | | |
|---|---|---|---|
| WO 84/00875 | 3/1984 | WIPO | A01N 43/80 |
| WO 96/40728 | 12/1996 | WIPO | A61K 31/575 |

OTHER PUBLICATIONS

European Search Report, mailed May 21, 1999.
"Quantitative Assessment of Antimalarial Activity In Vitro by a Semiautomated Microdulution Technique," E. Desjardins et al., *Antimicrobial Agents and Chemotherapy*, 16(6), Dec. 1979, pp. 710–718.

"Synchronization of *Plasmodium falciparum* Erythrocytic Stages in Culture," Chris Lambros and Jerome P. Vanderberg, *J. Parasitol.*, 65 (3), 1979, pp. 418–420.

"Human Malaria Parasites in Continuous Culture," William Trager et al., *Science*, vol. 193, Apr. 1976, pp. 673–675.

*Primary Examiner*—Kevin E. Weddington
*Attorney, Agent, or Firm*—Finnegan, Henderson, Farabow, Garrett & Dunner, L.L.P.

[57] ABSTRACT

Inhibitors of the sodium-hydrogen exchanger are suitable on their own or in combination with other classes of active compound for the production of a medicament for the treament of diseases which are caused by protozoa; thus of diseases which are caused by animal- and human-pathogenic protozoa, such as by intracellularly active parasites of the classes Apicomplexa and Zoomastigophorea, in particular trypanosomes, plasmodia (malaria pathogens), leishmanias, babesias and theilerias, cryptosporidiidae, sarcocystidae, amoebae, coccidia and trichomonads. NHE inhibitors are particularly preferably suitable for the production of a medicament for the treatment of tropical malaria, of tertian malaria, of quartan malaria, as well as toxoplasmosis, of coccidiosis, of intestinal sarcosporidosis, of cryptosporidosis, of Chargas' disease and of the cutaneous and visceral as well as other forms of leishmaniases; and also for the production of a medicament for the treatment of animals which have been infected by animal-pathogenic protozoa, such as by *Theileria parva*, the pathogen of East Coast fever of cattle, *Babesia begemina*, the pathogen of Texas fever in cattle and buffalo, *Babesia bovis*, the pathogen of European bovine babesiosis, and babesioses in dogs, cats and sheep, sarcocystidae, the pathogens of sarcocystoses in sheep, cattle and pigs, cryptosporidiidae, the pathogens of cryptosporidosis in cattle and birds, coccidia, the pathogens of coccidioses of rabbits, cattle, sheep, goats and pigs, but in particular of chickens and turkeys.

14 Claims, No Drawings

USE OF INHIBITORS OF THE SODIUM-HYDROGEN EXCHANGER FOR THE PRODUCTION OF A PHARMACEUTICAL FOR THE TREATMENT OF DISORDERS WHICH ARE CAUSED BY PROTOZOA

DESCRIPTION

Use of inhibitors of the sodium-hydrogen exchanger for the production of a pharmaceutical for the treatment of disorders which are caused by protozoa.

The invention relates to the use of inhibitors of the cellular sodium-hydrogen exchanger for the production of a pharmaceutical for the treatment of diseases which occur as a result of attack of humans and animals by protozoa.

Inhibitors of the sodium-hydrogen exchanger (NHE) have in recent years been characterized in numerous preclinical studies as substances which in the case of restricted circulation of the heart are suitable in a superior manner to protect endangered heart tissue from death. The protection of the heart tissue in this case includes all forms of heart damage caused by inadequate circulation, starting with cardiac arrhythmias via hypercontraction of the heart muscle and temporary loss of function up to death of the heart tissue and permanent damage associated therewith.

The mechanism of action of the NHE inhibitors is that they decrease the increased influx of sodium ions which arises in inadequately supplied tissues as a result of intracellular acidification and subsequent activation of the NHE. Since sodium and calcium ion transport are coupled to one another in mammalian tissue, the life-threatening calcium overloading of the cells is thus also prevented. This unique mechanism relates relatively specifically, in particular, to heart tissue.

It was therefore surprising, as could now be found, that NHE inhibitors are able to kill protozoa having a pathogenic action on humans and animals or to significantly restrict the survival ability of protozoa. Inhibitors of the sodium-hydrogen exchanger are therefore suitable on their own or in combination with other classes of active compound for the treatment of diseases which are caused by protozoa.

Animal- and human-pathogenic protozoa of this type are preferably intracellularly active parasites of the classes Apicomplexa and Zoomastigophorea, in particular trypanosomes, plasmodia (malaria pathogens), leishmanias, babesias and theilerias, cryptosporidiidae, sarcocystidae, ameeba, coccidia and trichomonads.

Particularly preferably, NHE inhibitors are suitable for the treatment of tropical malaria, which is caused by *Plasmodium falciparum*, for the treatment of tertian malaria, induced by *Plasmodium vivax* and *Plasmodium ovale*, for the treatment of quartan malaria, caused by *Plasmodium malariae*, and for the treatment of toxoplasmosis, caused by *Toxoplasma gondii*, of coccidiosis, caused by *Isospora belli*, of intestinal sarcosporidosis, caused by *Sarcocystis suihominis*, of cryptosporidosis, caused by *Cryptosporidium parvum*, of Chargas' disease, which is caused by *Trypanosoma cruzi*, of the cutaneous and visceral and also other forms of leishmaniases, and also for the treatment of animals which have been infected by animal-pathogenic protozoa, such as by *Theileria parva*, the pathogen of East Coast fever of cattle, *Babesia begemina*, the pathogen of Texas fever in cattle and buffalo, *Babesia bovis*, the pathogen of European bovine babesiosis, and also babesiosis in dogs, cats and sheep, sarcocystidae, the pathogens of sarcocystoses in sheep, cattle and pigs, cryptosporidiidae, the pathogens of cryptosporidosis in cattle and birds, coccidia, the pathogens of coccidioses of rabbits, cattle, sheep, goats and pigs, but in particular of chickens and turkeys.

In the treatment of diseases which are caused by human- and animal-pathogenic protozoa, the NHE inhibitors can be administered both orally and parenterally. In this case, NHE inhibitors are used as monosubstances and in combination with other active compounds. Since with NHE a novel principle of action is concerned, combinations with pharmaceuticals which are already used for the treatment of the respective protozoa-related disorder are also advantageously utilizable, a favorable, additively reinforcing action being observed.

Very particularly preferably, the NHE inhibitors are suitable for the treatment of forms of malaria, in particular for the treatment of malaria tropica. At present, between 300–500 million people suffer from malaria, and every twelve seconds a person dies from the consequences of this infectious disease. The number of cases of malaria will in-all probability increase still further in the next few years, since effective methods for the control of malaria are lacking at present. Medicaments which have been employed up to now against malaria have largely lost their efficacy. The malaria pathogens, protozoa of the genus Plasmodium, have become resistant. In order to avert the impending catastrophe, according to the World Health Organization novel pharmaceuticals are urgently needed for the prophylactic and curative treatment of malaria. In this connection, the development of novel medicaments against malaria has proven to be very difficult.

It was therefore surprising that NHE inhibitors have proven effective not only against chloroquine-sensitive but also against chloroquine-resistant *Plasmodium falciparum* strains. In addition to the treatment of the later erythrocytic stage of the malaria pathogen, which was customary up to now, with NHE inhibitors the treatment of the early form of malaria also appears to be very particularly advantageous due to destruction of the pathogens even in the liver.

In what follows, the activity of NHE inhibitors against protozoa is described:

Culture of *Plasmodium falciparum*

Erythrocytic stages of the human malaria parasite *Plasmodium falciparum* were cultured in RPMI 1640 medium, with L-glutamine, 25 mM HEPES, 4 µg/ml of gentamycin, 10% human serum and 5% human erythrocytes, according to Trager and Jensen (1976). The cultures were kept in Petri dishes (10 ml per dish with 10 cm diameter) and incubated at 37° C. in an atmosphere of 92% nitrogen, 3% carbon dioxide and 5% oxygen. The medium of the cultures was changed daily. At a parasitemia of at most 10%, the cultures were diluted. In order to synchronize the cultures, the infected erythrocytes were washed in 5% strength sorbitol solution according to Lambros and Vanderberg (1979). Only the ring stages survive this treatment.

Determination of the $IC_{50}$ values of the various NHE inhibitors

The half-maximal inhibitory concentration of various NHE inhibitors for the growth of *Plasmodium flaciparum* was measured in 96-well microtiter plates by incorporation of radioactive hypoxanthine according to Desjardins et al. (1979). In this case, the parasites were cultured for a complete erythrocyte cycle lasting 48 hours in the presence of the corresponding NHE inhibitors.

The NHE inhibitors were dissolved in DMSO and prediluted in physiological saline solution (150 mM NaCl). The dilution series of the NHE inhibitors in 10-fold concentrated 20 µl aliquots was initially introduced onto the microtiter plates, 180 µl of parasite suspension in culture medium were then added to each one. The parasites were in the ring stage with a parasitemia of 1%. The microtiter plates were then incubated for 24 hours. In order to change the culture medium, 150 μl each of supernatant from each well were removed and replaced by 135 μl of new medium, additionally supplemented with 2 μCi/ml of [3H]-hypoxanthine. The concentration of the NHE inhibitors was again adjusted by adding 10-fold concentrated stock solutions in 15 μl aliquots. After incubation for a further 24 hours, the cultures were harvested by filtration on glass fiber filters and the incorporated radioactivity was measured. The percentage inhibition of the tritium incorporation was related to a control without NHE inhibitor.

The $IC_{50}$ values of the various NHE inhibitors were measured on a chloroquine-sensitive (HB3) and a chloroquine-resistant (Dd2) strain.

| Substance | HB3 $IC_{50}$ [μm] | Dd2 $IC_{50}$ [μm] |
|---|---|---|
| 3-trifluoromethyl-5-N,N-dimethylaminobenzoylguanidine dihydrochloride | 9,97 ± 0.12 | 1.3 ± 0.10 |
| 3-trifluoromethyl-4-(3-pyridyloxy)benzoylguanidine dihydrochloride | 12 ± 1.7 | 6.5 ± 1.5 |
| 4-[4-(2-aminoethyl)phenoxy]-3-methylsulfonylbenzoylguanidine dihydrochloride | 2.9 ± 0.79 | 3.5 ± 0.04 |

References

Desjardins, R. E., Canfield, C. J. Haynes, J. D. and Chulay, J. D. (1979) Quantitative assessment of antimalarial activity in vitro by semiautomated microdilution technique, Antimicrob. Agents Chemother. 16: 710–718.

Lambros, C. J. and Vanderberg, J. (1979) Synchronization of *Plasmodium falciparum* erythrocytic stages in culture, J. Parasitol. 65: 418–420.

Trager, W. and Jensen, J. B. (1976) Human malaria parasites in continuous culture. Science 193: 673–675

The active compounds known and identified as NHE inhibitors are guanidine derivatives, preferably acylguanidines, inter alia as described in the following publications and patent disclosures: Edward J. Cragoe, Jr., "DIURETICS, Chemistry, Pharmacology and Medicine", J. WILEY & Sons (1983), 303–341, additionally compounds of the following formulae:

1. (HOE 89/F 288—U.S. Pat. No. 5,292,755)
   a) benzoylguanidines of the formula I

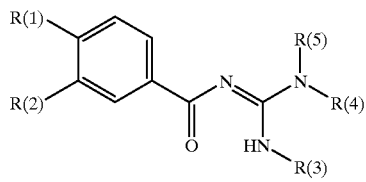

I in which:
R(1) or R(2) is R(6)—S(O)$_n$— or R(7)R(8)N—O$_2$S—;
and the other substituent R(1) or R(2) in each case is H, F, Cl, Br, (C$_1$–C$_4$)-alkyl, (C$_1$–C$_4$)-alkoxy or phenoxy, which is unsubstituted or substituted by 1–3 substituents selected from the group consisting of fluorine, chlorine, methyl and methoxy;

or the other substituent R(1) or R(2) in each case is R(6)—S(O)$_n$ or R(7)R(8)N—;
n is zero, 1 or 2;
R(6) is (C$_1$–C$_6$)-alkyl, (C$_5$–C$_7$)-cycloalkyl, cyclopentylmethyl, cyclohexylmethyl or phenyl, which is unsubstituted or substituted by 1–3 substituents selected from the group consisting of fluorine, chlorine, methyl and methoxy;
R(7) and R(8) identically or differently are H or (C$_1$–C$_6$)-alkyl; or
R(7) is phenyl-(CH$_2$)$_m$;
m is 1–4; or
R(7) is phenyl, which is unsubstituted or substituted by 1–2 substituents selected from the group consisting of fluorine, chlorine, methyl and methoxy; or
R(7) and R(8) together are a straight-chain or branched (C$_4$–C$_7$)-chain, where the chain can additionally be interrupted by O, S or NR(9);
R(9) is H or methyl; or
R(7) and R(8) together with the nitrogen atom to which they are bonded, are a dihydroindole, tetrahydroquinoline or tetrahydroisoquinoline system;
R(3), R(4) and R(5) independently of one another are H or (C$_1$–C$_2$)-alkyl, or
R(3) and R(4) together are a (C$_2$–C$_4$)-alkylene chain; or
R(4) and R(5) together are a (C$_4$–C$_7$)-alkylene chain;
and their pharmaceutically tolerable salts;
(HOE 92/F 34 - U.S. Pat. No. 5,373,924)
b) benzoylguanidines of the formula I

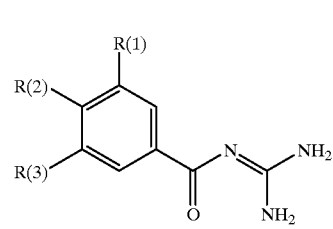

(I)

in which:
R(1) is R(4)—SO$_m$ or R(5)R(6)N—SO$_2$—;
m is zero, 1 or 2;
R(4) and R(5) are C$_1$–C$_8$-alkyl, C$_3$–C$_6$-alkenyl or —C$_n$H$_{2n}$—R(7);
n is zero, 1, 2, 3 or 4;
R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);
R(8) and R(9) are H or C$_1$–C$_4$-alkyl; or
R(5) is H;
R(6) is H or C$_1$–C$_4$-alkyl, or
R(5) and R(6) together are 4 or 5 methylene groups, of which one CH$_2$ group can be replaced by an O, S, NH, N—CH$_3$ or N-benzyl;
R(2) is hydrogen, F, Cl, Br, (C$_1$–C$_4$)-alkyl-, O—(CH$_2$)$_m$C$_p$F$_{2p+1}$ or—X—R(10);
m is zero or 1;
p is 1, 2 or 3;
x is O, S or NR(11);
R(10) is H, C$_1$–C$_6$-alkyl, C$_5$–C$_7$-cycloalkyl, cyclohexylmethyl, cyclopentylmethyl or —C$_n$H$_{2n}$—R(12);

n is zero, 1, 2, 3 or 4;

R(12) is phenyl, which is unsubstituted or substituted by 1–3 substituents selected from the group consisting of F, Cl, $CF_3$, methyl, methoxy and NR(8)R(9);

R(8) and R(9) are H or $C_1$–$C_4$-alkyl;

R(11) is hydrogen or $C_1$–$C_3$-alkyl; or

R(10) and R(11) together are 4 or 5 methylene groups, of which one $CH_2$ group can be replaced by O, S, NH, N—$CH_3$ or N-benzyl;

R(3) is defined as R(1), or is $C_1$–$C_6$-alkyl, nitro, cyano, trifluoromethyl, F, Cl, Br, I or —X—R(10);

X is O, S or NR(11);

R(10) is H, $C_1$–$C_6$-alkyl, $C_5$–$C_7$-cycloalkyl, cyclohexylmethyl, cyclopentylmethyl or —$C_nH_{2n}$—R(12);

n is zero to 4;

R(12) is phenyl, which is unsubstituted or substituted by 1–3 substituents selected from the group consisting of F, Cl, $CF_3$, methyl, methoxy und NR(8)R(9);

R(8) and R(9) are H or $C_1$–$C_4$-alkyl;

R(11) is $C_1$–$C_3$-alkyl, or

R(10) and R(11) together are 4 or 5 methylene groups, of which one $CH_2$ group can be replaced by O, S, NH, N—$CH_3$ or N-benzyl;

and their pharmaceutically tolerable salts;

(HOE 92/F 035 EP-A 556 673)

c) ortho-substituted benzoylguanidines of the formula I in which:

R(1) is F, Cl, Br, I, $C_1$–$C_6$-alkyl or —X—R(6);

X is O, S, NR(7) or Y—ZO;

Y is O or NR(7);

Z is C or SO;

R(6) is H, $C_1$–$C_6$-alkyl, $C_5$–$C_7$-cycloalkyl, cyclohexylmethyl, cyclopentylmethyl, —$(CH_2)_m$$C_pF_{2p+1}$ or —$C_nH_{2n}$—R(8);

m is zero or 1;

p is 1–3;

n is zero to4;

R(8) is phenyl, which is unsubstituted or substituted by 1–3 substituents selected from the group consisting of the groups F, Cl, $CF_3$, methyl, methoxy and NR(9)R(10);

R(9) and R(10) are H or $C_1$–$C_4$-alkyl;

R(7) is H or $C_1$–$C_3$-alkyl; or

R(6) and R(7) together are 4 or 5 methylene groups, of which one $CH_2$ group can be replaced by O, S, NH, N—$CH_3$ or N-benzyl;

R(3) is H or —X—R(6);

X is O, S, NR(7) or Y—ZO;

R(7) is H or $C_1$–$C_3$-alkyl;

Y is O or NR(7);

where Y is bonded to the phenyl radical of the formula I,

Z is C or SO;

R(6) is H, $C_1$–$C_6$-alkyl, $C_5$–$C_7$-cycloalkyl, cyclohexylmethyl, cyclopentylmethyl, —$(CH_2)_mC_pF_{2p+1}$ or —$C_nH_{2n}$—R(8);

m is zero or 1;

p is 1–3;

n is zero to 4;

R(8) is phenyl, which is unsubstituted or substituted by 1–3 substituents selected from the group consisting of F, Cl, $CF_3$, methyl, methoxy and NR(9)R(10);

R(9) and R(10) are H or $C_1$–$C_4$-alkyl; or

R(6) and R(7) together are 4 or 5 methylene groups, of which one $CH_2$ group can be replaced by O, S, NH, N—$CH_3$ or N-benzyl;

R(2) and R(4) identically or differently are R(11)—$SO_q$— or R(12)R(13)N—$SO_2$—;

q is zero –2;

R(11) is$C_1$–$C_4$-alkyl, which is unsubstituted or carries phenyl as a substituent, where phenyl is unsubstituted or substituted by 1–3 substituents selected from the group consisting of F, Cl, $CF_3$, methyl, methoxy and NR(9)R(10);

R(9) and R(10) are H or $C_1$–$C_4$-alkyl;

R(12) and R(13) are defined as R(6) and R(7);

or one of the two radicals R(2) or R(4) is hydrogen or is defined as R(1);

R(5) is H, methyl, F, Cl or methoxy, and their pharmaceutically tolerable salts;

(HOE 92/F 036 - U.S. Pat. No. 5,364,868)

d) benzoylguanidines of the formula I in which:

R(1) or R(2) is an amino group —NR(3)R(4);

R(3) and R(4) identically or differently are H, $C_1$–$C_6$-alkyl or $C_3$–$C_7$-cycloalkyl; or R(3) is phenyl—$(CH_2)_p$—;

p is 1, 1, 2, 3 or 4; or

R(3) is phenyl, where the phenyl in each case is unsubstituted or carries one to two substituents selected from the group consisting of fluorine, chlorine, methyl and methoxy; or R(3) and R(4) together can be a straight-chain or branched $C_4$–$C_7$-methylene chain, where one —$CH_2$— member of the methylene chain can be replaced by oxygen, S or NR(5);

R(5) is H or lower alkyl;

the other substituent R(1) or R(2) in each case is H, F, Cl, $C_1$–$C_4$-alkyl, $C_1$–$C_4$-alkoxy, $CF_3$, $C_mF_{2m+1}$—$CH_2$—, benzyl or phenoxy, where the respective phenyl radical is unsubstituted or carries one to two substituents selected from the group consisting of methyl, methoxy, fluorine and chlorine;

m is 1, 2 or 3;

and their pharmaceutically tolerable salts;

(92/F 197 K - NZ 248 013)

e) benzoylguanidines of the formula I

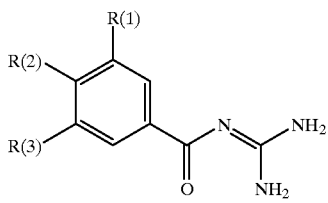

(I)

in which:

R(1) is R(4)—SO$_m$ or R(5)R(6)N—SO$_2$—;

m is zero, 1 or 2;

R(4) and R(5) are C$_1$–C$_8$-alkyl, C$_3$–C$_6$-alkenyl or —C$_n$H$_{2n}$—R(7);

n is zero, 1, 2, 3 or 4;

R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);

R(8) and R(9) are H or C$_1$–C$_4$-alkyl; or

R(5) is H;

R(6) is H or C$_1$–C$_4$-alkyl; or

R(5) and R(6) together are 4 or 5 methylene groups, of which one CH$_2$ group can be replaced by an O, S, NH, N—CH$_3$ or N-benzyl;

R(2) is hydrogen, straight-chain or branched (C$_5$–C$_8$)-alkyl, —CR(13)=CHR(12) or —C≡CR(12);

R(12) is phenyl, which is unsubstituted or substituted by 1–3 substituents selected from the group consisting of F, Cl, CF$_3$, methyl, methoxy and NR(14)R(15);

R(14) and R(15) are H or (C$_1$–C$_4$)-alkyl; or

R(12) is (C$_1$–C$_9$)-heteroaryl, which is unsubstituted or substituted as phenyl, or R(12) is (C$_1$–C$_6$)-alkyl, which is unsubstituted or substituted by 1–3 OH, or R(12) is (C$_3$–C$_8$)-cycloalkyl;

R(13) is hydrogen or methyl, or

R(12) is (C$_3$–C$_8$)-cycloalkyl, (C$_3$–C$_8$)-cycloalkyl-(C$_1$–C$_4$)-alkyl, phenyl, C$_6$H$_5$-(C$_1$–C$_4$)-alkyl, naphthyl, biphenylyl, 1,1-diphenyl-(C$_1$–C$_4$)-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl or cinnolinyl;

R(3) is defined as R(2); and where the aromatic substituents R(2) and R(3) are unsubstituted or substituted by 1–3 substituents from the groups F, Cl, CF$_3$, (C$_1$–C$_4$)-alkyl or -alkoxy, or NR(10)R(11) with R(10) and R(11) being H or (C$_1$–C$_4$)-alkyl;

and their pharmaceutically tolerable salts;

(HOE 92/F 303 K - EP-A 589 336, NZ 248 703)

f) benzoylguanidines of the formula I

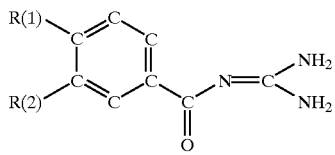

I in which:

R(1) or R(2) is R(3)—S(O)$_n$— or R(4)R(5)N—SO$_2$— the other substituent R(1) or R(2) in each case is H, OH, F, Cl, Br, I, C$_1$–C$_4$-alkyl, C$_1$–C$_4$-alkoxy, benzyloxy or phenoxy, which is unsubstituted or carries one to three substituents selected from the group consisting of fluorine, chlorine, methyl, methoxy, hydroxyl or benzyloxy, R(3)—S(O)$_n$, —NR(4)R(5) or 3,4-dehydropiperidine R(3) is C$_1$–C$_6$-alkyl, C$_5$–C$_7$-cycloalkyl, cyclopentylmethyl, cyclohexylmethyl or phenyl, which is unsubstituted or carries one to three substituents selected from the group consisting of fluorine, chlorine, methyl and methoxy;

R(4) and R(5) identically or differently, are H or C$_1$–C$_6$-alkyl; or

R(4) is phenyl—(CH$_2$)$_m$—;

m is 1, 2, 3 or 4; or

R(4) is phenyl, which is unsubstituted or carries one to two substituents selected from the group consisting of fluorine, chlorine, methyl and methoxy; or R(4) and R(5) together are a straight-chain or branched C$_4$–C$_7$-chain, where the chain can additionally be interrupted by O, S or NR(6), R(6) is H or methyl; or R(4) and R(5) together with the nitrogen atom to which they are bonded, are a dihydroindole, tetrahydroquinoline or tetrahydroisoquinoline system;

n is zero, 1 or 2;

and their pharmaceutically tolerable salts;

(92/F 304 - U.S. Pat. No. 5,416,094)

g) isoquinolines of the formula I

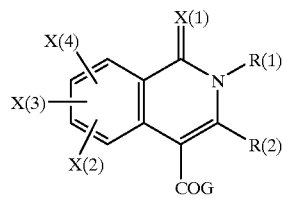

I in which:

R(1) is hydrogen, alkyl, cycloalkyl, arylalkyl, alkenyl, substituted aminoalkyl or an aryl or heteroaryl ring;

where the rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, trifluoromethyl, R(2) is hydrogen, halogen, alkyl or aryl;

which is unsubstituted or substituted by 1–3 groups selected from the group consisting of halogen, nitro, amino, mono(lower alkyl)amino, di(lower alkyl)

amino, lower alkyl, lower alkoxy, benzyloxy, phenoxy, hydroxyl,

G is

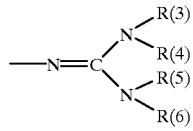

(VII)

X(2), X(3) and X(4) independently of one another are hydrogen, halogen, nitro, amino, alkyl, sulfonamide, mono(lower alkyl)amino, di(lower alkyl)amino, lower alkyl, benzyloxy, hydroxyl;

X(1) is hydrogen, oxygen, sulfur or NR(7);

R(7) is hydrogen, alkyl, cycloalkyl, arylalkyl, alkenyl, substituted aminoalkyl or an aryl or a heteroaryl ring; which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;

in which substituents each alkyl chain or alkenyl chain can be interrupted by oxygen, sulfur or NR(8);

R(8) is hydrogen, alkyl, cycloalkyl, arylalkyl, alkenyl, substituted aminoalkyl or an aryl or heteroaryl ring, which rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl and trifluoromethyl;

and their pharmaceutically acceptable salts;

(92/F 404 - EP 602 522, NZ 250 438)

h) compounds of the formula I

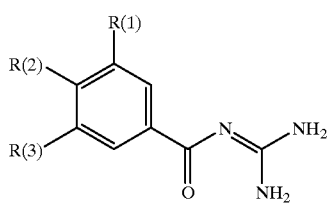

(I)

in which:

R(1) is hydrogen, F, Cl, Br, I, —NO$_2$, —C≡N, —CF$_3$, R(4)—SO$_m$ or R(5)R(6)N—SO$_2$—;

m is zero, 1 or 2;

R(4) and R(5) are (C$_1$–C$_8$)-alkyl, (C$_3$–C$_6$)-alkenyl, —C$_n$H$_{2n}$—R(7) or CF$_3$;

n is zero, 1, 2, 3 or 4;

R(7) is (C$_3$–C$_7$)-cycloalkyl or phenyl, which is not substituted or is substituted by 1–3 substituents selected from the group consisting of F, Cl, CF$_3$, methyl, methoxy and NR(8)R(9);

R(8) and R(9) are H or C$_1$–C$_4$-alkyl; or

R(5) is H;

R(6) is H or (C$_1$–C$_4$)-alkyl; or

R(5) and R(6) together are 4 or 5 methylene groups, of which one CH$_2$ group can be replaced by oxygen, S, NH, N—CH$_3$ or N-benzyl;

R(2) is —SR(10), —OR(10), —NHR(10), —NR(10)R(11), —CHR(10)R(12), —[CR(12)R(13)OR(13')],

—{C-[CH$_2$—OR(13')]R(12) (R(13)} or —[CR(18)R(17)]$_p$—(CO)—[CR(19)R(20)]$_q$—R(14);

R(10) and R(11) identically or differently are —[CHR(16)]$_s$—(CH$_2$)$_p$—(CHOH)q—(CH2)$_r$—(CHOH)$_t$—R(21) or —(CH$_2$)$_p$—O—(CH$_2$—CH$_2$O)$_q$—R(21), R(21) is hydrogen, methyl, p, q, r identically or differently are zero, 1, 2, 3 or 4;

s is zero or 1;

t is 1, 2, 3 or 4;

R(12) and R(13) identically or differently are hydrogen, (C$_1$–C$_6$)-alkyl or, together with the carbon atom carrying them, are a (C$_3$–C$_8$)-cycloalkyl, R(13) is hydrogen or (C$_1$–C$_4$)-alkyl;

R(1 4) is H, (C$_1$–C$_6$)-alkyl, (C$_3$–C$_8$)-cycloalkyl or —C$_a$H$_{2a}$—R(15);

a is zero, 1, 2, 3 or 4;

R(15) is phenyl, which is unsubstituted or substituted by 1–3 substituents selected from the group consisting of F, Cl, CF$_3$, methyl, methoxy and NR(8)R(9);

R(8) and R(9) are H or (C$_1$–C$_4$)-alkyl; or

R(15) is (C$_1$–C$_9$)-heteroaryl, which is unsubstituted or substituted as phenyl, or R(15) is (C$_1$–C$_6$)-alkyl, which is unsubstituted or substituted by 1–3 OH;

R(16), R(17), R(18), R(19) and R(20) are hydrogen or (C,-C$_3$)-alkyl;

(3) is defined as R(1), or (3) is (C$_1$–C$_6$)-alkyl or —X—R(22);

X is oxygen, S or NR(16);

R(16) is H or (C$_1$–C$_3$)-alkyl; or

R(22) and R(16) together are 4 or 5 methylene groups, of which one CH$_2$ group can be replaced by oxygen, S, NH, N—CH$_3$ or N-benzyl;

R(22) is defined as R(14);

and their pharmaceutically tolerable salts;

(HOE 92/F 405 - EP 602 523, NZ 250 437)

i) benzoylguanidines of the formula I

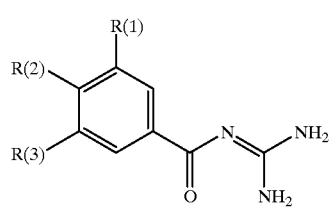

(I)

in which:

R(1) is hydrogen, F, Cl, Br, I, —NO$_2$, —C≡N, R(16)—C$_p$H$_{2p}$—O$_q$, R(4)—SO$_m$ or R(5)R(6)N—SO$_2$—;

m is zero, 1 or 2;

p is zero or 1;

q is zero, 1, 2 or 3;

R(16) is C$_r$F$_{2r+1}$;

r is 1, 2 or 3;

R(4) and R(5) are (C$_1$–C$_8$)-alkyl, (C$_3$–C$_6$)-alkenyl, —C$_n$H$_{2n}$—R(7) or CF$_3$;

n is zero, 1, 2, 3 or 4;

R(7) is (C$_3$–C$_7$)-cycloalkyl or phenyl, which is not substituted or is substituted by 1–3 substituents selected from the group consisting of F, Cl, CF$_3$, methyl, methoxy and NR(8)R(9);

R(8) and R(9) are H or C$_1$–C$_4$-alkyl; or

R(5) is H;

R(6) is H or (C$_1$–C$_4$)-alkyl; or

R(5) and R(6) together are 4 or 5 methylene groups, of which one CH$_2$ group can be replaced by oxygen, S, NH, N—CH$_3$ or N-benzyl, R(2) is (C$_1$–C$_9$)-heteroaryl, which is linked via C or N and which is unsubstituted or substituted by 1–3 substituents selected from the group consisting of F, Cl, CF$_3$, CH$_3$, methoxy, hydroxyl, amino, methylamino and dimethylamino; or R(2) is —SR(10), —OR(10), —NR(10)R(11), —CR(10)R(11)R(12);

R(10) is —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

a is zero, 1 or 2;

R(11) and R(12) independently of one another are defined as R(10) or are hydrogen or (C$_1$–C$_4$)-alkyl;

R(3) is defined as R(1), or is (C$_1$–C$_6$)-alkyl or —X—R(13);

X is oxygen, S, or NR(14);

R(14) is H or (C$_1$–C$_3$)-alkyl;

R(13) is H, (C$_1$–C$_6$)-alkyl, (C$_3$–C$_8$)-cycloalkyl or —C$_b$H$_{2b}$—R(15);

b is zero, 1, 2, 3 or 4; or

R(13) and R(14) together are 4 or 5 methylene groups, of which one CH$_2$ group can be replaced by oxygen, S, NH, N—CH$_3$ or N-benzyl;

R(15) is phenyl, which is unsubstituted or substituted by 1–3 substituents selected from the group consisting of F, Cl, CF$_3$, methyl, methoxy and NR(8)R(9);

R(8) and R(9) are H or (C$_1$–C$_4$)-alkyl;

and their pharmaceutically tolerable salts;

(HOE 92/F 411 - NZ 250 450, EP 603 650)

k) benzoylguanidines of the formula I

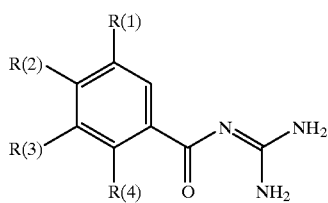

(I)

in which:

one of the substituents R(1), R(2), R(3) or R(4):

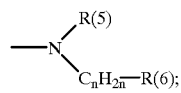

R(5) is hydrogen or C$_{(1-6)}$-alkyl;

n is zero, 1, 2, 3 or 4;

R(6) is H or C$_{(1-4)}$-alkyl; in which one CH$_2$ group can be replaced by 1 sulfur atom or a group NR(7);

R(7) is hydrogen, methyl or ethyl; or

R(6) is C$_{(3-8)}$-cycloalkyl or phenyl, which is unsubstituted or carries 1, 2 or 3 substituents selected from the group consisting of F, Cl, Br, methyl, methoxy, —NR(8)R(9);

R(8) and R(9) are H, methyl or ethyl; or

R(5) and R(6) together with the nitrogen atom are a 5-, 6- or 7-membered ring, in which 1 carbon atom can be replaced by oxygen, S or NR(10);

R(10) is H, C$_{(1-3)}$-alkyl or benzyl;

and the other substituents R(1), R(2), R(3), R(4) in each case are:

hydrogen, F, Cl, Br, I, CN, CF$_3$, NO$_2$, CF$_3$—O—, C$_m$F$_{2m+1}$—CH$_2$—O— or R(11)—C$_q$H$_{2q}$—X$_p$—;

m is 1, 2 or 3;

q is zero, 1, 2, 3 or 4;

p is zero or 1;

X is oxygen or NR(12);

R(12) is H or C$_{(1-3)}$-alkyl;

R(11) is hydrogen, C$_{(1-6)}$-alkyl, C$_{(3-8)}$-cycloalkyl or phenyl, which is unsubstituted or substituted by 1, 2 or 3 substituents selected from the group consisting of F, Cl, CH$_3$, CH$_3$—O— and NR(13)R(14);

R(13), R(14) are H, methyl or ethyl;

and their pharmaceutically tolerable salts;

(HOE 92/F 422 - EP 604 852)

l) benzoylguanidines of the formula I

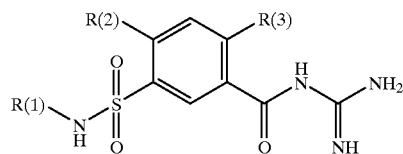

I in which

R(1) is R(4)R(5)N—C(X)—;

X is oxygen, S or N—R(6);

R(4) and R(5) identically or differently, are H, (C$_1$–C$_8$)-alkyl, (C$_3$–C$_6$)-alkenyl or —C$_n$H$_{2n}$—R(7);

n is zero, 1, 2, 3 or 4;

R(7) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or R(4) and R(5) together are 4 or 5 methylene groups, of which one CH$_2$ group can be replaced by oxygen, S, NH, N—CH$_3$ or N-benzyl;

R(6) is defined as R(4) or is amidine;

R(2) is H, F, Cl, Br, I, (C$_1$–C$_8$)-alkyl, 1-alkenyl or 1-alkynyl, (C$_3$–C$_8$)-cycloalkyl, (C$_3$–C$_8$)-cycloalkyl-(C$_1$–C$_4$)-alkyl, phenyl, C$_6$H$_5$-(C$_1$–C$_4$)-alkyl, naphthyl, biphenylyl, 1,1-diphenyl-(C$_1$–C$_4$)-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);

W is oxygen, S or NR(9);

R(8) is H, (C$_1$–C$_6$)-alkyl, (C$_5$–C$_7$)-cycloalkyl, cyclohexylmethyl, cyclopentylmethyl, —(CH$_2$)$_m$C$_p$F$_{2p+1}$ or —C$_q$H$_{2q}$—R(10);

m is zero or 1;

p is 1, 2 or 3;

q is zero, 1, 2, 3 or 4;

R(10) is phenyl, which is unsubstituted or substituted by 1–3 substituents selected from the group consisting of F, Cl, CF$_3$, methyl, methoxy and NR(11)R(12);

R(11) and R(12) are H or (C$_1$–C$_4$)-alkyl;

R(9) is H or (C$_1$–C$_3$)-alkyl; or

R(8) and R(9) together are 4 or 5 methylene groups, of which one $CH_2$ group can be replaced by oxygen, S, NH, N—$CH_3$ or N-benzyl;

R(3) is H, F, Cl, Br, I, ($C_1$–$C_6$)-alkyl or —W—R(8) as defined for R(2), and their pharmaceutically acceptable salts;

(93/F 054 - NZ 250 919, EP-A 612 723)

m) benzoylguanidines of the formula I

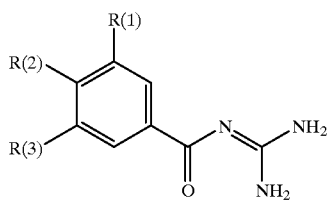

(I)

in which:
R(1), R(2), R(3) are hydrogen, F, Cl, Br, I or ($C_1$–$C_{12}$)-alkyl;
one of the substituents R(1), R(2) or R(3) is $N_3$, CN, OH or ($C_1$–$C_{10}$)-alkyloxy, if at least one of the remaining substituents R(1), R(2) or R(3) is a sufficiently lipophilic alkyl radical having 3 to 12 carbon atoms; or
one of the substituents R(1), R(2) or R(3) is R(4)-$C_nH_{2n}$—$O_m$—;
m is zero or 1;
n is zero, 1, 2 or 3;
R(4) is $C_pF_{2p+1}$;
p is 1, 2 or 3, if n is zero or 1; or
R(4) is ($C_3$–$C_{12}$)-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);
R(5) and R(6) are hydrogen or ($C_1$–$C_4$)-alkyl;
or one of the substituents R(1), R(2) or R(3) is —C≡CR(5) or —C[R(6)]=CR(5);
R(5) is phenyl, which is unsubstituted or substituted by 1–3 substituents selected from the group consisting of F, Cl, $CF_3$, methyl, methoxy, hydroxyl, amino, methylamino and dimethylamino, ($C_1$–$C_9$)-heteroaryl, which is unsubstituted or substituted as phenyl, or
R(5) is ($C_1$–$C_6$)-alkyl, which is unsubstituted or substituted by 1–3 OH; or
R(5) is ($C_3$–$C_8$)-cycloalkyl,
R(6) is hydrogen or methyl;
and their pharmacologically acceptable salts;

(93/F 153 - EP-A 627 413, NZ 260 660)

o) benzoylguanidines of the formula I

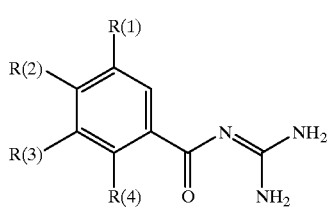

(I)

in which:
R(1) is hydrogen, F, Cl, Br, I, —$NO_2$, —C≡N, $X_o$—$(CH_2)_p$—$(CF_2)_q$—$CF_3$, R(5)—$SO_m$, R(6)—CO— or R(6)R(7)N—$SO_2$—, where X is oxygen, S or NR(14);
m is zero, 1 or 2;
o is zero or 1;
p is zero, 1 or 2;
q is zero, 1, 2, 3, 4, 5 or 6;
R(5) and R(6) are ($C_1$–$C_8$)-alkyl, ($C_3$–$C_6$)-alkenyl, -$C_nH_{2n}$—R(8) or $CF_3$;
n is zero, 1, 2, 3 or 4;
R(8) is ($C_3$–$C_7$)-cycloalkyl or phenyl, which is not substituted or is substituted by 1–3 substituents selected from the group consisting of F, Cl, $CF_3$, methyl, methoxy and NR(9)R(10);
R(9) and R(10) are H or $C_1$–$C_4$-alkyl; or
R(6) is H;
R(7) is H or ($C_1$–$C_4$)-alkyl; or
R(6) and R(7) together are 4 or 5 methylene groups, of which one $CH_2$ group can be replaced by oxygen, S, NH, N—$CH_3$ or N-benzyl;

R(2) is

—Y—⟨phenyl⟩—$(C)_h$—$(CHOH)_i$—$(CH_2)_j$—$(CHOH)_k$—R(11)
‖
O or

⟨phenyl⟩—$(C)_h$—$(CHOH)_i$—$(CH_2)_j$—$(CHOH)_k$—R(11)
‖
O
—Y or

⟨phenyl⟩—$(C)_h$—$(CHOH)_i$—$(CH_2)_j$—$(CHOH)_k$—R(11)
‖
O
Y—

Y is oxygen, —S— or —NR(12)—;
R(11) and R(12) are hydrogen or ($C_1$–$C_3$)-alkyl;
h is zero or 1;
i, j, and k independently are zero, 1, 2, 3 or 4; but where h, i and k are not simultaneously zero,
R(3) is defined as R(1), or is ($C_1$–$C_6$)-alkyl or —X—R(13);
X is oxygen, S or NR(14);
R(14) is H or ($C_1$–$C_3$)-alkyl;
R(13) is H, ($C_1$–C6)-alkyl, ($C_3$–$C_8$)-cycloalkyl or —$C_bH_{2b}$—R(15);
b is zero, 1, 2, 3 or 4; or
R(13) and R(14) together are 4 or 5 methylene groups, where one $CH_2$ group can be replaced by oxygen, S, NH, N—$CH_3$ or N-benzyl;
R(15) is phenyl, which is unsubstituted or substituted by 1–3 substituents selected from the group consisting of F, Cl, $CF_3$, methyl, methoxy and NR(9)R(10);
R(9) and R(10) are H or ($C_1$–$C_4$)-alkyl;
R(4) is hydrogen, —OR(16) or —NR(16)R(17);
R(16) and R(17) independently are hydrogen or ($C_1$–$C_3$)-alkyl;
and their pharmaceutically tolerable salts;
(HOE 93/F 154 - EP-A 628 543, NZ 260 681)

p) benzoylguanidines of the formula I

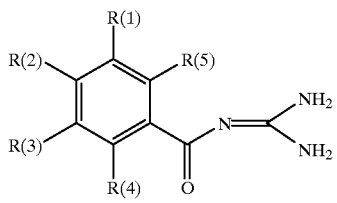

in which:

R(1) is R(6)—CO or R(7)R(8)N—CO;
 R(6) is $(C_1-C_8)$-alkyl, $(C_1-C_8)$-perfluoroalkyl, $(C_3-C_8)$-alkenyl or $-C_nH_{2n}-R(9)$;
 n is zero, 1, 2, 3 or 4;
 R(9) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11);
 R(10) and R(11) are H, $(C_1-C_4)$-alkyl or $(C_1-C_4)$-perfluoro-alkyl;
 R(7) is H, $(C_1-C_8)$-alkyl, $(C_1-C_8)$-perfluoroalkyl, $(C_3-C_8)$-alkenyl or $-C_nH_{2n}-R(12)$;
 n is zero, 1, 2, 3 or 4;
 R(12) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
 R(13) and R(14) are H, $(C_1-C_4)$-alkyl or $(C_1-C_4)$-perfluoro-alkyl;
R(8) is H, $(C_1-C_4)$-alkyl or $(C_1-C_4)$-perfluoroalkyl; or
R(7) and R(8) together are 4 or 5 methylene groups, of which one $CH_2$ group can be replaced by oxygen, S, NH, N—$CH_3$ or N-benzyl;
R(2) is defined as R(1), or is H, F, Cl, Br, I, CN, $NO_2$, $(C_1-C_8)$-alkyl, $(C_1-C_8)$-perfluoroalkyl, $(C_3-C_8)$-alkenyl or $-C_nH_{2n}R(15)$;
 n is zero, 1, 2, 3 or 4;
 R(15) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);
 R(16) and R(17) are H, $(C_1-C_4)$-alkyl or $(C_1-C_4)$-perfluoro-alkyl; or
R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
R(2) is SR(18), —OR(18), —NR(18)R(19), —CR(18)R(19)R(20);
 R(18) is $-C_aH_{2a}-(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
 a is zero, 1 or 2;
 R(19) and R(20) independently of one another are defined as R(18) or are hydrogen, $(C_1-C_4)$-alkyl or $(C_1-C_4)$-perfluoroalkyl; or R(2) is R(21)—$SO_m$ or R(22)R(23)N—$SO_2$—;
 m is 1 or 2;
 R(21) is $(C_1-C_8)$-alkyl, $(C_1-C_8)$-perfluoroalkyl, $(C_3-C_8)$-alkenyl, $-C_nH_{2n}-R(24)$,
 n is zero, 1, 2, 3 or 4;
 R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
  R(27) and R(28) are H, $(C_1-C_4)$-alkyl or $(C_1-C_4)$-perfluoro-alkyl;
 R(22) is H, $(C_1-C_8)$-alkyl, $(C_1-C_8)$-perfluoroalkyl, $(C_3-C_8)$-alkenyl, $-C_nH_{2n}-R(29)$;
 n is zero, 1, 2, 3 or 4;
 R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);
  R(30) and R(31) are H, $(C_1-C_4)$-alkyl or $(C_1-C_4)$-perfluoro-alkyl;
 R(23) is H, $(C_1-C_4)$-alkyl or $(C_1-C_4)$-perfluoroalkyl; or
 R(22) and R(23) together are 4 or 5 methylene groups, of which one $CH_2$ group can be replaced by oxygen, S, NH, N—$CH_3$ or N-benzyl; or
R(2) is R(33)X—;
 X is oxygen, S, NR(34), (D=O)A—, NR(34)C=MN$^{(*)}$R(35)—;
 M is oxygen or S;
 A is oxygen or NR(34);
 D is C or SO;
 R(33) is $(C_1-C_8)$-alkyl, $(C_3-C_8)$-alkenyl, $(CH_2)_bC_dF_{2d+1}$, $-C_nH_{2n}-R(36)$,
 b is zero or 1;
 d is 1, 2, 3, 4, 5, 6 or 7;
 n is zero, 1, 2, 3 or 4;
 R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
  R(37) and R(38) are H, $(C_1-C_4)$-alkyl or $(C_1-C_4)$-perfluoro-alkyl;
 R(34) is H, $(C_1-C_4)$-alkyl or $(C_1-C_4)$-perfluoroalkyl;
 R(35) is defined as R(33); or
 R(33) and R(34) together are 4 or 5 methylene groups, of which one $CH_2$ group can be replaced by oxygen, S, NH, N—$CH_3$ or N-benzyl;
 where A and $N^{(*)}$ are bonded to the phenyl nucleus of the benzoylguanidine parent structure; or
R(2) is —SR(40), —OR(40), —NHR(40), —NR(40)R(41), —CHR(40)R(42), —C[R(42)R(43)OH], —C≡CR(45), —CR(46)=CHR(45), —[CR(47)R(48)]$_u$—(CO)—[CR(49)R(50)]$_v$—R(44);
 R(40), R(41) identically or differently are —$(CH_2)_p$—$(CHOH)_q$—$(CH_2)_r$—$(CHOH)_t$—R(51) or —$(CH_2)_p$—O—$(CH_2-CH_2O)q$—R(51);
 R(51) is hydrogen or methyl;
 u is 1, 2, 3 or 4;
 v is zero, 1, 2, 3 or 4;
 p, q, r identically or differently are zero, 1, 2 or 3;
 t is 1, 2,3 or 4;
 R(42) and R(43) identically or differently are hydrogen or $(C_1-C_6)$-alkyl; or
 R(42) and R(43) together with the carbon atom carrying them form a $(C_3-C_8)$-cycloalkyl;
 R(44) is H, $(C_1-C6)$-alkyl, $(C_3-C_8)$-cycloalkyl or —$C_eH_{2e}$—R(45);

e is zero, 1, 2, 3 or 4;
R(45) is phenyl, which is unsubstituted or substituted by 1–3 substituents from the group consisting of F, Cl, CF$_3$, methyl, methoxy and NR(52)R(53) where R(52) and R(53) are H or (C$_1$–C$_4$)-alkyl, or R(45) is (C$_1$–C$_9$)-heteroaryl, which is unsubstituted or substituted as phenyl; or
R(45) is (C$_1$–C$_6$)-alkyl, which is unsubstituted or substituted by 1–3 OH;
R(46), R(47), R(48), R(49) and R(50) are hydrogen or methyl; or R(2) is R(55)—NH—SO$_2$—;
R(55) is R(56)R(57)N—(C=Y)—;
Y is oxygen, S or N—R(58);
R(56) and R(57) identically or differently are H, (C$_1$–C$_8$)-alkyl, (C$_3$–C$_6$)-alkenyl or —C$_f$H$_{2f}$—R(59);
f is zero, 1, 2, 3 or 4;
R(59) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or
R(56) and R(57) together are 4 or 5 methylene groups, of which one CH$_2$ group can be replaced by oxygen, S, NH, N—CH$_3$ or N-benzyl;
R(58) is defined as R(56) or is amidine;
R(3), R(4) and R(5) independently of one another are defined as R(1) or R(2);
and their pharmaceutically tolerable salts;
(HOE 93/F 220 - EP-A 640 593, NZ 264 117)

q) benzoylguanidines of the formula I

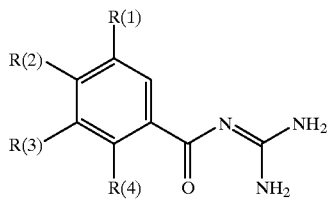

(I)

in which:

R(1) is hydrogen, F, Cl, Br, I, —NO$_2$, —C≡N, —X$_o$—(CH$_2$)$_p$—(CF$_2$)$_q$—CF$_3$, R(5)—SO$_m$—, R(6)—CO—, R(6)R(7)N—CO— or R(6)R(7)N—SO$_2$—;
X is oxygen, —S— or NR(14);
m is zero, 1 or 2;
o is zero or 1;
p is zero, 1 or 2;
q is zero, 1, 2, 3, 4, 5 or 6;
R(5) and R(6) are (C$_1$–C$_8$)-alkyl, (C$_3$–C$_6$)-alkenyl, —C$_n$H$_{2n}$—R(8) or CF$_3$;
n is zero, 1, 2, 3 or 4;
R(8) is (C$_3$–C$_7$)-cycloalkyl, phenyl, which is not substituted or is substituted by 1 to 3 substituents selected from the group consisting of F, Cl, CF$_3$, methyl, methoxy and NR(9)R(10);
R(9) and R(10) are H or (C$_1$–C$_4$)-alkyl; or
R(6) is hydrogen;
R(7) is hydrogen or (C$_1$–C$_4$)-alkyl; or
R(6) and R(7) together are 4 or 5 methylene groups, of which one CH$_2$ group can be replaced by oxygen, S, NH, N—CH$_3$ or N-benzyl;

R(2) is

—Y—⌬—R(11), ⌬—R(11) or
                    |
                    Y

⌬—R(11)
|
Y—

R(11) is (C$_1$–C$_9$)-heteroaryl, which is linked via C or N and which is unsubstituted or substituted by 1 to 3 substituents selected from the group consisting of F, Cl, CF$_3$, CH$_3$, methoxy, hydroxyl, amino, methylamino, dimethylamino and benzyl;
Y is oxygen, —S— or NR(12);
R(12) is H or (C$_1$–C$_4$)-alkyl;
R(3) is defined as R(1); or
R(3) is (C$_1$–C$_6$)-alkyl or —X—R(13);
X is oxygen, —S— or NR(14);
R(14) is H or (C$_1$–C$_3$)-alkyl;
R(13) is H, (C$_1$–C$_6$)-alkyl, (C$_3$–C$_8$)-cycloalkyl or —C$_b$H$_{2b}$—R(15);
b is zero, 1, 2, 3 or 4; or
R(13) and R(14) together are 4 or 5 methylene groups, of which one CH$_2$ group can be replaced by oxygen, S, NH, N—CH$_3$ or N-benzyl;
R(15) is phenyl, which is unsubstituted or substituted by 1–3 substituents selected from the group consisting of F, Cl, CF$_3$, methyl, methoxy and NR(9)R(10);
R(9) and R(10) are H or (C$_1$–C$_4$)-alkyl;
R(4) is hydrogen, —OR(16), —NR(16)R(17) or C$_r$F$_{2r+1}$;
R(16) and R(17) independently are hydrogen or (C$_1$–C$_3$)-alkyl;
r is 1, 2, 3 or 4;
and their pharmaceutically tolerable salts;
(HOE 93/F 223 K - EP 639 573, NZ 264 130)

r) benzo-fused 5-membered ring heterocycles of the formula I (I)

[structure with R(2), R(3), R(4), R(5), B, X, Y, A, R(1)]

in which:
X is N or CR(6);
Y is oxygen, S or NR(7);
A, B together are a bond or
A, B are both hydrogen, if X is CR(6) and Y is NR(7) simultaneously; one of the substituents R(1) to R(6) is a —CO—N=C(NH$_2$)$_2$ group;
the other substituents R(1) to R(6) in each case are hydrogen, F, Cl, Br, I or (C$_1$–C$_6$)-alkyl;
up to two of the other substituents R(1) to R(6) are CN, NO$_2$, N$_3$, (C$_1$–C$_4$)-alkyloxy or CF$_3$;

up to one of the other substituents is R(8)—$C_nH_2$,—Z—;
n is zero to 10; where the alkylene chain —$C_nH_{2n}$— is straight-chain or branched and where one carbon atom can be replaced by an oxygen or sulfur atom or by a nitrogen atom;
R(8) is hydrogen, ($C_2$–$C_6$)-alkenyl or ($C_3$–$C_{10}$)-cycloalkyl, which is unsubstituted or substituted by 1 to 4 methyl groups or an OH group, or can contain an ethylene group —CH=CH—, and in which one methylene group can be replaced by an oxygen or sulfur atom or by a nitrogen atom; or
R(8) is phenyl, which is unsubstituted or substituted by 1 to 3 substituents selected from the group consisting of F, Cl, Br, I, $CF_3$, $CH_3$—S(O)$_s$— or R(9)—$W_y$—;
s is zero, 1 or 2;
R(9) is H, methyl, ethyl,
W is oxygen or NR(10);
R(10) is H or methyl;
y is zero or 1; or
R(8) is $C_mF_{2m+1}$;
m is 1 to 3; or
R(8) is 1- or 2-naphthyl, pyridyl, quinolyl or isoquinolyl;
Z is —CO—, —$CH_2$— or —[CR(11)(OH)]$_q$—;
q is 1, 2 or 3;
R(11) is H or methyl; or
Z is oxygen or —NR(12)—;
R(12) is H or methyl; or
Z is —S(O)$_s$—;
s is zero, 1 or 2; or
Z is —$SO_2$—NR(13)—;
R(13) is H or ($C_1$–$C_4$)-alkyl;
R(7) is hydrogen, ($C_1$–$C_{10}$)-alkyl, ($C_2$–$C_{10}$)-alkenyl or R(8)—$C_nH_{2n}$—;
and their pharmaceutically tolerable salts;
(HOE 93/F 236 - EP-A 638 548, NZ 264 216)
s) benzoylguanidines of the formula I

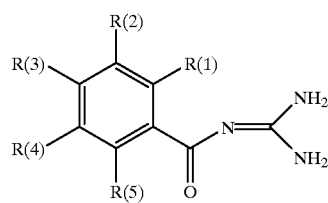

(I)

in which:
R(1), R(3) or R(4) is —NR(6) C=X NR(7)R(8);
X is oxygen or S;
R(6) is hydrogen, ($C_1$–$C_8$)-alkyl, ($C_1$–$C_8$)-perfluoroalkyl, ($C_3$–$C_8$)-alkenyl or —$C_nH_{2n}$—R(9);
n is zero, 1, 2, 3 or 4;
R(9) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11);
R(10) and R(11) are H, ($C_1$–$C_4$)-alkyl or ($C_1$–$C_4$)-perfluoroalkyl;
R(7) is hydrogen, ($C_1$–$C_8$)-alkyl, ($C_1$–$C_8$)-perfluoroalkyl, ($C_3$–$C_8$)-alkenyl or —$C_oH_{2o}$—R(12);
o is zero, 1, 2, 3 or 4;
R(12) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
R(13) and R(14) are H, ($C_1$–$C_4$)-alkyl or ($C_1$–$C_4$)-perfluoroalkyl;
R(8) is defined as R(7); or
R(7) and R(8) together are 4 or 5 methylene groups, of which one $CH_2$ group can be replaced by oxygen, S, NH, N—$CH_3$ or N-benzyl;
the remaining substituents R(2), R(3), R(4), R(5) or R(1), R(2), R(4), R(5) or R(1), R(2), R(3), R(5) in each case independently of one another are hydrogen, F, Cl, Br, I, —$O_{ta}$($C_1$–$C_8$)-alkyl, —$O_{tb}$($C_3$–$C_8$)-alkenyl, —$O_{tc}$($CH_2$)$_b$$C_dF_{2d+1}$, —$O_{td}C_pH_{2p}$R(18), or up to 2 groups CN, $NO_2$, NR(16)R(17),
b is zero or 1;
d is 1, 2, 3, 4, 5, 6 or 7;
ta is zero or 1;
tb is zero or 1;
tc is zero or 1;
td is zero or 1;
p is zero, 1, 2, 3 or 4;
R(18) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(19)R(20);
R(19) and R(20) are hydrogen or ($C_1$–$C_4$)-alkyl or ($C_1$–$C_4$)-perfluoroalkyl;
R(16) is hydrogen, ($C_1$–$C_8$)-alkyl, ($C_1$–$C_8$)-perfluoroalkyl, ($C_3$–$C_8$)-alkenyl, —$c_qH_{2q}$—R($^2$1),
q is zero, 1, 2, 3 or 4;
R(21) is ($C_3$–$C_8$)-cycloalkyl, phenyl, biphenylyl or naphthyl, where the aromatics are not substituted or are substituted by 1–3 substituents from the group F, Cl, $CF_3$, methyl, methoxy or NR(22)R(23), R(22) and R(23) are hydrogen, ($C_1$–$C_4$)-alkyl or ($C_1$–$C_4$)-perfluoroalkyl;
R(17) is hydrogen, ($C_1$–$C_8$)-alkyl, ($C_1$–$C_8$)-perfluoroalkyl, ($C_3$–$C_8$)-alkenyl, —$C_rH_{2r}$—R(24);
r is zero, 1, 2, 3 or 4;
R(24) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(25)R(26);
R(25) and R(26) are hydrogen, ($C_1$–$C_4$)-alkyl or ($C_1$–$C_4$)-perfluoroalkyl; or
R(16) and R(17) together are 4 or 5 methylene groups, of which one $CH_2$ group can be replaced by oxygen, S, NH, N—$CH_3$ or N-benzyl;
and their pharmaceutically tolerable salts;
(HOE 93/F 249 - EP-A 640 587, NZ 264 282)
t) diacyl-substituted guanidines of the formula I

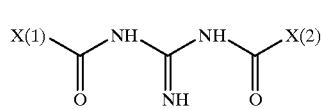

I in which:

X(1) and X(2) are

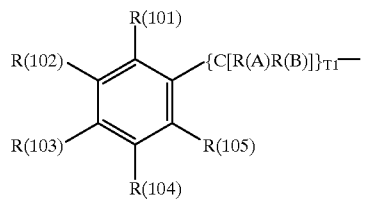

T1 is zero, 1, 2, 3 or 4;

R(A) and R(B) independently of one another are hydrogen, F, Cl, Br, I, CN, OR(106), $(C_1-C_8)$-alkyl, $(C_3-C_8)$-cycloalkyl, $O_{zk}(CH_2)_{zl}C_{zm}F_{2zm+1}$, NR(107)R(108), phenyl or benzyl, where the aromatics are not substituted or are substituted by 1–3 substituents selected from the group consisting of F, Cl, $CF_3$, methyl, methoxy and NR(109)R(110);

R(109) and R(110) are hydrogen, $(C_1-C_4)$-alkyl or $(C_1-C_4)$-perfluoroalkyl;

zl is zero, 1, 2, 3 or 4;

zk is zero or 1;

zm is 1, 2, 3, 4, 5, 6, 7 or 8;

R(106) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(111)R(112);

R(111) and R(112) are hydrogen, $(C_1-C_4)$-alkyl or $(C_1-C_4)$-perfluoro-alkyl;

R(107) and R(108) independently of one another are defined as R(106), or

R(107) and R(108) together are 4 or 5 methylene groups, of which one $CH_2$ group can be replaced by oxygen, S, NH, N—$CH_3$ or N-benzyl; or X(1) and X(2) are

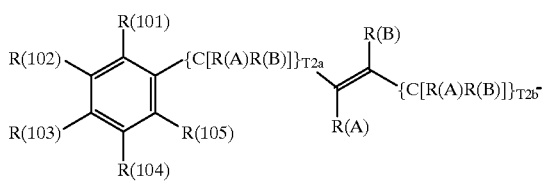

T2a and T2b independently of one another are zero, 1 or 2;

where the double bond can have the (E)- or (Z)-configuration; or

X(1) and X(2) are

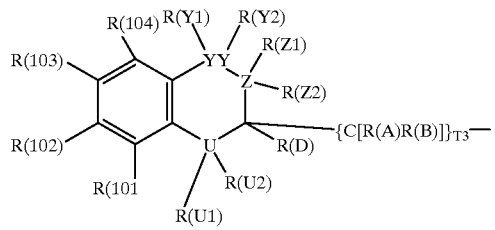

T3 is zero, 1 or 2;

U, YY and Z independently of one another are C or N, where U, YY, Z can carry the following number of substituents:

| U, YY or Z | Bonded in the ring to a double bond | Number of permitted substituents |
|---|---|---|
| C | yes | 1 |
| C | no | 2 |
| N | yes | 0 |
| N | no | 1 |

R(D) is hydrogen, $(C_1-C_8)$-alkyl or $(C_1-C_8)$-perfluoroalkyl, R(U1), R(U2), R(Y1), R(Y2), R(Z1), R(Z2) independently of one another are hydrogen, F, Cl, Br, I, CN, OR(114), $(C_1-C_8)$-alkyl, $(C_3-C_8)$-cycloalkyl, $O_{zka}(CH_2)_{zla}C_{zma}F_{2zma+1}$, NR(115)R(116), phenyl or benzyl, where the aromatics are not substituted or are substituted by 1–3 substituents selected from the group consisting of F, Cl, $CF_3$, methyl, methoxy, NR(117)R(118), R(117) and R(118) are hydrogen, $(C_1-C_4)$-alkyl or $(C_1-C_4)$-perfluoroalkyl, zka is zero or 1;

zla is zero, 1, 2, 3 or 4;

zma is 1, 2, 3, 4, 5, 6, 7 or 8;

R(114) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(119)R(120);

R(119) and R(120) are hydrogen, $(C_1-C_4)$-alkyl or $(C_1-C_4)$-perfluoro-alkyl;

R(115) and R(116) independently of one another are defined as R(114); or

R(115) and R(116) together are 4 or 5 methylene groups, of which one $CH_2$ group can be replaced by oxygen, S, NH, N—$CH_3$ or N-benzyl; but where the constitution of U is nitrogen (N), YY is nitrogen (N) and Z is carbon (C) is excluded, R(101), R(102), R(103), R(104) and R(105) independently of one another are hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(110c) N—CO, R(111a)—CO— or R(112a)R(113a)N—$SO_2$—, where the perfluoroalkyl group is straight-chain or branched, X is oxygen, S or NR(114a);
  R(114a) is H or $(C_1–C_3)$-alkyl;
zoa is zero or 1;
zbm is zero, 1 or 2;
zpa is zero, 1, 2, 3 or 4;
zqa is 1, 2, 3, 4, 5, 6, 7 or 8;
R(110a), R(110b), R(111a) and R(112a) independently of one another are $(C_1–C_8)$-alkyl, $(C_3–C_8)$-alkenyl, —$C_{zn}H_{2zn}$—R(115a) or $(C_1–C_8)$-perfluoroalkyl;
  zn is zero, 1, 2, 3 or 4;
  R(115a) is $(C_3–C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(116a)R(117a);
    R(116a) and R(117a) are hydrogen, $(C_1–C_4)$-perfluoroalkyl or $(C_1–C_4)$-alkyl; or
R(110b), R(111a) and R(112a) are hydrogen;
R(110c) and R(113a) independently are hydrogen, $(C_1–C_4)$-perfluoroalkyl or $(C_1–C_4)$-alkyl; or
R(110b) and R(110c) and R(112a) and R(113a) together are 4 or 5 methylene groups, of which one $CH_2$ group can be replaced by oxygen, sulfur, NH, N—$CH_3$ or N-benzyl; or
R(101), R(102), R(103), R(104), R(105) independently of one another are $(C_1–C_8)$-alkyl, —$C_{zal}H_{2zal}$R(118a) or $(C_3–C_8)$-alkenyl,
  zal is zero, 1, 2, 3 or 4;
  R(118a) is $(C_3–C_8)$-cycloalkyl, phenyl, biphenylyl or naphthyl, where the aromatics are not substituted or are substituted by 1–3 substituents from the group consisting of F, Cl, $CF_3$, methyl, methoxy or NR(119a)R(119b);
    R(119a) and R(119b) are hydrogen, $(C_1–C_4)$-alkyl or $(C_1–C_4)$-perfluoroalkyl; or
R(101), R(102), R(103), R(104), R(105) independently of one another are $(C_1–C_9)$-heteroaryl, which is linked via C or N and which is unsubstituted or substituted by 1–3 substituents from the group consisting of F, Cl, $CF_3$, $CH_3$, methoxy, hydroxyl, amino, methylamino and dimethylamino; or
R(101), R(102), R(103), R(104), R(105) independently of one another are —C≡C—R(193);
  R(193) is phenyl which is not substituted or is substituted by 1–3 substituents from the group consisting of F, Cl, $CF_3$, methyl, methoxy or NR(194)R(195);
  R(194) and R(195) are hydrogen or $CH_3$; or
R(101), R(102), R(103), R(104), R(105) independently of one another are
  —Y—para—$C_6H_4$—$(CO)_{zh}$—$(CHOH)_{zi}$—$(CH_2)_{zj}$—$(CHOH)_{zk}$—R(123),
  —Y—meta—$C_6H_4$—$(CO)_{zad}$—$(CHOH)_{zae}$—$(CH_2)_{zaf}$—$(CHOH)_{zag}$—R(124) or
  —Y—ortho—$C_6H_4$—$(CO)_{zah}$—$(CHOH)_{zao}$—$(CH_2)_{zap}$—$(CHOH)_{zak}$—R(125);
  Y is oxygen, —S— or —NR(122d)—;
  zh, zad, zah independently are zero or 1;
  zi, zj, zk, zae, zaf, zag, zao, zap and zak independently are zero, 1, 2, 3 or 4;
  but where in each case zh, zi and zk are not simultaneously zero, zad, zae and zag are not simultaneously zero, and zah, zao and zak are not simultaneously zero,
  R(123), R(124), R(125) and R(122d) independently are hydrogen or $(C_1–C_3)$-alkyl; or
R(101), R(102), R(103), R(104) and R(105) independently of one another are SR(129), —OR(130), —NR(131)R(132) or —CR(133)R(134)R(135);

R(129), R(130), R(131) and R(133) independently are —$C_{zab}H_{2zab}$—$(C_1–C_9)$-heteroaryl, which is unsubstituted or substituted by 1–3 substituents from the group consisting of F, Cl, $CF_3$, $CH_3$, methoxy, hydroxyl, amino, methylamino and dimethylamino;
  zab is zero, 1 or 2;
R(132), R(134) and R(135) independently of one another are defined as R(129) or are hydrogen, $(C_1–C_4)$-alkyl or $(C_1–C_4)$-perfluoroalkyl; or
R(101), R(102), R(103), R(104) and R(105) independently of one another are —W—para—$(C_6H_4)$—R(196), —W—meta—$(C_6H_4)$—R(197) or —W—ortho—$(C_6H_4)$—R(198);
  R(196), R(197) and R(198) independently are $(C_1–C_9)$-heteroaryl, which is linked via C or N and which is unsubstituted or substituted by 1 to 3 substituents from the group consisting of F, Cl, $CF_3$, $CH_3$, methoxy, hydroxyl, amino, methylamino, dimethylamino and benzyl;
  W is oxygen, S or NR(136)—;
    R(136) is hydrogen or $(C_1–C_4)$-alkyl; or
R(101), R(102), R(103), R(104) and R(105) independently of one another are R(146)X(1a)—;
  X(1a) is oxygen, S, NR(147), (D=O)A—, NR(148)C=MN$^{(*)}$R(149)—;
  M is oxygen or sulfur;
  A is oxygen or NR(150);
  D is C or SO;
  R(146) is $(C_1–C_8)$-alkyl, $(C_3–C_8)$-alkenyl, $(CH_2)_{zbz}C_{zdz}F_{2zdz+1}$ or —$C_{zxa}H_{2zxa}$—R(151);
    zbz is zero or 1;
    zdz is 1, 2, 3, 4, 5, 6 or 7;
    zxa is zero, 1, 2, 3 or 4;
    R(151) is $(C_3–C_8)$-cycloalkyl, phenyl, biphenylyl or naphthyl, where the aromatics are not substituted or are substituted by 1–3 substituents from the group consisting of F, Cl, $CF_3$, methyl, methoxy and NR(152)R(153);
      R(152) and R(153) are hydrogen, $(C_1–C_4)$-alkyl or $(C_1–C_4)$-perfluoroalkyl;
    R(147), R(148) and R(150) independently are hydrogen, $(C_1–C_4)$-alkyl, $(C_1–C_4)$-perfluoroalkyl;
    R(149) is defined as R(146), or
  R(146) and R(147), or R(146) and R(148) together are 4 or 5 methylene groups, of which one $CH_2$ group can be replaced by oxygen, sulfur, NH, N—$CH_3$ or N-benzyl;
  where A and N$^{(*)}$ are bonded to the phenyl nucleus of the alkanoyl parent structure; or
R(101), R(102), R(103), R(104) and R(105) independently of one another are —SR(164), —OR(165), —NHR(166), —NR(167)R(168), —CHR(169)R(170), —CR(154)R(155)OH, —C≡CR(156), —CR(158)=CR(157) or —$[CR(159)R(160)]_{zu}$—(C=O)—$[CR(161)R(162)]_{zv}$—R(163);
  R(164), R(165), R(166), R(167), R(169) identically or differently are —$(CH_2)_{zy}$—$(CHOH)_{zz}$—$(CH_2)_{zaa}$—$(CHOH)_{zt}$—R(171) or —$(CH2)_{zab}$—O—$(CH_2$—$CH_2O)_{zac}$—R(172);
    R(171) and R(172) are hydrogen or methyl;
    zu is 1, 2, 3 or 4;
    zv is zero, 1, 2, 3 or 4;
    zy, zz, zaa, zab, zac identically or differently are zero, 1, 2, 3 or 4;
    zt is 1, 2, 3 or 4;

R(168), R(170), R(154), R(155) identically or differently are hydrogen or (C$_1$–C$_6$)-alkyl, or R(169) and R(170), or R(154) and R(155) together with the carbon atom carrying them are a (C$_3$–C$_8$)-cycloalkyl;

R(163) is hydrogen, (C$_1$–C$_6$)-alkyl, (C$_3$–C$_8$)-cycloalkyl or —C$_{zeb}$H$_{2zeb}$—R(173);

zeb is zero, 1, 2, 3 or 4;

R(156), R(157) and R(173) independently are phenyl which is unsubstituted or is substituted by 1–3 substituents from the group consisting of F, Cl, CF$_3$, methyl, methoxy and NR(174)R(175);

R(174) and R(175) are hydrogen or (C$_1$–C$_4$)-alkyl; or

R(156), R(157) and R(173) independently are (C$_1$–C$_9$)-heteroaryl, which is unsubstituted or substituted as phenyl;

R(158), R(159), R(160), R(161) and R(162) are hydrogen or methyl, or

R(101), R(102), R(103), R(104), R(105) independently of one another are R(176)—NH—SO$_2$—;

R(176) is R(177)R(178)N—(C=Y')—;

Y' is oxygen, S or N—R(179);

R(177) and R(178) identically or differently are hydrogen, (C$_1$–C$_8$)-alkyl, (C$_3$–C$_6$)-alkenyl or —C$_{zfa}$H$_{2zfa}$—R(180);

zfa is zero, 1, 2, 3 or 4;

R(180) is (C$_5$–C$_7$)-cycloalkyl or phenyl, which is unsubstituted or substituted by 1–3 substituents selected from the group consisting of F, Cl, CF$_3$, methoxy or (C$_1$–C$_4$)-alkyl; or R(177) and R(178) together are 4 or 5 methylene groups, of which one CH$_2$ group can be replaced by oxygen, sulfur, NH, N—CH$_3$ or N-benzyl;

R(179) is defined as R(177) or is amidine, or

R(101), R(102), R(103), R(104), R(105) independently of one another are NR(184a)R(185), OR(184b), SR(184c) or —C$_{znx}$H$_{2znx}$—R(184d);

znx is zero, 1, 2, 3 or 4;

R(184d) is (C$_3$–C$_7$)-cycloalkyl or phenyl, which is not substituted or is substituted by 1–3 substituents from the group consisting of F, Cl, CF$_3$, methyl, methoxy and NR(116k)R(117k);

R(116k) and R(117k) are hydrogen or C$_1$–C$_4$-alkyl;

R(184a), R(184b), R(184c), R(185) independently of one another are hydrogen, (C$_1$–C$_8$)-alkyl, (C$_1$–C$_8$)-perfluoroalkyl or (CH$_2$)$_{zao}$—R(184g);

zao is zero, 1, 2, 3 or 4;

184g is (C$_3$–C$_7$)-cycloalkyl or phenyl, which is not substituted or is substituted by 1–3 substituents from the group consisting of F, Cl, CF$_3$, methyl, methoxy and NR(184u)R(184v);

R(184u) and R(184v) are hydrogen or C$_1$–C$_4$-alkyl; or

R(184a) and R(185) together are 4 or 5 methylene groups, of which one CH$_2$ group can be replaced by oxygen, sulfur, NH, N—CH$_3$ or N-benzyl;

and their pharmaceutically tolerable salts;

(HOE 93/F 254 - EP-A 640 588, NZ 264 307)

u) benzoylguanidines of the formula I

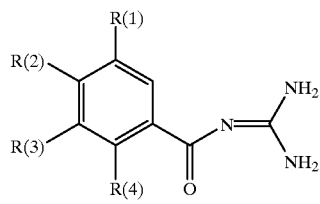

in which:

R(1) is H, F, Cl, Br, I, CN, NO$_2$, (C$_1$–C$_8$)-alkyl, (C$_3$–C$_8$)-cycloalkyl or X$_a$—(CH$_2$)b—(CF$_2$)$_c$—CF$_3$;

X is oxygen, S or NR(5);

a is zero or 1;

b is zero, 1 or 2;

c is zero, 1, 2 or 3;

R(5) is H, (C$_1$–C$_4$)-alkyl or —C$_d$H$_{2d}$R(6);

d is zero, 1, 2, 3 or 4;

R(6) is (C$_3$–C$_8$)-cycloalkyl, phenyl, biphenylyl or naphthyl, where the aromatics are not substituted or are substituted by 1 to 3 substituents selected from the group consisting of F, Cl, CF$_3$, methyl, methoxy and NR(7)R(8);

R(7) and R(8) independently are H or (C$_1$–C$_4$)-alkyl; or

R(1) is —SR(10), —OR(10) or —CR(10)R(11)R(12);

R(10) is —C$_f$H$_{2f}$—(C$_3$–C$_8$)-cycloalkyl, —(C$_1$–C$_9$)-heteroaryl or phenyl, where the aromatic systems are unsubstituted or substituted by 1 to 3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are defined as R(10) or are hydrogen or (C$_1$–C$_4$)-alkyl; or R(1) is phenyl, naphthyl, biphenylyl or (C$_1$–C$_9$)-heteroaryl, the latter linked via C or N, and which are unsubstituted or substituted by 1 to 3 substituents selected from the group consisting of F, Cl, CF$_3$, CH$_3$, methoxy, hydroxyl, amino, methylamino and dimethylamino; or R(1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$ (CO)—[CR(22)R(23)R(24)]$_j$ R(13) and R(14) identically or differently are —(CH$_2$)$_g$—(CHOH)$_h$—(CH$_2$)$_i$—(CHOH)$_j$—R(17), R(17) is hydrogen or methyl;

—(CH$_2$)$_g$—O—(CH$_2$—CH$_2$O)$_h$—R(24), g, h, i identically or differently are zero, 1, 2, 3 or 4;

j is 1, 2, 3 or 4;

R(15) and R(16) identically or differently are hydrogen, (C$_1$–C$_6$)-alkyl or together with the carbon atom carrying them are a (C$_3$–C$_8$)-cycloalkyl;

R(18) is phenyl, which is unsubstituted or substituted by 1 to 3 substituents selected from the group consisting of F, Cl, CF$_3$, methyl, methoxy and NR(25)R(26);

R(25) and R(26) are H or (C$_1$–C$_4$)-alkyl; or

R(18) is (C$_1$—C$_9$)-heteroaryl, which is unsubstituted or substituted as phenyl; or R(18) is (C$_1$–C$_6$)-alkyl, which is unsubstituted or substituted by 1 to 3 OH; or R(18) is $(C_3-C_8)$-cycloalkyl;
R(19), R(20), R(21), R(22) and R(23) are hydrogen or methyl;
k is zero, 1, 2, 3 or 4;
l is zero, 1, 2, 3 or 4;
R(24) is H, $(C_1-C_6)$-alkyl, $(C_3-C_8)$-cycloalkyl or —$C_mH_{2m}$—R(18);
m is 1, 2, 3 or 4;
R(2) and R(3) independently of one another are defined as R(1);
R(4) is $(C_1-C_3)$-alkyl, F, Cl, Br, I, CN or —$(CH_2)_n$—$(CF_2)_o$—$CF_3$;
n is zero or 1;
o is zero, 1 or 2;
and their pharmaceutically tolerable salts;
(HOE 93/F 436 - EP-A 659 748), NZ 270 264)
v) acylguanidines of the formula I in which:
X is carbonyl, sulfonyl,
R(1) is H, $(C_1-C_8)$-alkyl, unsubstituted or substituted by hydroxyl,
$(C_3-C_8)$-cycloalkyl, phenyl, which is unsubstituted or substituted by 1–3 substituents from the group F, Cl, $CF_3$, $CH_3$, methoxy, hydroxyl, amino, methylamino or dimethylamino,
R(2) is H, $(C_1-C_4)$-alkyl,
and their pharmaceutically tolerable salts;
(HOE 94/F 014 K - EP-A 666 252, NZ 270 370)
w) phenyl-substituted alkylcarboxylic acid guanidides, carrying perfluoroalkyl groups, of the formula I in which:
R(A) is hydrogen, F, Cl, Br, I, CN, OR(6), $(C_1-C_8)$-alkyl, $(C_3-C_8)$-cycloalkyl, $O_r(CH_2)_aC_bF_{2b+1}$ or NR(7)R(8);
r is zero or 1;
a is zero, 1, 2, 3 or 4;
b is 1, 2, 3, 4, 5, 6, 7 or 8;
R(6) is hydrogen, $(C_1-C_8)$-alkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(9)R(10);
R(9) and R(10) are H, $(C_1-C_4)$-alkyl or $(C_1-C_4)$-perfluoroalkyl;
R(7) and R(8) independently of one another are defined as R(6);

R(B) independently is defined as R(A);
x is 1, 2 or 3;
R(1) is hydrogen, $(C_1-C_8)$-alkyl, $(C_3-C_8)$-cycloalkyl, —$O_t(CH_2)_dC_eF_{2e+1}$, F, Cl, Br, I or CN;
t is zero or 1;
d is zero, 1, 2, 3 or 4;
e is 1, 2, 3, 4, 5, 6, 7 or 8;
R(2), R(3), R(4) and R(5) independently of one another are defined as R(1);
but with the condition that at least one of the substituents R(1), R(2), R(3), R(4), R(5), R(A) and R(B) is an —$O_t(CH_2)_dC_eF_{2e+1}$ or an $O_r(CH_2)_aC_bF_{2b+1}$ group, and their pharmaceutically tolerable salts;
(HOE 94/F 094 - EP-A 676 395, NZ 270 894)
x) heteroaroylguanidines of the formula I in which:
HA is $SO_m$, O or NR(5);
m is zero, 1 or 2;
R(5) is hydrogen, $(C_1-C_8)$-alkyl or —$C_{am}H_{2am}$R(81);
am is zero, 1 or 2;
R(81) is $(C_3-C_8)$-cycloalkyl or phenyl, which is not substituted or is substituted by 1–3 substituents selected from the group consisting of F, Cl, $CF_3$, methyl, methoxy and NR(82)R(83);
R(82) and R(83) is H or $CH_3$; or
R(81) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;
one of the two substituents R(1) and R(2) is —CO—N=C(NH$_2$)$_2$;
and the other in each case is hydrogen, F, Cl, Br, I, $(C_1-C_3)$-alkyl, —OR(6), $C_rF_{2r+1}$, —CO—N=C(NH$_2$)$_2$ or —NR(6)R(7);
R(6) and R(7) independently are hydrogen or $(C_1-C_3)$-alkyl;
r is 1, 2, 3 or 4;
R(3) and R(4) independently of one another are hydrogen, F, Cl, Br, I, —C≡N, X—$(CH_2)_p$—$(C_q$—$F_{2q+1})$, R(8)—$SO_{bm}$, R(9)R(10)N—CO, R(11)—CO— or R(12)R(13)N—$SO_2$—, where the perfluoroalkyl group is straight-chain or branched,
X is oxygen, S or NR(14);
R(14) is H or $(C_1-C_3)$-alkyl;
bm is zero, 1 or 2;
p is zero, 1 or 2;
q is zero, 1, 2, 3, 4, 5 or 6;
R(8), R(9), R(11) and R(12) independently are $(C_1-C_8)$-alkyl, $(C_3-C_6)$-alkenyl, —$C_nH_{2n}$—R(15), $CF_3$;
n is zero, 1, 2, 3 or 4;
R(15) is $(C_3-C_7)$-cycloalkyl or phenyl, which is not substituted or is substituted by 1–3 substituents selected from the group consisting of F, Cl, $CF_3$, methyl, methoxy or NR(16)R(17);
R(16) and R(17) are H or $C_1-C_4$-alkyl; or R(9), R(11) and R(12) are H;

R(10) and R(13) independently are H or $(C_1-C_4)$-alkyl; or

R(9) and R(10), and R(12) and R(13) together are 4 or 5 methylene groups, of which one $CH_2$ group can be replaced by oxygen, S, NH, N—$CH_3$ or N-benzyl, or R(3) and R(4) independently of one another are $(C_1-C_8)$-alkyl or —$C_{al}H_{2al}R(18)$;

al is zero, 1 or 2;

R(18) is $(C_3-C_8)$-cycloalkyl or phenyl; which is not substituted or is substituted by 1–3 substituents selected from the group consisting of F, Cl, $CF_3$, methyl, methoxy and NR(19)R(20);

R(19) and R(20) are H or $CH_3$; or

R(3) and R(4) independently of one another are $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or R(3) and R(4) independently of one another are

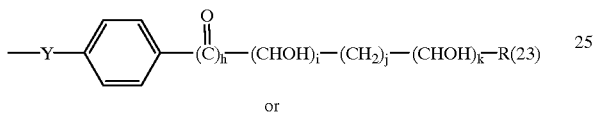

or

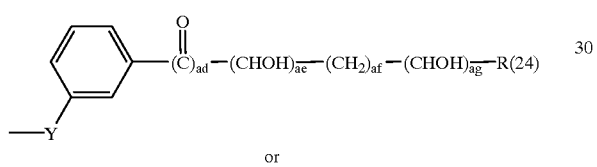

or

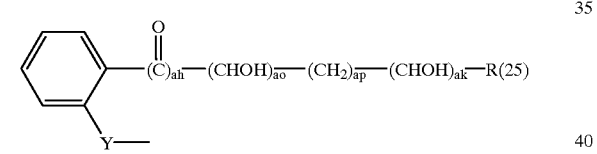

Y is oxygen, —S— or —NR(22)—;

h, ad, ah independently are zero or 1;

i, j, k, ae, af, ag, ao, ap and ak independently are zero, 1, 2, 3, 4, but where in each case h, i and k are not simultaneously zero, ad, ae and ag are not simultaneously zero, ah, ao and ak are not simultaneously zero, R(23), R(24), R(25) and R(22) independently are hydrogen or $(C_1-C_3)$-alkyl; or R(3) and R(4) independently of one another are hydrogen, F, Cl, Br, I, CN, $(C_1-C_8)$-alkyl, $(C_1-C_8)$-perfluoroalkyl, $(C_3-C_8)$-alkenyl or —$C_gH_{2g}R(26)$;

g is zero, 1, 2, 3 or 4;

R(26) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);

R(27) and R(28) are H, $(C_1-C_4)$-alkyl or $(C_1-C_4)$-pefluoroalkyl; or

R(3) and R(4) independently of one another are SR(29), —OR(30), —NR(31)R(32) or —CR(33)R(34)R(35);

R(29), R(30), R(31) and R(33) independently are —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(32), R(34) and R(35) independently of one another are defined as R(29) or are hydrogen, $(C_1-C_4)$-alkyl or $(C_1-C_4)$-perfluoroalkyl; or R(3) and R(4) independently of one another are

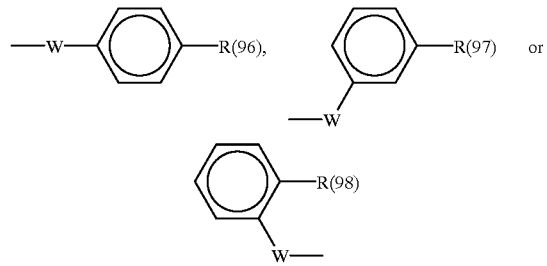

R(96), R(97) and R(98) independently are $(C_1-C_9)$-heteroaryl, which is linked via C or N and which is unsubstituted or substituted by 1 to 3 substituents selected from the group consisting of F, Cl, $CF_3$, $CH_3$, methoxy, hydroxyl, amino, methylamino, dimethylamino or benzyl;

W is oxygen, S or NR(36)—;

R(36) is H or $(C_1-C_4)$-alkyl; or

R(3) and R(4) independently of one another are R(37)—$SO_{cm}$ or R(38)R(39)N—$SO_2$—;

cm is 1 or 2;

R(37) is $(C_1-C_8)$-alkyl, $(C_1-C_8)$-perfluoroalkyl, $(C_3-C_8)$-alkenyl or —$C_sH_{2s}R(40)$;

s is zero, 1, 2, 3 or 4;

R(40) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(41)R(42);

R(41) and R(42) are H, $(C_1-C_4)$-alkyl or $(C_1-C_4)$-perfluoroalkyl;

R(38) is H, $(C_1-C_8)$-alkyl, $(C_1-C_8)$-perfluoroalkyl, $(C_3-C_8)$-alkenyl or —$C_wH_{2w}$—R(43);

w is zero, 1, 2, 3 or 4;

R(43) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(44)R(45);

R(44) and R(45) are H, $(C_1-C_4)$-alkyl or $(C_1-C_4)$-perfluoroalkyl;

R(39) is H, $(C_1-C_4)$-alkyl or $(C_1-C_4)$-perfluoroalkyl; or

R(38) and R(39) together are 4 or 5 methylene groups, of which one $CH_2$ group can be replaced by oxygen, S, NH, N—$CH_3$ or N-benzyl; or R(3) and R(4) independently of one another are R(46)X(1)—;

X(1) is oxygen, S, NR(47), (D=O)A—, NR(48)C=MN$^{(*)}$R(49)—,

M is oxygen or S;

A is oxygen or NR(50);

D is C or SO;

R(46) is $(C_1-C_8)$-alkyl, $(C_3-C_8)$-alkenyl, $(CH_2)_bC_dF_{2d+1}$ or —$C_xH_{2x}$—R(51);

b is zero or 1;

d is 1, 2, 3, 4, 5, 6 or 7;

x is zero, 1, 2, 3 or 4;

R(51) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);

R(52) and R(53) are H, $(C_1-C_4)$-alkyl or $(C_1-C_4)$-perfluoroalkyl;

R(47), R(48) and R(50) independently are hydrogen, $(C_1-C_4)$-alkyl or $(C_1-C_4)$-perfluoroalkyl;

R(49) is defined as R(46); or

R(46) and R(47), or R(46) and R(48) together are 4 or 5 methylene groups, of which one $CH_2$ group can be replaced by oxygen, S, NH, N—$CH_3$ or N-benzyl, where A and $N^{(*)}$ are bonded to the phenyl nucleus of the benzoylguanidine parent structure; or R(3) and R(4) independently of one another are —SR(64), —OR(65), —NHR(66), —NR(67)R(68), —CHR(69)R(70), —C(OH)R(54)R(55), —C≡CR(56), —CR(58)=CHR(57), —[CR(59)R(60)]$_u$—(CO)—[CR(61)R(62)]$_v$—R(63);

R(64), R(65), R(66), R(67) and R(69) identically or differently are —(CH$_2$)$_y$—(CHOH)$_z$—(CH$_2$)$_{aa}$—(CH$_2$OH)$_t$—R(71) or —(CH$_2$)$_{ab}$—O—(CH$_2$—CH$_2$O)$_{ac}$—R(72), R(71) and R(72) are hydrogen or methyl;

u is 1, 2, 3 or 4;

v is zero, 1, 2, 3 or 4;

y, z, aa identically or differently are zero, 1, 2, 3 or 4;

t is 1, 2, 3 or 4;

R(68), R(70), R(54) and R(55) identically or differently are hydrogen, $(C_1-C_6)$-alkyl; or R(69) and R(70), or R(54) and R(55) together with the carbon atom carrying them are a $(C_3-C_8)$-cycloalkyl;

R(63) is H, $(C_1-C_6)$-alkyl, $(C_3-C_8)$-cycloalkyl or —C$_e$H$_{2e}$—R(73);

e is zero, 1, 2, 3 or 4;

R(56), R(57) and R(73) independently are phenyl, which is unsubstituted or substituted by 1–3 substituents selected from the group consisting of F, Cl, $CF_3$, methyl, methoxy and NR(74)R(75);

R(74) and R(75) are H or $(C_1-C_4)$-alkyl; or

R(56), R(57) and R(73) independently are $(C_1-C_9)$-heteroaryl, which is unsubstituted or substitued as phenyl;

R(58), R(59), R(60), R(61) and R(62) are hydrogen or methyl, or

R(3) and R(4) independently of one another are R(76)-NH—SO$_2$—;

R(76) is R(77)R(78)N—(C=Y')—;

Y' is oxygen, S or N—R(79);

R(77) and R(78) identically or differently are H, $(C_1-C_8)$-alkyl, $(C_3-C_6)$-alkenyl, —C$_f$H$_{2f}$—R(80);

f is zero, 1, 2, 3 or 4;

R(80) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl; or R(77) and R(78) together are 4 or 5 methylene groups, of which one $CH_2$ group can be replaced by oxygen, S, NH, N—$CH_3$ or N-benzyl, R(79) is defined as R(77) or is amidine; or R(3) and R(4) independently of one another are NR(84)R(85);

R(84) and R(85) independently of one another are H, $(C_1-C_4)$-alkyl, or together are 4 or 5 methylene groups, of which one $CH_2$ group can be replaced by oxygen, S, NH, N—$CH_3$ or N-benzyl; or of which one or two $CH_2$ groups can be replaced by CH—C$_{dm}$H$_{2dm+1}$, and their pharmaceutically tolerable salts;

(HOE 94/F 123 - EP-A 682 017, NZ 272 058)

y) bicyclic heteroaroylguanidines of the formula I

I in which:

T, U, V, W, X, Y and Z independently of one another are nitrogen or carbon; but with the restriction that X and Z are not simultaneously nitrogen, and that T, U, V, W, X, Y and Z carry no substituents if they are nitrogen, and that no more than four of them are simultaneously nitrogen, R(1) and R(2) independently of one another are hydrogen, F, Cl, Br, I, $(C_1-C_3)$-alkyl, $(C_1-C_3)$-perfluoroalkyl, OR(8), NR(8)R(9) or C(=O)N=C(NH$_2$)$_2$;

R(8) and R(9) independently of one another are hydrogen or $(C_1-C_3)$-alkyl, or R(8) and R(9) together are 4 or 5 methylene groups, of which one $CH_2$ group can be replaced by oxygen, S, NH, N—$CH_3$ or N-benzyl;

R(3), R(4), R(5), R(6) and R(7) independently of one another are hydrogen, F, Cl, Br, I, —C≡N, X$_k$—(CH$_2$)$_p$—(C$_q$F$_{2q+1}$), R(10a)—SO$_{bm}$, R(10b)R(10c)N—CO, R(11)—CO— or R(12)R(13)N—SO$_2$—, where the perfluoroalkyl group is straight-chain or branched;

X is oxygen, S or NR(14);

R(14) is H or $(C_1-C_3)$-alkyl;

bm is zero, 1 or 2;

p is zero, 1 or 2;

k is zero or 1;

q 1, 2, 3, 4, 5 or 6;

R(10a), R(10b), R(11) and R(12) independently of one another are $(C_1-C_8)$-alkyl, $(C_3-C_6)$-alkenyl, —C$_n$H$_{2n}$—R(15) or $(C_1-C_8)$-perfluoroalkyl;

n is zero, 1, 2, 3 or 4;

R(15) is $(C_3-C_7)$-cycloalkyl or phenyl, which is not substituted or is substituted by 1–3 substituents selected from the group consisting of F, Cl, $CF_3$, methyl, methoxy and NR(16)R(17);

R(16) and R(17) are H or $C_1-C_4$-alkyl; or

R(10b), R(11) and R(12) are hydrogen;

R(10c) and R(13) independently are hydrogen or $(C_1-C_4)$-alkyl; or

R(10b) and R10c) and R(12) and R(13) together are 4 or 5 methylene groups, of which one $CH_2$ group can be replaced by oxygen, sulfur, NH, N—$CH_3$ or N-benzyl; or R(3), R(4), R(5), R(6) and R(7) independently of one another are $(C_1-C_8)$-alkyl, —C$_{al}$H$_{2al}$R(18) or $(C_3-C_8)$-alkenyl;

al is zero, 1 or 2;

R(18) is $(C_3–C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(19a)R(19b);

R(19a) and R(19b) are hydrogen, $(C_1–C_4)$-alkyl or $(C_1–C_4)$-perfluoroalkyl; or R(3), R(4), R(5), R(6) and R(7) independently of one another are $(C_1–C_9)$-heteroaryl, which is linked via C or N and which is unsubstituted or substituted by 1–3 substituents from the group consisting of F, Cl, $CF_3$, $CH_3$, methoxy, hydroxyl, amino, methylamino or dimethylamino; or R(3), R(4), R(5), R(6) and R(7) independently of one another are

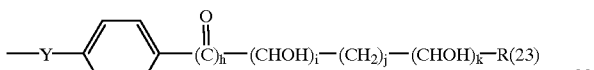

or

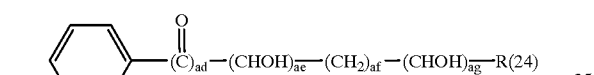

or

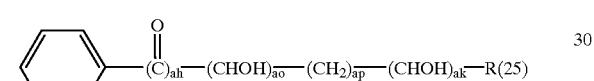

Y is oxygen, —S— or —NR(22)—;

h, ad, ah independently of one another are zero or 1;

i, j, k, ae, af, ag, ao, ap and ak independently of one another are zero, 1, 2, 3 or 4;

but where in each case h, i and k are not simultaneously zero, ad, ae and ag are not simultaneously zero, and ah, ao and ak are not simultaneously zero, R(23), R(24), R(25) and R(22) independently of one another are hydrogen or $(C_1–C_3)$-alkyl; or R(3), R(4), R(5), R(6) and R(7) independently of one another are SR(29), —OR(30), —NR(31)R(32) or —CR(33)R(34)R(35);

R(29), R(30), R(31) and R(33) independently of one another are —$C_aH_{2a}$—$(C_1–C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(32), R(34) and R(35) independently of one another are defined as R(29) or are hydrogen, $(C_1–C_4)$-alkyl or $(C_1–C_4)$-perfluoroalkyl; or R(3), R(4), R(5), R(6) and R(7) independently of one another are

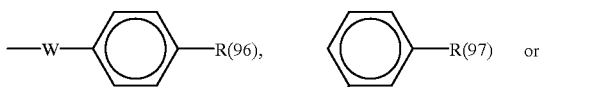

-continued

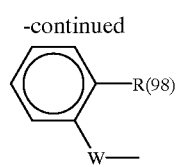

R(96), R(97) and R(98) independently of one another are $(C_1–C_9)$-heteroaryl, which is linked via C or N and which is unsubstitued or substituted by 1 to 3 substituents from the group consisting of F, Cl, $CF_3$, $CH_3$, methoxy, hydroxyl, amino, methylamino, dimethylamino or benzyl;

W is oxygen, S or NR(36)—;

R(36) is H or $(C_1–C_4)$-alkyl; or

R(3), R(4), R(5), R(6) and R(7) independently of one another are R(46)X(1)—;

X(1) is oxygen, S, NR(47), (D=O)A— or NR(48)C=MN$^{(*)}$R(49)—;

M is oxygen or sulfur;

A is oxygen or NR(50);

D is C or SO;

R(46) is $(C_1–C_8)$-alkyl, $(C_3–C_8)$-alkenyl, $(CH_2)_bC_dF_{2d+1}$ or —$C_xH_{2x}$—R(51);

b is zero or 1;

d is 1, 2, 3, 4, 5, 6 or 7;

x is zero, 1, 2, 3 or 4;

R(51) is $(C_3–C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);

R(52) and R(53) are hydrogen, $(C_1–C_4)$-alkyl or $(C_1–C_4)$-perfluoroalkyl;

R(47), R(48) and R(50) independently are hydrogen, $(C_1–C_4)$-alkyl or $(C_1–C_4)$-perfluoroalkyl;

R(49) is defined as R(46); or

R(46) and R(47), or R(46) and R(48) together are 4 or 5 methylene groups, of which one $CH_2$ group can be replaced by oxygen, sulfur, NH, N—$CH_3$ or N-benzyl;

where A and N$^{(*)}$ are bonded to the phenyl nucleus of the heteroaroylguanidine parent structure; or R(3), R(4), R(5), R(6) and R(7) independently of one another are —SR(64), —OR(65), —NHR(66), —NR(67)R(68), —CHR(69)R(70) or —CR(54)R(55)OH, —C≡CR(56), —CR(58)=CR(57) or —[CR(59)R(60)]$_u$—CO—[CR(61)R(62)]$_v$—R(63);

R(64), R(65), R(66), R(67) and R(69) identically or differently are —$(CH_2)_y$—$(CHOH)_z$—$(CH_2)_{aa}$—$(CHOH)_t$—R(71) or —$(CH_2)_{ab}$—O—$(CH_2$—$CH_2O)_{ac}$—R(72);

R(71) and R(72) independently of one another are hydrogen or methyl;

u is 1, 2, 3 or 4;

v is zero, 1, 2, 3 or 4;

y, z, aa identically or differently are zero, 1, 2, 3 or 4;

t is 1, 2, 3 or 4;

R(68), R(70), R(54) and R(55) identically or differently are hydrogen or $(C_1–C_6)$-alkyl; or R(69) and R(70), or R(54) and R(55) together with the carbon atom carrying them are $(C_3–C_8)$-cycloalkyl;

R(63) is hydrogen, $(C_1–C_6)$-alkyl, $(C_3–C_8)$-cycloalkyl or —$C_eH_{2e}$—R(73);

e is zero, 1, 2, 3 or 4;

R(56), R(57) and R(73) independently are phenyl, which is unsubstituted or substituted by 1–3 substituents selected from the group consisting of F, Cl, CF$_3$, methyl, methoxy and NR(74)R(75);
R(74) and R(75) are hydrogen or (C$_1$–C$_4$)-alkyl; or
R(56), R(57) and R(73) independently are (C$_1$–C$_9$)-heteroaryl, which is unsubstituted or substituted as phenyl;
R(58), R(59), R(60), R(61) and R(62) are hydrogen or methyl; or R(3), R(4), R(5), R(6) and R(7) independently of one another are R(76)—NH—SO$_2$—;
R(76) is R(77)R(78)N—(C=Y')—;
Y' is oxygen, S or N—R(79);
R(77) and R(78) identically or differently are hydrogen, (C$_1$–C$_8$)-alkyl, (C$_3$–C$_6$)-alkenyl or —C$_f$H$_{2f}$—R(80);
f is zero, 1, 2, 3 or 4;
R(80) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl; or
R(77) and R(78) together are 4 or 5 methylene groups, of which one CH$_2$ group can be replaced by oxygen, sulfur, NH, N—CH$_3$ or N-benzyl;
R(79) is defined as R(77) or is amidine; or R(3), R(4), R(5), R(6) and R(7) independently of one another are NR(84a)R(85), OR(84b), SR(84c) or —C$_n$H$_{2n}$—R(84d);
n is zero, 1, 2, 3 or 4;
R(84d) is (C$_3$–C$_7$)-cycloalkyl or phenyl, which is not substituted or is substituted by 1–3 substituents from the group consisting of F, Cl, CF$_3$, methyl, methoxy and NR(16)R(17);
R(16) and R(17) are hydrogen, or C$_1$–C$_4$-alkyl;
R(84a), R(84b), R(84c) and R(85) independently of one another are hydrogen, (C$_1$–C$_8$)-alkyl, (C$_1$–C$_8$)-perfluoroalkyl or (CH$_2$)$_{ax}$R(84g);
ax is zero, 1, 2, 3 or 4;
R(84g) is (C$_3$–C$_7$)-cycloalkyl or phenyl, which is not substituted or is substituted by 1–3 substituents selected from the group consisting of F, Cl, CF$_3$, methyl, methoxy and NR(84u)R(84v);
R(84u) and R(84v) are hydrogen or C$_1$–C$_4$-alkyl; or
R(84a) and R(85) together are 4 or 5 methylene groups, of which one CH$_2$ group can be replaced by oxygen, sulfur, NH, N—CH$_3$ or N-benzyl,
and their pharmaceutically tolerable salts;
(HOE 94/F 134 - EP-A 686 627, NZ 272 103)

z) benzoylguanidines of the formula I

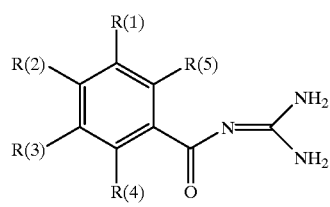

in which:
R(1) is R(6)—SO$_m$;
m is zero, 1 or 2;
R(6) is perfluoroalkyl having 1, 2, 3, 4, 5 or 6 carbon atoms, which is straight-chain or branched;

R(2) and R(3) independently of one another are hydrogen, F, Cl, Br, I, alkyl having 1, 2, 3 or 4 carbon atoms, alkoxy having 1, 2, 3 or 4 carbon atoms or phenoxy, which is unsubstituted or substituted by 1–3 substituents selected from the group consisting of F, Cl, methyl and methoxy; or
R(2) and R(3) independently of one another are pyrrol-1-yl, pyrrol-2-yl- or pyrrol-3-yl, which is not substituted or is substituted by 1 to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, CF$_3$, methyl and methoxy;
R(4) and R(5) independently of one another are hydrogen, alkyl having 1, 2 or 3 carbon atoms, F, Cl, Br, I, CN, OR(7), NR(8)R(9) or —(CH$_2$)$_n$—(CF$_2$)$_o$—CF$_3$;
R(7), R(8) and R(9) independently of one another are hydrogen or alkyl having 1, 2, 3 or 4 carbon atoms;
n is zero or 1;
o is zero, 1 or 2;
and their pharmacologically acceptable salts;
(HOE 94/F 168 - EP-A 690 048, NZ 272 373)

aa) phenyl-substituted alkenylcarboxylic acid guanidides, carrying perfluoroalkyl groups, of the formula I

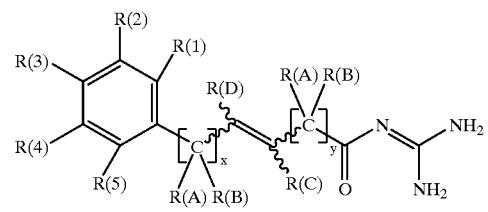

in which
R(A) is hydrogen, F, Cl, Br, I, CN, OH, OR(6), (C$_1$–C$_8$)-alkyl, O$_r$(CH$_2$)$_a$C$_b$F$_{2b+1}$, (C$_3$–C$_8$)-cycloalkyl or NR(7)R(8);
r is zero or 1;
a is zero, 1, 2, 3 or 4;
b is 1, 2, 3, 4, 5, 6, 7 or 8;
R(6) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl; where the aromatics are not substituted or are substituted by 1–3 substituents from the group consisting of F, Cl, CF$_3$, methyl, methoxy and NR(9)R(10);
R(9) and R(10) are H, (C$_1$–C$_4$)-alkyl or (C$_1$–C$_4$)-perfluoroalkyl;
R(7) and R(8) independently of one another are defined as R(6); or
R(7) and R(8) together are 4 or 5 methylene groups, of which one CH$_2$ group can be replaced by oxygen, sulfur, NH, N—CH$_3$ or N-benzyl;
R(B) independently is defined as R(A);
X is zero, 1 or 2;
Y is zero, 1 or 2;
R(C) is hydrogen, F, Cl, Br, I, CN, OR(12), (C$_1$–C$_8$)-alkyl, O$_p$(CH$_2$)$_f$C$_g$F$_{2g+1}$ or (C$_3$–C$_8$)-cycloalkyl;
p is zero or 1;
f is zero, 1, 2, 3 or 4;
g is 1, 2, 3, 4, 5, 6, 7 or 8;
R(12) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl; where the aromatics phenyl or benzyl are not substituted or are substituted by 1–3 substituents from the group consisting of F, Cl, $CF_3$, methyl, methoxy and NR(13)R(14);

R(13) and R(14) independently of one another are H, $(C_1-C_4)$-alkyl or $(C_1-C_4)$-perfluoroalkyl;

R(D) independently is defined as R(C),

R(1) is hydrogen, $(C_1-C_8)$-alkyl, $-O_t(CH_2)_dC_eF_{2e+1}$, $(C_3-C_8)$-cycloalkyl, F, Cl, Br, I or CN;

t is zero or 1;

d is zero, 1, 2, 3 or 4;

e is 1, 2, 3, 4, 5, 6, 7 or 8;

R(2), R(3), R(4) and R(5) independently of one another are defined as R(1);

but with the condition that at least one of the substituents R(A), R(B), R(C), R(D), R(1), R(2), R(4) or R(5) is an $O_r(CH_2)_aC_bF_{2b+1}$, $O_p(CH_2)_fC_gF_{2g+1}$ or $O_t(CH_2)_dC_eF_{2e+1}$ group and R(3) is not an $O_t(CH_2)_dC_eF_{2e+1}$ group;

and their pharmaceutically tolerable salts;

(HOE 94/F 182 - EP-A 690 048, NZ 272 449)

ab) ortho-amino-substituted benzoylguanidines of the formula I

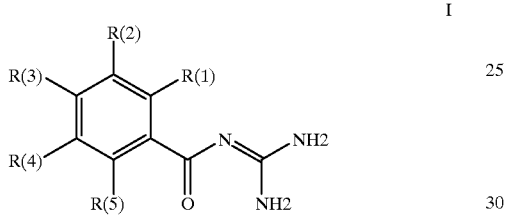

I in which:

R(1) is NR(50)R(6), R(50) and R(6) independently of one another are hydrogen, $(C_1-C_8)$-alkyl or $(C_1-C_8)$-perfluoroalkyl;

R(2), R(3), R(4) and R(5) independently of one another are R(10)—$SO_a$—, R(11)R(12)N—CO—, R(13)—CO— or R(14)R(15)N—$SO_2$—;

a is zero, 1 or 2,

R(10), R(11), R(12), R(13), R(14) and R(15) independently of one another are $(C_1-C_8)$-alkyl, $(C_1-C_8)$-perfluoroalkyl, $(C_3-C_6)$-alkenyl or —$C_{ab}H_{2ab}$—R(16);

ab is zero, 1, 2, 3 or 4;

R(16) is $(C_3-C_7)$-cycloalkyl, phenyl, which is not substituted or is substituted by 1–3 substituents selected from the group consisting of F, Cl, $CF_3$, methyl, methoxy or NR(17)R(18);

R(17) and R(18) independently of one another are H, $CF_3$ or $(C_1-C_4)$-alkyl; or R(11), R(12), and also R(14) and R(15) together are 4 or 5 methylene groups, of which one $CH_2$ group can be replaced by oxygen, S, NH, N—$CH_3$ or N-benzyl; or R(11), R(12), R(14) and R(15) independently of one another are hydrogen; or R(2), R(3), R(4) and R(5) independently of one another are SR(21), —OR(22), —NR(23)R(24) or —CR(25)R(26)R(27);

R(21), R(22), R(23) and R(25) independently of one another are —$C_bH_{2b}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

b is zero, 1 or 2;

R(24), R(26) and R(27) independently of one another are hydrogen, $(C_1-C_4)$-alkyl or $(C_1-C_4)$-perfluoroalkyl; or R(2), R(3), R(4) and R(5) independently of one another are hydrogen, F, Cl, Br, I, CN, —$(Xa)_{dg}$—$C_{da}H_{2da+1}$, —$(Xb)_{dh}$—$(CH_2)_{db}$—$C_{de}F_{2de+1}$, $(C_3-C_8)$-alkenyl or —$C_{df}H_{2df}R(^{30})$;

(Xa) is O, S or NR(33);

R(33) is H, $(C_1-C_4)$-alkyl or $(C_1-C_4)$-perfluoroalkyl;

dg is zero or 1;

(Xb) is O, S or NR(34);

R(34) is H, $(C_1-C_4)$-alkyl or $(C_1-C_4)$-perfluoroalkyl;

dh is zero or 1;

da is zero, 1, 2, 3, 4, 5, 6, 7, 8;

db is zero, 1, 2, 3, 4;

de is zero, 1, 2, 3, 4, 5, 6, 7;

df is zero, 1, 2, 3, 4;

R(30) is $(C_3-C_8)$-cycloalkyl, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(31)R(32);

R(31) and R(32) are H, $(C_1-C_4)$-alkyl or $(C_1-C_4)$-perfluoroalkyl; or

R(2), R(3), R(4) and R(5) independently of one another are NR(40)R(41) or —(Xe)—$(CH_2)_{eb}$R(45);

R(40) and R(41) independently of one another are hydrogen, $(C_1-C_8)$-alkyl, $(C_1-C_8)$-perfluoroalkyl or $(CH_2)_e$—R(42);

e is zero, 1, 2, 3 or 4;

R(42) is $(C_3-C_7)$-cycloalkyl, phenyl, which is not substituted or is substituted by 1–3 substituents selected from the group consisting of F, Cl, $CF_3$, methyl, methoxy and NR(43)R(44);

R(43) and R(44) independently of one another are H, $CF_3$ or $(C_1-C_4)$-alkyl; or R(40) and R(41) together are 4 or 5 methylene groups, of which one $CH_2$ group can be replaced by oxygen, sulfur, NH, N—$CH_3$ or N-benzyl;

(Xe) is O, S or NR(47);

R(47) is H, $(C_1-C_4)$-alkyl or $(C_1-C_4)$-perfluoroalkyl; ≦eb is zero, 1, 2, 3 or 4;

R(45) is $(C_3-C_7)$-cycloalkyl, phenyl, which is not substituted or is substituted by 1–3 substituents selected from the group consisting of F, Cl, $CF_3$, methyl, methoxy, NR(50)R(51) and —(Xfa)—$(CH_2)_{ed}$—(Xfb)R(46);

Xfa is $CH_2$, O, S or NR(48);

Xfb is O, S or NR(49);

ed is 1, 2, 3 or 4;

R(46) is H, $(C_1-C_4)$-alkyl or $(C_1-C_4)$-perfluoroalkyl;

R(48), R(49), R(50) and R(51) independently of one another are H or $(C_1-C_4)$-alkyl or $(C_1-C_4)$-perfluoroalkyl;

where R(3) and R(4), however, cannot be hydrogen, and their pharmaceutically tolerable salts;

(HOE 94/F 265 - NZ 272 946, EP-A 700 904)

ac) benzoylguanidines of the formula I

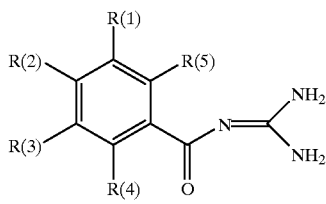

in which:
one of the three substituents R(1), R(2) and R(3) is ($C_1$–$C_9$)-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino; or one of the three substituents R(1), R(2) and R(3) is —SR(10), —OR(10), —NR(10)R(11) or —CR(10)R(11)R(12);

R(10) is —$C_aH_{2a}$—($C_1$–$C_9$)-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(11) and R(12) independently of one another are defined as R(10), are hydrogen or ($C_1$–$C_4$)-alkyl;

and the other substituents R(1), R(2) and R(3) in each case independently of one another are ($C_1$–$C_8$)-alkyl, ($C_2$–$C_8$)-alkenyl or —$C_mH_{2m}$R(14);

m is zero, 1 or 2;

R(14) is ($C_3$–$C_8$)-cycloalkyl or phenyl, which is not substituted or is substituted by 1–3 substituents selected from the group consisting of F, Cl, $CF_3$, methyl, methoxy and NR(15)R(16), R(15) and R(16) are hydrogen or $CH_3$; or the other substituents R(1), R(2) and R(3) in each case independently of one another are hydrogen, F, Cl, Br, I, —C≡N, X—($CH_{2p}$—($C_qF_{2q+1}$), R(22)—$SO_u$, R(23)R(24)N—CO, R(25)—CO— or R(26)R(27)N—$SO_2$—, where the perfluoroalkyl group is straight-chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently are ($C_1$–$C_8$)-alkyl, ($C_2$–$C_6$)-alkenyl, —$C_nH_{2n}$—R(29) or $CF_3$;

n is zero, 1, 2, 3 or 4;

R(28) is hydrogen or ($C_1$–$C_3$)-alkyl;

R(29) is ($C_3$–$C_7$)-cycloalkyl or phenyl; which is not substituted or is substituted by 1–3 substituents selected from the group consisting of F, Cl, $CF_3$, methyl, methoxy and NR(30)R(31);

R(30) and R(31) are hydrogen or $C_1$–$C_4$-alkyl, or

R(23), R(25) and R(26) are also hydrogen;

R(24) and R(27) independently of one another are hydrogen or ($C_1$–$C_4$)-alkyl; or R(23) and R(24), and also R(26) and R(27) together are 4 or 5 methylene groups, of which one $CH_2$ group can be replaced by oxygen, S, NH, N—$CH_3$ or N-benzyl; or the other substituents R(1), R(2) and R(3) in each case independently of one another are OR(35) or NR(35)R(36);

R(35) and R(36) independently of one another are hydrogen or ($C_1$–$C_6$)-alkyl; or R(35) and R(36) together are 4–7 methylene groups, of which one $CH_2$ group can be replaced by oxygen, S, NH, N—$CH_3$ or N-benzyl, R(4) and R(5) independently of one another are hydrogen, ($C_1$–$C_4$)-alkyl, F, Cl, —OR(32), —NR(33)R(34) or $C_rF_{2r+1}$;

R(32), R(33) and R(34) independently of one another are hydrogen or ($C_1$–$C_3$)-alkyl;

r is 1, 2, 3 or 4;

and their pharmaceutically tolerable salts;

(HOE 94/F 266 - EP-A 702 001, NZ 272 948)

ad) benzoylguanidines of the formula I

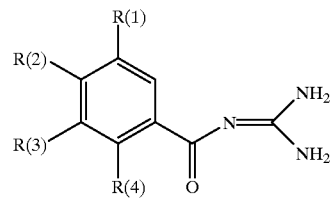

in which

R(1) is hydrogen, F, Cl, Br, I, CN, $NO_2$, OH, ($C_1$–$C_8$)-alkyl, ($C_3$–$C_8$)-cycloalkyl, $O_a$—($CH_2$)$_b$—($CF_2$)$_c$—$CF_3$;

a is zero or 1;

b is zero, 1 or 2;

c is zero, 1, 2 or 3; or

R(1) is R(5)—$SO_m$ or R(6)R(7)N—$SO_2$—;

m is zero, 1 or 2;

R(5) and R(6) independently of one another are ($C_1$–$C_8$)-alkyl, ($C_3$–$C_6$)-alkenyl, $CF_3$ or —$C_nH_{2n}$—R(8);

n is zero, 1, 2, 3 or 4;

R(7) is hydrogen or ($C_1$–$C_4$)-alkyl;

R(8) is ($C_3$–$C_7$)-cycloalkyl or phenyl, which is not substituted or is substituted by 1–3 substituents selected from the group consisting of F, Cl, $CF_3$, methyl, methoxy and NR(9)R(10);

R(9) and R(10) independently of one another are hydrogen or ($C_1$–$C_4$)-alkyl; or R(6) is H;

or R(6) and R(7) together are 4 or 5 methylene groups, of which one $CH_2$ group can be replaced by oxygen, S, NH, N—$CH_3$ or N-benzyl, or R(1) is —SR(11), —OR(11) or —CR(11)R(12)R(13);

R(11) is —$C_pH_{2p}$—($C_3$–$C_8$)-cycloalkyl, -($C_1$–$C_9$)-heteroaryl or phenyl, where the aromatic systems are unsubstituted or substituted by 1–3 substituents selected from the group consisting of F, Cl, $CF_3$, $CH_3$, methoxy, hydroxyl, amino, methylamino and dimethylamino;

R(12), R(13) independently of one another are defined as R(11) or are hydrogen or ($C_1$–$C_4$)-alkyl;

p is zero, 1 or 2; or

R(1) is phenyl, naphthyl, biphenylyl or ($C_1$–$C_9$)-heteroaryl, the latter linked via C or N, which are unsubstituted or substituted by 1–3 substituents selected from the group consisting of F, Cl, $CF_3$, $CH_3$, methoxy, hydroxyl, amino, methylamino and dimethylamino;

R(2) is $—CF_2R(14)$, $—CF[R(15)][R(16)]$, $—CF[(CF_2)_q—CF_3)][R(15)]$, $—C[(CF_2)_r—CF_3]=CR(15)R(16)$;

R(14) is $(C_1-C_4)$-alkyl or $(C_3-C_6)$-cycloalkyl;

R(15) and R(16) independently of one another are hydrogen or $(C_1-C_4)$-alkyl;

q is zero, 1 or 2;

r is zero, 1 or 2;

R(3) is defined as R(1);

R(4) is hydrogen, $(C_1-C_3)$-alkyl, F, Cl, Br, I, CN, $—(CH_2)_s—(CF_2)_t—CF_3$;

s is zero or 1;

t is zero, 1 or 2;

and their pharmaceutically tolerable salts;

(HOE 94/F 267 - EP-A 700 899, NZ 272 947)

ae) benzoylguanidines of the formula I

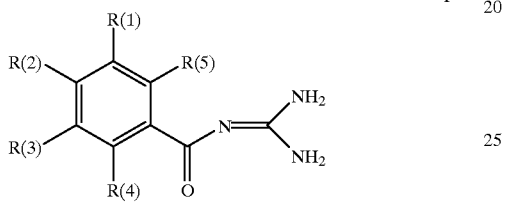

I in which:

one of the three substituents R(1), R(2) and R(3) is $—Y—4-[(CH_2)_k—CHR(7)—(C=O)R(8)]$-phenylen, $—Y—3-(CH_2)_k—CH R(7)—(C=O)R(8)]$-phenylen or $—Y—2-[(CH_2)_k—CHR(7)—(C=O)R(8)]$-phenylen, where the phenyl in each case is unsubstituted or substituted by 1–2 substituents from the group F, Cl, $—CF_3$, methyl, hydroxyl, methoxy, or $—NR(37)R(38)$;

R(37) and R(38) independently of one another are hydrogen or $—CH_3$;

Y is a bond, oxygen, —S— or —NR(9);

R(9) is hydrogen or $—(C_1-C_4)$-alkyl;

R(7) is —OR(10) or —NR(10)R(11);

R(10) and R(11) independently of one another are hydrogen, $-(C_1-C_8)$-alkyl, $—(C_1-C_8)$-alkanoyl, $—(C_1-C_8)$-alkoxycarbonyl, benzyl, benzyloxycarbonyl; or R(10) is trityl;

R(8) is —OR(12) or —NR(12)R(13);

R(12) and R(13) independently of one another are hydrogen, $—(C_1-C_8)$-alkyl or benzyl;

k is zero, 1, 2, 3 or 4;

and the other radicals R(1), R(2) and R(3) in each case independently of one another are $-(C_1-C_8)$-alkyl, $-(C_2-C_8)$-alkenyl or $—(CH_2)_mR(14)$;

m is zero, 1 or 2;

R(14) is $—(C_3-C_8)$-cycloalkyl or phenyl, which is not substituted or is substituted by 1–3 substituents selected from the group consisting of F, Cl, $—CF_3$, methyl, methoxy and —NR(15)R(16);

R(15) and R(16) are hydrogen or $—CH_3$; or the other radicals R(1), R(2) and R(3) in each case independently of one another are R(18)R(19)N—(C=Y')—NH—$SO_2$—;

Y' is oxygen, —S— or —N—R(20);

R(18) and R(19) independently of one another are hydrogen, $—(C_1-C_8)$-alkyl, $—(C_3—C6)$-alkenyl or $—(CH_2)_t—R(21)$;

t is zero, 1, 2, 3 or 4;

R(21) is $—(C_5-C_7)$-cycloalkyl or phenyl, which is unsubstituted or substituted by 1–3 substituents selected from the group consisting of F, Cl, $—CF_3$, methoxy and $—(C_1-C_4)$-alkyl; or R(18) and R(19) together are 4 or 5 methylene groups, of which one $CH_2$ group can be replaced by oxygen, —S—, —NH—, —N—$CH_3$ or —N-benzyl;

R(20) is defined as R(18) or is amidine; or the other radicals R(1), R(2) and R(3) in each case independently of one another are hydrogen, F, Cl, Br, I, $—C≡N$, $X—(CH_2)_p—(C_qF_{2q+1})$, $R(22)—SO_u—$, $R(23)R(24)N—CO—$, $R(25)—CO—$ or $R(26)R(27)N—SO_2—$, where the perfluoroalkyl group is straight-chain or branched;

X is a bond, oxygen, —S— or —NR(28);

u is zero, 1 or 2;

p is zero, 1 or 2;

q is 1, 2, 3, 4, 5 or 6;

R(22), R(23), R(25) and R(26) independently of one another are $—(C_1-C_8)$-alkyl, $—(C_3-C_6)$-alkenyl, $—(CH_2)_n—R(29)$ or $—CF_3$;

n is zero, 1, 2, 3 or 4;

R(28) is hydrogen or $—(C_1-C_3)$-alkyl;

R(29) is $—(C_3-C_7)$-cycloalkyl or phenyl, which is not substituted or is substituted by 1–3 substituents selected from the group consisting of F, Cl, $—CF_3$, methyl, methoxy and —NR(30)R(31);

R(30) and R(31) are hydrogen or $—(C_1-C_4)$-alkyl; or

R(23), R(25) and R(26) are hydrogen;

R(24) and R(27) independently of one another are hydrogen or $—(C_1-C_4)$-alkyl; or R(23) and R(24), and also R(26) and R(27) together are 4 or 5 methylene groups, of which one $CH_2$ group can be replaced by oxygen, —S—, —NH—, —N—$CH_3$ or —N-benzyl; or the other radicals R(1), R(2) and R(3) in each case independently of one another are —OR(35) or —NR(35)R(36);

R(35) and R(36) independently of one another are hydrogen or $—(C_1-C_6)$-alkyl; or R(35) and R(36) together are 4–7 methylene groups, of which one $CH_2$ group can be replaced by oxygen, —S—, —NH—, —N—$CH_3$ or —N-benzyl;

R(4) and R(5) independently of one another are hydrogen, $—(C_1-C_4)$-alkyl, F, Cl, —OR(32), —NR(33)R(34) or $—C_rF_{2r+1}$;

R(32), R(33) and R(34) independently of one another are hydrogen or $—(C_1-C_3)$-alkyl;

r is 1, 2, 3 or 4;

and their pharmaceutically tolerable salts;

(HOE 94/F 352 - EP-A 713 684, NZ 280 517)

af) benzoylguanidines of the formula I

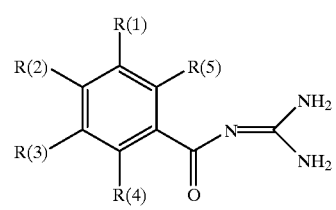

I in which:

R(1) is R(6)—CO or R(7)R(8)N—CO;
  R(6) is $(C_1-C_8)$-alkyl, $(C_1-C_8)$-perfluoroalkyl, $(C_3-C_8)$-alkenyl or $-C_nH_{2n}$—R(9),
  n is zero, 1, 2, 3 or 4;
    R(9) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11),
      R(10) and R(11) are H, $(C_1-C_4)$-alkyl or $(C_1-C_4)$-perfluoroalkyl;
  R(7) is H, $(C_1-C_8)$-alkyl, $(C_1-C_8)$-perfluoroalkyl, $(C_3-C_8)$-alkenyl or $-C_nH_{2n}$—R(12);
  n is zero, 1, 2, 3 or 4;
    R(12) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
      R(13) and R(14) are H, $(C_1-C_4)$-alkyl or $(C_1-C_4)$-perfluoroalkyl;
  R(8) is H, $(C_1-C_4)$-alkyl or $(C_1-C_4)$-perfluoroalkyl; or
  R(7) and R(8) together are 4 or 5 methylene groups, of which one $CH_2$ group can be replaced by oxygen, S, NH, N—$CH_3$ or N-benzyl;
R(2) is defined as R(1), or is H, OH, F, Cl, Br, I, CN, $NO_2$, $(C_1-C_8)$-alkyl, $(C_1-C_8)$-perfluoroalkyl, $(C_3-C_8)$-alkenyl or $-C_nH_{2n}$R(I15);
  n is zero, 1, 2, 3 or 4;
    R(15) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);
      R(16) and R(17) are H, $(C_1-C_4)$-alkyl or $(C_1-C_4)$-perfluoroalkyl; or
  R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino; or
  R(2) is SR(18), —OR(18), —NR(18)R(19) or —CR(18)R(19)R(20);
    R(18) is $-C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino, dimethylamino;
    a is zero, 1 or 2;
    R(19) and R(20) independently of one another are defined as R(18) or are hydrogen, $(C_1-C_4)$-alkyl or $(C_1-C_4)$-perfluoroalkyl; or
  R(2) is R(21)—$SO_m$ or R(22)R(23)N—$SO_2$—;
    m is 1 or 2;
    R(21) is $(C_1-C_8)$-alkyl, $(C_1-C_8)$-perfluoroalkyl, $(C_3-C_8)$-alkenyl or $-C_nH_{2n}$—R(24);
    n is zero, 1, 2, 3 or 4;
      R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
        R(27) and R(28) are H, $(C_1-C_4)$-alkyl or $(C_1-C_4)$-perfluoroalkyl;
    R(22) is H, $(C_1-C_8)$-alkyl, $(C_1-C_8)$-perfluoroalkyl, $(C_3-C_8)$-alkenyl or $-C_nH_{2n}$—R(29);
    n is zero, 1, 2, 3 or 4;
      R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);
        R(30) and R(31) are H, $(C_1-C_4)$-alkyl or $(C_1-C_4)$-perfluoroalkyl;
    R(23) is hydrogen, $(C_1-C_4)$-alkyl or $(C_1-C_4)$-perfluoroalkyl; or
    R(22) and R(23) together are 4 or 5 methylene groups, of which one $CH_2$ group can be replaced by oxygen, S, NH, N—$CH_3$ or N-benzyl; or
  R(2) is R(33)X—;
    X is oxygen, S, NR(34), (D=O)A— or NR(34)C=$MN^{(+)}$R(35)—;
    M is oxygen or S;
    A is oxygen or NR(34);
    D is C or SO;
    R(33) is $(C_1-C_8)$-alkyl, $(C_3-C_8)$-alkenyl, $(CH_2)_bC_dF_{2d+1}$ or $-C_nH_{2n}$—R(36);
    b is zero or 1;
    d is 1, 2, 3, 4, 5, 6 or 7;
    n is zero, 1, 2, 3, or 4;
      R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
        R(37) and R(38) are H, $(C_1-C_4)$-alkyl or $(C_1-C_4)$-perfluoroalkyl;
    R(34) is hydrogen, $(C_1-C_4)$-alkyl or $(C_1-C_4)$-perfluoroalkyl;
    R(35) is defined as R(33); or
    R(33) and R(34) together are 4 or 5 methylene groups, of which one $CH_2$ group can be replaced by oxygen, S, NH, N—$CH_3$ or N-benzyl;
    where A and $N^{(+)}$ are bonded to the phenyl nucleus of the benzoylguanidine parent structure; or
R(2) is —SR(40), —OR(40), —NHR(40), —NR(40)R(41), —CHR(40)R(42), —CR(42)R(43)OH, —C≡CR(45), —CR(46)=CR(45) or —[CR(47)R(48)]$_u$—CO—[C(R49)R(50)]$_v$—R(44);
  R(40) and R(41) independently of one another are —$(CH_2)_p$—$(CHOH)_q$—$(CH_2)_r$—$(CHOH)_t$—R(51) or —$(CH_2)_p$—O—$(CH_2$—$CH_2O)_q$—R(51);
  R(51) is hydrogen or methyl;
  u is 1, 2, 3 or 4;
  v is zero, 1, 2, 3 or 4;
    p, q and r independently of one another are zero, 1, 2, 3 or 4;
    t is 1, 2, 3 or 4;
  R(42) and R(43) independently of one another are hydrogen or $(C_1-C_6)$-alkyl; or
  R(42) and R(43) together with the carbon atom carrying them are a $(C_3-C_8)$-cycloalkyl;
  R(44) is hydrogen, $(C_1-C_6)$-alkyl, $(C_3-C_8)$-cycloalkyl, —$C_eH_{2e}$—R(45);
  e is zero, 1, 2, 3 or 4;
    R(45) is phenyl, which is unsubstituted or substituted by 1–3 substituents selected from the group consisting of F, Cl, $CF_3$, methyl, methoxy and NR(52)R(53);
      R(52) and R(53) are H or $(C_1-C_4)$-alkyl; or
    R(45) is $(C_1-C_9)$-heteroaryl, which is unsubstituted or substituted as phenyl; or R(45) is $(C_1-C_6)$-alkyl, which is unsubstituted or substituted by 1–3 OH;

R(46), R(47), R(48), R(49) and R(50) independently of one another are hydrogen or methyl; or R(2) is R(55)—NH—SO$_2$—;

R(55) is R(56)R(57)N—(C=Y)—;

Y is oxygen, S or N—R(58);

R(56) and R(57) independently of one another are hydrogen, $(C_1-C_8)$-alkyl, $(C_3-C_6)$-alkenyl or —C$_f$H$_{2f}$—R(59);

f is zero, 1, 2, 3 or 4;

R(59) is $(C_5-C_7)$-cycloalkyl, phenyl, which is unsubstituted or substituted by 1–3 substituents selected from the group consisting of F, Cl, CF$_3$, methoxy and $(C_1-C_4)$-alkyl; or R(56) and R(57) together are 4 or 5 methylene groups, of which one CH$_2$ group can be replaced by oxygen, S, NH, N—CH$_3$ or N-benzyl;

R(58) is defined as R(56) or is amidine;

R(3), R(4) and R(5) are independently of one another defined as R(1) or R(2), but where at least one of the substituents R(2), R(3), R(4) and R(5) must be OH;

and their pharmaceutically tolerable salts;

(HOE 95/F 007 K - EP-A 723 956, NZ 280 887)

ag) benzoylguanidines of the formula I

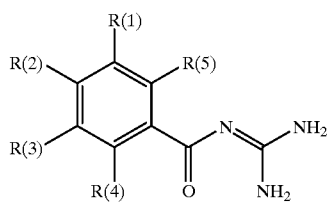

in which:

one of the three substituents R(1), R(2) and R(3) is R(6)—A—B—D—;

R(6) is a basic protonatable radical, i.e. an amino group —NR(7)R(8), an amidino group R(7)R(8)N—C[=N—R(9)]— or a guanidino group

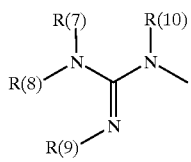

R(7), R(8), R(9) and R(10) independently of one another are hydrogen or alkyl having 1, 2, 3 or 4 carbon atoms; or R(7) and R(8) together are $C_aH_{2a}$;

a is 4, 5, 6 or 7;

where if a=5, 6 or 7 a methylene group of the group $C_aH_{2a}$ can be replaced by a heteroatom group O, SO$_m$ or NR(11), or R(8) and R(9) or R(9) and R(10) or R(7) and R(10) are a group $C_aH_{2a}$;

a is 2, 3, 4 or 5; where if a =3, 4 or 5 a methylene group of the group $C_aH_2a$ can be replaced by a heteroatom group O, SO$_m$ or NR(11);

m is zero, 1 or 2;

R(11) is hydrogen or methyl; or

R(6) is a basic heteroaromatic ring system having 1–9 carbon atoms;

A is $C_bH_{2b}$;

b is 1, 2, 3, 4, 5, 6, 7, 8, 9 or 10; where in the group $C_bH_{2b}$ one or two methylene groups can be replaced by one of the groupings selected from the group consisting of —O—, —CO—, —CH[OR(20)]—, —SO$_m$—, —NR(20)—, —NR(20)—CO—, —NR(20)—CO—NH—, —NR(20)—CO—NH—SO$_2$—

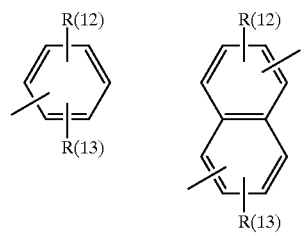

and —SO$_{aa}$[NR(19)]$_{bb}$—; and where in the group $C_bH_{2b}$ a methylene group can be replaced by —CH—R(99), where R(99) together with R(7) forms a pyrrolidine or piperidine ring;

aa is 1 or 2;

bb is 0 or 1;

aa+bb=2;

R(19) is hydrogen or alkyl having 1, 2, 3 or 4 carbon atoms;

R(20) is hydrogen or methyl;

B is a phenylene or naphthylene radical

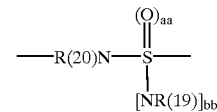

R(12) and R(13) independently of one another are hydrogen, methyl, F, Cl, Br, I, CF$_3$ or —SO$_w$—R(14);

R(14) is methyl or NR(15)R(16);

R(15) and R(16) independently of one another are hydrogen or alkyl having 1, 2, 3 or 4 carbon atoms;

w is zero, 1 or 2;

D is —C$_d$H$_{2d}$—X$_r$—;

d is zero, 1, 2, 3 or 4;

X is —O—, —CO—, —CH[OR(21)]—, —SO$_m$— or —NR(21)—;

f is zero or 1;

R(21) is hydrogen or methyl;

m is zero, 1 or 2;

and the other substituents R(1) and R(2) and R(3) in each case independently of one another are hydrogen, F, Cl, Br, I, —CN, —$(C_1-C_8)$-alkyl, —$(C_2-C_8)$-alkenyl, —NR(35)R(36) or R($^{17}$)—C$_g$H$_{2g}$—Z$_h$—;

g is zero, 1, 2, 3 or 4;

h is zero or 1;

R(35) and R(36) independently of one another are hydrogen or alkyl having 1, 2, 3, 4, 5 or 6 carbon atoms; or R(35) and R(36) together are 4–7 methylene groups, of which one CH$_2$group can be replaced by oxygen, —S—, —NH—, —NCH$_3$ or —N-benzyl;

Z is —O—, —CO—, —SO$_v$—, —NR(18)—, —NR(18)—CO—, —NR(18)—CO—NH— or —NR(18)—SO$_2$—;

R(18) is hydrogen or methyl;

v is zero, 1 or 2;
R(17) is hydrogen, cycloalkyl having 3, 5 or 6 carbon atoms or $C_kF_{2k+1}$—;
k is 1, 2 or 3, or
R(17) is pyrrol-1-yl, pyrrol-2-yl or pyrrol-3-yl, which is not substituted or is substituted by 1–4 substituents selected from the group consisting of F, Cl, Br, I, —CN, $(C_2-C_8)$-alkanoyl, $(C_2-C_8)$-alkoxycarbonyl, formyl, carboxyl, —$CF_3$, methyl and methoxy; or
R(1 7) -is $(C_3-C_8)$-cycloalkyl or phenyl, which is not substituted or is substituted by 1–3 substituents selected from the group consisting of F and Cl, —$CF_3$, methyl, hydroxyl, methoxy, —NR(37)R(38), $CH_3SO_2$— and $H_2NO_2S$—;
R(37) and R(38) are hydrogen or —$CH_3$;
R(4) and R(5) independently of one another are hydrogen, alkyl having 1, 2, 3 or 4 carbon atoms, F, Cl, —OR(32), —NR(33)R(34) or —$C_rF_{2r+1}$;
R(32), R(33) and R(34) independently of one another are hydrogen or alkyl having 1, 2 or 3 carbon atoms;
r is 1, 2, 3 or 4;
and their pharmacologically tolerable salts;
(HOE 95/F 072 - EP-A 738 712, NZ 286 380)
ah) indenoylguanidines of the formula I

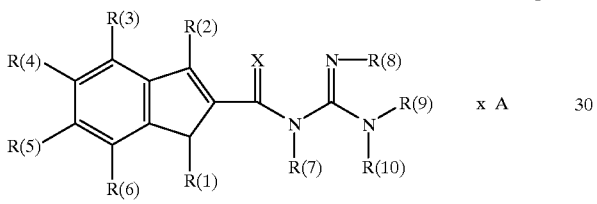

in which
R(1) and R(2) independently of one another are hydrogen, alkyl having 1, 2, 3, 4, 5, 6, 7, 8, 9 or 10 carbon atoms, cycloalkyl having 3, 4, 5 or 6 carbon atoms, O-alkyl having 1, 2, 3 or 4 carbon atoms, O—C(=O)— alkyl having 1, 2, 3 or 4 carbon atoms or $C_mH_{2m}$—NR(12)R(13);
R(12) and R(13) independently of one another are hydrogen or alkyl having 1, 2, 3 or 4 carbon atoms;
m is zero, 1, 2, 3 or 4;
NH—C(=O)—$NH_2$, C(=O)—O-alkyl having 1, 2, 3 or 4 carbon atoms, C(=O)-$NH_2$, C(=O)—NH-alkyl having 1, 2, 3 or 4 carbon atoms, C(=O)-N(alkyl)$_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenylaryl having 2, 3, 4, 5, 6, 7, 8, 9 or 10 carbon atoms in the alkenyl group, alkynylaryl having 2, 3, 4, 5, 6, 7, 8, 9 or 10 carbon atoms in the alkynyl group, $C_1-C_4$-alkyl-substituted aryl, $C_1-C_4$-alkylheteroaryl, $C_1-C_4$-alkenylheteroaryl, aminoalkylaryl having 1, 2, 3 or 4 carbon atoms in the alkyl group, substituted aryl, heteroaryl and substituted heteroaryl;
R(3), R(4), R(5) and R(6) independently of one another are hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogen, (such as F, Cl, Br, I), OH, aryl, substituted aryl, heteroaryl, substituted heteroaryl, O-lower alkyl, O-aryl, O-lower alkylaryl, O-substituted aryl, O-lower alkyl-substituted aryl, O—C(=O)—$C_1-C_4$-alkylaryl, O—C(=O)—NH—$C_1-C_4$-alkyl, O—C(=O)—N($C_1-C_4$-alkyl)$_2$, $NO_2$, CN, $CF_3$, $NH_2$, NH—C(=O)—$C_1-C_4$-alkyl, NH—C(=O)—$NH_2$, COOH, C(=O)—O—$C_1-C_4$-alkyl, C(=O)—$NH_2$, C(=O)— NH—$C_1-C_4$-alkyl, C(=O)-N($C_1-C_4$-alkyl)$_2$, $C_1-C_4$—COOH, $C_1-C_4$-alkyl-C(=O)—O—$C_1-C_4$-alkyl, $SO_3H$, $SO_2$-alkyl, $SO_2$-alkylaryl, $SO_2$—N—(alkyl)$_2$, $SO_2$-N(alkyl)(alkylaryl), C(=O)—R(11), $C_1-C_{10}$-alkyl—C(=O)—R(11), $C_2-C_{10}$-alkenyl—C(=O)-R(11), $C_2-C_{10}$-alkynyl—C(=O)—R(11), NH—C(=O)—$C_1-C_{10}$-alkyl—C(=O)—R(11), O—$C_1-C_{11}$-alkyl—C(=O)—R(11);
R(11) is $C_1-C_4$-alkyl, $C_1-C_4$-alkynyl, aryl, substituted aryl, $NH_2$, NH—$C_1-C_4$-alkyl, N—$(C_1-C_4$-alkyl)$_2$, $SO_3H$, $SO_2$-alkyl, $SO_2$-alkylaryl, $SO_2$—N— (alkyl)$_2$, $SO_2$-N(alkyl)(alkylaryl);
X is O, S or NH;
R(7), R(8), R(9) and R(10) independently of one another are hydrogen, alkyl, cycloalkyl, aryl, alkylaryl; or
R(8) and R(9) together are part of a 5-, 6- or 7-membered heterocyclic ring;
A is absent or is a nontoxic organic or inorganic acid;
(HOE 95/F 109 - EP 748 795, NZ 286 583)
ai) benzyloxycarbonylguanidines of the formula I

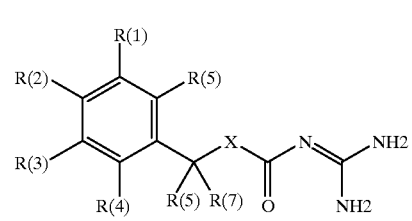

in which:
R(1), R(2) and R(3) independently of one another are —Y—[4—R(8)-phenyl], —Y—[3—R(8)-phenyl] or —Y—[2—R(8)-phenyl], where the phenyl is in each case unsubstituted or substituted by 1–2 substituents from the group consisting of F, Cl, —$CF_3$, methyl, hydroxyl, methoxy and —NR(96)R(97);
R(96) and R(97) independently of one another are hydrogen or —$CH_3$;
Y is a bond, $CH_2$, oxygen, —S— or —NR(9);
R(9) is hydrogen or alkyl having 1, 2, 3 or 4 carbon atoms;
R(8) is $SO_a[NR(98)]_bNR(99)R(10)$;
a is 1 or 2;
b is 0 or 1;
a+b=2;
R(98), R(99) and R(10) independently of one another are hydrogen, —$(C_1-C_8)$-alkyl, benzyl, —$(C_2-C_8)$-alkylene-NR(11)R(12), $(C_2-C_8)$-alkylene-NR(13)—$(C_2-C_8)$-alkylene-NR(37)R(38) or $(C_0-C_8)$-alkylene—CR(39)R(40)CR(41)R(42)$(C_0-C_8)$-alkylene-NR(43)R(44);
R(11), R(12), R(13), R(37), R(38), R(43) and R(44) independently of one another are hydrogen, —$(C_1-C_8)$-alkyl or benzyl;
R(39), R(40), R(41) and R(42) independently of one another are hydrogen, —$(C_1-C_8)$-alkyl or —$(C_0-C_3)$-alkylenephenyl, where the phenyl is not substituted or is substituted by 1–3 substituents selected from the group consisting of F, Cl, —$CF_3$, methyl and methoxy; or

49

R(99) and R(10) together are 4–6 methylene groups, of which one $CH_2$ group can be replaced by oxygen, —S—, —NH—, —N—$CH_3$ or —N—benzyl; or R(8) is $SO_a[NR(98)]_bNR(95)$—C[=N—R(94)]—NR(93)R(92);
R(92), R(93), R(94) and R(95) independently of one another are hydrogen or alkyl having 1, 2, 3 or 4 carbon atoms; or R(1), R(2) and R(3) independently of one another are pyrrol-1-yl, pyrrol-2-yl or pyrrol-3-yl, which is not substituted or is substituted by 1–4 substituents selected from the group consisting of F, Cl, Br, I, —CN, ($C_2$–$C_8$)-alkanoyl, ($C_2$–$C_8$)-alkoxycarbonyl, formyl, carboxyl, —$CF_3$, methyl, methoxy; or R(1), R(2) and R(3) independently of one another are hydrogen, —($C_1$–$C_8$)-alkyl, —($C_2$–$C_8$)-alkenyl or —$(CH_2)_m$R(14);
m is zero, 1 or 2;
R(14) is —($C_3$–$C_8$)-cycloalkyl or phenyl, which is not substituted or is substituted by 1–3 substituents selected from the group consisting of F and Cl, —$CF_3$, methyl, methoxy and —NR(15)R(16);
R(15) and R(16) are hydrogen or —$CH_3$; or R(1), R(2) and R(3) independently of one another are —Q—4-[$(CH_2)_k$—CHR(17)—(C=O)R(20)]-phenylen, —Q—3—$(CH_2)_k$—CHR(17)—(C=O)R(20)]-phenylen or —Q—2-[$(CH_2)_k$—CHR(17)—(C=O)R(20)]-phenylen, where the phenyl in each case is unsubstituted or substituted by 1–2 substituents from the group F, Cl, —$CF_3$, methyl, hydroxyl, methoxy and —NR(35)R(36);
R(35) and R(36) independently of one another are hydrogen or —$CH_3$;
Q is a bond, oxygen, —S— or —NR(18);
R(18) is hydrogen or —($C_1$–$C_4$)-alkyl;
R(17) is —OR(21) or —NR(21)R(22);
R(21) and R(22) independently of one another are hydrogen, —($C_1$–$C_8$)-alkyl, —($C_1$–$C_8$)-alkanoyl, —($C_1$–$C_8$)-alkoxycarbonyl, benzyl, benzyloxycarbonyl; or
R(21) is trityl;
R(20) is —OR(23) or —NR(23)R(24);
R(23), R(24) independently of one another are hydrogen, —($C_1$–$C_8$)-alkyl or benzyl;
k is zero, 1, 2, 3 or 4; or R(1), R(2) and R(3) independently of one another are ($C_1$–$C_9$)-heteroaryl, which is linked via C or N and which is unsubstituted or substituted by 1–3 substituents from the group F, Cl, $CF_3$, $CH_3$, methoxy, hydroxyl, amino, methylamino and dimethylamino; or R(1), R(2) and R(3) are —SR(25), —OR(25), —NR(25)R(26), —CR(25)R(26)R(27);
R(25) is —$C_fH_{2f}$($C_1$–$C_9$)-heteroaryl, which is unsubstituted or substituted by 1–3 substituents from the group F, Cl, $CF_3$, $CH_3$, methoxy, hydroxyl, amino, methylamino and dimethylamino;
f is zero, 1 or 2;
R(26) and R(27) independently of one another are defined as R(25) or are hydrogen or ($C_1$–$C_4$)-alkyl, or R(1), R(2) and R(3) independently of one another are ($C_1$–$C_9$)-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino; or

50

R(1), R(2) and R(3) independently of one another are —SR(28), —OR(28), —NR(28)R(29) or —CR(28)R(29)R(30);
R(28) is —$C_gH_{2g}$—($C_1$–$C_9$)-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;
g is zero, 1 or 2;
R(29), R(30) independently of one another are defined as R(28), hydrogen or ($C_1$–$C_4$)-alkyl; or R(1), R(2) and R(3) independently of one another are hydrogen, F, Cl, Br, I, —C≡N, T—$(CH_2)_h$—($C_iF_{2i+1}$), R(31)$SO_l$—, R(32)R(33)N—CO—, R(34)—CO— or R(45)R(46)N—$SO_2$, where the perfluoroalkyl group is straight-chain or branched;
T is a bond, oxygen, —S— or —NR(47);
l is zero, 1 or 2;
h is zero, 1 or 2;
i is 1, 2, 3, 4, 5 or 6;
R(31), R(32), R(34) and R(45) independently of one another are —($C_1$–$C_8$)-alkyl, —($C_3$–$C_6$)-alkenyl, $(CH_2)_n$R(48) or —$CF_3$;
n is zero, 1, 2, 3 or 4;
R(47) is hydrogen or alkyl with 1, 2 or 3 carbon atoms;
R(48) is —($C_3$–$C_7$)-cycloalkyl or phenyl, which is not substituted or is substituted by 1–3 substituents selected from the group consisting of F, Cl, —$CF_3$, methyl, methoxy and —NR(49)R(50);
R(49) and R(50) are hydrogen or alkyl having 1, 2, 3 or 4 carbon atoms; or
R(32), R(34) and R(45) are hydrogen;
R(33) and R(46) independently of one another are hydrogen or alkyl having 1, 2, 3 or 4 carbon atoms; or
R(32) and R(33), and R(45) and R(46) together are 5 or 6 methylene groups, of which one $CH_2$ group can be replaced by oxygen, —S—, —NH—, —$NCH_3$ or —N-benzyl; or R(1), R(2) and R(3) independently of one another are R(51)—A—G—D—;
R(51) is a basic protonatable radical, i.e. an amino group —NR(52)R(53), an amidino group R(52)R(53)N—C[=N—R(54)]-or a guanidino group R(52)R(53)N—C[=N—R(54)]—NR(55)—;
R(52), R(53), R(54) and R(55) independently of one another are hydrogen or alkyl having 1, 2, 3 or 4 carbon atoms; or
R(52) and R(53) are a group $C_\alpha H_{2\alpha}$;
α is 4, 5, 6 or 7;
where if α=5, 6 or 7 a carbon atom of the group $C_\alpha H_{2\alpha}$ can be replaced by a heteroatom group O, $SO_d$ or NR(56), or
R(53) and R(54) or R(54) and R(55) or R(52) and R(55) are a group $C_\gamma H_{2\gamma}$;
γ is 2, 3, 4 or 5;
where if γ=3, 4 or 5 a carbon atom of the group $C_\gamma H_{2\gamma}$ can be replaced by a heteroatom group O, $SO_d$ or NR(56);
d is zero, 1 or 2;
R(56) is hydrogen or methyl; or
R(51) is a basic heteroaromatic ring system having 1–9 carbon atoms;
A is a group $C_e H_{2e}$;
e is zero, 1, 2, 3, 4, 5, 6, 7, 8, 9 or 10; where in the group $C_e H_{2e}$ a carbon atom can be replaced by one of the groupings —O—, —CO—, —CH[OR(57)]—, —SO$_r$—, —NR(57)—, —NR(57)—CO—, —NR(57)—CO—NH—, —NR(57)—CO—NH—SO$_2$— or —NR(57)—SO$_2$—;
r is zero, 1 or 2;
G is a phenylene radical

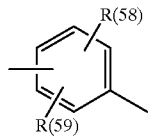

R(58) and R(59) independently of one another are hydrogen, methyl, methoxy, F, Cl, Br, I, CF$_3$ or —SO$_s$—R(60);
R(60) is methyl or NR(61)R(62);
R(61) and R(62) independently of one another are hydrogen or alkyl having 1, 2, 3 or 4 carbon atoms;
D is —C$_v$H$_{2v}$—E$_w$—;
v is zero, 1, 2, 3 or 4;
E is —O—, —CO—, —CH[OR(63)]—, —SO$_{aa}$— or —NR(63)—;
w is zero or 1;
aa is zero, 1 or 2
R(63) is hydrogen or methyl, or
R(1), R(2) and R(3) independently of one another are —CF$_2$R(64), —CF[R(65)][R(66)], —CF[(CF$_2$)$_q$—CF$_3$][R(65)], —C[(CF$_2$)$_p$—CF$_3$]=CR(65)R(66);
R(64) is alkyl having 1, 2, 3 or 4 carbon atoms or cycloalkyl having 3, 4, 5, 6 or 7 carbon atoms;
R(65) and R(66) independently of one another are hydrogen or alkyl having 1, 2, 3 or 4 carbon atoms;
q is zero, 1 or 2;
p is zero, 1 or 2; or
R(1), R(2) and R(3) independently of one another are —OR(67) or —NR(67)R(68);
R(67) and R(68) independently of one another are hydrogen or alkyl having 1, 2, 3, 4, 5 or 6 carbon atoms; or
R(67) and R(68) together are 4, 5, 6 or 7 methylene groups, of which one CH$_2$ group can be replaced by oxygen, —S—, SO$_2$, —NH—, —NCH$_3$ or —N-benzyl;
R(4) and R(5) independently of one another are hydrogen, alkyl having 1, 2, 3 or 4 carbon atoms, F, Cl, —OR(69), —NR(70)R(71) or —C$_z$F$_{2z+1}$;
R(69), R(70) and R(71) independently of one another are hydrogen or alkyl having 1, 2 or 3 carbon atoms;
z is 1, 2, 3 or 4;
R(6) and R(7) independently of one another are hydrogen or alkyl having 1, 2, 3 or 4 carbon atoms;
X is oxygen or NR(72);
R(72) is hydrogen or alkyl having 1, 2, 3 or 4 carbon atoms;
and their pharmaceutically tolerable salts;
(HOE 95/F 115 - EP 744 397, NZ 286 622)

ak) alkenylcarboxylic acid guanidides, carrying fluorophenyl groups, of the formula I

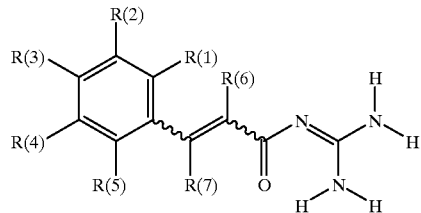

in which:
R(6) is hydrogen, (C$_1$–C$_8$)-alkyl, (C$_3$–C$_8$)-cycloalkyl or phenyl, where the phenyl group is not substituted or is substituted by 1–3 substituents selected from the group consisting of F, Cl, CF$_3$, methyl, methoxy and NR(9)R(10);
R(9) and R(10) are hydrogen, (C$_1$–C$_4$)-alkyl or (C$_1$–C$_4$)-perfluoroalkyl;
R(7) independently is defined as R(6);
R(1), R(2), R(3), R(4) and R(5) independently of one another are hydrogen or F; where, however, at least one of the radicals R(1), R(2), R(3), R(4) and R(5) must be fluorine;
and their pharmaceutically tolerable salts;
(HOE 95/F 167 - NZ 299 015)

al) benzoylguanidines of the formula I

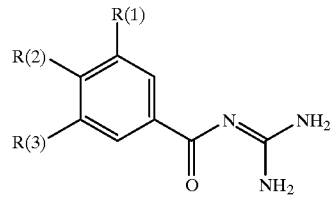

in which:
R(1) is R(4)—SO$_m$ or R(5)R(6)N—SO$_2$—;
m is 1 or 2;
R(4) and R(5) independently of one another are alkyl having 1, 2, 3, 4, 5, 6, 7 or 8 carbon atoms, alkenyl having 3, 4, 5 or 6 carbon atoms, CF$_3$ or —C$_n$H$_{2n}$—R(7);
n is zero, 1, 2, 3 or 4;
R(6) is H or alkyl having 1, 2, 3 or 4 carbon atoms;
R(7) is cycloalkyl having 3, 4, 5, 6, 7 or 8 carbon atoms or phenyl, which is not substituted or is substituted by 1–3 substituents selected from the group consisting of F, Cl, CF$_3$, methyl, methoxy and NR(8)R(9);
R(8) and R(9) are H or alkyl having 1, 2, 3 or 4 carbon atoms; or
R(5) is also hydrogen; or
R(5) and R(6) together are 4 or 5 methylene groups, of which a CH$_2$ group can be replaced by oxygen, S, NH, N—CH$_3$ or N-benzyl; or
R(1) is —O$_p$—(CH$_2$)$_q$—(CF$_2$)$_r$—CF$_3$;
p is zero or 1;
q is zero, 1 or 2;
r is zero, 1, 2 or 3; or
R(1) is —SR(10), —OR(10) or —CR(10)R(11)R(12);
R(10), R(11) and R(12) independently of one another are hydrogen, alkyl having 1, 2, 3, 4, 5, 6, 7 or 8 carbon atoms, —C$_s$H$_{2s}$—(C$_3$–C$_8$)-cycloalkyl or an aromatic system selected from the group consisting of pyridyl, pyrrolyl, quinolyl, isoquinolyl, imidazolyl or phenyl;
  s is zero, 1 or 2; where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;
R(2) is —$(CH_2)_u$—$(CF_2)_t$—$CF_3$;
  t is zero, 1, 2 or 3;
  u is zero or 1;
R(3) is hydrogen or independently is defined as R(1);
and their pharmaceutically tolerable salts;
(HOE 95/F 173 - NZ 299 052)
am) substituted cinnamic acid guanidides of the formula I

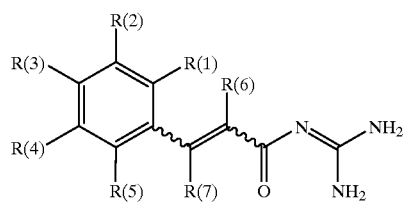

in which:
  at least one of the substituents R(1), R(2), R(3), R(4) and R(5) is —$X_a$—$Y_b$—$L_n$—U;
  X is CR(16)R(17), O, S or NR(18);
    R(16), R(17) and R(18) independently of one another are H, alkyl having 1, 2, 3 or 4 carbon atoms or perfluoroalkyl having 1, 2, 3 or 4 carbon atoms;
  a is zero or 1;
  Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;
  T is NR(20), O, S or phenylene, where the phenylene is not substituted or is substituted by 1–3 substituents selected from the group consisting of F, Cl, $CF_3$, methyl, methoxy and NR(21)R(22);
    R(20), R(21) and R(22) independently of one another are H, alkyl having 1, 2, 3 or 4 carbon atoms or perfluoroalkyl having 1, 2, 3 or 4 carbon atoms;
  b is zero or 1;
  L is O, S, NR(23) or $C_kH_{2k}$;
    k is 1, 2, 3, 4, 5, 6, 7 or 8;
  n is zero or 1;
  U is NR(24)R(25) or an N-containing heterocycle having 1, 2, 3, 4, 5, 6, 7, 8 or 9 carbon atoms;
    R(24) and R(25) independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms; or
    R(24) and R(25) together are 4 or 5 methylene groups, of which one $CH_2$ group can be replaced by oxygen, S, NH, N—$CH_3$ or N-benzyl;
    where the N-containing heterocycles are N- or C-bridged and are not substituted or are substituted by 1–3 substituents selected from the group consisting of F, Cl, $CF_3$, methyl, methoxy and NR(27)R(28);
    R(23), R(27) and R(28) independently of one another are H, alkyl having 1, 2, 3 or 4 carbon atoms or perfluoroalkyl having 1, 2, 3 or 4 carbon atoms;
  and the other substituents R(1), R(2), R(3), R(4) and R(5) in each case independently of one another are H, F, Cl, Br, I, CN, —$O_n$—$C_mH_{2m+1}$, —$O_p$—$(CH_2)_s$—$C_qF_{2q+1}$ or $C_rH_{2r}R$ (10);
  n is zero or 1;
  m is zero, 1, 2, 3, 4, 5, 6, 7 or 8;
  p is zero or 1;
  q is 1, 2, 3, 4, 5, 6, 7 or 8;
  s is zero, 1, 2, 3 or 4;
  r is zero, 1, 2, 3 or 4;
  R(10) is cycloalkyl having 3, 4, 5, 6, 7 or 8 carbon atoms, or phenyl, where the phenyl is not substituted or is substituted by 1–3 substituents selected from the group consisting of F, Cl, $CF_3$, methyl, methoxy and NR(11)R(12);
    R(11) and R(12) independently of one another are H, alkyl having 1, 2, 3 or 4 carbon atoms or perfluoroalkyl having 1, 2, 3 or 4 carbon atoms;
  R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
    which is not substituted or is substituted by 1–3 substituents selected from the group consisting of F, Cl, $CF_3$, methyl, methoxy and NR(14)R(15);
    R(14) and R(15) independently of one another are H, alkyl having 1, 2, 3 or 4 carbon atoms or perfluoroalkyl having 1, 2, 3 or 4 carbon atoms;
and their pharmaceutically tolerable salts;
(HOE 95/F 220 - NZ 299 052)
an) benzoylguanidines of the formula I

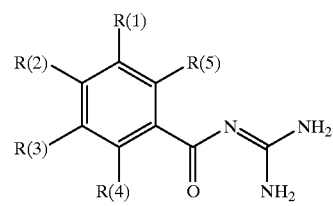

in which: at least one of the substituents R(1), R(2) and R(3) is R(6)—C(OH)$_2$—;
  R(6) is perfluoroalkyl having 1, 2 or 3 carbon atoms, which is straight-chain or branched;
  and the other substituents R(1), R(2) and R(3) independently of one another are hydrogen, OH, F, Cl, Br, I, alkyl having 1, 2, 3, 4, 5 or 6 carbon atoms, cycloalkyl having 3, 4, 5 or 6 carbon atoms, alkoxy having 1, 2, 3 or 4 carbon atoms, or phenoxy, which is unsubstituted or is substituted by 1–3 substituents selected from the group consisting of F, Cl, methyl and methoxy; or
    the other substituents R(1), R(2) and R(3) independently of one another are alkyl—$SO_x$, —CR(7)=CR(8)R(9) or —C≡—CR(9);
    x is zero, 1 or 2;
    R(7) is hydrogen or methyl;
    R(8) and R(9) independently of one another are hydrogen, ajkyl having 1, 2, 3 or 4 carbon atoms, cycloalkyl having 3, 4, 5, 6, 7 or 8 carbon atoms, or phenyl, which is unsubstituted or is substituted by 1–3 substituents selected from the group consisting of F, Cl, CF$_3$, methyl and methoxy; or the other substituents R(1), R(2) and R(3) independently of one another are phenyl, C$_6$H$_5$—(C$_1$–C$_4$)-alkyl, naphthyl, biphenylyl, quinolinyl, isoquinolinyl or imidazolyl, where quinolinyl, isoquinolinyl or imidazolyl are bonded via C or N and where phenyl, C$_6$H$_5$—(C$_1$–C$_4$)-alkyl, naphthyl, biphenylyl, quinolinyl, isoquinolinyl and imidazolyl are unsubstituted or are substituted by 1–3 substituents selected from the group consisting of F, Cl, CF$_3$, CH$_3$, methoxy, hydroxyl, amino, methylamino and dimethylamino; or the other substituents R(1), R(2) and R(3) independently of one another are SR(10), —OR(10), —CR(10)R(11)R(12);

R(10) is —C$_f$H$_{2f}$—(C$_3$–C$_8$)-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are defined as R(10), hydrogen or alkyl having 1, 2, 3 or 4 carbon atoms;

R(4) and R(5) independently of one another are hydrogen, alkyl having 1, 2 or 3 carbon atoms, F, Cl, Br, I, CN, OR(13), NR(14)R(15), —(CH$_2$)n—(CF$_2$)$_o$—CF$_3$;

R(13), R(14) and R(15) independently of one another are hydrogen or alkyl having 1, 2, 3 or 4 carbon atoms;

n is zero or 1;

o is zero, 1 or 2;

and their pharmacologically acceptable salts;

(HOE 95/F 253 - NZ 299 682)

ao) sulfonimidamides of the formula I

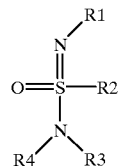

I in which:

at least one of the three substituents R(1), R(2) and R(3) is a benzoylguanidine,

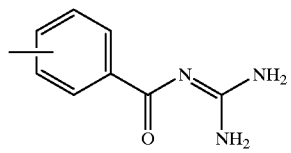

which is unsubstituted or substituted in the phenyl moiety by 1–4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$—R(14), F, Cl, Br, I, —C≡N, CF$_3$, R(22)SO$_2$—, R(23)R(24)N—CO—, R(25)—CO—, R(26)R(27) N—SO$_2$, —OR(35), —SR(35) or —N R(35)R(36);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$;

R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —CF$_3$;

n is zero, 1, 2, 3 or 4;

R(29) is —(C$_3$–C$_7$)-cycloalkyl or phenyl, which is not substituted or is substituted by 1–3 substituents selected from the group consisting of F, Cl, —CF$_3$, methyl, methoxy and —NR(30)R(31);

R(30) and R(31) are hydrogen or alkyl having 1, 2, 3 or 4 carbon atoms;

or

R(23), R(25) and R(26) are hydrogen;

R(24) and R(27) independently of one another are hydrogen or alkyl having 1, 2, 3 or 4 carbon atoms;

or

R(23) and R(24), and also R(26) and R(27) together are 5 or 6 methylene groups, of which one CH$_2$ group can be replaced by oxygen, —S—, —NH—, —NCH$_3$ or —N-benzyl;

R(35) and R(36) independently of one another are hydrogen or alkyl having 1, 2, 3, 4, 5 or 6 carbon atoms;

or

R(35) and R(36) together are 4–7 methylene groups, of which one CH$_2$ group can be replaced by oxygen, —S—, —NH—, —NCH$_3$ or —N-benzyl;

or

R(35) is phenyl, which is not substituted or is substituted by 1–3 substituents selected from the group consisting of F, Cl, —CF$_3$, methyl, methoxy, SO$_2$R(5), SO$_2$NR(6)R(7) and —NR(32)R(33);

R(5) is alkyl having 1, 2, 3, 4, 5 or 6 carbon atoms;

R(6) and R(7) independently of one another are hydrogen or alkyl having 1, 2, 3 or 4 carbon atoms;

R(32) and R(33) independently of one another are hydrogen or alkyl having 1, 2, 3 or 4 carbon atoms;

or

R(35) is C$_1$–C$_1$-heteroaryl, which is unsubstituted or substituted by 1–3 substituents selected from the group consisting of F, Cl, CF$_3$, CH$_3$, methoxy, hydroxyl, amino, methylamino and dimethylamino;

and the other substituents R(1), R(2) and R(3) in each case independently of one another are alkyl having 1, 2, 3, 4, 5, 6, 7 or 8 carbon atoms, (CH$_2$)$_p$R(10);

p is zero, 1, 2, 3 or 4;

R(10) is phenyl, which is not substituted or is substituted by 1–3 substituents selected from the group consisting of F, Cl, —CF$_3$, methyl, methoxy, —SO$_2$NR(17)R(8) and —SO$_2$R(9);

R(17) and R(8) independently of one another are hydrogen or alkyl having 1, 2, 3 or 4 carbon atoms;

R(9) is alkyl having 1, 2, 3 or 4 carbon atoms;

or the other radical R(1) or R(3) in each case is hydrogen,

R(4) is hydrogen or alkyl having 1, 2, 3 or 4 carbon atoms;

and their pharmaceutically tolerable salts; (HOE 95/F 265 - NZ 299 739) ap) benzoylguanidines of the formula I in which:

R(1) is alkyl having 1, 2, 3, 4, 5, 6, 7 or 8 carbon atoms or NR(7)R(8);

R(7) and R(8) independently of one another are hydrogen or alkyl having 1, 2, 3, 4, 5, 6, 7 or 8 carbon atoms;
R(2) is hydrogen, alkyl having 1, 2, 3, 4, 5, 6, 7 or 8 carbon atoms or —SO$_2$R(9);

R(9) independently is defined as R(1);
R(3) is hydrogen, —SR(25), —OR(25), —NR(25)R(26) or —CR(25)R(26)R(27);

R(25) is hydrogen, alkyl having 1, 2, 3, 4, 5, 6, 7 or 8 carbon atoms, or phenyl,
which is unsubstituted or substituted by 1–3 substituents selected from the group consisting of F, Cl, CF$_3$, CH$_3$, methoxy, hydroxyl, amino, methylamino and dimethylamino;

or

R(25)

is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

(4) is hydrogen, F, Cl, Br, I, OH, —C≡N, CF$_3$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) independently of one another are hydrogen or —CH$_3$;
R(5) and R(6) independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;

and their pharmaceutically tolerable salts; (HOE 95/F 269 K- EP 774 458) aq) benzenedicarboxylic acid diguanidides of the formula I in which:
one of the radicals R(1), R(2), R(3) and R(4) is —CO—N=C(NH$_2$)$_2$;

and of the other radicals R(1), R(2), R(3) and R(4) in each case:
R(1) is hydrogen, alkyl having 1, 2, 3 or 4 carbon atoms, F, Cl, Br, I, —OR(32), —NR(33)R(34) or CF$_3$;
R(32), R(33) and R(34) independently of one another are hydrogen or alkyl having 1, 2, 3 or 4 carbon atoms;
R(2) and R(4) independently of one another are hydrogen, F, Cl, Br, I, OH, —CN, CF$_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is —(C$_3$–C$_8$)-cycloalkyl or phenyl,
which is not substituted or is substituted by 1–3 substituents selected from the group consisting of F and Cl, —CF$_3$, methyl, methoxy and —NR(15)R(16);
R(15) and R(16) are hydrogen or —CH$_3$;
or
R(2) and R(4) independently of one another are pyrrol-1-yl, pyrrol-2-yl or pyrrol-3-yl,
which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy;
or
R(2) and R(4) independently of one another are R(22)-SO$_2$—, R(23)R(24)N—CO—, R(28)—CO— or R(29)R(30)N—SO$_2$;
R(22) and R(28) independently of one another are methyl or —CF$_3$;
R(23), R(24), R(29) and R(30) independently of one another are hydrogen or methyl;
or
R(2) and R(4) independently of one another are —OR(35) or —NR(35)R(36);
R(35) and R(36) independently of one another are hydrogen or alkyl having 1, 2, 3, 4, 5 or 6 carbon atoms;
or
R(35) and R(36) together are 4–7 methylene groups, of which one CH$_2$ group can be replaced by oxygen, —S—, —NH—, —NCH$_3$ or —N-benzyl;
R(3) is hydrogen, —SR(25), —OR(25), —NR(25)R(26), —CR(25)R(26)R(27);
R(25) is hydrogen, alkyl having 1, 2, 3, 4, 5, 6, 7 or 8 carbon atoms or phenyl,
which is unsubstituted or substituted by 1–3 substituents selected from the group consisting of F, Cl, CF$_3$, CH$_3$, methoxy, hydroxyl, amino, methylamino and dimethylamino;
or
R(25) is —(C$_1$–C$_9$)-heteroaryl,
which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(5) is alkyl having 1, 2, 3 or 4 carbon atoms, F, Cl, Br, I, X—(CH$_2$)$_y$—CF$_3$ or phenyl, which is not substituted or is substituted by 1–3 substituents selected from the group consisting of F and Cl, —CF$_3$, methyl, methoxy and —NR(6)R(7);

R(6) and R(7) independently of one another are hydrogen or —CH$_3$;

X is a bond or oxygen;

y is zero, 1 or 2;

their pharmaceutically tolerable salts; (HOE 95/F 269 BK - EP 774 457) ar) benzenedicarboxylic acid diguanidides of the formula I in which:

one of the radicals R(1), R(2), R(3) and R(5) is —CO—N=C(NH$_2$)$_2$;

and of the other radicals R(1), R(2), R(3) and R(5) in each case:

R(1) and R(5) independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;

R(2) is hydrogen, F, Cl, Br, I, OH, —CN, CF$_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$;

or

R(2) is R(22)—SO$_2$—, R(23)R(24)N—CO—, R(28)—CO— or R(29)R(30)N—SO$_2$;

R(22) and R(28) independently of one another are methyl or —CF$_3$;

R(23), R(24), R(29) and R(30) independently of one another are hydrogen or methyl;

or

R(2) is —OR(35) or —NR(35)R(36);

R(35) and R(36) independently of one another are hydrogen or alkyl having 1, 2, 3, 4, 5 or 6 carbon atoms;

or

R(35) and R(36) together are 4–7 methylene groups, of which one CH$_2$ group can be replaced by oxygen, —S—, —NH—, —NCH$_3$ or-N-benzyl;

R(3) is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino;

or

R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is CF$_3$, alkyl having 1, 2, 3, 4, 5, 6, 7 or 8 carbon atoms, alkenyl having 2, 3, 4, 5, 6, 7 or 8 carbon atoms, —(C$_3$–C$_8$)-cycloalkyl or —(CH$_2$)$_m$R(14);

m is 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$;

or

R(4) is phenyl, which is substituted by 2, 3, 4 or five substituents selected from the group consisting of F, Cl, CF$_3$, methyl, methoxy and —NR(1 5)R(16);

R(15) and R(16) independently of one another are hydrogen or CH$_3$;

and their pharmaceutically tolerable salts; (HOE 96/F 013 - EP-A 787 717) as) diaryldicarboxylic acid diguanidides of the formula I in which:

one of the radicals R(1), R(2), R(3), R(4) and R(5) is —CO—N=C(NH$_2$)$_2$;

the other radicals R(1) and R(5) in each case independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;

the other radicals R(2) and R(4) in each case independently of one another are hydrogen, F, Cl, Br, I, OH, —CN, CF$_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) are hydrogen or —CH$_3$;

or the other radicals R(2) and R(4) in each case independently of one another are pyrrol-1-yl, pyrrol-2-yl or pyrrol-3-yl, which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy;

or the other radicals R(2) and R(4) in each case are R(22)—SO₂—, R(23)R(24)N—CO—, R(28)—CO— or R(29)R(30)N—SO₂;
  R(22) and R(28) independently of one another are methyl or —CF₃;
  R(23), R(24), R(29) and R(30) independently of one another are hydrogen or methyl;
or
the other radicals R(2) and R(4) in each case independently of one another are —OR(35) or —NR(35)R(36);
  R(35) and R(36) independently of one another are hydrogen or alkyl having 1, 2, 3, 4, 5 or 6 carbon atoms;
or
  R(35) and R(36) together are 4–7 methylene groups, of which one CH₂ group can be replaced by oxygen, —S—, —NH—, —NCH₃ or —N-benzyl;
the other radical R(3) in each case is hydrogen, —SR(25), —OR(25), —NR(25)R(26), —CR(25)R(26)R(27);
  R(25) is hydrogen, alkyl having 1, 2, 3, 4, 5, 6, 7 or 8 carbon atoms, or phenyl,
    which is unsubstituted or substituted by 1–3 substituents selected from the group consisting of F, Cl, CF₃, CH₃, methoxy, hydroxyl, amino, methylamino and dimethylamino;
or
  R(25) is —(C₁–C₉)-heteroaryl, which is unsubstituted or substituted by 1–3 substituents selected from the group consisting of F, Cl, CF₃, CH₃, methoxy, hydroxyl, amino, methylamino and dimethylamino;
  R(26) and R(27) independently of one another are defined as R(25) or are hydrogen or alkyl having 1, 2, 3, 4, 5, 6, 7 or 8 carbon atoms;
one of the radicals R(6), R(7), R(8), R(9) and R(10) is —CO—N═C(NH₂)₂;
the other radicals R(6) and R(10) in each case independently of one another are hydrogen, alkyl having 1, 2, 3 or 4 carbon atoms, F, Cl, —OR(132), —NR(133)R(134) or CF₃;
  R(132), R(133) and R(134) independently of one another are hydrogen or alkyl having 1, 2, 3 or 4 carbon atoms;
the other radicals R(7) and R(9) in each case independently of one another are hydrogen, F, Cl, Br, I, OH, —CN, CF₃, —CO—N═C(NH₂)₂, alkyl having 1, 2, 3, 4, 5, 6, 7 or 8 carbon atoms, alkenyl having 2, 3, 4, 5, 6, 7 or 8 carbon atoms or —(CH₂)ₘₘR(1 14);
  mm is zero, 1 or 2;
  R(114)
    is —(C₃–C₈)-cycloalkyl or phenyl, which is not substituted or is substituted by 1–3 substituents selected from the group consisting of F and Cl, —CF₃, methyl, methoxy and —NR(115)R(116);
    R(115) and R(116) are hydrogen or —CH₃;
or
the other radicals R(7) and R(9) in each case independently of one another are pyrrol-1-yl, pyrrol-2-yl or pyrrol-3-yl,
  which is not substituted or is substituted by 1–4 substituents selected from the group consisting of F, Cl, Br, I, —CN, (C₂–C₈)-alkanoyl, (C₂–C₈)-alkoxycarbonyl, formyl, carboxyl, —CF₃, methyl and methoxy;
or
  the other radicals R(7) and R(9) in each case are R(122)—SO₂—, R(123)R(124)N—CO—, R(128)—CO— or R(129)R(130)N—SO₂;
    R(122) and R(128) independently of one another are methyl or —CF₃;
    R(123), R(124), R(129) and R(130) independently of one another are hydrogen or methyl;

or
the other radicals R(7) and R(9) in each case independently of one another are —OR(135) or —NR(135)R(136);
  R(135) and R(136) independently of one another are hydrogen or alkyl having 1, 2, 3, 4, 5 or 6 carbon atoms;
or
  R(135) and R(136) together are 4–7 methylene groups, of which one CH₂ group can be replaced by oxygen, —S—, —NH—, —NCH₃ or —N-benzyl;
the other radical R(8) in each case is hydrogen, —SR(125), —OR(125), —NR(125)R(126) or —CR(125)R(126)R(127);
  R(125) is hydrogen, alkyl having 1, 2, 3, 4, 5, 6, 7 or 8 carbon atoms or phenyl,
    which is unsubstituted or substituted by 1–3 substituents selected from the group consisting of F, Cl, CF₃, CH₃, methoxy, hydroxyl, amino, methylamino and dimethylamino;
or
  R(1 25)
    is —(C₁–C₉)-heteroaryl, which is unsubstituted or substituted by 1–3 substituents selected from the group consisting of F, Cl, CF₃, CH₃, methoxy, hydroxyl, amino, methylamino and dimethylamino;
  R(126) and R(127) independently of one another are defined as R(125) or are hydrogen or alkyl having 1, 2, 3, 4, 5, 6, 7 or 8 carbon atoms;
A is absent or is —NR(11)—CO—, —NR(12)—CO—NR(13)—, —NR(17)—CO—NR(18)—SO₂—, —NR(19)—SO₂—, —SO₂—NR(19)—SO₂—, —SO₂—NR(19)—CO—, —O—CO—NR(19)—SO₂— or —CR(20)═CR(21)—;
  R(11), R(12), R(13), R(17), R(18), R(19), R(20) and R(21) independently of one another are hydrogen or alkyl having 1, 2, 3, 4, 5, 6, 7 or 8 carbon atoms
and their pharmaceutically tolerable salts; (HOE 96/F 026 - EP 790 245) at) substituted thiophenylalkenylcarboxylic acid guanidides of the formula I

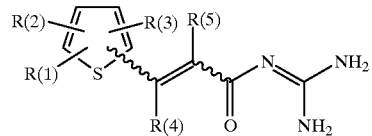

in which:
  at least one of the substituents R(1), R(2) and R(3) is —Oₚ—(CH₂)ₛ-C_qF_{2q+1}, R(40)CO— or R(31)SO_k—;
  p is zero or 1;
  s is zero, 1, 2, 3 or 4;
  q is 1, 2, 3, 4, 5, 6, 7 or 8;
  k is zero, 1 or 2;
  R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
    which is not substituted or is substituted by 1–3 substituents selected from the group consisting of F, Cl, CF₃, methyl and methoxy;
  R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
    which is not substituted or is substituted by 1–3 substituents selected from the group consisting of F, Cl, CF₃, methyl or methoxy;

or

R(31) is NR(41)R(42);

R(41) and R(42) independently of one another are hydrogen, alkyl having 1, 2, 3 or 4 carbon atoms, perfluoroalkyl having 1, 2, 3 or 4 carbon atoms, or R(41) and R(42) together are 4 or 5 methylene groups, of which one $CH_2$ group can be replaced by oxygen, S, NH, N—$CH_3$ or N-benzyl;

and the other substituents R(1), R(2) and R(3) in each case independently of one another are H, F, Cl, Br, I, CN, —$O_{na}$-$C_{ma}H_{2ma+1}$ or —$O_{ga}C_{ra}H_{2ra}$R(10);

na is zero or 1;

ma is zero, 1, 2, 3, 4, 5, 6, 7 or 8;

ga is zero or 1;

ra is zero, 1, 2, 3 or 4;

R(10) is cycloalkyl having 3, 4, 5, 6, 7 or 8 carbon atoms or phenyl, where the phenyl is not substituted or is substituted by 1–3 substituents selected from the group consisting of F, Cl, $CF_3$, methyl and methoxy;

R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl, which is not substituted or is substituted by 1–3 substituents selected from the group consisting of F, Cl, $CF_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

and their pharmaceutically tolerable salts; (HOE 96/F 032 - EP 791 577) au) ortho-substituted benzoylguanidines of the formula I

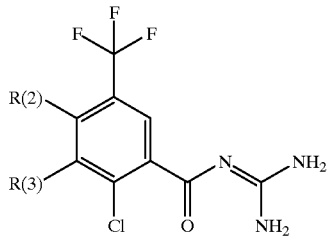

in which:

R(2) and R(3) independently of one another are hydrogen, Cl, Br, I, ($C_1$-$C_8$)-alkyl, ($C_3$-$C_8$)-cycloalkyl or —OR(5);

R(5) is ($C_1$-$C_8$)-alkyl or —$C_dH_{2d}$-($C_3$-$C_8$)-cycloalkyl; d is zero, 1 or 2;

where one of the two substituents R(2) and R(3) is always hydrogen but both substituents R(2) and R(3) are not simultaneously hydrogen, and their pharmaceutically tolerable salts; (HOE 96/F 042 - EP 794 171) av) benzoylguanidines of the formula I

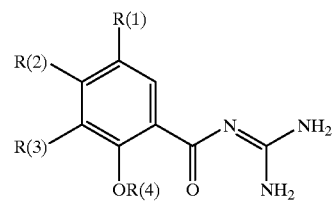

in which:

R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;

x is oxygen, S, NR(5), a is zero or 1;

b is zero, 1 or 2;

c is zero, 1, 2 or 3;

R(5) is H, alkyl having 1, 2, 3 or 4 carbon atoms or —$C_dH_{2d}$R(6);

d is zero, 1, 2, 3 or 4;

R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(7)R(8);

R(7) and R(8) independently are H or alkyl having 1, 2, 3 or 4 carbon atoms;

or

R(1) is —SR(10), —OR(10) or —CR(10)R(11)R(12);

R(10) is —$C_fH_2$f-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, $CF_3$, $CH_3$, methoxy, hydroxyl, amino, methylamino and dimethylamino;

f is zero, 1 or 2;

R(11) and R(12) independently of one another are defined as R(10) or are hydrogen or alkyl having 1, 2, 3 or 4 carbon atoms;

or

R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, $CF_3$, $CH_3$, methoxy, hydroxyl, amino, methylamino and dimethylamino, or R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$-(CO)—[CR(22)R(23)]$_l$-R(24), k is zero, 1, 2, 3 or 4;

l is zero, 1, 2, 3 or 4;

R(13) and R(14) identically or differently are —$(CH_2)_g$-(CHOH)$_h$-(CH$_2$)$_i$- (CHOH)$_j$-R(17) or —$(CH_2)_g$—O—(CH$_2$-CH$_2$O)$_h$-R(24); R(17) is hydrogen or methyl, g, h and i identically or differently are zero, 1, 2, 3 or 4; j is 1, 2, 3 or 4;

R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
R(18)
is phenyl, which is unsubstituted or substituted by 1–3 substituents selected from the group consisting of F, Cl, CF$_3$, methyl, methoxy and NR(25)R(26); R(25) and R(26)
are H or alkyl having 1, 2, 3 or 4 carbon atoms;
or
R(18) is heteroaryl having 1, 2, 3, 4, 5, 6, 7, 8 or 9 carbon atoms, which is unsubstituted or substituted as phenyl;
or
R(18) is alkyl having 1, 2, 3, 4, 5 or 6 carbon atoms, which is unsubstituted or substituted by 1–3 OH;
or
R(1 8) is cycloalkyl having 3, 4, 5, 6, 7 or 8 carbon atoms;
R(19), R(20), R(21), R(22) and R(23) identically or differently are hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_2$m-R(18);
m is 1, 2, 3 or 4;
R(2) and R(3) are defined as R(1);
R(4) is alkyl having 1, 2, 3 or 4 carbon atoms; and their pharmaceutically tolerable salts; (HOE 96/F 043 - EP 794 172) aw) ortho-substituted benzoylguanidines of the formula I

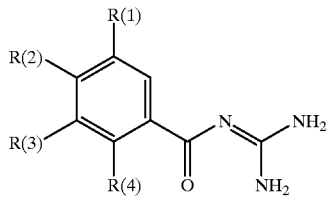

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, S, NR(5),
a is zero or 1;
b is zero, 1 or 2;
c is zero, 1, 2 or 3;
R (5) is H, alkyl having 1, 2, 3 or 4 carbon atoms or —C$_d$H$_{2d}$R($^6$);
d is zero, 1, 2, 3 or 4;
R(6) is cycloalkyl having 3, 4, 5, 6, 7 or 8 carbon atoms, phenyl, biphenylyl or naphthyl,
where the aromatics phenyl, biphenylyl or naphthyl are not substituted or are substituted by 1–3 substituents selected from the group consisting of F, Cl, CF$_3$, methyl, methoxy and NR(7)R(8);
R(7) and R(8) independently are H or alkyl having 1, 2, 3 or 4 carbon atoms;
or
R(1) is —SR(10), —OR(10) or —CR(10)R(11)R(12);
R(10) is —C$_f$H$_{2f}$-cycloalkyl having 3, 4, 5, 6, 7 or 8 carbon atoms in the cycloalkyl ring, or phenyl,
where phenyl is unsubstituted or substituted by 1–3 substituents selected from the group consisting of F, Cl, CF$_3$, CH$_3$, methoxy, hydroxyl, amino, methylamino and dimethylamino;

f is zero, 1 or 2;
R(11) and R(12) independently of one another are defined as R(10), or are hydrogen or alkyl having 1, 2, 3 or 4 carbon atoms;
or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring,
which are in each case unsubstituted or substituted by 1–3 substituents selected from the group consisting of F, Cl, CF$_3$, CH$_3$, methoxy, hydroxyl, amino, methylamino and dimethylamino,
or
R(1) is —SR(13), —OR(13), —NHR(13), —NR(13)R (14), —CHR(13)R(15), —C[R(15)R(16)OH], —C≡CR (18), —C[R(19)]=CHR(18), —C[R(20)R(2 1)]$_k$—(CO)—[CR(22)R(23)]$_l$—R(24),
k is zero, 1, 2, 3 or 4;
I is zero, 1, 2, 3 or 4;
R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);
R(17) is hydrogen or methyl,
g, h and i identically or differently are zero, 1, 2, 3 or 4;
j is 1, 2, 3 or 4;
R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
R(18) is phenyl,
which is unsubstituted or substituted by 1–3 substituents selected from the group consisting of F, Cl, CF$_3$, methyl, methoxy and NR(25)R(26);
R(25) and R(26) are H or alkyl having 1, 2, 3 or 4 carbon atoms;
or
R(1 8) is heteroaryl having 1, 2, 3, 4, 5, 6, 7, 8 or 9 carbon atoms, which is unsubstituted or substituted as phenyl;
or
R(18) is alkyl having 1, 2, 3, 4, 5 or 6 carbon atoms, which is unsubstituted or substituted by 1–3 OH;
or
R(18) is cycloalkyl having 3, 4, 5, 6, 7 or 8 carbon atoms;
R(19), R(20), R(21), R(22) and R(23) identically or differently are hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);
m is 1, 2, 3 or 4;
one of the two substituents R(2) and R(3) is hydroxyl; and
the other of the substituents R(2) and R(3) in each case is defined as R(1);
R(4) is alkyl having 1, 2, 3 or 4 carbon atoms; alkoxy having 1, 2, 3 or 4 carbon atoms, F, Cl, Br, I or —(CH$_2$)$_n$—(CF$_2$)$_o$—CF$_3$;
n is zero or 1;
o is zero or 1;
and their pharmaceutically tolerable salts; (HOE 96/F 135 - EP 810 207) ax) bis-ortho-substituted benzoylguanidines of the formula I

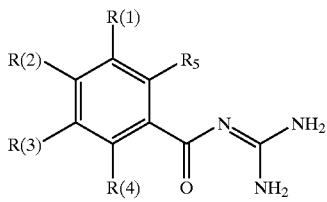

in which:

R(2) and R(3) independently of one another are R(10)—SOR$_a$— or R(14)R(15)N—SO$_2$—;

a is zero, 1 or 2,

R(10), R(14) and R(15) independently of one another are alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5 or 6 carbon atoms or —C$_{ab}$H$_{2ab}$—R(16);

ab is zero, 1, 2, 3 or 4;

R(16) is cycloalkyl having 3, 4, 5, 6 or 7 carbon atoms, or phenyl,
which is not substituted or is substituted by 1–3 substituents selected from the group consisting of F, Cl, CF$_3$, methyl, methoxy and NR(17)R(18);
R(17) and R(18) independently of one another are hydrogen, CF$_3$ or alkyl having 1, 2, 3 or 4 carbon atoms;

or

R(14) and R(15) together are 4 or 5 methylene groups, of which one CH$_2$ group can be replaced by oxygen, sulfur, NH, N—CH$_3$ or N-benzyl;

or

R(14) and R(15) are hydrogen;

or

R(1), R(2) and R(3) independently of one another are SR(21), —OR(22), —NR(23)R(24) or —CR(25)R(26)R(27);

R(21), R(22), R(23) and R(25) independently of one another are —C$_b$H$_{2b}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

b is zero, 1 or 2;

R(24), R(26) and R(27) independently of one another are hydrogen, alkyl having 1, 2, 3 or 4 carbon atoms or perfluoroalkyl having 1, 2, 3 or 4 carbon atoms;

or

R(1), R(2) and R(3) independently of one another are hydrogen, F, Cl, Br, I, CN, —(Xa)$_{dg}$—C$_{da}$H$_{2da+1}$, —(Xb)$_{dh}$—(CH$_2$)$_{db}$—C$_{de}$F$_{2de+1}$, alkenyl having 3, 4, 5, 6, 7 or 8 carbon atoms or —C$_{df}$H$_{2df}$R($^{30}$);

(Xa) is oxygen, sulfur or NR(33);

R(33) is hydrogen, alkyl having 1, 2, 3 or 4 carbon atoms or perfluoroalkyl having 1, 2, 3 or 4 carbon atoms;

dg is zero or 1;

(Xb) is oxygen, sulfur or NR(34);

R(34) is hydrogen, alkyl having 1, 2, 3 or 4 carbon atoms or perfluoroalkyl having 1, 2, 3 or 4 carbon atoms;

dh is zero or 1;

da is zero, 1, 2, 3, 4, 5, 6, 7 or 8;

db is zero, 1, 2, 3 or 4;

de is zero, 1, 2, 3, 4, 5, 6 or 7;

df is zero, 1, 2, 3 or 4;

R(30) is cycloalkyl having 3, 4, 5, 6, 7 or 8 carbon atoms, phenyl, biphenylyl or naphthyl, where the aromatics phenyl, biphenylyl and naphthyl are not substituted or are substituted by 1–3 substituents selected from the group consisting of F, Cl, CF$_3$, methyl, methoxy and NR(31)R(32);

R(31) and R(32) are hydrogen, alkyl having 1, 2, 3 or 4 carbon atoms or perfluoroalkyl having 1, 2, 3 or 4 carbon atoms;

or

R(1), R(2) and R(3) independently of one another are NR(40)R(41) or —(Xe)—(CH$_2$)$_{eb}$R(45);

R(40) and R(41) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms or (CH$_2$)$_e$—R(42);

e is zero, 1, 2, 3 or 4;

R(42) is cycloalkyl having 3, 4, 5, 6 or 7 carbon atoms or phenyl,
which is not substituted or is substituted by 1–3 substituents selected from the group consisting of F, Cl, CF$_3$, methyl, methoxy and NR(43)R(44);
R(43) and R(44) independently of one another are hydrogen, CF$_3$ or alkyl having 1, 2, 3 or 4 carbon atoms;

or

R(40) and R(41) together are 4 or 5 methylene groups, of which one CH$_2$ group can be replaced by oxygen, sulfur, NH, N—CH$_3$ or N-benzyl;

(Xe) is oxygen, sulfur or NR(47);

R(47) is hydrogen, alkyl having 1, 2, 3 or 4 carbon atoms or perfluoroalkyl having 1, 2, 3 or 4 carbon atoms;

eb is zero, 1, 2, 3 or 4;

R(45) is cycloalkyl having 3, 4, 5, 6 or 7 carbon atoms, or phenyl, which is not substituted or is substituted by 1–3 substituents selected from the group consisting of F, Cl, CF$_3$, methyl, methoxy, NR(50)R(51) and —(Xfa)—(CH$_2$)$_{ed}$—(Xfb)R(46);

Xfa is CH$_2$, oxygen, sulfur or NR(48);

Xfb is oxygen, sulfur or NR(49);

R(48), R(49), R(50) and R(51) independently of one another are hydrogen, alkyl having 1, 2, 3 or 4 carbon atoms or perfluoroalkyl having 1, 2, 3 or 4 carbon atoms;

ed is 1, 2, 3 or 4;

R(46) is hydrogen, alkyl having 1, 2, 3 or 4 carbon atoms or perfluoroalkyl having 1, 2, 3 or 4 carbon atoms;

or

R(1), R(2) and R(3) independently of one another are —CHR(52)R(53);

R(52) is —(CH$_2$)$_g$—(CHOH)$_h$—(CH)$_i$—(CHOH)$_k$—R(54) or —(CH$_2$)$_g$—O—(CH$_2$—CH$_2$O)$_h$—R(54);

R(54) is hydrogen or methyl; g, h, i identically or differently are zero, 1, 2, 3 or 4;

k is 1, 2, 3 or 4;

R(53) is hydrogen or alkyl having 1, 2, 3 or 4 carbon atoms;

or

R(1), R(2) and R(3) independently of one another are —C(OH)R(55)R(56);

R(55) and R(56) identically or differently are hydrogen or alkyl having 1, 2, 3 or 4 carbon atoms;

or
R(55) and R(56) together are cycloalkyl having 3, 4, 5 or 6 carbon atoms;
or
R(55) is —CH$_2$OH;
and
(4) and R(5) independently of one another are alkyl having 1, 2, 3 or 4 carbon atoms, alkoxy having 1, 2, 3 or 4 carbon atoms, OH, F, Cl, Br, I, CN, —O$_n$—(CH$_2$)$_o$—(CF$_2$)$_p$—CF$_3$;
n is zero or 1;
o is zero, 1 or 2;
p is zero, 1 or 2;
and their pharmaceutically tolerable salts; (96/F 136 - EP 810 205) ay) substituted 1-naphthoylguanidines of the formula I

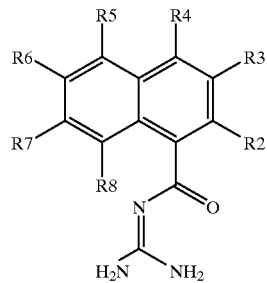

in which:
R2, R3, R4, R5, R6, R7 and R8 independently of one another are H, F, Cl, Br, I, CN, NO$_2$, CF$_3$, C$_2$F$_5$ or X$_a$Y$_b$Z;
X is O, S, NR(10), CR(11)R(12), C=O, C(=O)NR(10), C(=O)O, SO, SO$_2$, SO$_2$NR(10), OC=O, NR(10)C=O or NR(10)SO$_2$,
where the linkage with the naphthalene ring in each case takes place via the left atom;
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
a is zero or 1;
Y is alkylene having 1, 2, 3, 4, 5, 6, 7 or 8 CH$_2$ groups, where one of these CH$_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
b is zero or 1;
Z is H, alkyl having 1, 2, 3, 4, 5, 6 or 7 carbon atoms, cycloalkyl having 3, 4, 5, 6 or 7 carbon atoms, C(=O)R(15), SO$_2$R(15), NR(16)R(17) or phenyl,
which is not substituted or is substituted by 1–3 substituents selected from the group consisting of F, Cl, Br, CF$_3$, methyl, methoxy and NR(21)R(22);
R(21) and R(22) independently of one another are H or alkyl having 1, 2, 3 or 4 carbon atoms or perfluoroalkyl having 1, 2, 3 or 4 carbon atoms;
R(15) is N=C(NH$_2$)$_2$, NR(18)R(19), N(CH$_2$)$_c$NR(18)R(19) or OR (20);
c is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups, of which one CH$_2$ group can be replaced by oxygen, S, NH, N—CH$_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms;
or
R(16) and R(17) together are 4 or 5 methylene groups, of which one CH$_2$ group can be replaced by oxygen, S, NH, N—CH$_3$, N-benzyl or N-(p-chlorophenyl);
or
Z is an N-containing heterocycle having 1, 2, 3, 4, 5, 6, 7, 8 or 9 carbon atoms,
where the N-containing heterocycle is linked via N or C and is not substituted or is substituted by 1–3 substituents selected from the group consisting of F, Cl, Br, CF$_3$, methyl, methoxy and NR(21)R(22);
but where, in the case where R(4) is an alkoxy radical, at least one of the substituents R(2), R(3), R(5), R(6), R(7) and R(8) is not hydrogen; and their pharmaceutically tolerable salts; (96/F 137 - EP 810 206) az) substituted 2-naphthoylguanidines of the formula I

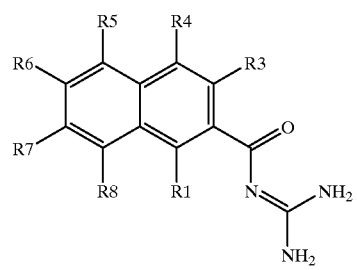

in which:
at least one of the substituents RI, R3, R4, R5, R6, R7 and R8 is XY$_a$WZ or X'Y$_a$WZ';
X is 0, S, NR(10) or CR(11)R(12);
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Y is alkylene having 1, 2, 3, 4, 5, 6, 7 or 8 CH$_2$ groups, where one of these CH$_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
a is zero or 1;
W is CH$_2$, SO$_2$, S(=O)(=NH) or—if W does not immediately follow a heteroatom of the group XY$_a$— alternatively O or NR(14);
R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
Z is C(=O)R(15), SO$_2$R(15) or—if W is not O or NR(14)—alternatively NR(16)R(17);
R(15) is N=C(NH$_2$)$_2$, NR(18)R(19), N(CH$_2$)$_b$NR(18)R(19) or OR(20);
b is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms;

or
R(18) and R(19) together are 4 or 5 methylene groups,
of which one CH$_2$ group can be replaced by oxygen, S, NH, N—CH$_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms;
or,
R(16) and R(17) together are 4 or 5 methylene groups,
of which one CH$_2$ group can be replaced by oxygen, S, NH, N—CH$_3$, N-benzyl or N-(p-chlorophenyl);
X' is C=O, C(=O)NR(30), C(=O)O, SO, SO$_2$, SO$_2$NR(30), OC=O,
NR(30)C=O or NR(30)SO$_2$, where the linkage with the naphthalene ring in each case takes place via the left atom;
R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Z' is C(=O)R(15), SO$_2$R(15), an N-containing heterocycle having 1, 2, 3, 4, 5, 6, 7, 8 or 9 carbon atoms,
where the N-containing heterocycle is linked via N or C and is not substituted or is substituted by 1–3 substituents selected from the group consisting of F, Cl, Br, CF$_3$, methyl, methoxy and NR(21)R(22);
R(21) and R(22) independently of one another are H, alkyl having 1, 2, 3 or 4 carbon atoms or perfluoroalkyl having 1, 2, 3 or 4 carbon atoms;
R(15) is N=C(NH$_2$)$_2$, NR1)(19), N(CH$_2$)$_b$NR(18)R(19) or OR(20);
R(18)and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups,
of which one CH$_2$ group can be replaced by oxygen, S, NH, N—CH$_3$, N-benzyl or N-(p-chlorophenyl);
b is 2 or 3;
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbor atoms;
or
Z'—if W is not O or NR(14)—is NR(16)R(17); R(16) and R(17) independently of one another are H, alkyl having 1, 2, 3, 4, 5, 6, 7 or 8 carbon atoms or perfluoroalkyl having 1, 2, 3 or 4 carbon atoms;
or
R(16) and R(17) together are 4 or 5 methylene groups,
of which one CH$_2$ group can be replaced by oxygen, S, NH, N—CH$_3$, N-benzyl or N-(p-chloro-phenyl);
and the other substituents R1, R3, R4, R5, R6, R7 and R8 in each case, which are still not allocated by the definitions given above,
independently of one another are H. F, Cl, Br, I, CN, NO$_2$, CF$_3$, C$_2$F$_5$ or V$_p$Q$_q$U;
V is O, S, SO, SO$_2$, NR(60), OC=O, C=O, C(=O)NR(60), C(=O)O or CR(66)R(67);
R(60), R(66) and R(67) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
p is zero or 1;

Q is alkylene having 1, 2, 3, 4, 5, 6, 7 or 8 CH$_2$ groups, where one of these CH$_2$ groups can be replaced by O, S, NR(68) or o-, p- or m-phenylene;
R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
q is zero or 1;
U is H, alkyl having 1, 2, 3, 4, 5, 6 or 7 carbon atoms, cycloalkyl having 3, 4, 5, 6 or 7 carbon atoms, C(=O)R(65), SO$_2$R(65), NR(61)R(62) or phenyl,
which is not substituted or is substituted by 1–3 substituents selected from the group consisting of F, Cl, Br, CF$_3$, methyl, methoxy and NR(63)R(64);
R(63) and R(64) independently of one another are H, alkyl having 1, 2, 3 or 4 carbon atoms or perfluoroalkyl having 1, 2, 3 or 4 carbon atoms;
R(65) is N=C(NH$_2$)$_2$, NR(61)R(62) or OR(60);
R(61) and R(62) independently of one another are H, alkyl having 1, 2, 3, 4, 5, 6, 7 or 8 carbon atoms or perfluoroalkyl having 1, 2, 3 or 4 carbon atoms;
or
R(61) and R(62) together are 4 or 5 methylene groups,
of which one CH$_2$ group can be replaced by oxygen, S, NH, N—CH$_3$, N-benzyl or N-(p-chlorophenyl);
or
U is an N-containing heterocycle having 1, 2, 3, 4, 5, 6, 7, 8 or 9 carbon atoms,
where the N-containing heterocycle is linked via N or C and is not substituted or is substituted by 1–3 substituents selected from the group consisting of F, Cl, Br, CF$_3$, methyl, methoxy and NR(63)R(64);
but where at least one of the substituents R5, R6, R7 and R8 is not hydrogen; and their pharmaceutically tolerable salts; (96/F 141 - EP 811 610) ba) ortho-substituted benzoylguanidines of the formula I $$\text{I}$$

in which:
(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
x is oxygen, sulfur or NR(9);
a is zero or 1;
b is zero, 1 or 2;
c is zero, 1, 2 or 3;
R(9) is H, alkyl having 1, 2, 3 or 4 carbon atoms or —C$_d$H$_{2d}$R(6);
d is zero, 1, 2, 3 or 4;
R(6) is cycloalkyl having 3, 4, 5, 6, 7 or 8 carbon atoms, phenyl, biphenylyl or naphthyl,
where the aromatics phenyl, biphenylyl or naphthyl are not substituted or are substituted by 1–3 substituents selected from the group consisting of F, Cl, CF$_3$, methyl, methoxy and NR(7)R(8);
R(7) and R(8) are independently, H or alkyl having 1, 2, 3 or 4 carbon atoms;

or
R(1) is —SR(10), —OR(10) or —CR(10)R(11)R(12);
R(10) is —C$_f$H$_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl,
where heteroaryl and phenyl are unsubstituted or are substituted by 1–3 substituents selected from the group consisting of F, Cl, CF$_3$, CH$_3$, methoxy, hydroxyl, amino, methylamino and dimethylamino;
f is zero ,1 or 2;
R(11) and (R12), independently of each other, are defined as R(10) or are hydrogen or alkyl having 1, 2, 3 or 4 carbon atoms;
or
R(1) is phenyl, naphthyl, biphenylyl or heteroaryl having 1, 2, 3, 4, 5, 6, 7, 8, or 9 carbon atoms, the latter linked via a carbon or nitrogen atom of the ring,
each of which is unsubstituted or is substituted by 1–3 substituents selected from the group consisting of F, Cl, CF$_3$, CH$_3$, methoxy, hydroxyl, amino, methylamino and dimethyl-amino,
or
(R1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24),
k is zero, 1, 2, 3 or 4;
I is zero, 1, 2, 3 or 4;
R(13) and R(14), identically or differently, are —(CH$_2$)$_g$—(CHOH)$_h$—(CH$_2$)$_i$—(CHOH)$_{kk}$—R(17) or —(CH$_2$)$_g$—O—(CH$_2$—CH$_2$O)$_n$—R(24);
R(17) is hydrogen or methyl, g, h and i, identically or differently, are zero, 1, 2, 3 or 4;
kk is 1, 2, 3or4;
R(15) and R(16), identically or differently, are hydrogen, alkyl having 1, 2, 3, 4, 5 or 6 carbon atoms, or, together with the carbon atom carrying them, cycloalkyl having 3, 4, 5, 6, 7 or 8 carbon atoms;
R(18) is phenyl,
which is unsubstituted or is substituted by 1–3 substituents selected from the group consisting of F, Cl, CF$_3$, methyl, methoxy and NR(25)R(26);
R(25) and R(26) are H or alkyl having 1, 2, 3 or 4 carbon atoms;
or
R(18) is heteroaryl having 1, 2, 3, 4, 5, 6, 7, 8 or 9 carbon atoms, which is unsubstituted or is substituted as phenyl;
or
R(18) is alkyl having 1, 2, 3, 4, 5 or 6 carbon atoms, which is unsubstituted or is substituted by 1–3 OH;
or
R(18) is cycloalkyl having 3, 4, 5, 6, 7 or 8 carbon atoms;
R(19), R(20), R(21), R(22) and R(23), identically or differently, are hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);
m is 1, 2, 3 or 4;
one of the two substituents R(2) and R(3) is
—O—CO—R(27);
R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl,
where phenyl, biphenylyl, naphthyl, pyridyl or quinolyl are unsubstituted or substituted by 1–3 substituents selected from the group consisting of F, Cl, CF$_3$, methyl, methoxy and NR(7)R(8);

R(7) and R(8) independently of one another are hydrogen or alkyl having 1, 2, 3 or 4 carbon atoms;
where one of the substituents R(2) and R(3) is always defined as R(1);
R(4) and R(5) independently of one another are hydrogen, alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$,
n is zero or 1,
o is zero or 1,
and their pharmaceutically tolerable salts; (HOE 96/F 154 - EP 814 077) bb) benzoylguanidines of the formula I

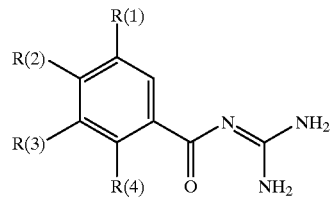

in which:
R(1) is R(13)—SO$_m$ or R (14)R(15)N—SO$_2$—;
m is 1 or 2;
R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(16),
n is zero, 1, 2, 3 or 4;
R(16) is cycloalkyl having 3, 4, 5, 6, 7 or 8 carbon atoms, phenyl, biphenylyl or naphthyl,
where phenyl, biphenylyl and naphthyl are not substituted or are substituted by 1–3 substituents selected from the group consisting of F, Cf, CF$_3$, methyl, methoxy and NR(25)R(26);
R(25) and R(26) are, independently of each other, hydrogen, alkyl having 1, 2, 3 or 4 carbon atoms or perfluoroalkyl having 1, 2, 3 or 4 carbon atoms;
R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(27),
n is zero, 1, 2, 3 or 4;
R(27) is cycloalkyl having 3, 4, 5, 6, 7 or 8 carbon atoms, phenyl, biphenylyl or naphthyl,
where phenyl, biphenylyl and naphthyl are not substituted or are substituted by 1–3 substituents selected from the group consisting of F, Cl, CF$_3$, methyl, methoxy and NR(28)R(29);
R(28) and R(29) are, independently of each other, hydrogen, alkyl having 1, 2, 3 or 4 carbon atoms or perfluoroalkyl having 1, 2, 3 or 4 carbon atoms;
R(15) is hydrogen, alkyl having 1, 2, 3 or 4 carbon atoms or perfluoroalkyl having 1, 2, 3 or 4 carbon atoms;
or
R(14) and R(15) are, together, 4 or 5 methylene groups of which one CH$_2$ group can be replaced by oxygen, S, NH, N—CH$_3$ or N-benzyl;
one of the substituents R(2) and R(3) is hydrogen;
and the other of the substituents R(2) and R(3) in each case is —CHR(30)R(31);
R(30) is —(CH$_2$)$_g$—(CHOH)$_h$—(CH$_2$)$_i$—(CHOH)$_k$—R(32) or —(CH$_2$)$_g$—O—(CH$_2$—CH$_2$O)$_n$—R(24);
R(24) and R(32) are, independently of each other, hydrogen or methyl;

g, h and i are, identically or differently, zero, 1, 2, 3 or 4;

k is 1, 2, 3 or 4;

or the other of the substituents R(2) and R(3) in each case is —C(OH)R(33)R(34);

R(31), R(33) and R(34) are, identically or differently, hydrogen or alkyl having 1, 2, 3 or 4 carbon atoms, or R(33) and R(34) are, together, cycloalkyl having 3, 4, 5 or 6 carbon atoms;

or

R(33) is —CH$_2$OH;

R(4) is alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$;

n is zero or 1;

o is zero, 1 or 2;

and their pharmaceutically tolerable salts; (HOE 96/F 202 - EP 837 055) bc) indanylidineacetylguanidines of the formula I

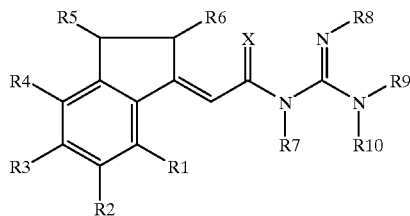

in which:

R1, R2, R3, R4, R5 and R6 independently of one another are H, C$_1$–C$_{10}$-alkyl; haloalkyl having 1–6 carbon atoms, O—C$_1$–C$_{10}$-alkyl, haloalkoxy having 1–6 carbon atoms, F, Cl, Br, I, aryl, substituted aryl, heteroaryl, substituted heteroaryl, OH, O-lower alkyl, O-aryl, O-lower alkylaryl, O-substituted aryl, O-lower alkyl-substituted aryl, O—C(=O)—C$_1$–C$_4$-alkylaryl, O—C(=O)—NH—C$_1$–C$_4$-alkyl, O—C(=O)—N(C$_1$–C$_4$-alkyl)$_2$, NO$_2$, CN, CF$_3$, NH$_2$, NH—C(=O)—C$_1$–C$_4$-alkyl, NH—C(=O)—NH$_2$, COOH, C(=O)—O—C$_1$–C$_4$-alkyl, C(=O)—NH$_2$, C(=O)—NH—C$_1$–C$_4$-alkyl, C(=O)—N(C$_1$–C$_4$-alkyl)$_2$, C$_1$–C$_4$—COOH, C$_1$–C$_4$-alkyl—C(=O)—O—C$_1$–C$_4$-alkyl, SO$_3$H, SO$_2$-alkyl; SO$_2$-alkylaryl, SO$_2$—N—(alkyl)$_2$, SO$_2$-N(alkyl)(alkylaryl), C(=O)—R11, C$_1$–C$_{10}$-alkyl-C(=O)—R11, C$_2$–C$_{10}$-alkenyl-C(=O)—R11, C$_2$–C$_{10}$-alkynyl-C(=O)—R11, NH—C(=O)—C$_1$–C$_{10}$-alkyl-C(=O)-R11 or O—C$_1$–C$_{11}$-alkyl-C(=O)—R11;

R11 is C$_1$–C$_4$-alkyl, C$_1$–C$_4$-alkynyl, aryl, substituted aryl, NH$_2$, NH—C$_1$–C$_4$-alkyl, N—(C$_1$–C$_4$-alkyl)$_2$, SO$_3$H, SO$_2$-alkyl, SO$_2$-alkylaryl, SO$_2$-N-(alkyl)$_2$ or SO$_2$-N(alkyl)(alkylaryl);

x is O, S or NH;

R7, R8, R9 and R10 independently of one another are H, alkyl, cycloalkyl, aryl, alkylaryl, or R8 and R9 together are part of a 5-, 6- or 7-membered heterocyclic ring; or their pharmaceutically acceptable salts; (HOE 96/F 226 - EP 825 178) bd) phenyl-substituted alkenylcarboxylic acid guanidides of the formula I

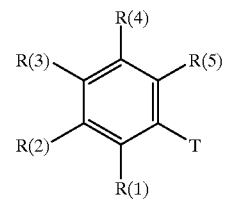

in which:

T is

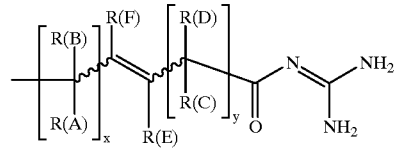

R(A) is hydrogen, F, Cl, Br, I, CN, OH, OR(6), (C$_1$–C$_4$)-alkyl, O$_r$(CH$_2$)$_a$C$_b$F$_{2b+1}$, (C$_3$–C$_8$)-cycloalkyl oder NR(7)R(8)

r is zero or 1;

a is zero, 1, 2, 3 or 4;

b is 1, 2, 3 or 4;

R(6) is (C$_1$–C$_4$)-alkyl, (C$_1$–C$_4$)-perfluoroalkyl, (C$_3$–C$_6$)-alkenyl, (C$_3$–C$_8$)-cycloalkyl, phenyl or benzyl, the phenyl nucleus not being substituted or being substituted by 1–3 substituents selected from the group consisting of F, Cl, CF$_3$, methyl, methoxy and NR(9)R(10);

R(9) and R(10) are H, (C$_1$–C$_4$)-alkyl or (C$_1$–C$_4$)-perfluoro-alkyl;

R(7) and R(8) independently of one another are defined as R(6);

or

R(7) and R(8) together are 4 or 5 methylene groups, of which one CH$_2$ group can be replaced by oxygen, sulfur, NH, N—CH$_3$ or N-benzyl;

R(B), R(C) and R(D) independently are defined as R(A);

x is zero, 1 or 2;

y is zero, 1 or 2;

R(F) is hydrogen, F, Cl, Br, I, CN, OR(12), (C$_1$–C$_8$)-alkyl, O$_p$(CH$_2$)$_f$C$_g$F$_{2g+1}$, (C$_3$–C$_8$)-cycloalkyl or (C$_1$–C$_9$)-heteroaryl;

p is zero or 1;

f is zero, 1, 2, 3 or 4;

g is 1, 2, 3, 4, 5, 6, 7 or 8;

R(12) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl, the phenyl nucleus not being substituted or being substituted by 1–3 substituents selected from the group consisting of F, Cl, CF$_3$, methyl, methoxy and NR(13)R(14);

R(13) and R(14) are H, (C$_1$–C$_4$)-alkyl or (C$_1$–C$_4$)-perfluoroalkyl;

R(E) is defined independently as R(F);

R(1) is defined independently as T;

or

R(1) is hydrogen, —O$_k$C$_m$H$_{2m+1}$, —O$_n$(CH$_2$)$_p$C$_q$F$_{2q+1}$, F, Cl, Br, I, CN, —(C=O)— N=C(N H$_2$)$_2$, —SO$_r$R(17), —SO$_{r2}$NR(31)R(32), —O$_u$(CH$_2$)$_v$C$_6$H$_5$, —O$_{u2}$—(C$_1$–C$_9$)-heteroaryl or —S$_{u2}$-(C$_1$–C$_9$)-heteroaryl;

k is zero or 1;

m is zero, 1, 2, 3, 4, 5, 6, 7 or 8;
n is zero or 1;
p is zero, 1, 2, 3 or 4;
q is 1, 2, 3, 4, 5, 6, 7 or 8;
r is zero, 1 or 2;
r2 is zero, 1 or 2;
R(31) and R(32) independently of one another are hydrogen, $(C_1-C_8)$-alkyl or $(C_1-C_8)$-perfluoroalkyl;
or
R(31) and R(32) are, together, 4 or 5 methylene groups of which one $CH_2$ group can be replaced by oxygen, S, NH, N—$CH_3$ or N-benzyl;
R(17) is $(C_1-C_8)$-alkyl;
U is zero or 1;
u2 is zero or 1;
v is zero, 1, 2, 3 or 4; where the phenyl nucleus is not substituted or is substituted by 1–3 substituents selected from the group consisting of F, Cl, $CF_3$, methyl, methoxy, —$(CH_2)_w$NR(21)R(22), NR(18)R(19) and $(C_1-C_9)$-heteroaryl;
R(18), R(19), R(21) and R(22) independently of one another are $(C_1-C_4)$-alkyl or $(C_1-C_4)$-perfluoroalkyl;
w is 1, 2, 3 or 4;
where the heterocycle of the $(C_1-C_9)$-heteroaryl is unsubstituted or substituted by 1–3 substituents selected from the group consisting of F, Cl, $CF_3$, methyl or methoxy;
R(2), R(3), R(4) and R(5) independently of one another are defined as R(1),
or
R(1) and R(2) or R(2) and R(3) in each case together are —CH—CH=CH—CH—,
which is not substituted or is substituted by 1–3 substituents selected from the group consisting of F, Cl, $CF_3$, methyl, methoxy, —$(CH_2)_{w2}$NR(24)R(25) and NR(26)R(27);
R(24), R(25), R(26) and R(27) are H, $(C_1-C_4)$-alkyl or $(C_1-C_4)$-perfluoroalkyl;
w2 is 1, 2, 3 or 4;
the radical T being present in the molecule at least twice, but only three times at most;
and their pharmaceutically tolerable salts; (HOE 97/F 082)
be) benzoylguanidines of the formula I

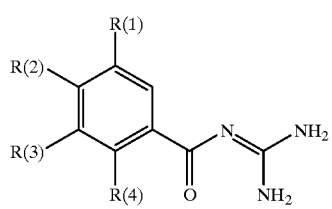

in which:
R(1) is $CF_3$;
one of the substituents R(2) and R(3) is hydrogen;
and the other substituent R(2) or R(3) in each case is —C(OH)($CH_3$)—$CH_2$OH, —CH($CH_3$)—$CH_2$OH or —C(OH)($CH_3$)$_2$;
R(4) is methyl, methoxy, Cl or $CF_3$; and their pharmaceutically tolerable salts.
(DE 195 02 895, DE 44 30 212, EP 667 341, DE 44 04 183, EP 708 088, EP 723 963, EP 0 694 537, DE 44 21 495, EP 699 660, EP 699 663, EP 699 666, DE 43 37 611, EP 0719 766, WO 94/26709, WO 96 04 241, EP 726 254, U.S. Pat. No. 4,251,545, DE 35 02 629, WO 84/00875, Kumamoto et al., Pharm. Bull. [1966], 7–13; U.S. Pat. No. 3,780,027, JP 8225513; EP 743 301)

II. Also suitable are compounds of the formula

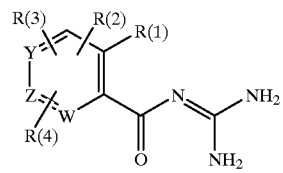

in which:
W, Y and Z are a nitrogen atom or a carbon atom substituted by R(2) or R(3) or R(4);
R(1) is hydrogen, A, Hal, —$CF_3$, —$CH_2$F, —$CHF_2$, —$CH_2CF_3$, —$C_2F_5$, —CN, —$NO_2$, -ethynyl, or an X-R';
A is alkyl having 1 to 6 carbon atoms;
Hal is F, Cl, Br or I;
X is oxygen, S or NR";
R" is hydrogen, A or a cyclic methylene chain having 3 to 7 carbon atoms;
R' is H, A, HO—A—, HOOC—A—, $(C_3-C_7)$-cycloalkyl, $(C_6-C_8)$-cycloalkylalkyl, $CF_3$, $CH_2F$, $CHF_2$, $CH_2$—$CF_3$, Ph, —$CH_2$—Ph or Het;
Ph is phenyl, naphthyl or biphenylyl which is unsubstituted or mono-, di- or trisubstituted by A, OA, NR'R", Hal, $CF_3$;
Het is a mono- or binuclear saturated, unsaturated or aromatic heterocycle having 1 to 4 nitrogen, oxygen and/or sulfur atoms,
which is unsubstituted or mono-, di- or trisubstituted by Hal, $CF_3$, A, OH, OA, —X—R', —CN, —$NO_2$, and/or carbonyl oxygen,
where Het is bonded via N or an alkylene chain $C_mH_{2m}$ where m=zero to 6;
or
R' and R" together are alkylene having 4–5 carbon atoms, in which one $CH_2$ group can also be replaced by oxygen, S, NH, N—A, N—Ph and N—$CH_2$—Ph;
R(2) and R(3) independently of one another are hydrogen, Hal, A, HO—A—, X—R', —C(=N—OH)—A, A—O—CO—$(C_1-C_4)$-alkyl-, CN, $NO_2$, COOH, halogen-substituted A, in particular $CF_3$, $CH_2F$, $CHF_2$, $C_2F_5$, $CH_2CF_3$, or $S(O)_nR'''$;
R''' is A, Ph or —Het;
n is zero, 1 or 2;
or
R(2) and R(3) independently of one another are $SO_2NR'R''$, Ph or —O—Ph, —O—$CH_2$—Ph, —CO—A, —CHO, —COOA, —CSNR'R", CONR'R", —CH=CH—COOH, —CH=CH—COOA, indenyl, indanyl, decahydronaphthyl, cyclopentenyl, dihydrothienyl, dihydrofuryl, heterobicyclyl, alkylthienyl, halothienyl, haloalkylthienyl, acylthienyl, halofuryl, haloalkylfuryl or pyrrolyl;
or
R(2) and R(3) independently of one another are R(5)—O—; R(5) is hydrogen, A, $(C_1-C_6)$-alkenyl or $(C_3-C_7)$-cycloalkyl;
R(4) is Ph, Het, —O—Het; $CF_3$, $S(O)_nR'''$, —$SO_2NR'R''$, alk;

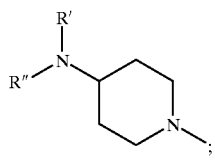

or
two of the substituents R(1) to R(4) together are a group —O—CR(6)R(7)—CO—NR(8)—,
or

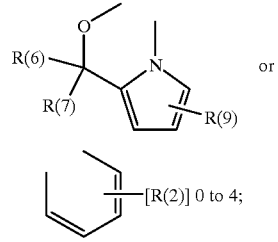

where R(2) has the meaning indicated;
R(6), R(7), R(8) and R(9) independently of one another are H or A;
or
R(8) is $(C_5-C_7)$-cycloalkyl;
or
R(9) is cyano;
alk is straight-chain or branched $(C_1-C_8)$-alkyl or $(C_3-C_8)$-cycloalkyl, which is unsubstituted or mono-, di- or trisubstituted by A;
or
alk is an ethenyl or ethynyl radical which is substituted by H, A, Ph or Het.
(EP 708 091, EP 622 356, JP 5-125085)
III. Likewise suitable are indoloylguanidine derivatives of the formula

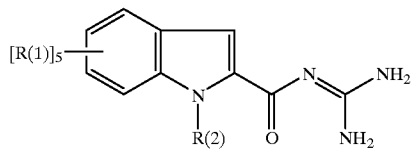

in which
R(2) is hydrogen, unsubstituted or substituted $(C_1-C_8)$-alkyl, $(C_3-C_7)$-cycloalkyl, OH, $(C_1-C_6)$-alkyl—O—, an aromatic radical or a group —CH$_2$—R(20);
R(20) is $(C_2-C_6)$-alkenyl or $(C_2-C_6)$-alkynyl;
R(1) is 1 to 5 identical or different substituents, which are: hydrogen, unsubstituted or substituted $(C_1-C_8)$-alkyl, $(C_2-C_6)$-alkenyl, $(C_2-C_6)$-alkynyl, $(C_3-C_7)$-cycloalkyl, halogen, —NO$_2$, $(C_2-C_8)$-alkanoyl, arylalkanoyl having up to 10 carbon atoms, aroyl having up to 11 carbon atoms, —COOH, $(C_2-C6)$-alkoxycarbonyl, an aromatic group or one of the following mentioned groups: —OR(3), —NR(6)R(7) or —S(O)$_n$R(40);
R(3) is hydrogen, $(C_1-C_8)$-alkyl, substituted $(C_1-C_8)$-alkyl, $(C_3-C_7)$-cycloalkyl, an aromatic radical or a group —CH$_2$—R(30); R(30) is alkenyl or alkynyl;
R(6) and R(7) independently of one another are hydrogen, unsubstituted or substituted $(C_1-C_8)$-alkyl, $(C_3-C_7)$-cycloalkyl, $(C_2-C_8)$-alkanoyl, an arylalkanoyl group having up to 10 carbon atoms, an aroyl group having up to 11 carbon atoms, an aromatic group or —CH$_2$—R(60);
R(60) is $(C_2-C_6)$-alkenyl or $(C_2-C_6)$-alkynyl;
or
R(6) and R(7) together with the nitrogen atom are a 5–7-membered cyclic amine, which can additionally contain further heteroatoms in the ring;
n is zero, 1 or 2;
R(40) is unsubstituted or substituted $(C_1-C_8)$-alkyl, or an aromatic group, or a group

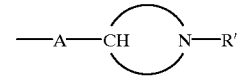

A is oxygen, —S(O)$_n$— or —N(R50)—;
R(50) is hydrogen or $(C_1-C_8)$-alkyl;
R' is hydrogen, unsubstituted or substituted $(C_1-C_8)$-alkyl, in which the ring represents a saturated 3–8-membered heterocycle having a nitrogen atom,
said substituted alkyl carries one or more groups selected from the group consisting of halogen, —OH, $(C_1-C_6)$-alkoxy, —CN, —COOH, $(C_2-C_6)$-alkoxycarbonyl, $(C_2-C_8)$-alkanoyl, arylalkanoyl having up to 10 carbon atoms, aroyl having up to 11 carbon atoms, an aromatic group, —CONR(4)(R5),
R(4) and R(5) identically or differently are hydrogen or $(C_1-C_8)$-alkyl;
or
R(4) and R(5) are connected to one another and together form a 5–7-membered cyclic amine which can additionally contain further heteroatoms in the ring,
or said substituted alkyl carries a group

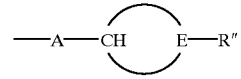

in which:
E is a nitrogen atom or a CH group;
R" is hydrogen, $(C_1-C_8)$-alkyl which is unsubstituted or substituted by OH or substituted $(C_1-C_8)$-alkyl, $(C_1-C_6)$-alkoxy, —CN, —COOH, $(C_2-C_6)$-alkoxycarbonyl, $(C_2-C_8)$-alkanoyl, aralkanoyl having up to 10 carbon atoms, aroyl having up to 11 carbon atoms, an aromatic group, —NR(6)R(7), —CONR(4)R(5);
R(4) and R(5) independently of one another are hydrogen or $(C_1-C_8)$-alkyl;
where the cyclic system of the formula

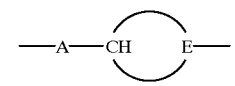

is a 3–8-membered saturated aliphatic or heterocyclic ring system having a nitrogen atom,
and where the aromatic groups mentioned are an aryl radical having up to 10 carbon atoms, a 5- or 6-membered heteroaryl radical having 1–4 nitrogen atoms, a 5- or 6-membered heteroaryl group containing 1 or 2 nitrogen atoms and a heteroatom which is oxygen or sulfur, or furyl, and where the aryl radicals mentioned can be unsubstituted or substituted by unsubstituted $(C_1-C_8)$-alkyl or substituted $(C_1-C_8)$-alkyl, halogen, —NO$_2$, $(C_2-C_6)$-alkoxycarbonyl, COOH, —OR(3), NR(6)R(7), —CONR(4)R(5), —SO₂NR(6)R(7) or S(O)$_n$R(40), where R(1) and the guanidinocarbonyl radical can be in any desired position of the 5- or 6-membered ring of the indole system, and the appropriate pharmaceutically tolerable salts. (WO 95 04052)

IV. Additionally suitable are heterocyclic guanidine derivatives of the formula

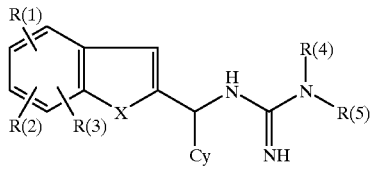

in which:

X is —O—, —S—, —NH—, —N[(C₁–C₄)-alkyl]- or —N(phenyl)-;

R(1), R(2) and R(3) are hydrogen, halogen, (C₁–C₄)-alkyl, (C₁–C₄)-alkyl—O—, phenyl, benzyl;

or two of the substituents R(1), R(2) and R(3) together with one side of the benzo system are a 4–6-membered carbocyclic ring;

R(4) and R(5) independently of one another are hydrogen, (C₁–C₁₂)-alkyl, benzhydryl, aralkyl, which is unsubstituted or substituted by one or more substituents from the groups halogen, (C₁–C₄)-alkyl, (C₁–C₄)-alkyl—O— or —CF₃, —(CH₂)$_m$—CH₂—T, m is zero to 3;

T is —CO—O—T(1);

T(1) is hydrogen or (C₁–C₄)-alkyl;

Cy is a benzo-fused saturated or dihydro-5-membered ring heterocycle

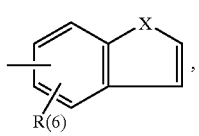, a pyrazole or imidazole ring of the formula

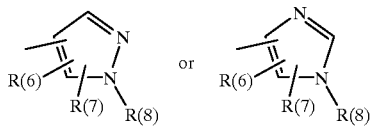

a naphthyl radical or a dihydro- or tetrahydronaphthyl radical

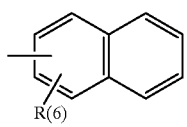

a 2-,3- or 4-pyridyl radical

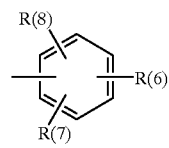

z is N— or CH;

a thienyl radical

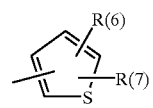

R(6) is hydrogen, halogen hydroxyl, (C₁–C₁₀)-alkyl, (C₁–C₁₀)-alkyl—O—, phenoxy, (C₁–C₁₀)-alkyloxymethyloxy- or —(O)$_n$S—R(9);

R(9) is (C₁–C₁₀)-alkyl, thienyl, pyridyl, thiazolyl, thiadiazolyl, imidazolyl, pyrazolyl or phenyl, each of which is unsubstituted or mono- or disubstituted by halogen, (C₁–C₄)-alkyl or (C₁–C₄)-alkyl—O—;

R(7) and R(8) are hydrogen, halogen, hydroxyl, (C₁–C₁₀)-alkyl, (C₁–C₁₀)-alkyl—O—, phenyl, phenoxy or (C₁–C₁₀)-alkoxymethyloxy;

or

Cy is phenyl, which is unsubstituted or is mono- or disubstituted by halogen, (C₁–C₄)-alkyl or (C₁–C₄)-alkyl—O—;

or

Cy is —Gr—Am;

Gr is —R(13)—R(12)—(CH₂)$_q$-C[W][W(1)]—(CH₂)$_{q'}$—; R(13)R(14)— or

—R(15)—;

R(12) is a single bond, —O—, —(O)$_n$S—, —CO— or —CONH—;

R(13) is a single bond, phenyl, thienyl, pyridyl, thiazolyl, thiadiazolyl, imidazolyl or pyrazolyl;

R(14) is a single bond or SO₂—;

R(15) is (C₂–C₁₀)-alkenyl or (C₂–C₁₀)-alkynyl;

W and W(1) independently of one another are hydrogen, (C₁–C₄)-alkyl;

or

W and W(1) cyclically connected to one another are a (C₃–C₈)-hydrocarbon ring;

q and q' are zero to 9;

Am is —NR(10)R(11); R(10) is hydrogen, (C₁–C₄)-alkyl or benzyl, R(1 1) is (C₁–C₄)-alkyl, phenyl or benzyl;

or

R(10) and R(11) together are a (C₃–C₁₀)-alkylene group, which is unsubstituted or substituted by —COOH, (C₁–C₅)-alkoxycarbonyl, (C₂–C₄)-hydroxylalkylene or benzyl;

or

Am is pyrrolyl, pyridyl, pyrazolyl, morpholinyl, dihydropyridyl, tetrahydropyridyl, quinuclidinyl, imidazolyl, 3-azabicyclo[3.2.1]octyl, which is unsubstituted or substituted by (C₁–C₄)-alkyl, or Am is azabicyclo[3.2.2]nonyl;

or

Am is a piperazine group of the formula

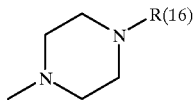

R(16) is hydrogen, $(C_1-C_4)$-alkyl, $(C_3-C_6)$-cycloalkyl, phenyl, tolyl, methoxyphenyl, halophenyl, diphenylmethylene, benzyl or pyridyl;

or

Am is an azido group —(O)t—(CH2)$_q$—C[W][W(1)]—(CH2)q'—N$_3$;

t is zero or 1;

where W and W(1) have the previously indicated meaning;

and the optical enantiomers and the pharmacologically tolerable salts.

V. Additionally suitable are the guanidine compounds such as are described in

EP-743 301 (DE 195 17 848), EP 758 644 (DE 195 29 612), EP 760 365 (DE 195 31 138)

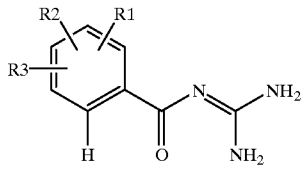

where R1=R2 is H, halo, alkyl, CN, NO$_2$, perfluoroalkyl, SO$_n$CF$_3$; R3 is CH=CH$_2$, CH$_2$—CH=CH$_2$, CH$_2$—CH$_2$—CH=CH$_2$, cycloalkenyl, cycloalkenylalkyl; R4 is alkyl, (substituted) phenyl, or as described in DE 195 48 708, WO 97 25 310, WO 97 27 183, DE 196 01 303, EP 787 728, JP 82 25 513, JP 090 59 245, JP 090 67 332, JP 690 67 340, WO 97 11 055 and EP 743 301.

Compounds which are particularly suitable for the use according to the invention are those selected from the group consisting of the compounds I. (HOE 89/F 288 - U.S. Pat. No. 5,292,755)

a) benzoylguanidines of the formula I

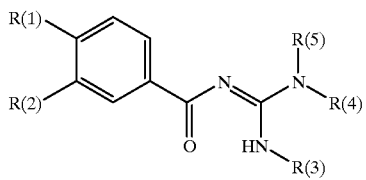

in which:

R(1) or R(2) is R(6)—S(O)$_n$— or R(7)R(8)N—O$_2$S—;

and the other substituent R(1) or R(2) in each case is H, F, Cl, Br, $(C_1-C_4)$-alkyl, $(C_1-C_4)$-alkoxy or phenoxy, which is unsubstituted or substituted by 1–3 substituents selected from the group consisting of fluorine, chlorine, methyl and methoxy;

or the other substituent R(1) or R(2) in each case is R(6)—S(O)$_n$ or R(7)R(8)N—;

n is zero, 1 or 2;

R(6) is $(C_1-C_6)$-alkyl, $(C_5-C_7)$-cycloalkyl, cyclopentylmethyl, cyclohexylmethyl or phenyl, which is unsubstituted or substituted by 1–3 substituents selected from the group consisting of fluorine, chlorine, methyl and methoxy;

R(7) and R(8) identically or differently are H or $(C_1-C_6)$-alkyl;

or

R(7) is phenyl—(CH$_2$)$_m$;

m is 1–4;

or

R(7) is phenyl, which is unsubstituted or substituted by 1–2 substituents selected from the group consisting of fluorine, chlorine, methyl and methoxy;

or

R(7) and R(8) together are a straight-chain or branched $(C_4-C_7)$-chain, where the chain can additionally be interrupted by O, S or NR(9);

R(9) is H or methyl;

or

R(7) and R(8) together with the nitrogen atom to which they are bonded, are a dihydroindole, tetrahydroquinoline or tetrahydroisoquinoline system;

R(3), R(4) and R(5) independently of one another are H or $(C_1-C_2)$-alkyl, or

R(3) and R(4) together are a $(C_2-C_4)$-alkylene chain;

or

R(4) and R(5) together are a $(C_4-C_7)$-alkylene chain; and their pharmaceutically tolerable salts; (HOE 92/F 34 - U.S. Pat. No. 5,373,924)

b) benzoylguanidines of the formula I

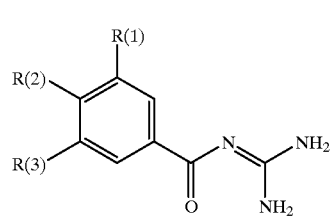

(I)

in which:

R(1) is R(4)—SO$_m$ or R(5)R(6)N—SO$_2$—;

m is zero, 1 or 2;

R(4) and R(5) are $C_1-C_8$-alkyl, $C_3-C_6$-alkenyl or —C$_n$H$_{2n}$—R(7);

n is zero, 1, 2, 3 or 4;

R(7) is $C_5-C_7$-cycloalkyl or phenyl, which is unsubstituted or substituted by 1–3 substituents selected from the group consisting of F, Cl, CF$_3$, methyl, methoxy and NR(8)R(9);

R(8) and R(9) are H or $C_1-C_4$-alkyl;

or

R(5) is H;

R(6) is H or $C_1-C_4$-alkyl, or

R(5) and R(6) together are 4 or 5 methylene groups, of which one CH$_2$ group can be replaced by an O, S, NH, N—CH$_3$ or N-benzyl;

R(2) is hydrogen, F, Cl, Br, $(C_1-C_4)$-alkyl-, O—(CH$_2$)$_m$C$_p$F$_{2p+1}$ or —X—R(10);

m is zero or 1;

p is 1, 2 or 3;

x is O, S or NR(11);

R(10) is H, $C_1-C_6$-alkyl, $C_5-C_7$-cycloalkyl, cyclohexylmethyl, cyclopentylmethyl or —C$_n$H$_{2n}$—R(12);

n is zero, 1, 2, 3 or 4;

R(12) is phenyl, which is unsubstituted or substituted by 1–3 substituents selected from the group consisting of F, Cl, CF₃, methyl, methoxy and NR(8)R(9);

R(8) and R(9) are H or C₁–C₄-alkyl;

R(1 1) is hydrogen or C₁–C₃-alkyl;

or

R(10) and R(11) together are 4 or 5 methylene groups, of which one CH₂ group can be replaced by O, S, NH, N—CH₃ or N-benzyl;

R(3) is defined as R(1), or is C₁–C₆-alkyl, nitro, cyano, trifluoromethyl, F, Cl, Br, I or —X—R(10);

x is O, S or NR(11);

R(10) is H, C₁–C₆-alkyl, C₅–C₇-cycloalkyl, cyclohexylmethyl, cyclopentylmethyl or —CₙH₂ₙ—R(12);

n is zero to 4;

R(12) is phenyl, which is unsubstituted or substituted by 1–3 substituents selected from the group consisting of F, Cl, CF₃, methyl, methoxy und NR(8)R(9);

R(8) and R(9) are H or C₁–C₄-alkyl;

R(11) is C₁–C₃-alkyl, or

R(10) and R(11) together are 4 or 5 methylene groups, of which one CH₂ group can be replaced by O, S, NH, N-CH₃ or N-benzyl;

and their pharmaceutically tolerable salts; (HOE 92/F 303 K - EP-A 589 336, NZ 248 703)

f) benzotylguanidines of the formula I

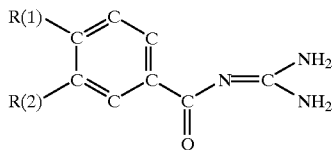

in which:

R(1) or R(2) is R(3)—S(O)ₙ— or R(4)R(5)N—SO₂— the other substituent R(1) or R(2) in each case is H, OH, F, Cl, Br, I, C₁–C₄-alkyl, C₁–C₄-alkoxy, benzyloxy or phenoxy, which is unsubstituted or carries one to three substituents selected from the group consisting of fluorine, chlorine, methyl, methoxy, hydroxyl or benzyloxy, R(3)-S(O)ₙ, —NR(4)R(5) or 3,4-dehydropiperidine R(3) is C₁–C₆-alkyl, C₅–C₇-cycloalkyl, cyclopentylmethyl, cyclohexylmethyl or phenyl, which is unsubstituted or carries one to three substituents selected from the group consisting of fluorine, chlorine, methyl and methoxy;

R(4) and R(5) identically or differently, are H or C₁–C₆-alkyl;

for

R(4) is phenyl-(CH₂)ₘ—;

m is 1, 2, 3 or 4;

or

R(4) is phenyl, which is unsubstituted or carries one to two substituents selected from the group consisting of fluorine, chlorine, methyl and methoxy;

or

R(4) and R(5) together are a straight-chain or branched C₄–C₇-chain, where the chain can additionally be interrupted by O, S or NR(6), R(6) is H or methyl;

or

R(4) and R(5) together with the nitrogen atom to which they are bonded, are a dihydroindole, tetrahydroquinoline or tetrahydroisoquinoline system;

n is zero, 1 or 2;

and their pharmaceutically tolerable salts; (HOE 92/F 411 - NZ 250 450, EP 603 650)

k) benzoylguanidines of the formula I

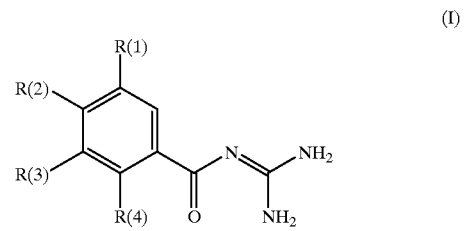

in which:

one of the substituents R(1), R(2), R(3) or R(4):

is an amino group

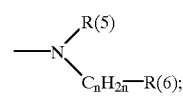

R(5) is hydrogen or C₍₁₋₆₎-alkyl;

n is zero, 1, 2, 3 or 4;

R(6) is H or C₍₁₋₄₎-alkyl;

in which one CH₂ group can be replaced by 1 sulfur atom or a group NR(7);

R(7) is hydrogen, methyl or ethyl;

or

R(6) is C₍₃₋₈₎-cycloalkyl or phenyl, which is unsubstituted or carries 1, 2 or 3 substituents selected from the group consisting of F, Cl, Br, methyl, methoxy, —NR(8)R(9);

R(8) and R(9) are H, methyl or ethyl;

or

R(5) and R(6) together with the nitrogen atom are a 5-, 6- or 7-membered ring, in which 1 carbon atom can be replaced by oxygen, S or NR(10);

R(10) is H, C₍₁₋₃₎-alkyl or benzyl;

and the other substituents R(1), R(2), R(3), R(4) in each case are: hydrogen, F, Cl, Br, I, CN, CF₃, NO₂, CF₃—O—, CₘF₂ₘ₊₁—CH₂—O— or R(11)—C_qH_{2q}—X_p—;

m is 1, 2 or 3;

q is zero, 1, 2, 3 or 4;

p is zero or 1;

X is oxygen or NR(12); R(12) is H or C(1–3)-alkyl;

R(11) is hydrogen, C₍₁₋₆₎-alkyl, C₍₃₋₈₎-cycloalkyl or phenyl, which is unsubstituted or substituted by 1, 2 or 3 substituents selected from the group consisting of F, Cl, CH₃, CH₃—O— and NR(13)R(14);

R(13), R(14) are H, methyl or ethyl;

and their pharmaceutically tolerable salts; (93/F 054 - NZ 250 919, EP-A 612 723)

m) benzoylguanidines of the formula I

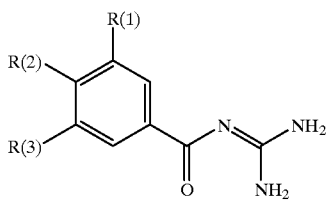

(I)

in which:
R(1), R(2), R(3) are hydrogen, F, Cl, Br, I or $(C_1-C_{12})$-alkyl;
one of the substituents R(1), R(2) or R(3) is $N_3$, CN, OH or $(C_1-C_{10})$-alkyloxy, if at least one of the remaining substituents R(1), R(2) or R(3) is a sufficiently lipophilic alkyl radical having 3 to 12 carbon atoms;
or
one of the substituents R(1), R(2) or R(3)
is R(4)-$C_nH_{2n}$—$O_m$—;
m is zero or 1;
n is zero, 1, 2 or 3;
R(4) is $C_pF_{2p+1}$;
p is 1, 2 or 3, if n is zero or 1;
or
R(4) is $(C_3-C_{12})$-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);
R(5) and R(6) are hydrogen or $(C_1-C_4)$-alkyl;
or one of the substituents R(1), R(2) or R(3) is —C≡CR(5) or —C[R(6)]=CR(5);
R(5) is phenyl, which is unsubstituted or substituted by 1–3 substituents selected from the group consisting of F, Cl, $CF_3$, methyl, methoxy, hydroxyl, amino, methylamino and dimethylamino,
$(C_1-C_9)$-heteroaryl, which is unsubstituted or substituted as phenyl,
or
R(5) is $(C_1-C_6)$-alkyl, which is unsubstituted or substituted by 1–3 OH;
or
R(5) is $(C_3-C_8)$-cycloalkyl,
R(6) is hydrogen or methyl; and their pharmacologically acceptable salts; (93/F 153 - EP-A 627 413, NZ 260 660)

o) benzoylguanidines of the formula I

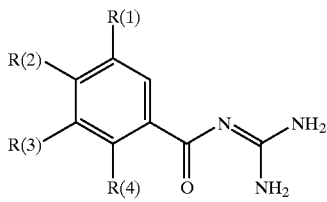

(I)

in which:
R(1) is hydrogen, F, Cl, Br, I, —$NO_2$, —C≡N, $X_o$—$(CH_2)_p$—$(CF_2)_q$—$CF_3$, R(5)—$SO_m$, R(6)—CO— or R(6)R(7)N—$SO_2$—, where
X is oxygen, S or NR(14);
m is zero, 1 or 2;
o is zero or 1;

p is zero, 1 or 2;
q is zero, 1, 2, 3, 4, 5 or 6;
R(5) and R(6) are $(C_1-C_8)$-alkyl, $(C_3-C_6)$-alkenyl, -$C_nH_{2n}$-R(8) or $CF_3$;
n is zero, 1, 2, 3 or 4;
R(8) is $(C_3-C_7)$-cycloalkyl or phenyl, which is not substituted or is substituted by 1–3 substituents selected from the group consisting of F, Cl, $CF_3$, methyl, methoxy and NR(9)R(10);
R(9) and R(10) are H or $C_1-C_4$-alkyl;
or
R(6) is H;
R(7) is H or $(C_1-C_4)$-alkyl;
or
R(6) and R(7) together are 4 or 5 methylene groups, of which one $CH_2$ group can be replaced by oxygen, S, NH, N—$CH_3$ or N-benzyl;

R(2) is

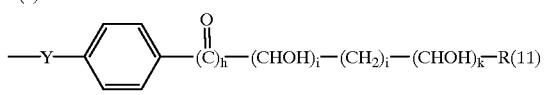

or

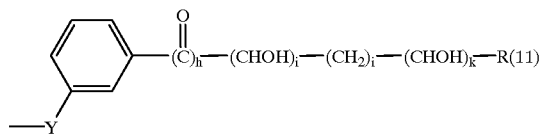

or

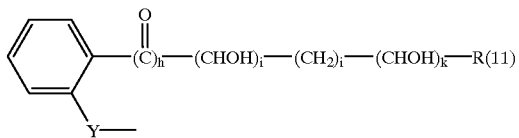

Y is oxygen, —S— or —NR(12)—;
R(11) and R(12) are hydrogen or $(C_1-C_3)$-alkyl;
h is zero or 1;
i, j and k independently are zero, 1, 2, 3 or 4;
but where h, i and k are not simultaneously zero,
R(3) is defined as R(1), or is $(C_1-C_6)$-alkyl or —X—R(13);
x is oxygen, S or NR(14);
R(14) is H or $(C_1-C_3)$-alkyl;
R(13) is H, $(C_1-C_6)$-alkyl, $(C_3-C_8)$-cycloalkyl or —$C_bH_{2b}$—R(15);
b is zero, 1, 2, 3 or 4;
or
R(13) and R(14) together are 4 or 5 methylene groups, where one $CH_2$ group can be replaced by oxygen, S, NH, N—$CH_3$ or N-benzyl;
R(15) is phenyl, which is unsubstituted or substituted by 1–3 substituents selected from the group consisting of F, Cl, $CF_3$, methyl, methoxy and NR(9)R(10);
R(9) and R(10) are H or $(C_1-C_4)$-alkyl;
R(4) is hydrogen, —OR(16) or —NR(16)R(17);
R(16) and R(17) independently are hydrogen or $(C_1-C_3)$-alkyl; and their pharmaceutically tolerable salts;
(HOE 93/F 223 K - EP 639 5 3, NZ 264 130)

r) benzo-fused 5-membered ring heterocycles of the formula I z) benzoylguanidines of the formula I

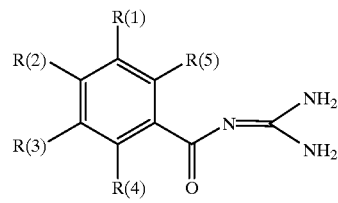

(I)

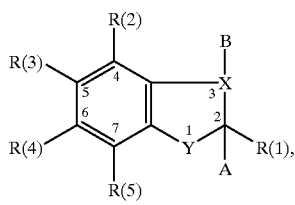

in which:
x is N or CR(6);
Y is oxygen, S or NR(7);
A, B together are a bond
or

A, B are both hydrogen, if X is CR(6) and Y is NR(7) simultaneously; one of the substituents R(1) to R(6) is a —CO—N═C(NH$_2$)$_2$ group; the other substituents R(1) to R(6) in each case are hydrogen, F, Cl, Br, I or (C$_1$–C$_6$)-alkyl;

up to two of the other substituents R(1) to R(6) are CN, NO$_2$, N$_3$, (C$_1$–C$_4$)-alkyloxy or CF$_3$;

up to one of the other substituents is R(8)—C$_n$H$_{2n}$—Z—;
n is zero to 10;

where the alkylene chain —C$_n$H$_{2n}$— is straight-chain or branched and where one carbon atom can be replaced by an oxygen or sulfur atom or by a nitrogen atom;

R(8) is hydrogen, (C$_2$–C$_6$)-alkenyl or (C$_3$–C$_{10}$)-cycloalkyl, which is unsubstituted or substituted by 1 to 4 methyl groups or an OH group, or can contain an ethylene group —CH═CH—, and in which one methylene group can be replaced by an oxygen or sulfur atom or by a nitrogen atom;

or
R(8) is phenyl,
which is unsubstituted or substituted by 1 to 3 substituents selected from the group consisting of F, Cl, Br, I, CF$_3$, CH$_3$—S(O)$_s$— or R(9)—W$_y$—;
s is zero, 1 or 2;
R(9) is H, methyl, ethyl,
W is oxygen or NR(10); R(10) is H or methyl;
y is zero or 1;
or
R(8) is C$_m$F$_{2m+1}$;
m is 1 to 3;
or
R(8) is 1- or 2-naphthyl, pyridyl, quinolyl or isoquinolyl;
Z is —CO—, —CH$_2$— or —[CR(11)(OH)]$_q$—;
q is 1, 2 or 3;
R(11) is H or methyl;
or
z is oxygen or —NR(12)—;
R(12) is H or methyl;
or
Z is —S(O)$_s$—;
s is zero, 1 or 2;
or
Z is —SO$_2$—NR(13)—;
R(13) is H or (C$_1$–C$_4$)-alkyl;
R(7) is hydrogen, (C$_1$–C$_{10}$)-alkyl, (C$_2$–C$_{10}$)-alkenyl or R(8)-C$_n$H$_{2n}$—; and their pharmaceutically tolerable salts;
(HOE 94/F 134 - EP-A 686 627, NZ 272 103)

in which:
R(1) is R(6)—SO$_m$;
m is zero, 1 or 2;
R(6) is perfluoroalkyl having 1, 2, 3, 4, 5 or 6 carbon atoms, which is straight-chain or branched;
R(2) and R(3) independently of one another are hydrogen, F, Cl, Br, I, alkyl having 1, 2, 3 or 4 carbon atoms, alkoxy having 1, 2, 3 or 4 carbon atoms or phenoxy, which is unsubstituted or substituted by 1–3 substituents selected from the group consisting of F, Cl, methyl and methoxy;

or

R(2) and R(3) independently of one another are pyrrol-1-yl, pyrrol-2-yl- or pyrrol-3-yl, which is not substituted or is substituted by 1 to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, CF$_3$, methyl and methoxy;

R(4) and R(5) independently of one another are hydrogen, alkyl having 1, 2 or 3 carbon atoms, F, Cl, Br, I, CN, OR(7), NR(8)R(9) or —(CH$_2$)$_n$—(CF$_2$)$_o$—CF$_3$;

R(7), R(8) and R(9) independently of one another are hydrogen or alkyl having 1, 2, 3 or 4 carbon atoms;

n is zero or 1;
o is zero, 1 or 2;

and their pharmacologically acceptable salts; (HOE 95/F 007 K - EP-A 723 956, NZ 280 887)

ag) benzoylguanidines of the formula I

I in which:
one of the three substituents R(1), R(2) and R(3) is R(6)—A—B—D—;

R(6) is a basic protonatable radical, i.e. an amino group —NR(7)R(8), an amidino group R(7)R(8)N—C[═N—R(9)]— or a guanidino group

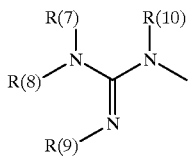

R(7), R(8), R(9) and R(10) independently of one another are hydrogen or alkyl having 1, 2, 3 or 4 carbon atoms;
or
R(7) and R(8) together are $C_aH_{2a}$;
a is 4, 5, 6 or 7;
where if a=5, 6 or 7 a methylene group of the group $C_aH_{2a}$ can be replaced by a heteroatom group O, $SO_m$ or NR(11),
or
R(8) and R(9) or R(9) and R(10) or R(7) and R(10) are a group $C_aH_{2a}$;
a is 2, 3, 4 or 5;
where if a=3, 4 or 5 a methylene group of the group $C_aH_{2a}$ can be replaced by a heteroatom group O, $SO_m$ or NR(11);
m is zero, 1 or 2;
R(1 1) is hydrogen or methyl;
or
R(6) is a basic heteroaromatic ring system having 1–9 carbon atoms;
A is $C_bH_{2b}$;
b is 1, 2, 3, 4, 5, 6, 7, 8, 9 or 10; where in the group $C_bH_{2b}$ one or two methylene groups can be replaced by one of the groupings selected from the group consisting of —O—, —CO—, —CH[OR(20)]—, —$SO_m$—, —NR(20)—, —NR(20)—CO—, —NR(20)—CO—NH—, —NR(20)—CO—NH—$SO_2$—

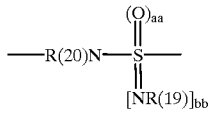

and —$SO_{aa}$[NR(19)]$_{bb}$—;
and where in the group $C_bH_{2b}$ a methylene group can be replaced by —CH—R(99), where R(99) together with R(7) forms a pyrrolidine or piperidine ring;
aa is 1 or 2;
bb is 0 or 1;
aa+bb=2;
R(1 9) is hydrogen or alkyl having 1, 2, 3 or 4 carbon atoms;
R(20) is hydrogen or methyl;
B is a phenylene or naphthylene radical

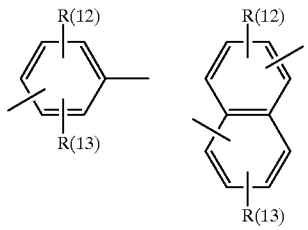

R(12) and R(13) independently of one another are hydrogen, methyl, F, Cl, Br, I, $CF_3$ or —$SO_w$—R(14);
R(14) is methyl or NR(15)R(16);
R(15) and R(16) independently of one another are hydrogen or alkyl having 1, 2, 3 or 4 carbon atoms;

w is zero, 1 or 2;
D is —$C_dH2d$—$X_f$—;
d is zero, 1, 2, 3 or 4;
x is —O—, —CO—, —CH[OR(21)]—, —$SO_m$— or —NR(21)—;
f is zero or 1;
R(21) is hydrogen or methyl;
m is zero, 1 or 2;
and the other substituents R(1) and R(2) and R(3) in each case independently of one another are hydrogen, F, Cl, Br, I, —CN, —($C_1$–$C_8$)-alkyl, —($C_2$–$C_8$)-alkenyl, —NR(35)R(36) or R(17)—$C_gH_{2g}$—$Z_h$—;
g is zero, 1, 2, 3 or 4;
h is zero or 1;
R(35) and R(36) independently of one another are hydrogen or alkyl having 1, 2, 3, 4, 5 or 6 carbon atoms;
or
R(35) and R(36) together are 4–7 methylene groups, of which one $CH_2$ group can be replaced by oxygen, —S—, —NH—, —$NCH_3$ or —N-benzyl;
Z is —O—, —CO—, —$SO_v$—, —NR(18)—, —NR(18)—CO—, —NR(18)—CO—NH— or —NR(18)—$SO_2$—;
R(18) is hydrogen or methyl;
v is zero, 1 or 2;
R(17) is hydrogen, cycloalkyl having 3, 5 or 6 carbon atoms or $C_kF_{2k+1}$—;
k is 1, 2 or 3,
or
R(17) is pyrrol-1-yl, pyrrol-2-yl or pyrrol-3-yl, which is not substituted or is substituted by 1–4 substituents selected from the group consisting of F, Cl, Br, I, —CN, ($C_2$–$C_8$)-alkanoyl, ($C_2$–$C_8$)-alkoxycarbonyl, formyl, carboxyl, —$CF_3$, methyl and methoxy;
or
R(17) -is ($C_3$–$C_8$)-cycloalkyl or phenyl, which is not substituted or is substituted by 1–3 substituents selected from the group consisting of F and Cl, —$CF_3$, methyl, hydroxyl, methoxy, —NR(37)R(38), $CH_3SO_2$— and $H_2NO_2S$—;
R(37) and R(38) are hydrogen or —$CH_3$;
R(4) and R(5) independently of one another are hydrogen, alkyl having 1, 2, 3 or 4 carbon atoms, F, Cl, —OR(32), —NR(33)R(34) or —$C_rF_{2r+1}$;
R(32), R(33) and R(34) independently of one another are hydrogen or alkyl having 1, 2 or 3 carbon atoms;
r is 1, 2, 3 or 4;
and their pharmacologically tolerable salts; (HOE 95/F 173 - NZ 299 052)
am) substituted cinnamic acid guanidides of the formula I

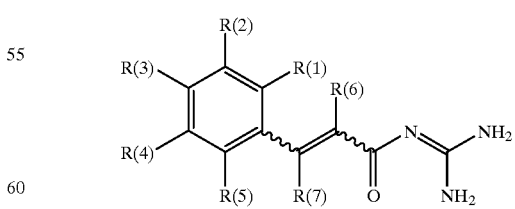

I in which:
at least one of the substituents R(1), R(2), R(3), R(4) and R(5) is
—$X_a$—$Y_b$—$L_n$—U;
x is CR(16)R(17), O, S or NR(18);

R(16), R(17) and R(18) independently of one another are H, alkyl having 1, 2, 3 or 4 carbon atoms or perfluoroalkyl having 1, 2, 3 or 4 carbon atoms;
a is zero or 1;
Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;
T is NR(20), O, S or phenylene, where the phenylene is not substituted or is substituted by 1–3 substituents selected from the group consisting of F, Cl, $CF_3$, methyl, methoxy and NR(21)R(22);
R(20), R(21) and R(22) independently of one another are H, alkyl having 1, 2, 3 or 4 carbon atoms or perfluoroalkyl having 1, 2, 3 or 4 carbon atoms;
b is zero or 1;
L is O, S, NR(23) or $C_kH_{2k}$;
k is 1, 2, 3, 4, 5, 6, 7 or 8;
n is zero or 1;
U is NR(24)R(25) or an N-containing heterocycle having 1, 2, 3, 4, 5, 6, 7, 8 or 9 carbon atoms;
R(24) and R(25) independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms;
or
R(24) and R(25) together are 4 or 5 methylene groups, of which one $CH_2$ group can be replaced by oxygen, S, NH, N—$CH_3$ or N-benzyl;
where the N-containing heterocycles are N- or C-bridged and are not substituted or are substituted by 1–3 substituents selected from the group consisting of F, Cl, $CF_3$, methyl, methoxy and NR(27)R(28);
R(23), R(27) and R(28) independently of one another are H, alkyl having 1, 2, 3 or 4 carbon atoms or perfluoroalkyl having 1, 2, 3 or 4 carbon atoms;
and the other substituents R(1), R(2), R(3), R(4) and R(5) in each case independently of one another are H, F, Cl, Br, I, CN, —$O_n$—$C_mH_{2m+1}$, —$O_p$—$(CH_2)_s$—$C_qF_{2q+1}$ or —$C_rH_{2r}R(10)$;
n is zero or 1;
m is zero, 1, 2, 3, 4, 5, 6, 7 or 8;
p is zero or 1;
q is 1, 2, 3, 4, 5, 6, 7 or 8;
s is zero, 1, 2, 3 or 4;
r is zero, 1, 2, 3 or 4;
R(10)
is cycloalkyl having 3, 4, 5, 6, 7 or 8 carbon atoms, or phenyl, where the phenyl is not substituted or is substituted by 1–3 substituents selected from the group consisting of F, Cl, $CF_3$, methyl, methoxy and NR(11)R(12);
R(11) and R(12) independently of one another are H, alkyl having 1, 2, 3 or 4 carbon atoms or perfluoroalkyl having 1, 2, 3 or 4 carbon atoms;
R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
which is not substituted or is substituted by 1–3 substituents selected from the group consisting of F, Cl, $CF_3$, methyl, methoxy and NR(14)R(15);
R(14) and R(15) independently of one another are H, alkyl having 1, 2, 3 or 4 carbon atoms or perfluoroalkyl having 1, 2, 3 or 4 carbon atoms;
and their pharmaceutically tolerable salts; (HOE 96/F 226 - EP 825 178)

bd) phenyl-substituted alkenylcarboxylic acid guanidides of the formula I

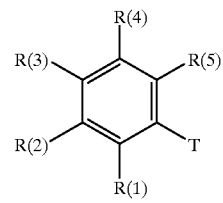

in which:
T is

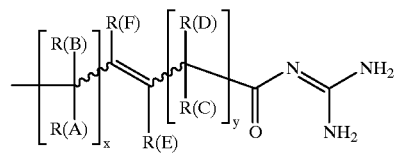

R(A) is hydrogen, F, Cl, Br, I, CN, OH, OR(6), ($C_1$–$C_4$)-alkyl, $O_r(CH_2)_aC_bF_{2b+1}$, ($C_3$–$C_8$)-cycloalkyl oder NR(7)R(8)
r is zero or 1;
a is zero, 1, 2, 3 or 4;
b is 1, 2, 3 or 4;
R(6) is ($C_1$–$C_4$)-alkyl, ($C_1$–$C_4$)-perfluoroalkyl, ($C_3$–$C_6$)-alkenyl, ($C_3$–$C_8$)-cycloalkyl, phenyl or benzyl,
the phenyl nucleus not being substituted or being substituted by 1–3 substituents selected from the group consisting of F, Cl, $CF_3$, methyl, methoxy and NR(9)R(10);
R(9) and R(10) are H, ($C_1$–$C_4$)-alkyl or ($C_1$–$C_4$)-perfluoro-alkyl;
R(7) and R(8) independently of one another are defined as R(6);
or
R(7) and R(8) together are 4 or 5 methylene groups, of which one $CH_2$ group can be replaced by oxygen, sulfur, NH, N—$CH_3$ or N-benzyl;
R(B), R(C) and R(D) independently are defined as R(A);
x is zero, 1 or 2;
y is zero, 1 or 2;
R(F) is hydrogen, F, Cl, Br, I, CN, OR(12), ($C_1$–$C_8$)-alkyl, $O_p(CH_2)_fC_gF_{2g+1}$, ($C_3$–$C_8$)-cycloalkyl or ($C_1$–$C_9$)-heteroaryl;
p is zero or 1;
f is zero, 1, 2, 3 or 4;
g is 1, 2, 3, 4, 5, 6, 7 or 8;
R(1 2) is ($C_1$–$C_8$)-alkyl, ($C_1$–$C_4$)-perfluoroalkyl, ($C_3$–$C_8$)-alkenyl, ($C_3$–$C_8$)-cycloalkyl, phenyl or benzyl,
the phenyl nucleus not being substituted or being substituted by 1–3 substituents selected from the group consisting of F, Cl, $CF_3$, methyl, methoxy and NR(13)R(14);
R(13) and R(14) are H, ($C_1$–$C_4$)-alkyl or ($C_1$–$C_4$)-perfluoroalkyl;
R(E) is defined independently as R(F);
R(1) is defined independently as T;
or
R(1) is hydrogen, —$O_kC_mH_{2m+1}$, —$O_n(CH_2)_pC_qF_{2q+1}$, F, Cl, Br, I, CN, —(C=O)— N=C(N $H_2)_2$, —$So_rR(17)$, —$SO_{r2}N$ R(31) R(32), —$O_u(CH_2)_vC_6H_5$, —$O_{u2}$—($C_1$–$C_9$)-heteroaryl or —$S_{u2}$—($C_1$–$C_9$)-heteroaryl;

k is zero or 1;
m is zero, 1, 2, 3, 4, 5, 6, 7 or 8;
n is zero or 1;
p is zero, 1, 2, 3 or 4;
q is 1, 2, 3, 4, 5, 6, 7 or 8;
r is zero, 1 or 2;
r2 is zero, 1 or 2;
R(31) and R(32) independently of one another are hydrogen, $(C_1-C_8)$-alkyl or $(C_1-C_8)$-perfluoroalkyl;
or
R(31) and R(32) are, together, 4 or 5 methylene groups of which one $CH_2$ group can be replaced by oxygen, S, NH, N—$CH_3$ or N-benzyl;
R(17) is $(C_1-C_8)$-alkyl;
u is zero or 1;
u2 is zero or 1;
v is zero, 1, 2, 3 or 4;
where the phenyl nucleus is not substituted or is substituted by 1–3 substituents selected from the group consisting of F, Cl, $CF_3$, methyl, methoxy, —$(CH_2)_w$NR(21)R(22), NR(18)R(19) and $(C_1-C_9)$-heteroaryl;
R(18), R(19), R(21) and R(22) independently of one another are $(C_1-C_4)$-alkyl or $(C_1-C_4)$-perfluoroalkyl;
w is 1, 2, 3 or 4;
where the heterocycle of the $(C_1-C_9)$-heteroaryl is unsubstituted or substituted by 1–3 substituents selected from the group consisting of F, Cl, $CF_3$, methyl or methoxy;
R(2), R(3), R(4) and R(5) independently of one another are defined as R(1),
or
R(1) and R(2) or R(2) and R(3) in each case together are —CH—CH=CH—CH—, which is not substituted or is substituted by 1–3 substituents selected from the group consisting of F, Cl, $CF_3$, methyl, methoxy, —$(CH_2)_{w2}$NR(24)R(25) and NR(26)R(27);
R(24), R(25), R(26) and R(27) are H, $(C_1-C_4)$-alkyl or $(C_1-C_4)$-perfluoroalkyl;
w 2 is 1, 2, 3 or 4;
the radical T being present in the molecule at least twice, but only three times at most;
and their pharmaceutically tolerable salts.
Very particularly suitable compounds are those which are selected from the group consisting of
3-dimethylamino-5-trifluoromethylbenzoylguanidine,
3-phenyl-5-trifluoromethylbenzoylguanidine,
3-isopropyl-4-fluoro-5-trifluoromethylbenzoylguanidine,
3-chloro-5-(1-pyrrolyl)benzoylguanidine,
3-chloro-5-trifluoromethylbenzoylguanidine,
3-dimethylamino-5-(1-pyrrolyl)benzoylguanidine,
3-dimethylamino4-tert-butylbenzoylguanidine,
4-(3-chloroanilino)-3-methylsulfonylbenzoylguanidine,
4-(4-aminoethylphenoxy)-3-methylsulfonylbenzoylguanidine,
4-(4-aminoethylsulfonylmethylphenoxy)-3-trifluoromethylbenzoylguanidine,
4-(4-aminoethylthiophenoxy)-3-trifluoromethylbenzoylguanidine,
3,5-di-tert-butylbenzoylguanidine,
3,5-di-tert-butyl4-hydroxybenzoylguanidine,
5-chloro-2-indoloylguanidine,
3,5-dichloro-2-indoloylguanidine,
5-chloro-3-phenylthio-2-indoloylguanidine,
5-chloro-3-phenylsulfonyl-2-indoloylguanidine,
5-methoxy-3-isopropyl-2-indoloylguanidine,
4-benzyloxy-2-indoloylguanidine,
5-chloro-1-(4-picolyl)-2-indoloylguanidine,
2-(4-hydroxyphenyl)4-benzimidazolylguanidine,
n-{3-[3-(3-guanidino-2-methyl-3-oxopropenyl)phenyl]-2-methylacryloyl}guandine,
and their pharmacologically tolerable salts.

What is claimed is:
1. A method for the treatment or prophylaxis of a disease which is caused by protozoa, comprising administering to a patient in need thereof a medicament comprising a pharmaceutically effective amount of a $Na^+/H^+$ exchange inhibitor selected from the group consisting of

I. a) benzoylguanidine of the formula

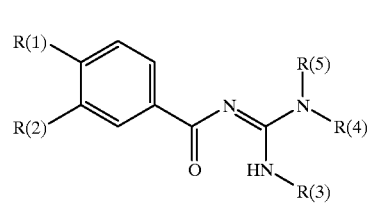

I in which:

R(1) or R(2) is R(6)—S(O)$_n$— or R(7)R(8)N—$O_2$S—;

and the other substituent R(1) or R(2) in each case is H, F, Cl, Br, $(C_1-C_4)$-alkyl, $(C_1-C_4)$-alkoxy or phenoxy, which is unsubstituted or substituted by 1–3 substituents selected from the group consisting of fluorine, chlorine, methyl and methoxy;

or the other substituent R(1) or R(2) in each case is R(6)—S(O)$_n$ or R(7)R(8)N—;

n is zero, 1 or 2;

R(6) is $(C_1-C_6)$-alkyl, $(C_5-C_7)$-cycloalkyl, cyclopentylmethyl, cyclohexylmethyl or phenyl, which is unsubstituted or substituted by 1–3 substituents selected from the group consisting of fluorine, chlorine, methyl and methoxy;

R(7) and R(8) identically or differently are H or $(C_1-C_6)$-alkyl;

or

R(7) is phenyl-$(CH_2)_m$;

m is 1–4;

or

R(7) is phenyl, which is unsubstituted or substituted by 1–2 substituents selected from the group consisting of fluorine, chlorine, methyl and methoxy;

or

R(7) and R(8) together are a straight-chain or branched $(C_4-C_7)$-chain, where the chain can additionally be interrupted by O, S or NR(9); R(9) is H or methyl;

or

R(7) and R(8) together with the nitrogen atom to which they are bonded, are a dihydroindole, tetrahydroquinoline or tetrahydroisoquinoline system;

R(3), R(4) and R(5) independently of one another are H or $(C_1-C_2)$-alkyl, or

R(3) and R(4) together are a $(C_2-C_4)$-alkylene chain;

or

R(4) and R(5) together are a $(C_4-C_7)$-alkylene chain;

or a pharmaceutically tolerable salt thereof;

b) a benzoylguanidine of the formula

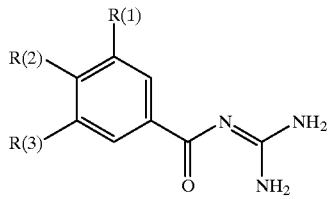

(I)

in which:
R(1) is R(4)—SO$_m$ or R(5)R(6)N—SO$_2$—;
m is zero, 1 or 2;
R(4) and R(5) are C$_1$-C$_8$-alkyl, C$_3$-C$_6$-alkenyl or —C$_n$H$_{2n}$—R(7);
n is zero, 1, 2, 3 or 4;
R(7) is C$_5$-C$_7$-cycloalkyl or phenyl, which is unsubstituted or substituted by 1–3 substituents selected from the group consisting of F, Cl, CF$_3$, methyl, methoxy and NR(8)R(9); R(8) and R(9) are H or C$_1$-C$_4$-alkyl;
or
R(5) is H;
R(6) is H or C$_1$-C$_4$-alkyl,
or
R(5) and R(6) together are 4 or 5 methylene groups, of which one CH$_2$ group can be replaced by an O, S, NH, N-CH$_3$ or N-benzyl;
R(2) is hydrogen, F, Cl, Br, (C$_1$-C$_4$)-alkyl-, O—(CH$_2$)$_m$C$_p$F$_{2p+1}$ or —X—R(10);
m is zero or 1;
p is 1, 2 or 3;
X is O, S or NR(11);
R(10) is H, C$_1$-C$_6$-alkyl, C$_5$-C$_7$-cycloalkyl, cyclohexylmethyl, cyclopentylmethyl or —C$_n$H$_{2n}$—R(12);
n is zero, 1, 2, 3 or 4;
R(12) is phenyl, which is unsubstituted or substituted by 1–3 substituents selected from the group consisting of F, Cl, CF$_3$, methyl, methoxy and NR(8)R(9); R(8) and R(9) are H or C$_1$-C$_4$-alkyl;
R(11) is hydrogen or C$_1$-C$_3$-alkyl;
or
R(10) and R(11) together are 4 or 5 methylene groups, of which one CH$_2$ group can be replaced by O, S, NH, N—CH$_3$ or N-benzyl;
R(3) is defined as R(1), or is C$_1$-C$_6$-alkyl, nitro, cyano, trifluoromethyl, F, Cl, Br, I or —X—R(10);
x is O, S or NR(11);
R(10) is H, C$_1$-C$_6$-alkyl, C$_5$-C$_7$-cycloalkyl, cyclohexylmethyl, cyclopentylmethyl or —C$_n$H$_{2n}$—R(12);
n is zero to 4;
R(12) is phenyl, which is unsubstituted or substituted by 1–3 substituents selected from the group consisting of F, Cl, CF$_3$, methyl, methoxy und NR(8)R(9); R(8) and R(9) are H or C$_1$-C$_4$-alkyl;
R(11) is C$_1$-C$_3$-alkyl,
or
R(10) and R(11) together are 4 or 5 methylene groups, of which one CH$_2$ group can be replaced by O, S, NH, N—CH$_3$ or N-benzyl;

or a pharmaceutically tolerable salt thereof;
c) an ortho-substituted benzoylguanidine of the formula

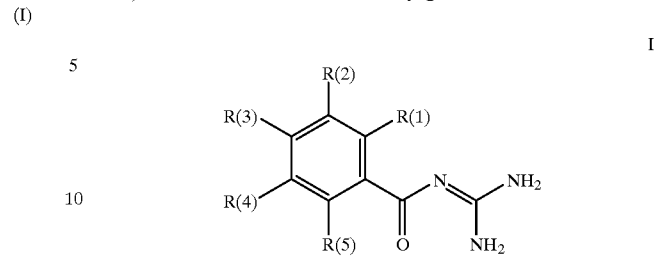

I in which:
R(1) is F, Cl, Br, I, C$_1$-C$_6$-alkyl or —X—R(6);
X is O, S, NR(7) or Y—ZO;
Y is or NR(7);
Z is C or SO;
R(6) is H, C$_1$-C$_6$-alkyl, C$_5$-C$_7$-cycloalkyl, cyclohexylmethyl, cyclopentylmethyl, —(CH$_2$)$_m$C$_p$F$_{2p+1}$ or —C$_n$H$_{2n}$—R(8);
m is zero or 1;
p is 1–3;
n is zero to 4;
R(8) is phenyl, which is unsubstituted or substituted by 1–3 substituents selected from the group consisting of the groups F, Cl, CF$_3$, methyl, methoxy and NR(9)R(10);
R(9) and R(10) are H or C$_1$-C$_4$-alkyl;
R(7) is H or C$_1$-C$_3$-alkyl;
or
R(6) and R(7) together are 4 or 5 methylene groups, of which one CH$_2$ group can be replaced by O, S, NH, N-CH$_3$ or N-benzyl;
R(3) is H or —X—R(6);
x is O, S, NR(7) or Y—ZO;
R(7) is H or C$_1$-C$_3$-alkyl;
Y is O or NR(7); where Y is bonded to the phenyl radical of the formula I,
Z is C or SO;
R(6) is H, C$_1$-C$_6$-alkyl, C$_5$-C$_7$-cycloalkyl, cyclohexylmethyl, cyclopentylmethyl, —(CH$_2$)$_m$C$_p$F$_{2p+1}$ or —C$_n$H$_{2n}$—R(8);
m is zero or 1;
p is 1–3;
n is zero to 4.
2. The method as claimed in claim 1, wherein the disease is tropical malaria.
3. The method as claimed in claim 1, wherein the disease is tertian malaria.
4. The method as claimed in claim 1, wherein the disease is quartan malaria.
5. The method as claimed in claim 1, wherein the disease is toxoplasmosis.
6. The method as claimed in claim 1, wherein the disease is coccidiosis.
7. The method as claimed in claim 1, wherein the disease is intestinal sarcosporidosis.
8. The method as claimed in claim 1, wherein the disease is cryptosporidosis.
9. The method as claimed in claim 1, wherein the disease is Chargas' disease.
10. The method as claimed in claim 1, wherein the disease is leishmaniasis.

11. The method according to claim 10, wherein the leishmaniasis is cutaneous or visceral.

12. The method as claimed in claim 1, wherein the patient is an animal which is infected by animal-pathogenic protozoa.

13. The method as claimed in any of claims 1, 2–12, wherein the Na$^+$/H$^+$ exchange inhibitor is selected from the group consisting of I. a) a benzoylguanidine of the formula

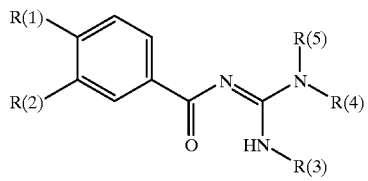

in which:

R(1) or R(2) is R(6)—S(O)$_n$— or R(7)R(8)N—O$_2$S—;

and the other substituent R(1) or R(2) in each case is H, F, Cl, Br, (C$_1$–C$_4$)-alkyl, (C$_1$–C$_4$)-alkoxy or phenoxy, which is unsubstituted or substituted by 1–3 substituents selected from the group consisting of fluorine, chlorine, methyl and methoxy;

or the other substituent R(1) or R(2) in each case is R(6)—S(O)$_n$ or R(7)R(8)N—;

n is zero, 1 or 2;

R(6) is (C$_1$–C$_6$)-alkyl, (C$_5$–C$_7$)-cycloalkyl, cyclopentylmethyl, cyclohexylmethyl or phenyl, which is unsubstituted or substituted by 1–3 substituents selected from the group consisting of fluorine, chlorine, methyl and methoxy;

R(7) and R(8) identically or differently are H or (C$_1$–C$_6$)-alkyl;

or

R(7) is phenyl-(CH$_2$)$_m$;

m is 1–4;

or

R(7) is phenyl, which is unsubstituted or substituted by 1–2 substituents selected from the group consisting of fluorine, chlorine, methyl and methoxy;

or

R(7) and R(8) together are a straight-chain or branched (C$_4$–C$_7$)-chain, where the chain can additionally be interrupted by O, S or NR(9);

R(9) is H or methyl;

or

R(7) and R(8) together with the nitrogen atom to which they are bonded, are a dihydroindole, tetrahydroquinoline or tetrahydroisoquinoline system;

R(3), R(4) and R(5) independently of one another are H or (C$_1$–C$_2$)-alkyl, or R(3) and R(4) together are a (C$_2$–C$_4$)-alkylene chain;

or

R(4) and R(5) together are a (C$_4$–C$_7$)-alkylene chain;

or a pharmaceutically tolerable salt thereof;

b) a benzoylguanidine of the formula

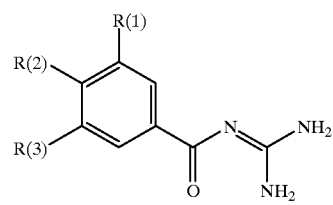

in which:

R(1) is R(4)—SO$_m$ or R(5)R(6)N—SO$_2$—;

m is zero, 1 or 2;

R(4) and R(5) are C$_1$–C$_8$-alkyl, C$_3$–C$_6$-alkenyl or -C$_n$H$_{2n}$—R(7);

n is zero, 1, 2, 3 or 4;

R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);

R(8) and R(9) are H or C$_1$–C$_4$-alkyl;

or

R(5) is H;

R(6) is H or C$_1$–C$_4$-alkyl, or

R(5) and R(6) together are 4 or 5 methylene groups, of which one CH$_2$ group can be replaced by an 0, S, NH, N—CH$_3$ or N-benzyl;

R(2) is hydrogen, F, Cl, Br, (C$_1$–C$_4$)-alkyl-, O—(CH$_2$)$_m$C$_p$F$_{2p+1}$ or —X—R(10);

m is zero or 1;

p is 1, 2 or 3;

x is O, S or NR(11);

R(10) is H, C$_1$–C$_6$-alkyl, C$_5$–C$_7$-cycloalkyl, cyclohexylmethyl, cyclopentylmethyl or —C$_n$H$_{2n}$—R(12);

n is zero, 1, 2, 3 or 4;

R(12) is phenyl, which is unsubstituted or substituted by 1–3 substituents selected from the group consisting of F, Cl, CF$_3$, methyl, methoxy and NR(8)R(9);

R(8) and R(9) are H or C$_1$–C$_4$-alkyl;

R(1 1) is hydrogen or C$_1$–C$_3$-alkyl;

or

R(10) and R(11) together are 4 or 5 methylene groups, of which one CH$_2$ group can be replaced by O, S, NH, N-CH$_3$ or N-benzyl;

R(3) is defined as R(1), or is C$_1$–C$_6$-alkyl, nitro, cyano, trifluoromethyl, F, Cl, Br, I or —X—R(10);

x is O, S or NR(11);

R(10) is H, C$_1$–C$_6$-alkyl, C$_5$–C$_7$-cycloalkyl, cyclohexylmethyl, cyclopentylmethyl or —C$_n$H$_{2n}$—R(12);

n is zero to 4;

R(12) is phenyl, which is unsubstituted or substituted by 1–3 substituents selected from the group consisting of F, Cl, CF$_3$, methyl, methoxy und NR(8)R(9);

R(8) and R(9) are H or C$_1$–C$_4$-alkyl;

R(11) is C$_1$–C$_3$-alkyl, or

R(10) and R(11) together are 4 or 5 methylene groups, of which one CH$_2$ group can be replaced by O, S, NH, N-CH$_3$ or N-benzyl;

or a pharmaceutically tolerable salt thereof;

f) a benzoylguanidine of the formula

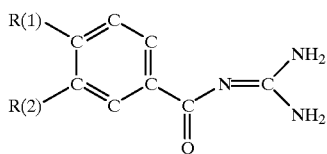

in which:

R(1) or R(2) is R(3)—S(O)$_n$— or R(4)R(5)N—SO$_2$— the other substituent R(1) or R(2) in each case is H, OH, F, Cl, Br, I, C$_1$–C$_4$-alkyl, C$_1$–C$_4$-alkoxy, benzyloxy or phenoxy, which is unsubstituted or carries one to three substituents selected from the group consisting of fluorine, chlorine, methyl, methoxy, hydroxyl or benzyloxy, R(3)—S(O)$_n$, —NR(4)R(5) or 3,4-dehydropiperidine R(3) is C$_1$–C$_6$-alkyl, C$_5$–C$_7$-cycloalkyl, cyclopentylmethyl, cyclohexylmethyl or phenyl, which is unsubstituted or carries one to three substituents selected from the group consisting of fluorine, chlorine, methyl and methoxy;

R(4) and R(5) identically or differently, are H or C$_1$–C$_6$-alkyl;

or

R(4) is phenyl-(CH$_2$)$_m$—;

m is 1, 2, 3 or 4;

or

R(4) is phenyl, which is unsubstituted or carries one to two substituents selected from the group consisting of fluorine, chlorine, methyl and methoxy;

or

R(4) and R(5) together are a straight-chain or branched C$_4$–C$_7$-chain, where the chain can additionally be interrupted by O, S or NR(6), R(6) is H or methyl;

or

R(4) and R(5) together with the nitrogen atom to which they are bonded, are a dihydroindole, tetrahydroquinoline or tetrahydroisoquinoline system;

n is zero, 1 or 2;

or a pharmaceutically tolerable salt thereof;

k) a benzoylguanidine of the formula

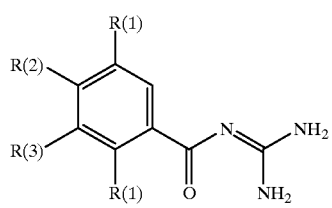

(I)

in which:

one of the substituents R(1), R(2), R(3) or R(4):

is an amino group

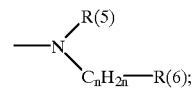

R(5) is hydrogen or C$_{(1–6)}$-alkyl;

n is zero, 1, 2, 3 or 4;

R(6) is H or C$_{(1–4)}$-alkyl;

in which one CH$_2$ group can be replaced by 1 sulfur atom or a group NR(7);

R(7) is hydrogen, methyl or ethyl:

or

R(6) is C$_{(3–8)}$-cycloalkyl or phenyl, which is unsubstituted or carries 1, 2 or 3 substituents selected from the group consisting of F, Cl, Br, methyl, methoxy, —NR(8)R(9);

R(8) and R(9) are H, methyl or ethyl;

or

R(5) and R(6) together with the nitrogen atom are a 5-, 6- or 7-membered ring, in which 1 carbon atom can be replaced by oxygen, S or NR(10);

R(10) is H, C$_{(1–3)}$-alkyl or benzyl;

and the other substituents R(1), R(2), R(3), R(4) in each case are: hydrogen, F, Cl, Br, I, CN, CF$_3$, NO$_2$, CF$_3$—O—, C$_m$F$_{2m+1}$—CH$_2$—O— or R(11)—

C$_q$H$_{2q}$—X$_p$—;

m is 1, 2 or 3;

q is zero, 1, 2, 3 or 4;

p is zero or 1;

X is oxygen or NR(12);

R(12) is H or C$_{(1–3)}$-alkyl;

R(11) is hydrogen, C$_{(1–6)}$-alkyl, C$_{(3–8)}$-cycloalkyl or phenyl, which is unsubstituted or substituted by 1, 2 or 3 substituents selected from the group consisting of F, Cl, CH$_3$, CH$_3$—O— and NR(13)R(14);

R(13), R(14) are H, methyl or ethyl;

or a pharmaceutically tolerable salt thereof;

m) a benzoylguanidine of the formula

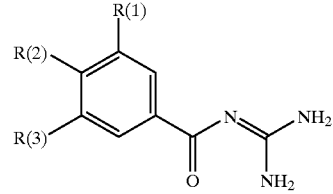

in which:

R(1), R(2), R(3) are hydrogen, F, Cl, Br, I or (C$_1$–C$_{12}$)-alkyl;

one of the substituents R(1), R(2) or R(3) is N$_3$, CN, OH or (C$_1$–C$_{10}$)-alkyloxy, if at least one of the remaining substituents R(1), R(2) or R(3) is a sufficiently lipophilic alkyl radical having 3 to 12 carbon atoms;

or one of the substituents R(1), R(2) or R(3)

is R(4)—C$_n$H$_{2n}$—O$_m$—;

m is zero or 1;

n is zero, 1, 2 or 3;

R(4) is $C_pF_{2p+1}$;

p is 1, 2 or 3, if n is zero or 1;

or

R(4) is $(C_3-C_{12})$-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);

R(5) and R(6) are hydrogen or $(C_1-C_4)$-alkyl;

or one of the substituents R(1), R(2) or R(3) is —C≡CR(5) or —C[R(6)]=CR(5);

R(5) is phenyl, which is unsubstituted or substituted by 1–3 substituents selected from the group consisting of F, Cl, $CF_3$, methyl, methoxy, hydroxyl, amino, methylamino and dimethylamino, $(C_1-C_9)$-heteroaryl, which is unsubstituted or substituted as phenyl, or R(5) is $(C_1-C_6)$-alkyl, which is unsubstituted or substituted by 1–3 OH;

or

R(5) is $(C_3-C_8)$-cycloalkyl,

R(6) is hydrogen or methyl;

or a pharmacologically acceptable salt thereof;

o) a benzoylguanidine of the formula

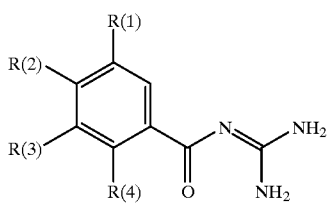

in which:

R(1) is hydrogen, F, Cl, Br, I, —$NO_2$, —C≡N, $X_o$—$(CH_2)_p$—$(CF_2)_q$—$CF_3$, R(5)—$SO_m$, R(6)—CO— or R(6)R(7)N—$SO_2$—, where x is oxygen, S or NR(14);

m is zero, 1 or 2;

o is zero or 1;

p is zero, 1 or 2;

q is zero, 1, 2, 3, 4, 5 or 6;

R(5) and R(6) are $(C_1-C_8)$-alkyl, $(C_3-C_6)$-alkenyl, —$C_nH_{2n}$—R(8) or $CF_3$;

n is zero, 1, 2, 3 or 4;

R(8) is $(C_3-C_7)$-cycloalkyl or phenyl, which is not substituted or is substituted by 1–3 substituents selected from the group consisting of F, Cl, $CF_3$, methyl, methoxy and NR(9)R(10);

R(9) and R(10) are H or $C_1-C_4$-alkyl;

or

R(6) is H;

R(7) is H or $(C_1-C_4)$-alkyl;

or

R(6) and R(7) together are 4 or 5 methylene groups, of which one $CH_2$ group can be replaced by oxygen, S, NH, N—$CH_3$ or N-benzyl;

R(2) is

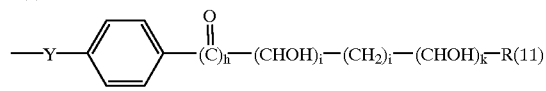

or

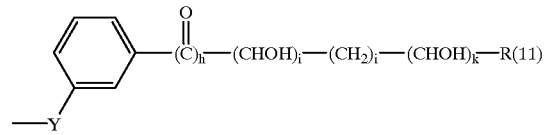

or

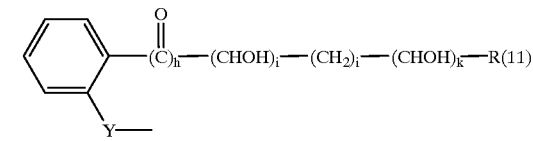

Y is oxygen, —S— or —NR(12)—;

R(11) and R(12) are hydrogen or $(C_1-C_3)$-alkyl;

h is zero or 1;

i, j and k independently are zero, 1, 2, 3 or 4;

but where h, i and k are not simultaneously zero,

R(3) is defined as R(1), or is $(C_1-C_6)$-alkyl or —X—R(13);

X is oxygen, S or NR(14);

R(14) is H or $(C_1-C_3)$-alkyl;

R(13) is H, $(C_1-C_6)$-alkyl, $(C_3-C_8)$-cycloalkyl or —$C_bH_{2b}$—R(15);

b is zero, 1, 2, 3 or 4;

or

R(13) and R(14) together are 4 or 5 methylene groups, where one $CH_2$ group can be replaced by oxygen, S, NH, N—$CH_3$ or N-benzyl;

R(15) is phenyl, which is unsubstituted or substituted by 1–3 substituents selected from the group consisting of F, Cl, $CF_3$, methyl, methoxy and NR(9)R(10);

R(9) and R(10) are H or $(C_1-C_4)$-alkyl;

R(4) is hydrogen, —OR(16) or —NR(16)R(17);

R(16) and R(17) independently are hydrogen or $(C_1-C_3)$-alkyl;

or a pharmaceutically tolerable salt thereof;

r) a benzo-fused 5-membered ring heterocycle of the formula

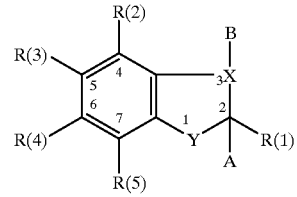

in which:

X is N or CR(6);

Y is oxygen, S or NR(7);

A, B together are a bond or

A, B are both hydrogen, if X is CR(6) and Y is NR(7) simultaneously; one of the substituents R(1) to R(6) is a —CO—N=C($NH_2$)$_2$ group;

the other substituents R(1) to R(6) in each case are hydrogen, F, Cl, Br, I or (C$_1$–C$_6$)-alkyl;
up to two of the other substituents R(1) to R(6) are CN, NO$_2$, N$_3$, (C$_1$–C$_4$)-alkyloxy or CF$_3$;
up to one of the other substituents
is R(8)—C$_n$H$_{2n}$—Z—;
n is zero to 10;
where the alkylene chain —C$_n$H$_{2n}$— is straight-chain or branched and where one carbon atom can be replaced by an oxygen or sulfur atom or by a nitrogen atom;
R(8) is hydrogen, (C$_2$–C$_6$)-alkenyl or (C$_3$–C$_{10}$)-cycloalkyl, which is unsubstituted or substituted by 1 to 4 methyl groups or an OH group, or can contain an ethylene group —CH═CH—, and in which one methylene group can be replaced by an oxygen or sulfur atom or by a nitrogen atom;
or
R(8) is phenyl, which is unsubstituted or substituted by 1 to 3 substituents selected from the group consisting of F, Cl, Br, I, CF$_3$, CH$_3$—S(O)$_s$— or R(9)-W$_y$—;
s is zero, 1 or 2;
R(9) is H, methyl, ethyl,
W is oxygen or NR(10);
R(10) is H or methyl;
y is zero or 1;
or
R(8) is C$_m$F$_{2m+1}$;
m is 1 to 3;
or
R(8) is 1- or 2-naphthyl, pyridyl, quinolyl or isoquinolyl;
Z is —CO—, —CH$_2$— or —[CR(11)(OH)]$_q$—;
q is 1, 2 or 3;
R(11) is H or methyl;
or
Z is oxygen or —NR(12)—;
R(12) is H or methyl;
or
Z is —S(O)$_s$—;
s is zero, 1 or 2;
or
Z is —SO$_2$—NR(13)—;
R(13) is H or (C$_1$–C$_4$)-alkyl;
R(7) is hydrogen, (C$_1$–C$_{10}$)-alkyl, (C$_2$–C$_{10}$)-alkenyl or R(8)-C$_n$H$_{2n}$—; or a pharmaceutically tolerable salt thereof;
z) a benzoylguanidine of the formula

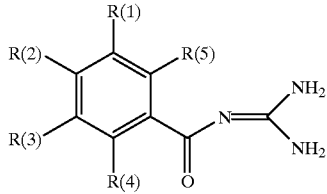

in which:
R(1) is 13(6)—SO$_m$;
m is zero, 1 or 2;
R(6) is perfluoroalkyl having 1, 2, 3, 4, 5 or 6 carbon atoms, which is straight-chain or branched;
R(2) and R(3) independently of one another are hydrogen, F, Cl, Br, I, alkyl having 1, 2, 3 or 4 carbon atoms, alkoxy having 1, 2, 3 or.4 carbon atoms or phenoxy, which is unsubstituted or substituted by 1–3 substituents selected from the group consisting of F, Cl, methyl and methoxy;
or
R(2) and R(3)
independently of one another are pyrrol-1-yl, pyrrol-2-yl- or pyrrol-3-yl, which is not substituted or is substituted by I to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, CF$_3$, methyl and methoxy;
R(4) and R(5) independently of one another are hydrogen, alkyl having 1, 2 or 3 carbon atoms, F, Cl, Br, I, CN, OR(7), NR(8)R(9) or —(CH$_2$)$_n$—(CF$_2$)$_o$—CF$_3$;
R(7), R(8) and R(9) independently of one another are hydrogen or alkyl having 1, 2, 3 or 4 carbon atoms;
n is zero or 1;
o is zero, 1 or 2;
or a pharmacologically acceptable salt thereof;
ag) a benzoylguanidine of the formula

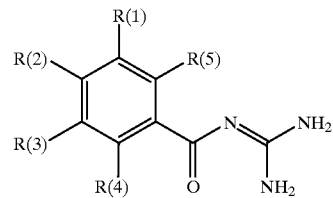

in which:
one of the three substituents R(1), R(2) and R(3) is R(6)—A—B—D—;
R(6) is a basic protonatable radical, i.e. an amino group —NR(7)R(8), an amidino group R(7)R(8)N—C[═N—R(9)]— or a guanidino group

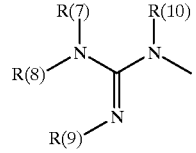

R(7), R(8), a R(9) and R(10) in dependently of one another are hydrogen or alkyl having 1, 2, 3 or 4 carbon atoms;
or
R(7) and R(8) together are C$_a$H2a;
a is 4, 5, 6 or 7;
where if a=5, 6 or 7 a methylene group of the group C$_a$H$_{2a}$ can be replaced by a heteroatom group O, SO$_m$ or NR(11),
or
R(8) and R(9) or R(9) and R(10) or R(7) and R(10) are a group CaH2a;
a is 2, 3, 4 or 5;
where if a=3, 4 or 5 a methylene group of the group C$_a$H$_{2a}$ can be replaced by a heteroatom group O, SO$_m$ or NR(11);
m is zero, 1 or 2;
R(1 1) is hydrogen or methyl;
or R(6) is a basic heteroaromatic ring system having 1–9 carbon atoms;

A is $C_bH_{2b}$;

b is 1, 2, 3, 4, 5, 6, 7, 8, 9 or 10;

where in the group $C_bH_{2b}$, one or two methylene groups can be replaced by one of the groupings selected from the group consisting of —O—, —CO—, —CH[OR(20)]—, —SO$_m$—, —NR(20)—, —NR(20)—CO—, —NR(20)—CO—NH—, —NR(20)—CO—NH—SO$_2$—

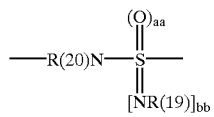

and —SO$_{aa}$[NR(19)]$_{bb}$—;

and where in the group $C_bH_{2b}$, a methylene group can be replaced by —CH—R(99), where R(99) together with R(7) forms a pyrrolidine or piperidine ring;

aa is 1 or 2;

bb is 0 or 1;

aa+bb=2;

R(19) is hydrogen or alkyl having 1, 2, 3 or 4 carbon atoms;

R(20) is hydrogen or methyl;

B is a phenylene or naphthylene radical

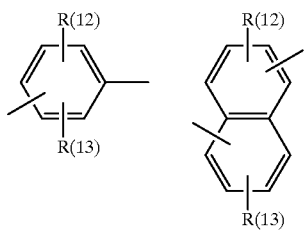

R(12) and R(13) independently of one another are hydrogen, methyl, F, Cl, Br, I, CF$_3$ or —SO$_w$—R(14);

R(14) is methyl or NR(15)R(16);

R(15) and R(16) independently of one another are hydrogen or alkyl having 1, 2, 3 or 4 carbon atoms;

w is zero, 1 or 2;

D is —$C_dH_{2d}$—$X_f$—;

d is zero, 1, 2, 3 or 4;

X is —O—, —CO—, —CH[OR(21)]—, —SO$_m$— or —NR(21)—;

f is zero or 1;

R(21) is hydrogen or methyl;

m is zero, 1 or 2;

and the other substituents R(1) and R(2) and R(3) in each case independently of one another are hydrogen, F, Cl, Br, I, —CN, —($C_1$-$C_8$)— alkyl, —($C_2$-$C_8$)-alkenyl, —NR(35)R(36) or R(17)-$C_gH_{2g}$—$Z_h$—;

g is zero, 1, 2, 3 or 4;

h is zero or 1;

R(35) and R(36) independently of one another are hydrogen or alkyl having 1, 2, 3, 4, 5 or 6 carbon atoms;

or

R(35) and R(36) together are 4–7 methylene groups, of which one CH$_2$ group can be replaced by oxygen, —S—, —NH—, —NCH$_3$ or —N-benzyl;

z is —O—, —CO—, —SO$_v$—, —NR(18)—, —NR(18)—CO—, —NR(18)—CO—NH— or —NR(18)—SO$_2$—;

R(18) is hydrogen or methyl;

v is zero, 1 or 2;

R(17) is hydrogen, cycloalkyl having 3, 5 or 6 carbon atoms or $C_kF_{2k+1}$—;

k is 1, 2 or 3, or

R(17) is pyrrol-1-yl, pyrrol-2-yl or pyrrol-3-yl, which is not substituted or is substituted by 1–4 substituents selected from the group consisting of F, Cl, Br, I, —CN, ($C_2$-$C_8$)-alkanoyl, ($C_2$-$C_8$)-alkoxycarbonyl, formyl, carboxyl, —CF$_3$, methyl and methoxy;

or

R(17) -is ($C_3$-$C_8$)-cycloalkyl or phenyl, which is not substituted or is substituted by 1–3 substituents selected from the group consisting of F and Cl, —CF$_3$, methyl, hydroxyl, methoxy, —NR(37)R(38), CH$_3$SO$_2$— and H$_2$NO$_2$S—;

R(37) and R(38) are hydrogen or —CH$_3$;

R(4) and R(5) independently of one another are hydrogen, alkyl having 1, 2, 3 or 4 carbon atoms, F, Cl, —OR(32), —NR(33)R(34) or —$C_rF_{2r+1}$;

R(32), R(33) and R(34) independently of one another are hydrogen or alkyl having 1, 2 or 3 carbon atoms;

r is 1, 2, 3 or 4;

and their pharmacologically tolerable salts;

am) a substituted cinnamic acid guanidide of the formula

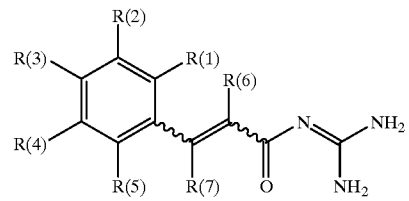

in which:

at least one of the substituents R(1), R(2), R(3), R(4) and R(5) is

—$X_a$—$Y_b$—$L_n$—U;

X is CR(16)R(17), O, S or NR(18);

R(16), R(17) and R(18) independently of one another are H, alkyl having 1, 2, 3 or 4 carbon atoms or perfluoroalkyl having 1, 2, 3 or 4 carbon atoms;

a is zero or 1;

Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;

T is NR(20), O, S or phenylene, where the phenylene is not substituted or is substituted by 1–3 substituents selected from the group consisting of F, Cl, CF$_3$, methyl, methoxy and NR(21)R(22);

R(20), R(21) and R(22) independently of one another are H, alkyl having 1, 2, 3 or 4 carbon atoms or perfluoroalkyl having 1, 2, 3 or 4 carbon atoms;

b is zero or 1;

L is O, S, NR(23) or $C_kH_{2k}$;

k is 1, 2, 3, 4, 5, 6, 7 or 8;

n is zero or 1;

U is NR(24)R(25) or an N-containing heterocycle having 1, 2, 3, 4, 5, 6, 7, 8 or 9 carbon atoms;
R(24) and R(25) independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms;

or

R(24) and R(25) together are 4 or 5 methylene groups, of which one $CH_2$ group can be replaced by oxygen, S, NH, N—$CH_3$ or N-benzyl;
where the N-containing heterocycles are N- or C-bridged and are not substituted or are substituted by 1–3 substituents selected from the group consisting of F, Cl, $CF_3$, methyl, methoxy and NR(27)R(28);
R(23), R(27) and R(28) independently of one another are H, alkyl having 1, 2, 3 or 4 carbon atoms or perfluoroalkyl having 1, 2, 3 or 4 carbon atoms;
and the other substituents R(1), R(2), R(3), R(4) and R(5) in each case independently of one another are H, F, Cl, Br, I, CN, —$O_n$—$C_mH_{2m+1}$, —$O_p$— $(CH_2)_s$—$C_qF_{2q+1}$ or —$C_rH_2$-R(10);

n is zero or 1;
m is zero, 1, 2, 3, 4, 5, 6, 7 or 8;
p is zero or 1;
q is 1, 2, 3, 4, 5, 6, 7 or 8;
s is zero, 1, 2, 3 or 4;
r is zero, 1, 2, 3 or 4;
R(10) is cycloalkyl hiving 3, 4, 5, 6, 7 or 8 carbon atoms, or phenyl, where the phenyl is not substituted or is substituted by 1–3 substituents selected from the group consisting of F, Cl, $CF_3$, methyl, methoxy and NR(11)R(12);
R(11) and R(12) independently of one another are H, alkyl having 1, 2, 3 or 4 carbon atoms or perfluoroalkyl having 1, 2, 3 or 4 carbon atoms;
R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
which is not substituted or is substituted by 1–3 substituents selected from the group consisting of F, Cl, $CF_3$, methyl, methoxy and NR(14)R(15);
R(14) and R(15) independently of one another are H, alkyl having 1, 2, 3 or 4 carbon atoms or perfluoroalkyl having 1, 2, 3 or 4 carbon atoms;

or a pharmaceutically tolerable salt thereof;

bd) phenyl-substituted alkenylcarboxylic acid guanidide of the formula I

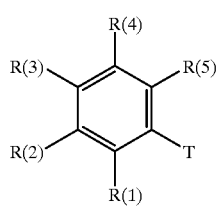

in which:
T is

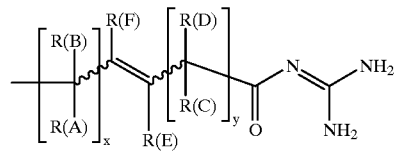

R(A) is hydrogen, F, Cl, Br, I, CN, OH, OR(6), $(C_1-C_4)$-alkyl, $O_r(CH_2)_aC_bF_{2b+1}$, $(C_3-C_8)$-cycloalkyl oder NR(7)R(8)
r is zero or 1;
a is zero, 1, 2, 3 or 4;
b is 1, 2, 3 or 4;
R(6) is $(C_1-C_4)$-alkyl, $(C_1-C_4)$-perfluoroalkyl, $(C_3-C_6)$-alkenyl,
$(C_3-C_8)$-cycloalkyl, phenyl or benzyl, the phenyl nucleus not being substituted or being substituted by 1–3 substituents selected from the group consisting of F, Cl, $CF_3$, methyl, methoxy and NR(9)R(l0);
R(9) and R(10) are H, $(C_1-C_4)$-alkyl or $(C_1-C_4)$-perfluoro-alkyl;
R(7) and R(8) independently of one another are defined as R(6);

or

R(7) and R(8) together are 4 or 5 methylene groups, of which one $CH_2$ group can be replaced by oxygen, sulfur, NH, N—$CH_3$ or N-benzyl;
R(B), R(C) and R(D) independently are defined as R(A);
x is zero, 1 or 2;
y is zero, 1 or 2;
R(F) is hydrogen, F, Cl, Br, I, CN, OR(12), $(C_1-C_8)$-alkyl, $O_p(CH_2)_fC_gF_{2g+1}$, $(C_3-C_8)$-cycloalkyl or $(C_1{}_{-C9})$-heteroaryl;
p is zero or 1;
f is zero, 1, 2, 3 or 4;
g is 1, 2, 3, 4, 5, 6, 7 or 8;
R(12) is $(C_1-C_8)$-alkyl, $(C_1-C_4)$-perfluoroalkyl, $(C_3-C_8)$-alkenyl,
$(C_3-C_8)$-cycloalkyl, phenyl or benzyl, the phenyl nucleus not being substituted or being substituted by 1–3 substituents selected from the group corisisting of F, Cl, $CF_3$, methyl, methoxy and NR(13)R(14);
R(13) and R(14) are H, $(C_1-C_4)$-alkyl or $(C_1-C_4)$-perfluoroalkyl;
R(E) is defined independently as R(F);
R(1) is defined independently as T;

or

R(1) is hydrogen, —$O_kC_mH_{2m+1}$, —$O_n(CH_2)_pC_qF_{2q+1}$, F, Cl, Br, I, CN, —(C=O)— N=C(N $H_2)_2$, —$SO_rR(17)$, —$SO_{r2}N$ R(31)R(32), —$O_u(CH_2)_vC_6H_5$, —$O_{u2}$—$(C_1-C_9)$-heteroaryl or —$S_{u2}$-$(C_1-C_9)$-heteroaryl;
k is zero or 1;
m is zero, 1, 2, 3, 4, 5, 6, 7 or 8;
n is zero or 1;
p is zero, 1, 2, 3 or 4;
q is 1, 2, 3, 4, 5, 6, 7 or 8;
r is zero, 1 or 2;
r2 is zero, 1 or 2;
R(31) and R(32) independently of one another are hydrogen, $(C_1-C_8)$-alkyl or $(C_1-C_8)$-perfluoroalkyl;

or

R(31) and R(32) are, together, 4 or 5 methylene groups of which one $CH_2$ group can be replaced by oxygen, S, NH, N—$CH_3$ or N-benzyl;

R(17) is ($C_1$–$C_8$)-alkyl;

u is zero or 1;

u2 is zero or 1;

v is zero, 1, 2, 3 or 4;

where the phenyl nucleus is not substituted or is substituted by 1–3 substituents selected from the group consisting of F, Cl, $CF_3$, methyl, methoxy, —$(CH_2)_w$NR(21)R(22), NR(18)R(19) and ($C_1$–$C_9$)-heteroaryl;

R(18), R(19), R(21) and R(22) independently of one another are ($C_1$–$C_4$)-alkyl or ($C_1$–$C_4$)-perfluoroalkyl;

w is 1, 2, 3 or 4;

where the heterocycle of the ($C_1$–$C_9$)-heteroaryl is unsubstituted or substituted by 1–3 substituents selected from the group consisting of F, Cl, $CF_3$, methyl or methoxy;

R(2), R(3), R(4) and R(5) independently of one another are defined as R(1), or

R(1) and R(2) or R(2) and R(3) in each case together are —CH—CH=CH—CH—, which is not substituted or is substituted by 1–3 substituents selected from the group consisting of F, Cl, $CF_3$, methyl, methoxy, —$(CH_2)_{w2}$NR(24)R(25) and NR(26)R(27);

R(24), R(25), R(26) and R(27) are H, ($C_1$–$C_4$)-alkyl or ($C_1$–$C_4$)-perfluoroalkyl;

w 2 is 1, 2, 3 or 4 the radical T being present in the molecule at least twice, but only three times at most;

or a pharmaceutically tolerable salt thereof.

14. The method as claimed in any of claims 1, 2–12, wherein the $Na^+/H^+$ exchange inhibitor is selected from the group consisting of 3-dimethylamino-5-trifluoromethylbenzoylguanidine, 3-phenyl-5-trifluoromethylbenzoylguanidine, 3-isopropyl-4-fluoro-5-trifluoromethylbenzoylguanidine, 3-chloro-5-(1-pyrrolyl)benzoylguanidine, 3-chloro-5-trifluoromethylbenzoylguanidine, 3-dimethylamino-5-(1-pyrrolyl)benzoylguanidine, 3-dimethylamino-4-tert-butylbenzoylguanidine, 4-(3-chloroanilino)-3-methylsulfonylbenzoylguanidine, 4-(4-aminoethylphenoxy)-3-methylsulfonylbenzoylguanidine, 4-(4-aminoethylsulfonylmethylphenoxy)-3-trifluoromethylbenzoyl-guanidine, 4-(4-aminoethylthiophenoxy)-3-trifluoromethylbenzoylguanidine, 3,5-di-tert-butylbenzoylguanidine, 3,5-di-tert-butyl-4-hydroxybenzoylguanidine, 5-chloro-2-indoloylguanidine, 3,5-dichloro-2-indoloylguanidine, 5-chloro-3-phenylthio-2-indoloylguanidine, 5-chloro-3-phenylsulfonyl-2-indoloylguanidine, 5-methoxy-3-isopropyl-2-indoloylguanidine, 4-benzyloxy-2-indoloylguanidine, 5-chloro-1-(4-picolyl)-2-indoloylguanidine, 2-(4-hydroxyphenyl)-4-benzimidazolylguanidine, N-{3-[3-(3-guanidino-2-methyl-3-oxopropenyl)phenyl] 2-methylacryloyl}guandine, and their pharmacologically tolerable salts.

R(8) is phenyl, which is unsubstituted or substituted by 1–3 substituents selected from the group consisting of F, Cl, $CF_3$, methyl, methoxy and NR(9)R(10);

R(9) and R(10) are H or $C_1$–$C_4$-alkyl;

or

R(6) and R(7) together are 4 or 5 methylene groups, of which one $CH_2$ group can be replaced by O, S, NH, N—$CH_3$ or N-benzyl;

R(2) and R(4) identically or differently are R(11)—$SO_q$— or R(12)R(13)N—$SO_2$—;

q is zero –2;

R(11) is $C_1$–$C_4$-alkyl, which is unsubstituted or carries phenyl as a substituent, where phenyl is unsubstituted or substituted by 1–3 substituents selected from the group consisting of F, Cl, $CF_3$, methyl, methoxy and NR(9)R(10);

R(9) and R(10) are H or $C_1$–$C_4$-alkyl;

R(12) and R(13) are defined as R(6) and R(7);

or one of the two radicals R(2) or R(4) is hydrogen or is defined as R(1);

R(5) is H, methyl, F, Cl or methoxy, or a pharmaceutically tolerable salt thereof;

d) a benzoylguanidine of the formula

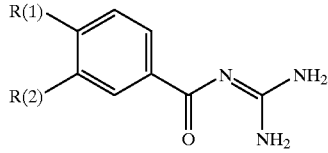

(I)

in which:

R(1) or R(2) is an amino group —NR(3)R(4);

R(3) and R(4) identically or differently are H, $C_1$–$C_6$-alkyl or $C_3$–$C_7$-cycloalkyl;

or

R(3) is phenyl—$(CH_2)_p$—;

p is 0, 1, 2, 3 or 4;

or

R(3) is phenyl, where the phenyl in each case is unsubstituted or carries one to two substituents selected from the group consisting of fluorine, chlorine, methyl and methoxy;

or

R(3) and R(4) together can be a straight-chain or branched $C_4$–$C_7$-methylene chain, where one —$CH_2$-member of the methylene chain can be replaced by oxygen, S or NR(5);

R(5) is H or lower alkyl;

the other substituent R(1) or R(2) in each case is H, F, Cl, $C_1$–$C_4$-alkyl, $C_1$–$C_4$-alkoxy, $CF_3$, $C_mF_{2m+1}$—$CH_2$—, benzyl or phenoxy, where the respective phenyl radical is unsubstituted or carries one to two substituents selected from the group consisting of methyl, methoxy, fluorine and chlorine;

m is 1, 2 or 3;

or a pharmaceutically tolerable salt thereof;

113 e) a benzoylguanidine of the formula

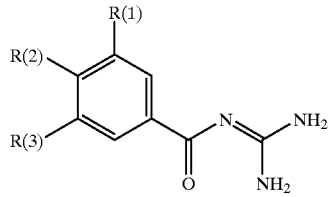
(I)

in which:

R(1) is R(4)—SO$_m$ or R(5)R(6)N—SO$_2$—;

m is zero, 1 or 2;

R(4) and R(5) are C$_1$–C$_8$-alkyl, C$_3$–C$_6$-alkenyl or —C$_n$H$_{2n}$—R(7);

n is zero, 1, 2, 3 or 4;

R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);

R(8) and R(9) are H or C$_1$–C$_4$-alkyl;

or

R(5) is H;

R(6) is H or C$_1$–C$_4$-alkyl;

or

R(5) and R(6) together are 4 or 5 methylene groups, of which one CH$_2$ group can be replaced by an O, S, NH, N—CH$_3$ or N-benzyl;

R(2) is hydrogen, straight-chain or branched (C$_5$–C$_8$)-alkyl, —CR(13)=CHR(12) or —C≡CR(1 2);

R(12) is phenyl, which is unsubstituted or substituted by 1–3 substituents selected from the group consisting of F, Cl, CF$_3$, methyl, methoxy and NR(14)R(1 5);

R(14) and R(15) are H or (C$_1$–C$_4$)-alkyl;

or

R(12) is (C$_1$–C$_9$)-heteroaryl, which is unsubstituted or substituted as phenyl, or R(12) is (C$_1$–C$_6$)-alkyl, which is unsubstituted or substituted by 1–3 OH, or R(12) is (C$_3$–C$_8$)-cycloalkyl;

R(13) is hydrogen or methyl, or

R(12) is (C$_3$–C$_8$)-cycloalkyl, (C$_3$–C$_8$)-cycloalkyl-(C$_1$–C$_4$)-alkyl, phenyl, C$_6$H$_5$—(C$_1$–C$_4$)-alkyl, naphthyl, biphenylyl, 1,1-diphenyl-(C$_1$–C$_4$)-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl or cinnolinyl;

R(3) is defined as R(2); and where the aromatic substituents R(2) and R(3) are unsubstituted or substituted by 1–3 substituents from the groups F, Cl, CF$_3$, (C$_1$–C$_4$)-alkyl or -alkoxy, or NR(10)R(11) with R(10) and R(11) being H or (C$_1$–C$_4$)-alkyl;

or a pharmaceutically tolerable salt thereof;

114 f) a benzoylguanidine of the formula

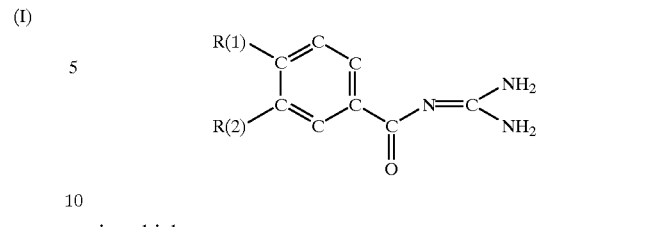
I in which:

R(1) or R(2) is R(3)—S(O)$_n$— or R(4)R(5)N—SO$_2$— the other substituent R(1) or R(2) in each case is H, OH, F, Cl, Br, I, C$_1$–C$_4$-alkyl, C$_1$–C$_4$-alkoxy, benzyloxy or phenoxy, which is unsubstituted or carries one to three substituents selected from the group consisting of fluorine, chlorine, methyl, methoxy, hydroxyl or benzyloxy, R(3)—S(O)$_n$, —NR(4)R(5) or 3,4-dehydropiperidine R(3) is C$_1$–C$_6$-alkyl, C$_5$–C$_7$-cycloalkyl, cyclopentylmethyl, cyclohexylmethyl or phenyl, which is unsubstituted or carries one to three substituents selected from the group consisting of fluorine, chlorine, methyl and methoxy;

R(4) and R(5) identically or differently, are H or C$_1$–C$_6$-alkyl;

or

R(4) is phenyl—(CH$_2$)$_m$—;

m is 1, 2, 3 or 4;

or

R(4) is phenyl, which is unsubstituted or carries one to two substituents selected from the group consisting of fluorine, chlorine, methyl and methoxy;

or

R(4) and R(5) together are a straight-chain or branched C$_4$–C$_7$-chain, where the chain can additionally be interrupted by O, S or NR(6), R(6) is H or methyl;

or

R(4) and R(5) together with the nitrogen atom to which they are bonded, are a dihydroindole, tetrahydroquinoline or tetrahydroisoquinoline system;

n is zero, 1 or 2;

or a pharmaceutically tolerable salt thereof;

g) an isoquinoline of the formula

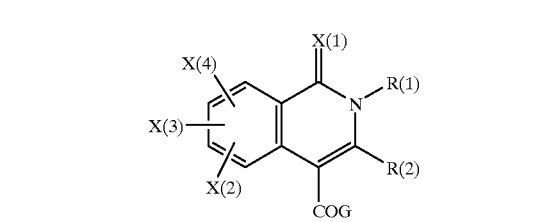
I in which:

R(1) is hydrogen, alkyl, cycloalkyl, arylalkyl, alkenyl, substituted aminoalkyl or an aryl or heteroaryl ring; where the rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, trifluoromethyl, R(2) is hydrogen, halogen, alkyl or aryl; which is unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, G is X(2), X(3) and X(4) independently of one another are hydrogen, halogen, nitro, amino, alkyl, sulfonamide, mono(lower alkyl)amino, di(lower alkyl)amino, lower alkyl, benzyloxy, hydroxyl;

X(1) is hydrogen, oxygen, sulfur or NR(7);

R(7) is hydrogen, alkyl, cycloalkyl, arylalkyl, alkenyl, substituted aminoalkyl or an aryl or a heteroaryl ring; which rings are unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl and trifluoromethyl;

in which substituents each alkyl chain or alkenyl chain can be interrupted by oxygen, sulfur or NR(8);

R(8) is hydrogen, alkyl, cycloalkyl, arylalkyl, alkenyl, substituted aminoalkyl or an aryl or heteroaryl ring, which rings are unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl and trifluoromethyl;

or a pharmaceutically acceptable salt thereof;

h) a compound of the formula

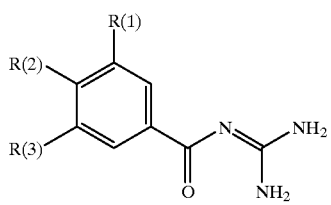

(I)

in which:

R(1) is hydrogen, F, Cl, Br, I, —NO$_2$, —C≡N, —CF$_3$, R(4)—SO$_m$ or R(5)R(6)N—SO$_2$—;

m is zero, 1 or 2;

R(4) and R(5) are (C$_1$–C$_8$)-alkyl, (C$_3$—C6)-alkenyl, —C$_n$H$_{2n}$—R(7) or CF$_3$;

n is zero, 1, 2, 3 or 4;

R(7) is (C$_3$–C$_7$)-cycloalkyl or phenyl, which is not substituted or is substituted by 1–3 substituents selected from the group consisting of F, Cl, CF$_3$, methyl, methoxy and NR(8)R(9);

R(8) and R(9) are H or C$_1$–C$_4$-alkyl;

or

R(5) is H;

R(6) is H or (C$_{1-C4}$)-alkyl;

or

R(5) and R(6) together are 4 or 5 methylene groups, of which one CH$_2$ group can be replaced by oxygen, S, NH, N—CH$_3$ or N-benzyl;

R(2) is —SR(10), —OR(10), —NHR(10), —NR(10)R (11), —CHR(10)R(12), —[CR(12)R(13)OR(13')], —{C—[CH$_2$—OR(13')]R(12) (R(13)} or —[CR(18)R (17)]$_p$—(CO)—[CR(19)R(20)]$_q$—R(14);

R(10) and R(11) identically or differently are —[CHR (16)]$_s$—(CH$_2$)$_p$—(CHOH)$_q$—(CH$_2$)$_r$—(CHOH)$_t$—R (21) or —(CH$_2$)$_p$—O—(CH$_2$—CH$_2$O)$_q$—R(21), R(21) is hydrogen, methyl, p, q, r identically or differently are zero, 1, 2, 3 or 4;

s is zero or 1;

t is 1, 2, 3 or 4;

R(12) and R(13) identically or differently are hydrogen, (C$_1$–C$_6$)-alkyl or, together with the carbon atom carrying them, are a (C$_3$–C$_8$)-cycloalkyl, R(13') is hydrogen or (C$_1$–C$_4$)-alkyl;

R(14) is H, (C$_1$–C$_6$)-alkyl, (C$_3$–C$_8$)-cycloalkyl or —C$_a$H$_{2a}$—R(15);

a is zero, 1, 2, 3 or 4;

R(15) is phenyl, which is unsubstituted or substituted by 1–3 substituents selected from the group consisting of F, Cl, CF$_3$, methyl, methoxy and NR(8)R(9);

R(8) and R(9) are H or (C$_1$–C$_4$)-alkyl;

or

R(15) is (C$_1$–C$_9$)-heteroaryl, which is unsubstituted or substituted as phenyl, or R(15) is (C$_1$–C$_6$)-alkyl, which is unsubstituted or substituted by 1–3 OH;

R(16), R(17), R(18), R(19) and R(20) are hydrogen or (C$_1$—C$_3$)-alkyl;

R(3) is defined as R(1), or

R(3) is (C$_1$–C$_6$)-alkyl or —X—R(22);

X is oxygen, S or NR(16);

R(16) is H or (C$_1$–C$_3$)-alkyl;

or

R(22) and R(16) together are 4 or 5 methylene groups, of which one CH$_2$ group can be replaced by oxygen, S, NH, N—CH$_3$ or N-benzyl;

R(22) is defined as R(14);

or a pharmaceutically tolerable salt thereof;

i) a benzoylguanidine of the formula

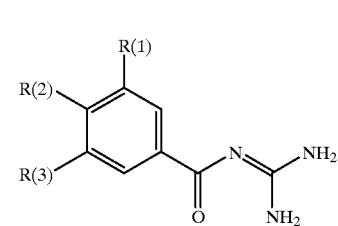

(I)

in which:

R(1) is hydrogen, F, Cl, Br, I, —NO$_2$, —C≡N, R(16)— C$_p$H$_{2p}$—O$_q$, R(4)—SO$_m$ or R(5)R(6)N—SO$_2$—;

m is zero, 1 or 2;

p is zero or 1;

q is zero, 1, 2 or 3;

R(16) is C$_r$F$_{2r+1}$;

r is 1, 2 or 3;

R(4) and R(5) are (C$_1$–C$_8$)-alkyl, (C$_3$–C$_6$)-alkenyl, —C$_n$H$_{2n}$—R(7) or CF$_3$;

n is zero, 1, 2, 3 or 4;

R(7) is (C$_3$–C$_7$)-cycloalkyl or phenyl, which is not substituted or is substituted by 1–3 substituents selected from the group consisting of F, Cl, CF$_3$, methyl, methoxy and NR(8)R(9);

R(8) and R(9) are H or C$_1$–C$_4$-alkyl;

or

R(5) is H;

R(6) is H or (C$_1$–C$_4$)-alkyl;

or

R(5) and R(6) together are 4 or 5 methylene groups, of which one CH$_2$ group can be replaced by oxygen, S, NH, N—CH$_3$ or N-benzyl, R(2) is (C$_1$—C$_9$)-heteroaryl, which is linked via C or N and which is unsubstituted or substituted by 1–3 substituents selected from the group consisting of F, Cl, CF$_3$, CH$_3$, methoxy, hydroxyl, amino, methylamino and dimethylamino;

or

R(2) is —SR(10), —OR(10), —NR(10)R(11), —CR(10)R(11)R(12);

R(10) is —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

a is zero, 1 or 2;

R(11) and R(12) independently of one another are defined as R(10) or are hydrogen or (C$_1$–C$_4$)-alkyl;

R(3) is defined as R(1), or is (C$_1$–C$_6$)-alkyl or —X—R(13);

X is oxygen, S, or NR(14);

R(14) is H or (C$_1$–C$_3$)-alkyl;

R(13) is H, (C$_1$–C$_6$)-alkyl, (C$_3$–C$_8$)-cycloalkyl or —C$_b$H$_{2b}$—R(15);

b is zero, 1 2, 3 or 4;

or

R(13) and R(14) together are 4 or 5 methylene groups, of which one CH$_2$ group can be replaced by oxygen, S, NH, N—CH$_3$ or N-benzyl;

R(15) is phenyl, which is unsubstituted or substituted by 1–3 substituents selected from the group consisting of F, Cl, CF$_3$, methyl, methoxy and NR(8)R(9);

R(8) and R(9) are H or (C$_1$–C$_4$)-alkyl;

or a pharmaceutically tolerable salt thereof;

k) a benzoylguanidine of the formula

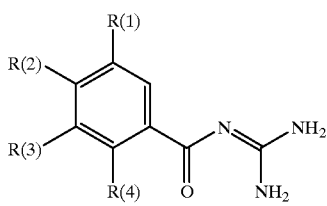

(I)

in which:

one of the substituents R(1), R(2), R(3) or R(4): is an amino group

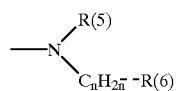

R(5) is hydrogen or C$_{(1-6)}$-alkyl;

n is zero, 1, 2, 3 or 4;

R(6) is H or C$_{(1-4)}$-alkyl;

in which one CH$_2$ group can be replaced by 1 sulfur atom or a group NR(7);

R(7) is hydrogen, methyl or ethyl;

or

R(6) is C$_{(3-8)}$-cycloalkyl or phenyl, which is unsubstituted or carries 1, 2 or 3 substituents selected from the group consisting of F, Cl, Br, methyl, methoxy, —NR(8)R(9);

R(8) and R(9) are H, methyl or ethyl;

or

R(5) and R(6) together with the nitrogen atom are a 5-, 6- or 7-membered ring, in which 1 carbon atom can be replaced by oxygen, S or NR(10);

R(10) is H, C$_{(1-3)}$-alkyl or benzyl;

and the other substituents R(1), R(2), R(3), R(4) in each case are:

hydrogen, F, Cl, Br, I, CN, CF$_3$, NO$_2$, CF$_3$—O—, C$_m$F$_{2m+1}$—CH$_2$—O— or R(11)— C$_q$H$_{2q}$—X$_p$—;

m is 1, 2 or 3;

q is zero, 1, 2, 3 or 4;

p is zero or 1;

X is oxygen or NR(12);

R(12) is H or C$_{(1-3)}$-alkyl;

R(11) is hydrogen, C$_{(1-6)}$-alkyl, C$_{(3-8)}$-cycloalkyl or phenyl, which is unsubstituted or substituted by 1, 2 or 3 substituents selected from the group consisting of F, Cl, CH$_3$, CH$_3$—O— and NR(13)R(14);

R(13) and R(14) are H, methyl or ethyl;

or a pharmaceutically tolerable salt thereof;

l) a benzoylguanidine of the formula

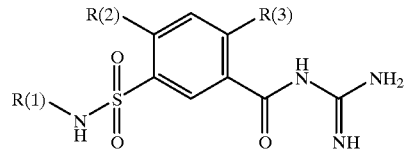

I in which

R(1) is R(4)R(5)N—C(X)—;

X is oxygen, S or N—R(6);

R(4) and R(5) identically or differently, are H, (C$_1$–C$_8$)-alkyl, (C$_3$–C$_6$)-alkenyl or —C$_n$H$_{2n}$—R(7);

n is zero, 1, 2, 3 or 4;

R(7) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl;

or

R(4) and R(5) together are 4 or 5 methylene groups, of which one CH$_2$ group can be replaced by oxygen, S, NH, N—CH$_3$ or N-benzyl;

R(6) is defined as R(4) or is amidine;

R(2) is H, F, Cl, Br, I, (C$_1$–C$_8$)-alkyl, 1-alkenyl or 1-alkynyl, (C$_3$–C$_8$)-cycloalkyl, (C$_3$–C$_8$)-cycloalkyl-(C$_1$–C$_4$)-alkyl, phenyl, C$_6$H$_5$-(C$_1$—C$_4$)-alkyl, naphthyl, biphenylyl, 1,1-diphenyl-(C$_1$–C$_4$)-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);

W is oxygen, S or NR(9);

R(8) is H, (C$_1$–C$_6$)-alkyl, (C$_5$–C$_7$)-cycloalkyl, cyclohexylmethyl, cyclopentylmethyl, —(CH$_2$)$_m$C$_p$F$_{2p+1}$ or —C$_q$H$_{2q}$—R(10);

m is zero or 1;

p is 1, 2 or 3;

q is zero, 1, 2, 3 or 4;

R(10) is phenyl, which is unsubstituted or substituted by 1–3 substituents selected from the group consisting of F, Cl, $CF_3$, methyl, methoxy and NR(11)R(12);

R(11) and R(12) are H or $(C_1-C_4)$-alkyl;

R(9) is H or $(C_1-C_3)$-alkyl;

or

R(8) and R(9) together are 4 or 5 methylene groups, of which one $CH_2$ group can be replaced by oxygen, S, NH, N—$CH_3$ or N-benzyl;

R(3) is H, F, Cl, Br, I, $(C_1-C_6)$-alkyl or —W—R(8) as defined for R(2), or a pharmaceutically acceptable salt thereof;

m) a benzoylguanidine of the formula

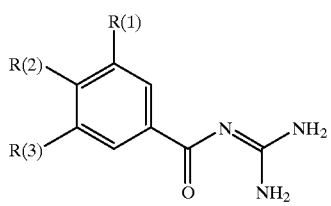

(I)

in which:

R(1), R(2), R(3)

are hydrogen, F, Cl, Br, I or $(C_1-C_{12})$-alkyl;

one of the substituents R(1), R(2) or R(3) is $N_3$, CN, OH or $(C_1-C_{10})$-alkyloxy, if at least one of the remaining substituents R(1), R(2) or R(3) is a sufficiently lipophilic alkyl radical having 3 to 12 carbon atoms;

or one of the substituents R(1), R(2) or R(3) is R(4)—$C_nH_{2n}$—$O_m$—;

m is zero or 1;

n is zero, 1, 2 or 3;

R(4) is $C_pF_{2p+1}$;

p is 1, 2 or 3, if n is zero or 1;

or

R(4) is $(C_3-C_{12})$-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);

R(5) and R(6) are hydrogen or $(C_1-C_4)$-alkyl;

or one of the substituents R(1), R(2) or R(3) is —C≡CR(5) or —C[R(6)]=CR(5);

R(5) is phenyl, which is unsubstituted or substituted by 1–3 substituents selected from the group consisting of F, Cl, $CF_3$, methyl, methoxy, hydroxyl, amino, methylamino and dimethylamino, $(C_1-C_9)$-heteroaryl, which is unsubstituted or substituted as phenyl, or R(5) is $(C_1-C_6)$-alkyl, which is unsubstituted or substituted by 1–3 OH;

or

R(5) is $(C_3-C_8)$-cycloalkyl,

R(6) is hydrogen or methyl;

or a pharmacologically acceptable salt thereof;

o) a benzoylguanidine of the formula

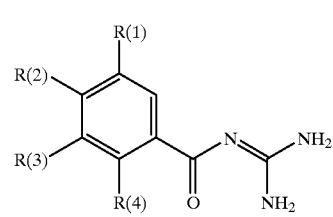

(I)

in which:

R(1) is hydrogen, F, Cl, Br, I, —$NO_2$, —C≡N, $X_o$—$(CH_2)_p$—$(CF_2)_q$—$CF_3$, R(5)—$SO_m$, R(6)—CO— or R(6)R(7)N—$SO_2$—, where X is oxygen, S or NR(14);

m is zero, 1 or 2;

O is zero or 1;

p is zero, 1 or 2;

q is zero, 1, 2, 3, 4, 5 or 6;

R(5) and R(6) are $(C_1-C_8)$-alkyl, $(C_3-C_6)$-alkenyl, —$C_nH_{2n}$—R(8) or $CF_3$;

n is zero, 1, 2, 3 or 4;

R(8) is $(C_3-C_7)$-cycloalkyl or phenyl, which is not substituted or is substituted by 1–3 substituents selected from the group consisting of F, Cl, $CF_3$, methyl, methoxy and NR(9)R(10);

R(9) and R(10) are H or $C_1-C_4$-alkyl;

or

R(6) is H;

R(7) is H or $(C_1-C_4)$-alkyl;

or

R(6) and R(7) together are 4 or 5 methylene groups, of which one $CH_2$ group can be replaced by oxygen, S, NH, N—$CH_3$ or N-benzyl;

R(2) is

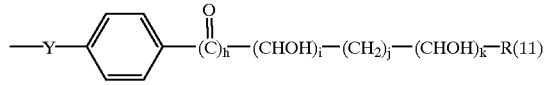

Y is oxygen, —S— or —NR(12)—;

R(11) and R(12) are hydrogen or $(C_1-C_3)$-alkyl;

h is zero or 1;

i, j and k independently are zero, 1, 2, 3 or 4;

but where h, i and k are not simultaneously zero,

R(3) is defined as R(1), or is $(C_1-C_6)$-alkyl or —X—R(13);

X is oxygen, S or NR(14);

R(14) is H or $(C_1-C_3)$-alkyl;

R(13) is H, $(C_1-C_6)$-alkyl, $(C_3-C_8)$-cycloalkyl or —$C_bH_{2b}$—R($^{15}$);

b is zero, 1, 2, 3 or 4;

or R(13) and R(14)

together are 4 or 5 methylene groups, where one $CH_2$ group can be replaced by oxygen, S, NH, N—$CH_3$ or N-benzyl;

R(15) is phenyl, which is unsubstituted or substituted by 1–3 substituents selected from the group consisting of F, Cl, CF$_3$, methyl, methoxy and NR(9)R(10);

R(9) and R(10) are H or (C$_1$–C$_4$)-alkyl;

R(4) is hydrogen, —OR(16) or —NR(16)R(17);

R(16) and R(17) independently are hydrogen or (C$_1$–C$_3$)-alkyl;

or a pharmaceutically tolerable salt thereof;

p) a benzoylguanidine of the formula

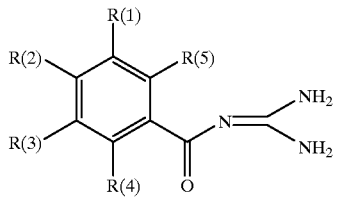

I in which:

R(1) is R(6)—CO or R(7)R(8)N—CO;

R(6) is (C$_1$–C$_8$)-alkyl, (C$_1$–C$_8$)-perfluoroalkyl, (C$_3$–C$_8$)-alkenyl or —C$_n$H$_{2n}$—R(9);

n is zero, 1, 2, 3 or 4;

R(9) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(10)R(11);

R(10) and R(11) are H, (C$_1$–C$_4$)-alkyl or (C$_1$–C$_4$)-perfluoroalkyl;

R(7) is H, (C$_1$–C$_8$)-alkyl, (C$_1$–C$_8$)-perfluoroalkyl, (C$_3$–C$_8$)-alkenyl or —C$_n$H2n—R(12);

n is zero, 1, 2, 3 or 4;

R(12) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(13)R(14);

R(13) and R(14) are H, (C$_1$–C$_4$)-alkyl or (C$_1$–C$_4$)-perfluoroalkyl;

R(8) is H, (C$_1$–C$_4$)-alkyl or (C$_1$–C$_4$)-perfluoroalkyl;

or

R(7) and R(8) together are 4 or 5 methylene groups, of which one CH$_2$ group can be replaced by oxygen, S, NH, N—CH$_3$ or N-benzyl;

R(2) is defined as R(1), or is H, F, Cl, Br, I, CN, NO$_2$, (C$_1$–C$_8$)-alkyl, (C$_1$–C$_8$)-perfluoroalkyl, (C$_3$–C$_8$)-alkenyl or —C$_n$H$_{2n}$R(15);

n is zero, 1, 2, 3 or 4;

R(15) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(16)R(17);

R(16) and R(17) are H, (C$_1$–C$_4$)-alkyl or (C$_1$–C$_4$)-perfluoroalkyl;

or

R(2) is (C$_1$–C$_9$)-heteroaryl, which is linked via C or N and which is unsubstituted or substituted by 1–3 substituents selected from the group consisting of F, Cl, CF$_3$, CH$_3$, methoxy, hydroxyl, amino, methylamino and dimethylamino;

or

R(2) is SR(18), —OR(18), —NR(18)R(19), —CR(18)R(19)R(20);

R(18) is —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

a is zero, 1 or 2;

R(19) and R(20) independently of one another are defined as R(18) or are hydrogen, (C$_1$–C$_4$)-alkyl or (C$_1$–C$_4$)-perfluoroalkyl;

or

R(2) is R(21)—SO$_m$ or R(22)R(23)N—SO$_2$—;

m is 1 or 2;

R(21) is (C$_1$–C$_8$)-alkyl, (C$_1$–C$_8$)-perfluoroalkyl, (C$_3$–C$_8$)-alkenyl, —C$_n$H$_{2n}$—R(24), n is zero, 1, 2, 3 or 4;

R(24) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(27)R(28);

R(27) and R(28) are H, (C$_1$–C$_4$)-alkyl or (C$_1$–C$_4$)-perfluoroalkyl;

R(22) is H, (C$_1$–C$_8$)-alkyl, (C$_1$–C$_8$)-perfluoroalkyl, (C$_3$–C$_8$)-alkenyl, —C$_n$H$_{2n}$—R(29);

n is zero, 1, 2, 3 or 4;

R(29) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(30)R(31);

R(30) and R(31) are H, (C$_1$–C$_4$)-alkyl or (C$_1$–C$_4$)-perfluoroalkyl;

R(23) is H, (C$_1$–C$_4$)-alkyl or (C$_1$–C$_4$)-perfluoroalkyl;

or

R(22) and R(23) together are 4 or 5 methylene groups, of which one CH$_2$ group can be replaced by oxygen, S, NH, N—CH$_3$ or N-benzyl;

or

R(2) is R(33)X—;

x is oxygen, S, NR(34), (D=O)A—, NR(34)C=MN(*)R(35)—;

M is oxygen or S;

A is oxygen or NR(34);

D is C or SO;

R(33) is (C$_1$–C$_8$)-alkyl, (C$_3$–C$_8$)-alkenyl, (CH$_2$)$_b$C$_d$F$_{2d+1}$, —C$_n$H$_{2n}$—R(36), b is zero or 1;

d is 1, 2, 3, 4, 5, 6 or 7;

n is zero, 1, 2, 3 or 4;

R(36) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(37)R(38);

R(37) and R(38) are H, (C$_1$–C$_4$)-alkyl or (C$_1$–C$_4$)-perfluoroalkyl;

R(34) is H, (C$_1$–C$_4$)-alkyl or (C$_1$–C$_4$)-perfluoroalkyl;

R(35) is defined as R(33);

or

R(33) and R(34) together are 4 or 5 methylene groups, of which one CH$_2$ group can be replaced by oxygen, S, NH, N—CH₃ or N-benzyl; where A and N(*) are bonded to the phenyl nucleus of the benzoylguanidine parent structure;

or

R(2) is —SR(40), —OR(40), —NHR(40), —NR(40)R(41), —CHR(40)R(42), —C[R(42)R(43)OH], —C≡CR(45), —CR(46)=CHR(45), —[CR(47)R(48)]$_u$—(CO)—[CR(49)R(50)]$_v$,—R(44);

R(40), R(41) identically or differently are —(CH$_2$)$_p$—(CHOH)$_q$—(CH$_2$)$_r$—(CHOH)$_t$—R(51) or —(CH$_2$)$_p$—O—(CH$_2$—CH$_2$O)$_q$—R(51);

R(51) is hydrogen or methyl;

u is 1, 2, 3 or 4;

v is zero, 1, 2, 3 or 4;

p, q, r identically or differently are zero, 1, 2, 3 or 4;

t is 1, 2, 3 or 4;

R(42) and R(43) identically or differently are hydrogen or (C$_1$–C$_6$)-alkyl;

or

R(42) and R(43) together with the carbon atom carrying them form a (C$_3$–C$_8$)-cycloalkyl;

R(44) is H, (C$_1$–C$_6$)-alkyl, (C$_3$–C$_8$)-cycloalkyl or —C$_e$H$_{2e}$—R(45);

e is zero, 1, 2, 3 or 4;

R(45) is phenyl, which is unsubstituted or substituted by 1–3 substituents from the group consisting of F, Cl, CF$_3$, methyl, methoxy and NR(52)R(53) where R(52) and R(53) are H or (C$_1$–C$_4$)-alkyl, or R(45) is (C$_1$–C$_9$)-heteroaryl, which is unsubstituted or substituted as phenyl;

or

R(45) is (C$_1$–C$_6$)-alkyl, which is unsubstituted or substituted by 1–3 OH;

R(46), R(47), R(48), R(49) and R(50) are hydrogen or methyl;

or

R(2) is R(55)—NH—SO$_2$—;

R(55) is R(56)R(57)N—(C=Y)—;

Y is oxygen, S or N—R(58);

R(56) and R(57) identically or differently are H, (C$_1$–C$_8$)-alkyl, (C$_3$–C$_6$)-alkenyl or —C$_f$H$_{2f}$—R(59);

f is zero, 1, 2, 3 or 4;

R(59) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl;

or

R(56) and R(57) together are 4 or 5 methylene groups, of which one CH$_2$ group can be replaced by oxygen, S, NH, N—CH$_3$ or N-benzyl;

R(58) is defined as R(56) or is amidine;

R(3), R(4) and R(5) independently of one another are defined as R(1) or R(2);

or a pharmaceutically tolerable salt thereof;

q) a benzoylguanidine of the formula

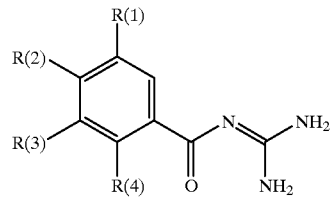

(I)

in which:

R(1) is hydrogen, F, Cl, Br, I, —NO$_2$, —C≡N, —X$_o$—(CH$_2$)$_p$—(CF$_2$)$_q$—CF$_3$, R(5)—SO$_m$—, R(6)—CO—, R(6)R(7)N—CO— or R(6)R(7)N—SO$_2$—;

X is oxygen, —S— or NR(14);

m is zero, 1 or 2;

o is zero or 1;

p is zero, 1 or 2;

q is zero, 1, 2, 3, 4, 5 or 6;

R(5) and R(6) are (C$_1$–C$_8$)-alkyl, (C$_3$–C$_6$)-alkenyl, —C$_n$H$_{2n}$—R(8) or CF$_3$;

n is zero, 1, 2, 3 or 4;

R(8) is (C$_3$–C$_7$)-cycloalkyl, phenyl, which is not substituted or is substituted by 1 to 3 substituents selected from the group consisting of F, Cl, CF$_3$, methyl, methoxy and NR(9)R(10);

R(9) and R(10) are H or (C$_1$–C$_4$)-alkyl;

or

R(6) is hydrogen;

R(7) is hydrogen or (C$_1$–C$_4$)-alkyl;

or

R(6) and R(7) together are 4 or 5 methylene groups, of which one CH$_2$ group can be replaced by oxygen, S, NH, N—CH$_3$ or N-benzyl;

R(2) is

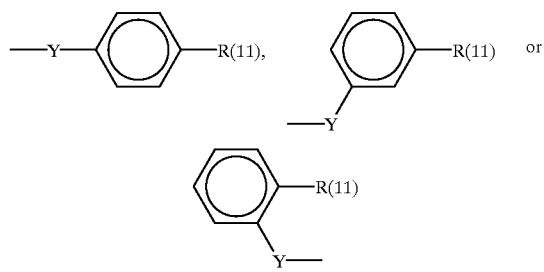

R(11) is (C$_1$–C$_9$)-heteroaryl, which is linked via C or N and which is unsubstituted or substituted by 1 to 3 substituents selected from the group consisting of F, Cl, CF$_3$, CH$_3$, methoxy, hydroxyl, amino, methylamino, dimethylamino and benzyl;

Y is oxygen, —S— or NR(12);

R(12) is H or (C$_1$–C$_4$)-alkyl;

R(3) is defined as R(1);

or

R(3) is (C$_1$–C$_6$)-alkyl or —X—R(13);

X is oxygen, —S— or NR(14);

R(14) is H or (C$_1$–C$_3$)-alkyl;

R(13) is H, $(C_1-C_6)$-alkyl, $(C_3-C_8)$-cycloalkyl or
—$C_bH_{2b}$—R(15);

b is zero, 1, 2, 3 or 4;

or

R(13) and R(14) together are 4 or 5 methylene groups, of which one $CH_2$ group can be replaced by oxygen, S, NH, N—$CH_3$ or N-benzyl;

R(15) is phenyl, which is unsubstituted or substituted by 1–3 substituents selected from the group consisting of F, Cl, $CF_3$, methyl, methoxy and NR(9)R(10);

R(9) and R(10) are H or $(C_1-C_4)$-alkyl;

R(4) is hydrogen, —OR(16), —NR(16)R(17) or $C_rF_{2r+1}$;

R(16) and R(17) independently are hydrogen or $(C_1-C_3)$-alkyl;

r is 1, 2, 3 or 4;

or a pharmaceutically tolerable salt thereof;

r) a benzo-fused 5-membered ring heterocycle of the formula

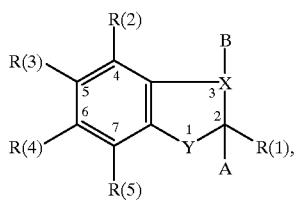

(I)

in which:

X is N or CR(6);

Y is oxygen, S or NR(7);

A, B together are a bond or

A, B are both hydrogen, if X is CR(6) and Y is NR(7) simultaneously; one of the substituents R(1) to R(6) is a —CO—N=C(NH$_2$)$_2$ group;

the other substituents R(1) to R(6) in each case are hydrogen, F, Cl, Br, I or $(C_1-C_6)$-alkyl;

up to two of the other substituents R(1) to R(6) are CN, NO$_2$, N$_3$, $(C_1-C_4)$-alkyloxy or CF$_3$;

up to one of the other substituents is R(8)—$C_nH_{2n}$—Z—;

n is zero to 10;

where the alkylene chain —$C_nH_{2n}$— is straight-chain or branched and where one carbon atom can be replaced by an oxygen or sulfur atom or by a nitrogen atom;

R(8) is hydrogen, $(C_2-C_6)$-alkenyl or $(C_3-C_{10})$-cycloalkyl, which is unsubstituted or substituted by 1 to 4 methyl groups or an OH group, or can contain an ethylene group —CH=CH—, and in which one methylene group can be replaced by an oxygen or sulfur atom or by a nitrogen atom;

or

R(8) is phenyl, which is unsubstituted or substituted by 1 to 3 substituents selected from the group consisting of F, Cl, Br, I, CF$_3$, CH$_3$—S(O)S— or R(9)—W$_y$—;

s is zero, 1 or 2;

R(9) is H, methyl, ethyl,

W is oxygen or NR(10);

R(10) is H or methyl;

y is zero or 1;

or

R(8) is $C_mF_{2m+1}$;

m is 1 to 3;

or

R(8) is 1- or 2-naphthyl, pyridyl, quinolyl or isoquinolyl;

Z is —CO—, —CH$_2$— or —[CR(11)(OH)]$_q$—;

q is 1, 2 or 3;

R(11) is H or methyl;

or

Z is oxygen or —NR(12)—;

R(12) is H or methyl;

or z is —S(O)$_s$—;

s is zero, 1 or 2;

or

Z is —SO$_2$—NR(13)—;

R(13) is H or $(C_1-C_4)$-alkyl;

R(7) is hydrogen, $(C_1-C_{10})$-alkyl, $(C_2-C_{10})$-alkenyl or R(8)—$C_nH_{2n}$—;

or a pharmaceutically tolerable salt thereof;

s) a benzoylguanidine of the formula

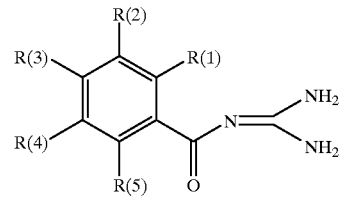

(I)

in which:

R(1), R(3) or R(4) is —NR(6) C=X NR(7)R(8);

x is oxygen or S;

R(6) is hydrogen, $(C_1-C_8)$-alkyl, $(C_1-C_8)$-perfluoroalkyl, $(C_3-C_8)$-alkenyl or —$C_nH_{2n}$—R(9);

n is zero, 1, 2, 3 or 4;

R(9) is $(C_3-C_8)$-cycloalkyl, phenyl, biphenylyl or naphthyl, where the aromatics are not substituted or are substituted by 1–3 substituents selected from the group consisting of F, Cl, CF$_3$, methyl, methoxy and NR(10)R(11);

R(10) and R(11) are H, $(C_1-C_4)$-alkyl or $(C_1-C_4)$-perfluoroalkyl;

R(7) is hydrogen, $(C_1-C_8)$-alkyl, $(C_1-C_8)$-perfluoroalkyl, $(C_3-C_8)$-alkenyl or —$C_oH_{2o}$—R(12);

o is zero, 1, 2, 3 or 4;

R(12) is $(C_3-C_8)$-cycloalkyl, phenyl, biphenylyl or naphthyl, where the aromatics are not substituted or are substituted by 1–3 substituents selected from the group consisting of F, Cl, CF$_3$, methyl, methoxy and NR(13)R(14);

R(13) and R(14) are H, $(C_1-C_4)$-alkyl or $(C_1-C_4)$-perfluoroalkyl;

R(8) is defined as R(7);

or

R(7) and R(8) together are 4 or 5 methylene groups, of which one CH$_2$ group can be replaced by oxygen, S, NH, N—CH$_3$ or N-benzyl;

the remaining substituents R(2), R(3), R(4), R(5) or R(1), R(2), R(4), R(5) or R(1), R(2), R(3), R(5) in each case independently of one another are hydrogen, F, Cl, Br, I, —$O_{ta}(C_1-C_8)$-alkyl, —$O_{tb}(C_3-C_8)$-alkenyl, —$O_{tc}$ $(CH_2)_b C_d F_{2d+1}$, —$O_{td} C_p H_{2p} R(18)$, or up to 2 groups CN, $NO_2$, NR(16)R(17), b is zero or 1;

d is 1, 2, 3, 4, 5, 6 or 7;

ta is zero or 1;

tb is zero or 1;

tc is zero or 1;

td is zero or 1;

p is zero, 1, 2, 3 or 4;

R(18) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(19)R(20);

R(19) and R(20) are hydrogen or $(C_1-C_4)$-alkyl or $(C_1-C_4)$-perfluoroalkyl;

R(16) is hydrogen, $(C_1-C_8)$-alkyl, $(C_1-C_8)$-perfluoroalkyl, $(C_3-C_8)$-alkenyl, —$C_q H_{2q}$—R(21), q is zero, 1, 2, 3 or 4;

R(21) is $(C_3-C_8)$-cycloalkyl, phenyl, biphenylyl or naphthyl, where the aromatics are not substituted or are substituted by 1–3 substituents from the group F, Cl, $CF_3$, methyl, methoxy or NR(22)R(23), R(22) and R(23) are hydrogen, $(C_1-C_4)$-alkyl or $(C1-C_4)$-perfluoroalkyl;

R(17) is hydrogen, $(C_1-C_8)$-alkyl, $(C_1-C_8)$-perfluoroalkyl, $(C_3-C_8)$-alkenyl, —$C_r H_{2r}$—R(24);

r is zero, 1, 2, 3 or 4;

R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(25)R(26);

R(25) and R(26) are hydrogen, $(C_1-C_4)$-alkyl or $(C_1-C_4)$-perfluoroalkyl;

or

R(16) and R(17) together are 4 or 5 methylene groups, of which one $CH_2$ group can be replaced by oxygen, S, NH, N—$CH_3$ or N-benzyl;

or a pharmaceutically tolerable salt thereof;

t) a diacyl-substituted guanidine of the formula

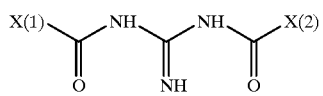

I in which:

X(1) and X(2) are

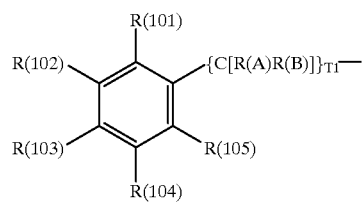

T1 is zero, 1, 2, 3 or 4;

R(A) and R(B) independently of one another are hydrogen, F, Cl, Br, I, CN, OR(106), $(C_1-C_8)$-alkyl, $(C_3-C_8)$-cycloalkyl, $O_{zk}(CH_2)_{z1} C_{zm} F_{2zm+1}$, NR(107)R(108), phenyl or benzyl, where the aromatics are not substituted or are substituted by 1–3 substituents selected from the group consisting of F, Cl, $CF_3$, methyl, methoxy and NR(109)R(110);

R(109) and R(110) are hydrogen, $(C_1-C_4)$-alkyl or $(C_1-C_4)$-perfluoroalkyl;

zl is zero, 1, 2, 3 or 4;

zk is zero or 1;

zm is 1, 2, 3, 4, 5, 6, 7 or 8;

R(106) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(111)R(112);

R(111) and R(112) are hydrogen, $(C_1-C_4)$-alkyl or $(C_1-C_4)$-perfluoroalkyl;

R(107) and R(108) independently of one another are defined as R(106), or

R(107) and R(108) together are 4 or 5 methylene groups, of which one $CH_2$ group can be replaced by oxygen, S, NH, N—$CH_3$ or N-benzyl;

or

X(1) and X(2) are

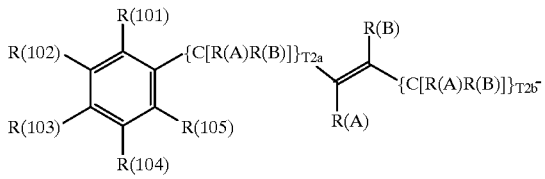

T2a and T2b independently of one another are zero, 1 or 2; where the double bond can have the (E)— or (Z)-configuration;

or

X(1) and X(2) are

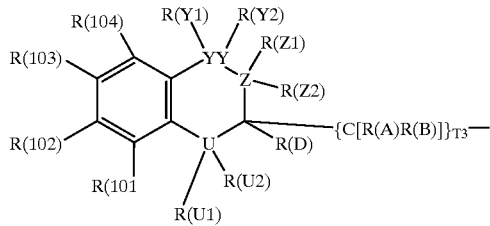

T3 is zero, 1 or 2;

U, YY and Z independently of one another are C or N, where U, YY, Z can carry the following number of substituents:

| U, YY or Z | Bonded in the ring to a double bond | Number of permitted substituents |
|---|---|---|
| C | yes | 1 |
| C | no | 2 |
| N | yes | 0 |
| N | no | 1 |

R(D) is hydrogen, $(C_1-C_8)$-alkyl or $(C_1-C_8)$-perfluoroalkyl, R(U1), R(U2), R(Y1), R(Y2), R(Z1), R(Z2) independently of one another are hydrogen, F, Cl, Br, I, CN, OR(114), $(C_1-C_8)$-alkyl, $(C_3-C_8)$-cycloalkyl, $O_{zka}(CH_2)_{zla}C_{zma}F_{2zma+1}$, NR(115)R(116), phenyl or benzyl, where the aromatics are not substituted or are substituted by 1–3 substituents selected from the group consisting of F, Cl, $CF_3$, methyl, methoxy, NR(117)R(118), R(117) and R(118) are hydrogen, $(C_1-C_4)$-alkyl or $(C_1-C_4)$-perfluoroalkyl, zka is zero or 1;
zla is zero, 1, 2, 3 or 4;
zma is 1, 2, 3, 4, 5, 6, 7 or 8;

R(114) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(119)R(120);

R(119) and R(120) are hydrogen, $(C_1-C_4)$-alkyl or $(C_1-C_4)$-perfluoroalkyl;

R(115) and R(116) independently of one another are defined as R(114);

or

R(115) and R(116) together are 4 or 5 methylene groups, of which one $CH_2$ group can be replaced by oxygen, S, NH, N—$CH_3$ or N-benzyl;

but where the constitution of U is nitrogen (N), YY is nitrogen (N) and Z is carbon (C) is excluded, R(101), R(102), R(103), R(104) and R(105) independently of one another are hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(1110c)N—CO, R(111a)—CO— or R(112a)R(113a)N—$SO_2$—, where the perfluoroalkyl group is straight-chain or branched, X is oxygen, S or NR(114a);
R(114a) is H or $(C_1-C_3)$-alkyl;
zoa is zero or 1;
zbm is zero, 1 or 2;
zpa is zero, 1, 2, 3 or 4;
zqa is 1, 2, 3, 4, 5, 6, 7 or 8;

R(110a), R(1110b), R(111a) and R(112a) independently of one another are $(C_1-C_8)$-alkyl, $(C_3-C_8)$-alkenyl, —$C_{zn}H_{2zn}$—R(115a) or $(C_1-C_8)$-perfluoroalkyl;

zn is zero, 1, 2, 3 or 4;

R(115a) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(116a)R(117a);

R(116a) and R(117a) are hydrogen, $(C_1-C_4)$-perfluoroalkyl or $(C_1-C_4)$-alkyl;

or

R(1110b), R(111a) and R(112a) are hydrogen;

R(110c) and R(113a) independently are hydrogen, $(C_1-C_4)$-perfluoroalkyl or $(C_1-C_4)$-alkyl;

or

R(1110b) and R(110c) and R(112a) and R(113a) together are 4 or 5 methylene groups, of which one $CH_2$ group can be replaced by oxygen, sulfur, NH, N—$CH_3$ or N-benzyl;

or

R(101), R(102), R(103), R(104), R(105) independently of one another are $(C_1-C_8)$-alkyl, —$C_{za1}H_{2za1}$R(118a) or $(C_3-C_8)$-alkenyl, za1 is zero, 1, 2, 3 or 4;

R(118a) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy or NR(119a)R(119b);

R(119a) and R(119b) are hydrogen, $(C_1-C_4)$-alkyl or $(C_1-C_4)$-perfluoroalkyl;

or

R(101), R(102), R(103), R(104), R(105) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino and dimethylamino;

or

R(101), R(102), R(103), R(104), R(105) independently of one another are —C≡C—R(193);

R(193) is phenyl which is not substituted or is substituted by 1–3 substituents from the group consisting of F, Cl, $CF_3$, methyl, methoxy or NR(194)R(195);

R(194) and R(195) are hydrogen or $CH_3$;

or

R(101), R(102), R(103), R(104), R(105) independently of one another are —Y—para—$C_6H_4$—$(CO)_{zh}$—$(CHOH)_{zi}$—$(CH_2)_{zj}$—$(CHOH)_{zk}$—R(123), —Y—meta—$C_6H_4$—$(CO)_{zad}$—$(CHOH)_{zae}$—$(CH_2)_{zaf}$—$(CHOH)_{zag}$—R(124)

or

—Y—ortho—$C_6H_4$—$(CO)_{zah}$—$(CHOH)_{zao}$—$(CH_2)_{zap}$—$(CHOH)_{zak}$—R(125);

Y is oxygen, —S— or —NR(122d)—;

zh, zad, zah independently are zero or 1;

zi, zj, zk, zae, zaf, zag, zao, zap and zak independently are zero, 1, 2, 3 or 4;

but where in each case zh, zi and zk are not simultaneously zero, zad, zae and zag are not simultaneously zero, and zah, zao and zak are not simultaneously zero, R(123), R(124), R(125) and R(122d) independently are hydrogen or $(C_1-C_3)$-alkyl;

or

R(101), R(102), R(103), R(104) and R(105) independently of one another are SR(129), —OR(130), —NR(131)R(132) or —CR(133)R(134)R(135);

R(129), R(130), R(131) and R(133) independently are —$C_{zab}H_{2zab}$—$(C_1-C_9)$-heteroaryl, which is unsubstituted or substituted by 1–3 substituents from the group consisting of F, Cl, $CF_3$, $CH_3$, methoxy, hydroxyl, amino, methylamino and dimethylamino;

zab is zero, 1 or 2;

R(132), R(134) and R(135) independently of one another are defined as R(129) or are hydrogen, $(C_1-C_4)$-alkyl or $(C_1-C_4)$-perfluoroalkyl;

or

R(101), R(102), R(103), R(104) and R(105) independently of one another are —W—para—$(C_6H_4)$—R(196), —W—meta—$(C_6H_4)$—R(197) or —W—ortho—$(C_6H_4)$—R(198);

R(196), R(197) and R(198) independently are $(C_1-C_9)$-heteroaryl, which is linked via C or N and which is unsubstituted or substituted by 1 to 3 substituents from the group consisting of F, Cl, $CF_3$, $CH_3$, methoxy, hydroxyl, amino, methylamino, dimethylamino and benzyl;

W is oxygen, S or NR(136)—;

R(136) is hydrogen or $(C_1-C_4)$-alkyl;

or

R(101), R(102), R(103), R(104) and R(105) independently of one another are R(146)X(1a)—;

X(1a) is oxygen, S, NR(147), (D=O)A—, NR(148)C=MN(*)R(149)—;

M is oxygen or sulfur;

A is oxygen or NR(150);

D is C or SO;

R(146) is $(C_1-C_8)$-alkyl, $(C_3-C_8)$-alkenyl, $(CH_2)_{zbz}C_{zdz}F_{2zdz+1}$ or —$C_{zxa}H_{2zxa}$—R(151);

zbz is zero or 1;

zdz is 1, 2, 3, 4, 5, 6 or 7;

zxa is zero, 1, 2, 3 or 4;

R(151) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy and NR(152)R(153);

R(152) and R(153) are hydrogen, $(C_1-C_4)$-alkyl or $(C_1-C_4)$-perfluoroalkyl;

R(147), R(148) and R(150) independently are hydrogen, $(C_1-C_4)$-alkyl, $(C_1-C_4)$-perfluoroalkyl;

R(149) is defined as R(146), or

R(146) and R(147), or R(146) and R(148) together are 4 or 5 methylene groups, of which one $CH_2$ group can be replaced by oxygen, sulfur, NH, N—$CH_3$ or N-benzyl;

where A and N(*) are bonded to the phenyl nucleus of the alkanoyl parent structure;

or

R(101), R(102), R(103), R(104) and R(105) independently of one another are —SR(164), —OR(165), —NHR(166), —NR(167)R(168), —CHR(169)R(170), —CR(154)R(155)OH, —C≡CR(156), —CR(158)=CR(157) or —[CR(159)R(160)]$_{zu}$—(C=O)—[CR(161)R(162)]$_{zv}$—R(163);

R(164), R(165), R(166), R(167), R(169) identically or differently are —$(CH_2)_{zy}$—$(CHOH)_{zz}$—$(CH_2)_{zaa}$—$(CHOH)_{zt}$—R(171) or —$(CH_2)_{zab}$—O—$(CH_2$—$CH_2O)_{zac}$—R(172);

R(171) and R(172) are hydrogen or methyl;

zu is 1, 2, 3 or 4;

zv is zero, 1, 2, 3 or 4;

zy, zz, zaa, zab, zac identically or differently are zero, 1, 2, 3 or 4;

zt is 1, 2, 3 or 4;

R(168), R(170), R(154), R(155) identically or differently are hydrogen or $(C_1-C_6)$-alkyl, or R(169) and R(170), or R(154) and R(155) together with the carbon atom carrying them are a $(C_3-C_8)$-cycloalkyl;

R(163) is hydrogen, $(C_1-C_6)$-alkyl, $(C_3-C_8)$-cycloalkyl or —$C_{zeb}H_{2zeb}$—R(173);

zeb is zero, 1, 2, 3 or 4;

R(156), R(157) and R(173) independently are phenyl which is unsubstituted or is substituted by 1–3 substituents from the group consisting of F, Cl, $CF_3$, methyl, methoxy and NR(174)R(175);

R(174) and R(175) are hydrogen or $(C_1-C_4)$-alkyl;

or

R(156), R(157) and R(173) independently are $(C_1-C_9)$-heteroaryl, which is unsubstituted or substituted as phenyl;

R(158), R(159), R(160), R(161) and R(162) are hydrogen or methyl, or

R(101), R(102), R(103), R(104), R(105) independently of one another are R(176)—NH—$SO_2$—;

R(1 76) is R(177)R(178)N—(C=Y')—;

Y' is oxygen, S or N—R(179);

R(177) and R(178) identically or differently are hydrogen, $(C_1-C_8)$-alkyl, $(C_3-C_6)$-alkenyl or —$C_{zfa}H_{2zfa}$—R(180);

zfa is zero, 1, 2, 3 or 4;

R(180) is $(C_5-C_7)$-cycloalkyl or phenyl, which is unsubstituted or substituted by 1–3 substituents selected from the group consisting of F, Cl, $CF_3$, methoxy or $(C_1-C_4)$-alkyl;

or

R(177) and R(178) together are 4 or 5 methylene groups, of which one $CH_2$ group can be replaced by oxygen, sulfur, NH, N—$CH_3$ or N-benzyl;

R(179) is defined as R(177) or is amidine, or

R(101), R(102), R(103), R(104), R(105) independently of one another are NR(184a)R(185), OR(184b), SR(184c) or —$C_{znx}H_{2znx}$—R(184d);

znx is zero, 1, 2, 3 or 4;

R(184d) is ($C_3$–$C_7$)-cycloalkyl or phenyl, which is not substituted or is substituted by 1–3 substituents from the group consisting of F, Cl, $CF_3$, methyl, methoxy and NR(116k)R(117k);

R(116k) and R(117k) are hydrogen or $C_1$–$C_4$-alkyl;

R(184a), R(184b), R(184c), R(185) independently of one another are hydrogen, ($C_1$–$C_8$)-alkyl, ($C_1$–$C_8$)-perfluoroalkyl or $(CH_2)_{zao}$—R(184g);

zao is zero, 1, 2, 3 or 4;

184g is ($C_3$–$C_7$)-cycloalkyl or phenyl, which is not substituted or is substituted by 1–3 substituents from the group consisting of F, Cl, $CF_3$, methyl, methoxy and N R(184u) R(184v);

R(184u) and R(184v) are hydrogen or $C_1$–$C_4$-alkyl;

or R(184a) and R(185) together are 4 or 5 methylene groups, of which one $CH_2$ group can be replaced by oxygen, sulfur, NH, N—$CH_3$ or N-benzyl;

or a pharmaceutically tolerable salt thereof;

u) a benzoylguanidine of the formula

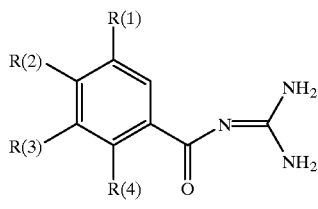

in which:

R(1) is H, F, Cl, Br, I, CN, $NO_2$, ($C_1$–$C_8$)-alkyl, ($C_3$–$C_8$)-cycloalkyl or $X_a$—$(CH_2)_b$—$(CF_2)_c$—$CF_3$;

X is oxygen, S or NR(5);

a is zero or 1;

b is zero, 1 or 2;

c is zero, 1, 2 or 3;

R(5) is H, ($C_1$–$C_4$)-alkyl or —$C_dH_{2d}R(6)$;

d is zero, 1, 2, 3 or 4;

R(6) is ($C_3$–$C_8$)-cycloalkyl, phenyl, biphenylyl or naphthyl, where the aromatics are not substituted or are substituted by 1 to 3 substituents selected from the group consisting of F, Cl, $CF_3$, methyl, methoxy and NR(7)R(8);

R(7) and R(8) independently are H or ($C_1$–$C_4$)-alkyl;

or

R(1) is —SR(10), —OR(10) or —CR(10)R(11)R(12);

R(10) is —$C_fH_{2f}$—($C_3$–$C_8$)-cycloalkyl, —($C_1$–$C_9$)-heteroaryl or phenyl,
where the aromatic systems are unsubstituted or substituted by 1 to 3 substituents selected from the group consisting of F, Cl, $CF_3$, $CH_3$, methoxy, hydroxyl, amino, methylamino and dimethylamino;

f is zero, 1 or 2;

R(11) and R(12) independently of one another are defined as R(10) or are hydrogen or ($C_1$–$C_4$)-alkyl;

or

R(1) is phenyl, naphthyl, biphenylyl or ($C_1$–$C_9$)-heteroaryl, the latter linked via C or N, and which are unsubstituted or substituted by 1 to 3 substituents selected from the group consisting of F, Cl, $CF_3$, $CH_3$, methoxy, hydroxyl, amino, methylamino and dimethylamino;

or

R(1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)—[CR(22)R(23)R(24)],

R(13) and R(14) identically or differently are —$(CH_2)_g$—$(CHOH)_h$—$(CH_2)_i$—$(CHOH)_j$—R(17), R(17) is hydrogen or methyl;

—$(CH_2)_g$—O—$(CH_2$—$CH_2O)_h$—R(24), g, h, i identically or differently are zero, 1, 2, 3 or 4;

is 1, 2, 3 or 4;

R(15) and R(16) identically or differently are hydrogen, ($C_1$–$C_6$)-alkyl or together with the carbon atom carrying them are a ($C_3$–$C_8$)-cycloalkyl;

R(18) is phenyl, which is unsubstituted or substituted by 1 to 3 substituents selected from the group consisting of F, Cl, $CF_3$, methyl, methoxy and NR(25)R(26);

R(25) and R(26) are H or ($C_1$–$C_4$)-alkyl;

or

R(18) is ($C_1$–$C_9$)-heteroaryl, which is unsubstituted or substituted as phenyl;

or

R(18) is ($C_1$–$C_6$)-alkyl, which is unsubstituted or substituted by 1 to 3 OH;

or

R(18) is ($C_3$–$C_8$)-cycloalkyl;

R(19), R(20), R(21), R(22) and R(23) are hydrogen or methyl;

k is zero, 1, 2, 3 or 4;

l is zero, 1, 2, 3 or 4;

R(24) is H, ($C_1$–$C_6$)-alkyl, ($C_3$–$C_8$)-cycloalkyl or —$C_mH_{2m}$—R(18);

m is 1, 2, 3 or 4;

R(2) and R(3) independently of one another are defined as R(1);

R(4) is ($C_1$–$C_3$)-alkyl, F, Cl, Br, I, CN or —$(CH_2)_n$—$(CF_2)_o$—$CF_3$;

n is zero or 1;

o is zero, 1 or 2;

or a pharmaceutically tolerable salt thereof;

v) an acylguanidine of the formula

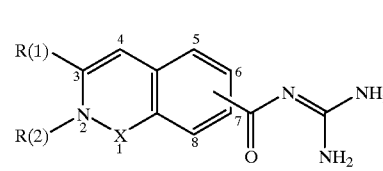

(I)

in which:

X is carbonyl, sulfonyl,

R(1) is H, ($C_1$–$C_8$)-alkyl, unsubstituted or substituted by hydroxyl, ($C_3$–$C_8$)-cycloalkyl, phenyl, which is unsubstituted or substituted by 1–3 substituents from the group F, Cl, $CF_3$, $CH_3$, methoxy, hydroxyl, amino, methylamino or dimethylamino, R(2) is H, ($C_1$–$C_4$)-alkyl, or a pharmaceutically tolerable salt thereof;

w) a phenyl-substituted alkylcarboxylic acid guanidide, carrying perfluoroalkyl groups, of the formula

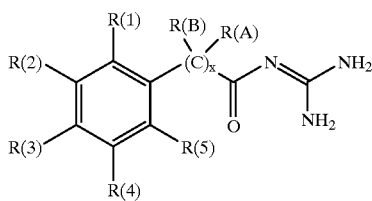
(I)

in which:

R(A) is hydrogen, F, Cl, Br, I, CN, OR(6), $(C_1-C_8)$-alkyl, $(C_3-C_8)$-cycloalkyl, $O_r(CH_2)_a C_b F_{2b+1}$ or NR(7)R(8);

r is zero or 1;

a is zero, 1, 2, 3 or 4;

b is 1, 2, 3, 4, 5, 6, 7 or 8;

R(6) is hydrogen, $(C_1-C_8)$-alkyl, $(C_3-C_8)$-alkenyl, $(C_3-C_8)$-cycloalkyl, phenyl or benzyl,
where the aromatics are not substituted or are substituted by 1–3 substituents selected from the group consisting of F, Cl, $CF_3$, methyl, methoxy and NR(9)R(10);

R(9) and R(10) are H, $(C_1-C_4)$-alkyl or $(C_1-C_4)$-perfluoroalkyl;

R(7) and R(8) independently of one another are defined as R(6);

R(B) independently is defined as R(A);

X is 1, 2 or 3;

R(1) is hydrogen, $(C_1-C_8)$-alkyl, $(C_3-C_8)$-cycloalkyl, $-O_t(CH_2)_d C_e F_{2e+1}$, F, Cl, Br, I or CN;

t is zero or 1;

d is zero, 1, 2 or 3 or 4;

e is 1, 2, 3, 4, 5, 6, 7 or 8;

R(2), R(3), R(4) and R(5) independently of one another are defined as R(1);

but with the condition that at least one of the substituents R(1I), R(2), R(3), R(4), R(5), R(A) and R(B) is an $-O_t(CH_2)_d C_e F_{2e+i}$ or an $O_r(CH_2)_a C_b F_{2b+1}$ group, or a pharmaceutically tolerable salt thereof;

x) a heteroaroylguanidine of the formula

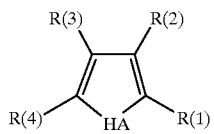
I in which:

HA is $SO_m$, O or NR(5);

m is zero, 1 or 2;

R(5) is hydrogen, $(C_1-C_8)$-alkyl or $-C_{am}H_{2am}R(81)$;

am is zero, 1 or 2;

R(81) is $(C_3-C_8)$-cycloalkyl or phenyl, which is not substituted or is substituted by 1–3 substituents selected from the group consisting of F, Cl, $CF_3$, methyl, methoxy and NR(82)R(83);

R(82) and R(83) is H or $CH_3$;

or

R(81) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

one of the two substituents R(1) and R(2) is $-CO-N=C(NH_2)_2$;

and the other in each case is hydrogen, F, Cl, Br, I, $(C_1-C_3)$-alkyl, $-OR(6)$, $C_rF_{2r+1}$, $-CO-N=C(NH_2)_2$ or $-NR(6)R(7)$;

R(6) and R(7) independently are hydrogen or $(C_1-C_3)$-alkyl;

r is 1, 2, 3 or 4;

R(3) and R(4) independently of one another are hydrogen, F, Cl, Br, I, $-C\equiv N$, $X-(CH_2)_p-(C_q-F_{2q+1})$, $R(8)-SO_{bm}$, $R(9)R(10)N-CO$, $R(11)-CO-$ or $R(12)R(13)N-SO_2-$, where the perfluoroalkyl group is straight-chain or branched, X is oxygen, S or NR(14);

R(14) is H or $(C_1-C_3)$-alkyl;

bm is zero, 1 or 2;

p is zero, 1 or 2;

q is zero, 1, 2, 3, 4, 5 or 6;

R(8), R(9), R(11) and R(12) independently are $(C_1-C_8)$-alkyl, $(C_3-C_6)$-alkenyl, $-C_nH_{2n}-R(15)$, $CF_3$;

n is zero, 1, 2, 3 or 4;

R(15) is $(C_3-C_7)$-cycloalkyl or phenyl, which is not substituted or is substituted by 1–3 substituents selected from the group consisting of F, Cl, $CF_3$, methyl, methoxy or NR(16)R(17);

R(16) and R(17) are H or $C_1-C_4$-alkyl;

or

R(9), R(11) and R(12) are H;

R(10) and R(13) independently are H or $(C_1-C_4)$-alkyl;

or

R(9) and R(10), and R(12) and R(13) together are 4 or 5 methylene groups, of which one $CH_2$ group can be replaced by oxygen, S, NH, $N-CH_3$ or N-benzyl, or R(3) and R(4) independently of one another are $(C_1-C_8)$-alkyl or $-C_{a1}H_{2a1}R(18)$;

a1 is zero, 1 or 2;

R(18) is $(C_3-C_8)$-cycloalkyl or phenyl; which is not substituted or is substituted by 1–3 substituents selected from the group consisting of F, Cl, $CF_3$, methyl, methoxy and NR(19)R(20);

R(19) and R(20) are H or $CH_3$;

or

R(3) and R(4) in dependently of one another are $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

or

R(3) and R(4) independently of one another are

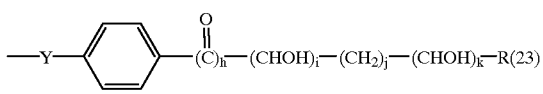

or

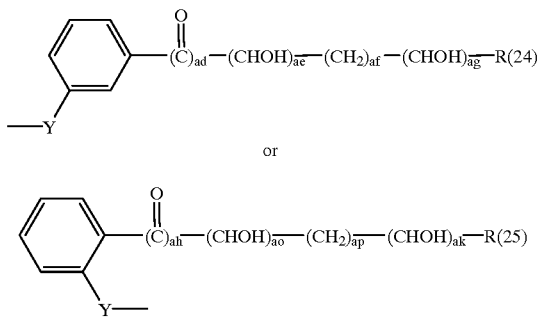

Y is oxygen, —S— or —NR(22)—;

h, ad, ah independently are zero or 1;

i, j, k, ae, af, ag, ao, ap and ak independently are zero, 1, 2, 3, 4, but where in each case h, i and k are not simultaneously zero, ad, ae and ag are not simultaneously zero, ah, ao and ak are not simultaneously zero, R(23), R(24), R(25) and R(22) independently are hydrogen or $(C_1-C_3)$-alkyl;

or

R(3) and R(4) independently of one another are hydrogen, F, Cl, Br, I, CN, $(C_1-C_8)$-alkyl, $(C_1-C_8)$-perfluoroalkyl, $(C_3-C_8)$-alkenyl or —$C_gH_{2g}R(26)$;

g is zero, 1, 2, 3 or 4;

R(26) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);

R(27) and R(28) are H, $(C_1-C_4)$-alkyl or $(C_1-C_4)$-pefluoroalkyl;

or

R(3) and R(4) independently of one another are SR(29), —OR(30), —NR(31)R(32) or —CR(33)R(34)R(35);

R(29), R(30), R(31) and R(33) independently are —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(32), R(34) and R(35) independently of one another are defined as R(29) or are hydrogen, $(C_1-C_4)$-alkyl or $(C_1-C_4)$-perfluoroalkyl;

or

R(3) and R(4) independently of one another are

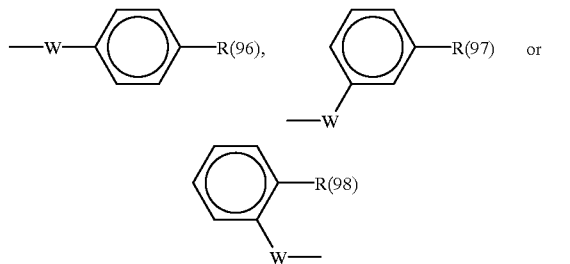

R(96), R(97) and R(98) independently are $(C_1-C_9)$-heteroaryl, which is linked via C or N and which is unsubstituted or substituted by 1 to 3 substituents selected from the group consisting of F, Cl, $CF_3$, $CH_3$, methoxy, hydroxyl, amino, methylamino, dimethylamino or benzyl;

W is oxygen, S or NR(36)—;

R(36) is H or $(C_1-C_4)$-alkyl;

or

R(3) and R(4) independently of one another are R(37)—$SO_{cm}$ or R(38)R(39)N—$SO_2$—;

cm is 1 or 2;

R(37) is $(C_1-C_8)$-alkyl, $(C_1-C_8)$-perfluoroalkyl, $(C_3-C_8)$-alkenyl or —$C_sH_{2s}R(40)$;

S is zero, 1, 2, 3 or 4;

R(40) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(41)R(42);

R(41) and R(42) are H, $(C_1-C_4)$-alkyl or $(C_1-C_4)$-perfluoroalkyl;

R(38) is H, $(C_1-C_8)$-alkyl, $(C_1-C_8)$-perfluoroalkyl, $(C_3-C_8)$-alkenyl or —$C_wH_{2w}$—R(43);

w is zero, 1, 2, 3 or 4;

R(43) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(44)R(45);

R(44) and R(45) are H, $(C_1-C_4)$-alkyl or $(C_1-C_4)$-perfluoroalkyl;

R(39) is H, $(C_1-C_4)$-alkyl or $(C_1-C_4)$-perfluoroalkyl;

or

R(38) and R(39) together are 4 or 5 methylene groups, of which one $CH_2$ group can be replaced by oxygen, S, NH, N—$CH_3$ or N-benzyl;

or

R(3) and R(4) independently of one another are R(46)X(1)—;

X(1) is oxygen, S, NR(47), (D=O)A—, NR(48)C=MN(*)R(49)—,

M is oxygen or S;

A is oxygen or NR(50);

D is C or SO;

R(46) is $(C_1-C_8)$-alkyl, $(C_3-C_8)$-alkenyl, $(CH_2)_bC_dF_{2d+1}$ or —$C_xH_{2x}$—R(51);

b is zero or 1;

d is 1, 2, 3, 4, 5, 6 or 7;

x is zero, 1, 2, 3 or 4;

R(51) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);

R(52) and R(53) are H, $(C_1-C_4)$-alkyl or $(C_1-C_4)$-perfluoroalkyl;

R(47), R(48) and R(50) independently are hydrogen, $(C_1-C_4)$-alkyl or $(C_1-C_4)$-perfluoroalkyl;

R(49) is defined as R(46);

or

R(46) and R(47), or R(46) and R(48) together are 4 or 5 methylene groups, of which one $CH_2$ group can be replaced by oxygen, S, NH, N—$CH_3$ or N-benzyl, where A and N(*) are bonded to the phenyl nucleus of the benzoylguanidine parent structure;

or

R(3) and R(4) independently of one another are —SR(64), —OR(65), —NHR(66), —NR(67) R(68), —CH R(69)R(70), —C(OH)R(54)R(55), —C≡CR(56), —CR(58)=CH R(57), —[CR(59) R(60)]$_u$—(CO)—[CR(61) R(62)]$_v$—R(63); R(64), R(65), R(66), R(67) and R(69)

identically or differently are —(CH$_2$)$_y$—(CHOH)$_z$—(CH$_2$)$_{aa}$—(CH$_2$OH)$_t$—R(71) or —(CH$_2$)$_{ab}$—O—(CH$_2$—CH$_2$O)$_{ac}$—R(72), R(71) and R(72) are hydrogen or methyl;

u is 1, 2, 3 or 4;

V is zero, 1, 2, 3 or 4;

y, z, aa identically or differently are zero, 1, 2, 3 or 4;

t is 1, 2, 3 or 4;

R(68), R(70), R(54) and R(55) identically or differently are hydrogen, (C$_1$–C$_6$)-alkyl;

or

R(69) and R(70), or R(54) and R(55) together with the carbon atom carrying them are a (C$_3$–C$_8$)—cycloalkyl;

R(63) is H, (C$_1$–C$_6$)-alkyl, (C$_3$–C$_8$)-cycloalkyl or —C$_e$H$_{2e}$—R(73);

e is zero, 1, 2, 3 or 4;

R(56), R(57) and R(73) independently are phenyl, which is unsubstituted or substituted by 1–3 substituents selected from the group consisting of F, Cl, CF$_3$, methyl, methoxy and NR(74)R(75);

R(74) and R(75) are H or (C$_1$–C$_4$)-alkyl;

or

R(56), R(57) and R(73) independently are (C$_1$–C$_9$)-heteroaryl, which is unsubstituted or substitued as phenyl;

R(58), R(59), R(60), R(61) and R(62) are hydrogen or methyl, or

R(3) and R(4) independently of one another are R(76)—NH—SO$_2$—;

R(76) is R(77)R(78)N—(C=Y')—;

Y' is oxygen, S or N—R(79);

R(77) and R(78) identically or differently are H, (C$_1$–C$_8$)-alkyl, (C$_3$–C$_6$)-alkenyl, -C$_f$H$_{2f}$—R(80);

f is zero, 1, 2, 3 or 4;

R(80) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl;

or

R(77) and R(78) together are 4 or 5 methylene groups, of which one CH$_2$ group can be replaced by oxygen, S, NH, N—CH$_3$ or N-benzyl, R(79) is defined as R(77) or is amidine;

or

R(3) and R(4) independently of one another are NR(84) R(85);

R(84) and R(85) independently of one another are H, (C$_1$–C$_4$)-alkyl, or together are 4 or 5 methylene groups, of which one CH$_2$ group can be replaced by oxygen, S, NH, N—CH3 or N-benzyl; or of which one or two CH$_2$ groups can be replaced by CH—C$_{dm}$H$_{2dm+1}$, or a pharmaceutically tolerable salt thereof;

y) a bicyclic heteroaroylguanidine of the formula

I

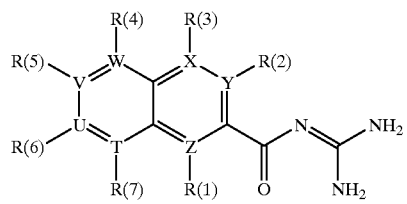

in which:

T, U, V, W, X, Y and Z independently of one another are nitrogen or carbon; but with the restriction that X and Z are not simultaneously nitrogen, and that T, U, V, W, X, Y and Z carry no substituents if they are nitrogen, and that no more thai four of them are simultaneously nitrogen, R(1) and R(2) independently of one another are hydrogen, F, Cl, Br, I, (C$_1$–C$_3$)-alkyl, (C$_1$–C$_3$)-perfluoroalkyl, OR(8), NR(8)R(9) or C(=O)N=C(NH$_2$)$_2$;

R(8) and R(9) independently of one another are hydrogen or (C$_1$–C$_3$)-alkyl, or R(8) and R(9) together are 4 or 5 methylene groups, of which one CH$_2$ group can be replaced by oxygen, S, NH, N—CH$_3$ or N-benzyl;

R(3), R(4), R(5), R(6) and R(7) independently of one another are hydrogen, F, Cl, Br, I, —C≡N, X$_k$—(CH$_2$)$_p$—(C$_q$F$_{2q+1}$), R(10a)—SO$_{bm}$, R(10b)R(10c)N—CO, R(11)—CO— or R(12)R(13)N—SO$_2$—, where the perfluoroalkyl group is straight-chain or branched;

X is oxygen, S or NR(14);

R(14) is H or (C$_1$–C3)-alkyl;

bm is zero, 1 or 2;

p is zero, 1 or 2;

k is zero or 1;

q 1, 2, 3, 4, 5 or 6;

R(10a), R(10b), R(11) and R(12) independently of one another are (C$_1$–C$_8$)-alkyl, (C$_3$–C$_6$)-alkenyl, —C$_n$H$_{2n}$—R(15) or (C$_1$–C$_8$)-perfluoroalkyl;

n is zero, 1, 2, 3 or 4;

R(15) is (C$_3$–C$_7$)-cycloalkyl or phenyl, which is not substituted or is substituted by 1–3 substituents selected from the group consisting of F, Cl, CF$_3$, methyl, methoxy and NR(16)R(17);

R(16) and R(17) are H or C$_1$–C$_4$-alkyl;

or

R(10b), R(11) and R(12) are hydrogen;

R(10c) and R(13) independently are hydrogen or (C$_1$–C$_4$)-alkyl;

or

R(10b) and R(10c) and R(12) and R(13) together are 4 or 5 methylene groups, of which one CH$_2$ group can be replaced by oxygen, sulfur, NH, N—CH$_3$ or N-benzyl;

or

R(3), R(4), R(5), R(6) and R(7) independently of one another are (C$_1$–C$_8$)-alkyl, —C$_{a1}$H$_{2a1}$R(18) or (C$_3$–C$_8$)—alkenyl;

a1 is zero, 1 or 2;

R(18) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(19a)R(19b);

R(19a) and R(19b) are hydrogen, (C$_1$–C$_4$)-alkyl or (C$_1$–C$_4$)-perfluoroalkyl;

or

R(3), R(4), R(5), R(6) and R(7) independently of one another are (C$_1$–C$_9$)-heteroaryl, which is linked via C or N and which is unsubstituted or substituted by 1–3 substituents from the group consisting of F, Cl, CF$_3$, CH$_3$, methoxy, hydroxyl, amino, methylamino or dimethylamino;

or

R(3), R(4), R(5), R(6) and R(7) independently of one another are

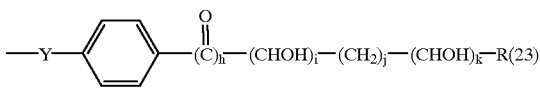

or

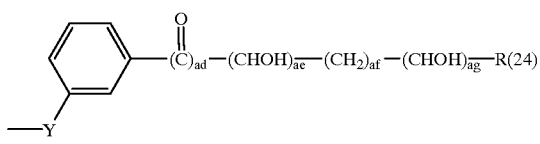

or

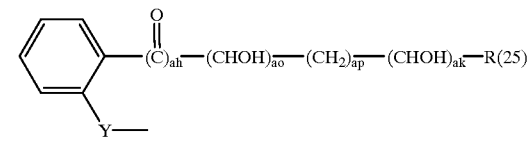

Y is oxygen, —S— or —NR(22)—;

h, ad, ah independently of one another are zero or 1;

i, j, k, ae, af, ag, ao, ap and ak independently of one another are zero, 1, 2, 3 or 4;

but where in each case h, i and k are not simultaneously zero, ad, ae and ag are not simultaneously zero, and ah, ao and ak are not simultaneously zero, R(23), R(24), R(25) and R(22) independently of one another are hydrogen or (C$_1$–C$_3$)-alkyl;

or

R(3), R(4), R(5), R(6) and R(7) independently of one another are SR(29), —OR(30), —NR(31)R(32) or —CR(33)R(34)R(35);

R(29), R(30), R(31) and R(33) independently of one another are —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

a is zero, 1 or 2;

R(32), R(34) and R(35) independently of one another are defined as R(29) or are hydrogen, (C$_1$–C$_4$)-alkyl or (C$_1$–C$_4$)-perfluoroalkyl;

or

R(3), R(4), R(5), R(6) and R(7) independently of one another are

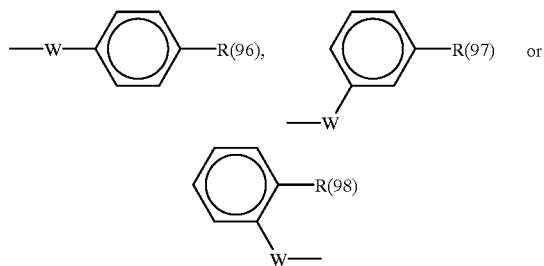

R(96), R(97) and R(98) independently of one another are (C$_1$–C$_9$)-heteroaryl, which is linked via C or N and which is unsubstitued or substituted by 1 to 3 substituents from the group consisting of F, Cl, CF$_3$, CH$_3$, methoxy, hydroxyl, amino, methylamino, dimethylamino or benzyl;

W is oxygen, S or NR(36)—;

R(36) is H or (C$_1$–C$_4$)-alkyl;

or

R(3), R(4), R(5), R(6) and R(7) independently of one another are R(46)X(1)—;

X(1) is oxygen, S, NR(47), (D=O)A— or NR(48)C=MN(*)R(49)—;

M is oxygen or sulfur;

A is oxygen or NR(50);

D is C or SO;

R(46) is (C$_1$–C$_8$)-alkyl, (C$_3$–C$_8$)-alkenyl, (CH$_2$)$_b$C$_d$F$_{2d+1}$ or —C$_x$H$_{2x}$—R(51);

b is zero or 1;

d is 1, 2, 3, 4, 5, 6 or 7;

x is zero, 1, 2, 3 or 4;

R(51) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(52)R(53);

R(52) and R(53) are hydrogen, (C$_1$–C$_4$)-alkyl or (C$_1$–C$_4$)-perfluoroalkyl;

R(47), R(48) and R(50) independently are hydrogen, (C$_1$–C$_4$)-alkyl or (C$_1$–C$_4$)-perfluoroalkyl;

R(49) is defined as R(46);

or

R(46) and R(47), or R(46) and R(48) together are 4 or 5 methylene groups, of which one CH$_2$ group can be replaced by oxygen, sulfur, NH, N—CH$_3$ or N-benzyl; where A and N(*) are bonded to the phenyl nucleus of the heteroaroylguanidine parent structure;

or

R(3), R(4), R(5), R(6) and R(7) independently of one another are —SR(64), —OR(65), —NHR(66), —NR(67)R(68), —CH R(69)R(70) or —CR(54)R(55)OH, —C≡CR(56), —CR(58)=CR(57) or —[CR(59)R(60)]$_u$, —CO—[CR(61)R(62)]$_v$—R(63); R(64), R(65), R(66), R(67) and R(69) identically or differently are —(CH$_2$)$_y$—(CHOH)$_z$—(CH$_2$)$_{aa}$—(CHOH)$_t$—R(71) or —(CH$_2$)$_{ab}$—O—(CH$_2$—CH$_2$O)$_{ac}$—R(72);

R(71) and R(72) independently of one another are hydrogen or methyl;

u is 1, 2, 3 or 4;
v is zero, 1, 2, 3 or 4;
y, z, aa identically or differently are zero, 1, 2, 3 or 4;
t is 1, 2, 3 or 4;
R(68), R(70), R(54) and R(55) identically or differently are hydrogen or ($C_1$–$C_6$)-alkyl;

or

R(69) and R(70), or R(54) and R(55) together with the carbon atom carrying them are ($C_3$–$C_8$)-cycloalkyl;
R(63) is hydrogen, ($C_1$–$C_6$)-alkyl, ($C_3$–$C_8$)-cycloalkyl or —$C_eH_{2e}$—R(73);
e is zero, 1, 2, 3 or 4;
R(56), R(57) and R(73) independently are phenyl, which is unsubstituted or substituted by 1–3 substituents selected from the group consisting of F, Cl, $CF_3$, methyl, methoxy and NR(74)R(75);
R(74) and R(75) are hydrogen or ($C_1$–$C_4$)-alkyl;

or

R(56), R(57) and R(73) independently are ($C_1$–$C_9$)-heteroaryl, which is unsubstituted or substituted as phenyl;
R(58), R(59), R(60), R(61) and R(62) are hydrogen or methyl;

or

R(3), R(4), R(5), R(6) and R(7) independently of one another are R(76)—NH—$SO_2$—;
R(76) is R(77)R(78)N—(C=Y')—;
Y' is oxygen, S or N—R(79);
R(77) and R(78) identically or differently are hydrogen, ($C_1$–$C_8$)-alkyl, ($C_3$–$C_6$)-alkenyl or —$C_fH_{2f}$R(80);
f is zero, 1, 2, 3 or 4;
R(80) is ($C_5$–$C_7$)-cycloalkyl or phenyl, which is unsubstituted or substituted by 1–3 substituents selected from the group consisting of F, Cl, $CF_3$, methoxy and ($C_1$–$C_4$)-alkyl;

or

R(77) and R(78) together are 4 or 5 methylene groups, of which one $CH_2$ group can be replaced by oxygen, sulfur, NH, N—$CH_3$ or N-benzyl;
R(79) is defined as R(77) or is amidine;

or

R(3), R(4), R(5), R(6) and R(7) independently of one another are NR(84a)R(85), OR(84b), SR(84c) or —$C_nH_{2n}$—R(84d);
n is zero, 1, 2, 3 or 4;
R(84d) is ($C_3$–$C_7$)-cycloalkyl or phenyl, which is not substituted or is substituted by 1–3 substituents from the group consisting of F, Cl, $CF_3$, methyl, methoxy and NR(16)R(17);
R(16) and R(17) are hydrogen, or $C_1$–$C_4$-alkyl;
R(84a), R(84b), R(84c) and R(85) independently of one another are hydrogen, ($C_1$–$C_8$)-alkyl, ($C_1$–$C_8$)-perfluoroalkyl or $(CH_2)_{ax}$—R(84g);
ax is zero, 1, 2, 3 or 4;
R(84g) is ($C_3$–$C_7$)-cycloalkyl or phenyl, which is not substituted or is substituted by 1–3 substituents selected from the group consisting of F, Cl, $CF_3$, methyl, methoxy and NR(84u)R(84v);
R(84u) and R(84v) are hydrogen or $C_1$–$C_4$-alkyl;

or

R(84a) and R(85) together are 4 or 5 methylene groups, of which one $CH_2$ group can be replaced by oxygen, sulfur, NH, N—$CH_3$ or N-benzyl, or a pharmaceutically tolerable salt thereof;

z) a benzoylguanidine of the formula

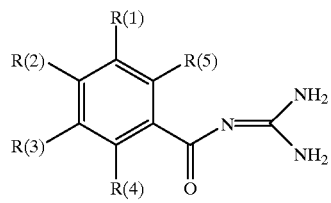

I in which:
R(1) is R(6)—$SO_m$;
m is zero, 1 or 2;
R(6) is perfluoroalkyl having 1, 2, 3, 4, 5 or 6 carbon atoms, which is straight-chain or branched;
R(2) and R(3) independently of one another are hydrogen, F, Cl, Br, I, alkyl having 1, 2, 3 or 4 carbon atoms, alkoxy having 1, 2, 3 or 4 carbon atoms or phenoxy, which is unsubstituted or substituted by 1–3 substituents selected from the group consisting of F, Cl, methyl and methoxy;

or

R(2) and R(3) independently of one another are pyrrol-1-yl, pyrrol-2-yl- or pyrrol-3-yl, which is not substituted or is substituted by 1 to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, $CF_3$, methyl and methoxy;
R(4) and R(5) independently of one another are hydrogen, alkyl having 1, 2 or 3 carbon atoms, F, Cl, Br, I, CN, OR(7), NR(8)R(9) or —$(CH_2)_n$—$(CF_2)_o$—$CF_3$;
R(7), R(8) and R(9) independently of one another are hydrogen or alkyl having 1, 2, 3 or 4 carbon atoms;
n is zero or 1;
o is zero, 1 or 2;

or a pharmacologically acceptable salt thereof;

aa) a phenyl-substituted alkenylcarboxylic acid guanidide, carrying perfluoroalkyl groups, of the formula

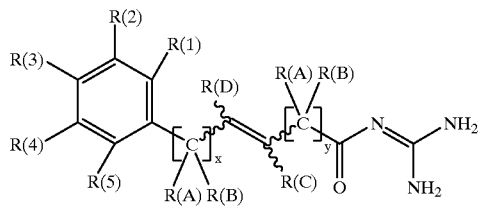

I in which:
R(A) is hydrogen, F, Cl, Br, I, CN, OH, OR(6), ($C_1$–$C_8$)-alkyl, $O_r(CH_2)_aC_bF_{2b+1}$, ($C_3$–$C_8$)-cycloalkyl or NR(7)R(8);
r is zero or 1;
a is zero, 1, 2, 3 or 4;
b is 1, 2, 3, 4, 5, 6, 7 or 8;
R(6) is ($C_1$–$C_8$)-alkyl, ($C_1$–$C_4$)-perfluoroalkyl, ($C_3$–$C_8$)-alkenyl, ($C_3$–$C_8$)-cycloalkyl, phenyl or benzyl;
where the aromatics are not substituted or are substituted by 1–3 substituents from the group consisting of F, Cl, $CF_3$, methyl, methoxy and NR(9)R(10);

R(9) and R(10) are H, $(C_1-C_4)$-alkyl or $(C_1-C_4)$-perfluoroalkyl;

R(7) and R(8) independently of one another are defined as R(6);

or

R(7) and R(8) together are 4 or 5 methylene groups, of which one $CH_2$ group can be replaced by oxygen, sulfur, NH, N—$CH_3$ or N-benzyl;

R(B) independently is defined as R(A);

X is zero, 1 or 2;

Y is zero, 1 or 2;

R(C) is hydrogen, F, Cl, Br, I, CN, OR(12), $(C_1-C_8)$-alkyl, $O_p(CH_2)_fC_gF_{2g+1}$ or $(C_3-C_8)$-cycloalkyl;

p is zero or 1;

f is zero, 1, 2, 3 or 4;

g is 1, 2, 3, 4, 5, 6, 7 or 8;

R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl;

where the aromatics phenyl or benzyl are not substituted or are substituted by 1–3 substituents from the group consisting of F, Cl, $CF_3$, methyl, methoxy and NR(13)R(14);

R(13) and R(14) independently of one another are H, $(C_1-C_4)$-alkyl or $(C_1-C_4)$-perfluoroalkyl;

R(D) independently is defined as R(C),

R(1) is hydrogen, $(C_1-C_8)$-alkyl, —$O_t(CH_2)_dC_eF_{2e+1}$, $(C_3-C_8)$-cycloalkyl, F, Cl, Br, I or CN;

t is zero or 1;

d is zero, 1, 2, 3 or 4;

e is 1, 2, 3, 4, 5, 6, 7 or 8;

R(2), R(3), R(4) and R(5) independently of one another are defined as R(1);

but with the condition that at least one of the substituents R(A), R(B), R(C), R(D), R(1), R(2), R(4) or R(5) is an $O_t(CH_2)_aC_bF_{2b+1}$, $O_p(CH_2)_fC_gF_{2g+1}$ or $O_t(CH_2)_dC_eF_{2e+1}$ group and R(3) is not an $O_t(CH_2)_dC_eF_{2e+1}$ group;

or a pharmaceutically tolerable salt thereof;

ab) an ortho-amino-substituted benzoylguanidine of the formula

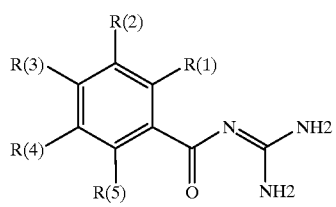

I in which:

R(1) is NR(50)R(6), R(50) and R(6) independently of one another are hydrogen, $(C_1-C_8)$-alkyl or $(C_1-C_8)$-perfluoroalkyl;

R(2), R(3), R(4) and R(5) independently of one another are R(10)—$SO_a$—, R(11)R(12)N—CO—, R(13)—CO— or R(14)R(15)N—$SO_2$—;

a is zero, 1 or 2,

R(10), R(11), R(12), R(13), R(14) and R(15) independently of one another are $(C_1-C_8)$-alkyl, $(C_1-C_8)$-perfluoroalkyl, $(C_3-C_6)$-alkenyl or —$C_{ab}H_{2ab}$—R(16);

ab is zero, 1, 2, 3 or 4;

R(16) is $(C_3-C_7)$-cycloalkyl, phenyl, which is not substituted or is substituted by 1–3 substituents selected from the group consisting of F, Cl, $CF_3$, methyl, methoxy or NR(17)R(18);

R(17) and R(18) independently of one another are H, $CF_3$ or $(C_1-C_4)$-alkyl;

or

R(11), R(12), and also R(14) and R(15) together are 4 or 5 methylene groups, of which one $CH_2$ group can be replaced by oxygen, S, NH, N—$CH_3$ or N-benzyl;

or

R(11), R(12), R(14) and R(15) independently of one another are hydrogen;

or

R(2), R(3), R(4) and R(5) independently of one another are SR(21), —OR(22), —NR(23)R(24) or —CR(25)R(26)R(27);

R(21), R(22), R(23) and R(25) independently of one another are —$C_bH_{2b}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

b is zero, 1 or 2;

R(24), R(26) and R(27) independently of one another are hydrogen, $(C_1-C_4)$-alkyl or $(C_1-C_4)$-perfluoroalkyl;

or

R(2), R(3), R(4) and R(5) independently of one another are hydrogen, F, Cl, Br, I, CN, —$(Xa)_{dg}$—$C_{da}H_{2da+1}$, —$(Xb)_{dh}$—$(CH_2)_{db}$—$C_{de}F_{2de+1}$, $(C_3-C_8)$-alkenyl or —$C_{df}H_{2df}R(30)$;

(Xa) is O, S or NR(33);

R(33) is H, $(C_1-C_4)$-alkyl or $(C_1-C_4)$-perfluoroalkyl;

dg is zero or 1;

(Xb) is O, S or NR(34);

R(34) is H, $(C_1-C_4)$-alkyl or $(C_1-C_4)$-perfluoroalkyl;

dh is zero or 1;

da is zero, 1, 2, 3, 4, 5, 6, 7, 8;

db is zero, 1, 2, 3, 4;

de is zero, 1, 2, 3, 4, 5, 6, 7;

df is zero, 1, 2, 3, 4;

R(30) is $(C_3-C_8)$-cycloalkyl, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(31)R(32);

R(31) and R(32) are H, $(C_1-C_4)$-alkyl or $(C_1-C_4)$-perfluoroalkyl;

or

R(2), R(3), R(4) and R(5) independently of one another are NR(40)R(41) or —(Xe)—$(CH_2)_{eb}R(45)$;

R(40) and R(41) independently of one another are hydrogen, $(C_1-C_8)$-alkyl, $(C_1-C_8)$-perfluoroalkyl or $(CH_2)_e$—R(42);

e is zero, 1, 2, 3 or 4;

R(42) is $(C_3-C_7)$-cycloalkyl, phenyl, which is not substituted or is substituted by 1–3 substituents selected from the group consisting of F, Cl, $CF_3$, methyl, methoxy and NR(43)R(44);

R(43) and R(44) independently of one another are H, $CF_3$ or $(C_1-C_4)$-alkyl;

or

R(40) and R(41) together are 4 or 5 methylene groups, of which one CH$_2$ group can be replaced by oxygen, sulfur, NH, N—CH$_3$ or N-benzyl;

(Xe) is O, S or NR(47);

R(47) is H, (C$_1$–C$_4$)-alkyl or (C$_1$–C$_4$)-perfluoroalkyl;

eb is zero, 1, 2, 3 or 4;

R(45) is (C$_3$–C$_7$)-cycloalkyl, phenyl, which is not substituted or is substituted by 1–3 substituents selected from the group consisting of F, Cl, CF$_3$, methyl, methoxy, NR(50)R(51) and —(Xfa)—(CH$_2$)$_{ed}$—(Xfb)R(46);

Xfa is CH$_2$, O, S or NR(48);

Xfb is O, S or NR(49);

ed is 1, 2, 3 or 4;

R(46) is H, (C$_1$–C$_4$)-alkyl or (C$_1$–C$_4$)-perfluoroalkyl;

R(48), R(49), R(50) and R(51) independently of one another are H or (C$_1$–C$_4$)-alkyl or (C$_1$–C$_4$)-perfluoroalkyl;

where R(3) and R(4), however, cannot be hydrogen, or a pharmaceutically tolerable salt thereof;

ac) a benzoylguanidine of the formula

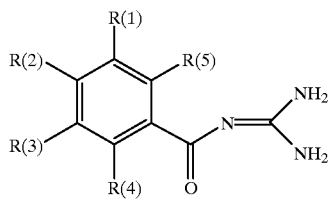

I in which:

one of the three substituents R(1), R(2) and R(3) is (C$_1$–C$_9$)-heteroaryl-N-oxide,
which is linked via C or N and which is unsubstituted or substituted by 1–3 substituents selected from the group consisting of F, Cl, CF$_3$, CH$_3$, methoxy, hydroxyl, amino, methylamino and dimethylamino;

or one of the three substituents R(1), R(2) and R(3) is —SR(10), —OR(10), —NR(10)R(11) or —CR(10)R(11)R(12);

R(10) is —C$_a$H$_{2a}$—(C$_1$–C$_9$)-heteroaryl-N-oxide, which is unsubstituted or substituted by 1–3 substituents selected from the group consisting of F, Cl, CF$_3$, CH$_3$, methoxy, hydroxyl, amino, methylamino and dimethylamino;

a is zero, 1 or 2;

R(11) and R(12) independently of one another are defined as R(10), are hydrogen or (C$_1$–C$_4$)-alkyl;

and the other substituents R(1), R(2) and R(3) in each case independently of one another are (C$_1$–C$_8$)-alkyl, (C$_2$–C$_8$)-alkenyl or —C$_m$H$_{2m}$R(14);

m is zero, 1 or 2;

R(14) is (C$_3$–C$_8$)-cycloalkyl or phenyl, which is not substituted or is substituted by 1–3 substituents selected from the group consisting of F, Cl, CF$_3$, methyl, methoxy and NR(15)R(16), R(15) and R(16) are hydrogen or CH$_3$;

or the other substituents R(1), R(2) and R(3) in each case independently of one another are hydrogen, F, Cl, Br, I, —C≡N, X—(CH$_2$)$_p$—(C$_q$F$_{2q+1}$), R(22)—SO$_u$, R(23)R(24)N—CO, R(25)—CO— or R(26)R(27)N—SO$_2$—,
where the perfluoroalkyl group is straight-chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently are (C$_1$–C$_8$)-alkyl, (C$_2$–C$_6$)-alkenyl, —C$_n$H$_{2n}$—R(29) or CF$_3$;

n is zero, 1, 2, 3 or 4;

R(28) is hydrogen or (C$_1$–C$_3$)-alkyl;

R(29) is (C$_3$–C$_7$)-cycloalkyl or phenyl; which is not substituted or is substituted by 1–3 substituents selected from the group consisting of F, Cl, CF$_3$, methyl, methoxy and NR(30)R(31);

R(30) and R(31) are hydrogen or C$_1$–C$_4$-alkyl, or

R(23), R(25) and R(26) are also hydrogen;

R(24) and R(27) independently of one another are hydrogen or (C$_1$–C$_4$)-alkyl;

or

R(23) and R(24), and also R(26) and R(27) together are 4 or 5 methylene groups, of which one CH$_2$ group can be replaced by oxygen, S, NH, N—CH$_3$ or N-benzyl;

or the other substituents R(1), R(2) and R(3) in each case independently of one another are OR(35) or NR(35)R(36); R(35) and R(36)
independently of one another are hydrogen or (C$_1$–C$_6$)-alkyl;

or

R(35) and R(36) together are 4–7 methylene groups, of which one CH$_2$ group can be replaced by oxygen, S, NH, N—CH$_3$ or N-benzyl, R(4) and R(5) independently of one another are hydrogen, (C$_1$–C$_4$)-alkyl, F, Cl, —OR(32), —NR(33)R(34) or C$_r$F$_{2r+1}$;

R(32), R(33) and R(34) independently of one another are hydrogen or (C$_1$–C$_3$)-alkyl;

r is 1, 2, 3 or 4;

or a pharmaceutically tolerable salt thereof;

ad) a benzoylguanidine of the formula

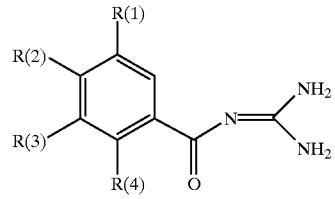

I in which:

R(1) is hydrogen, F, Cl, Br, I, CN, NO$_2$, OH, (C$_1$–C$_8$)-alkyl, (C$_3$–C$_8$)-cycloalkyl, O$_a$—(CH$_2$)$_b$—(CF$_2$)$_c$—CF$_3$;

a is zero or 1;

b is zero, 1 or 2;

c is zero, 1, 2 or 3;

or
R(1) is R(5)—SO$_m$— or R(6)R(7)N—SO$_2$—;
m is zero, 1 or 2;
R(5) and R(6) independently of one another are (C$_1$–C$_8$)-alkyl, (C$_3$–C$_6$)-alkenyl, CF$_3$ or —C$_n$H$_{2n}$—R(8);
n is zero, 1, 2, 3 or 4;
R(7) is hydrogen or (C$_1$–C$_4$)-alkyl;
R(8) is (C$_3$–C$_7$)-cycloalkyl or phenyl, which is not substituted or is substituted by 1–3 substituents selected from the group consisting of F, Cl, CF$_3$, methyl, methoxy and NR(9)R(10);
R(9) and R(10) independently of one another are hydrogen or (C$_1$–C$_4$)-alkyl;
or
R(6) is H;
or R(6) and R(7) together are 4 or 5 methylene groups, of which one CH$_2$ group can be replaced by oxygen, S, NH, N—CH$_3$ or N-benzyl,
or
R(1) is —SR(11), —OR(11) or —CR(11)R(12)R(13);
R(11) is —C$_p$H$_{2p}$—(C$_3$–C$_8$)-cycloalkyl, —(C$_1$–C$_9$)-heteroaryl or phenyl, where the aromatic systems are unsubstituted or substituted by 1–3 substituents selected from the group consisting of F, Cl, CF$_3$, CH$_3$, methoxy, hydroxyl, amino, methylamino and dimethylamino;
R(12), R(13) independently of one another are defined as R(11) or are hydrogen or (C$_1$–C$_4$)-alkyl;
p is zero, 1 or 2;
or
R(1) is phenyl, naphthyl, biphenylyl or (C$_1$–C$_9$)-heteroaryl, the latter linked via C or N,
which are unsubstituted or substituted by 1–3 substituents selected from the group consisting of F, Cl, CF$_3$, CH$_3$, methoxy, hydroxyl, amino, methylamino and dimethylamino;
R(2) is —CF$_2$R(14), —CF[R(15)][R(16)], —CF[(CF$_2$)$_q$—CF$_3$][R(15)], —C[(CF$_2$)$_r$—CF$_3$]=CR(15)R(16);
R(14) is (C$_1$–C$_4$)-alkyl or (C$_3$–C$_6$)-cycloalkyl;
R(15) and R(16) independently of one another are hydrogen or (C$_1$–C$_4$)-alkyl;
q is zero, 1 or 2;
r is zero, 1 or 2;
R(3) is defined as R(1);
R(4) is hydrogen, (C$_1$–C$_3$)-alkyl, F, Cl, Br, I, CN, —(CH$_2$)$_s$—(CF$_2$)$_t$—CF$_3$;
s is zero or 1;
t is zero, 1 or 2;
or a pharmaceutically tolerable salt thereof;
ae) a benzoylguanidine of the formula

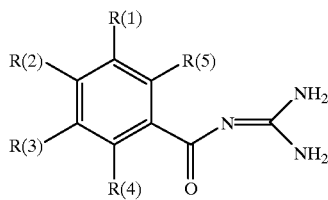

I in which:
one of the three substituents R(1), R(2) and R(3) is
—Y—4—[(CH$_2$)$_k$—CHR(7)—(C=O)R(8)]-phenyl,
—Y—3—(CH$_2$)$_k$—CHR(7)—(C=O)R(8)]-phenyl or
—Y—2—[(CH$_2$)$_k$—CHR(7)—(C=O)R(8)]—phenyl,
where the phenyl in each case is unsubstituted or substituted by 1–2 substituents from the group F, Cl, —CF$_3$, methyl, hydroxyl, methoxy, or —NR(37)R(38);
R(37) and R(38) independently of one another are hydrogen or —CH$_3$;
Y is a bond, oxygen, —S— or —NR(9);
R(9) is hydrogen or —(C$_1$–C$_4$)-alkyl;
R(7) is —OR(10) or —NR(10)R(11);
R(10) and R(11) independently of one another are hydrogen, —(C$_1$–C$_8$)-alkyl, —(C$_1$–C$_8$)-alkanoyl, —(C$_1$–C$_8$)-alkoxycarbonyl, benzyl, benzyloxycarbonyl;
or
R(10) is trityl;
R(8) is —OR(12) or —NR(12)R(13);
R(12) and R(13) independently of one another are hydrogen, —(C$_1$–C$_8$)-alkyl or benzyl;
k is zero, 1, 2, 3 or 4;
and the other radicals R(1), R(2) and R(3) in each case independently of one another are —(C$_1$–C$_8$)-alkyl, —(C$_2$–C$_8$)-alkenyl or —(CH$_2$)$_m$R(14);
m is zero, 1 or 2;
R(14) is —(C$_3$–C$_8$)-cycloalkyl or phenyl, which is not substituted or is substituted by 1–3 substituents selected from the group consisting of F, Cl, —CF$_3$, methyl, methoxy and —NR(15)R(16);
R(15) and R(16) are hydrogen or —CH$_3$;
or
the other radicals R(1), R(2) and R(3) in each case independently of one another are R(18)R(19)N—(C=Y')—NH—SO$_2$—;
Y' is oxygen, —S— or —N—R(20);
R(18) and R(19) independently of one another are hydrogen, —(C$_1$–C$_8$)-alkyl, —(C$_3$–C$_6$)—alkenyl or —(CH$_2$)$_t$—R(21);
t is zero, 1, 2, 3 or 4;
R(21) is —(C$_5$–C$_7$)-cycloalkyl or phenyl, which is unsubstituted or substituted by 1–3 substituents selected from the group consisting of F, Cl, —CF$_3$, methoxy and —(C$_1$–C$_4$)-alkyl;
or
R(18) and R(19) together are 4 or 5 methylene groups, of which one CH$_2$ group can be replaced by oxygen, —S—, —NH—, —N—CH$_3$ or —N—benzyl;
R(20) is defined as R(18) or is amidine;
or
the other radicals R(1), R(2) and R(3) in each case independently of one another are hydrogen, F, Cl, Br, 1, —C≡N, X—(CH$_2$)$_p$—(C$_q$F$_{2q+1}$), R(22)—SO$_u$—, R(23)R(24)N—CO—, R(25)—CO— or R(26)R(27)N—SO$_2$—, where the perfluoroalkyl group is straight-chain or branched;
X is a bond, oxygen, —S— or —NR(28);
u is zero, 1 or 2;
p is zero, 1 or 2;
q is 1, 2, 3, 4, 5 or 6;
R(22), R(23), R(25) and R(26) independently of one another are —(C$_1$–C$_8$)-alkyl, —(C$_3$–C$_6$)-alkenyl, —(CH$_2$)$_n$—R(29) or —CF$_3$;

n is zero, 1, 2, 3 or 4;

R(28) is hydrogen or —($C_1$–$C_3$)-alkyl;

R(29) is —($C_3$–$C_7$)-cycloalkyl or phenyl, which is not substituted or is substituted by 1–3 substituents selected from the group consisting of F, Cl, —$CF_3$, methyl, methoxy and —NR(30)R(31);

R(30) and R(31) are hydrogen or —($C_1$–$C_4$)-alkyl;

or

R(23), R(25) and R(26) are hydrogen;

R(24) and R(27) independently of one another are hydrogen or —($C_1$–$C_4$)-alkyl;

or

R(23) and R(24), and also R(26) and R(27) together are 4 or 5 methylene groups, of which one $CH_2$ group can be replaced by oxygen, —S—, —NH—, —N—$CH_3$ or —N-benzyl;

or the other radicals R(1), R(2) and R(3) in each case independently of one another are —OR(35) or —NR(35)R(36);

R(35) and R(36) independently of one another are hydrogen or —($C_1$–$C_6$)-alkyl;

or

R(35) and R(36) together are 4–7 methylene groups, of which one $CH_2$ group can be replaced by oxygen, —S—, —NH—, —N—$CH_3$ or —N—benzyl;

R(4) and R(5) independently of one another are hydrogen, —($C_1$–$C_4$)-alkyl, F, Cl, —OR(32), —NR(33)R(34) or —$C_rF_{2r+1}$;

R(32), R(33) and R(34) independently of one another are hydrogen or —($C_1$–$C_3$)-alkyl;

r is 1, 2, 3 or 4;

or a pharmaceutically tolerable salt thereof;

af) benzoylguanidines of the formula

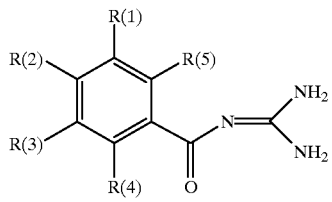

I in which:

R(1) is R(6)—CO or R(7)R(8)N—CO;

R(6) is ($C_1$–$C_8$)-alkyl, ($C_1$–$C_8$)-perfluoroalkyl, ($C_3$–$C_8$)-alkenyl or —$C_nH_{2n}$—R(9), n is zero, 1, 2, 3 or 4;

R(9) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11), R(10) and R(11) are H, ($C_1$–$C_4$)-alkyl or ($C_1$–$C_4$)-perfluoroalkyl;

R(7) is H, ($C_1$–$C_8$)-alkyl, ($C_1$–$C_8$)-perfluoroalkyl, ($C_3$–$C_8$)-alkenyl or —$C_nH_{2n}$—R(12);

n is zero, 1, 2, 3 or 4;

R(12) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);

R(13) and R(14) are H, ($C_1$–$C_4$)-alkyl or ($C_1$–$C_4$)—perfluoroalkyl;

R(8) is H, ($C_1$–$C_4$)-alkyl or ($C_1$–$C_4$)-perfluoroalkyl;

or

R(7) and R(8) together are 4 or 5 methylene groups, of which one $CH_2$ group can be replaced by oxygen, S, NH, N—$CH_3$ or N-benzyl;

R(2) is defined as R(1), or is H, OH, F, Cl, Br, I, CN, $NO_2$, ($C_1$–$C_8$)-alkyl, ($C_1$–$C_8$)-perfluoroalkyl, ($C_3$-$C_8$)-alkenyl or —$C_nH_{2n}$R(15);

n is zero, 1, 2, 3 or 4;

R(15) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);

R(16) and R(17) are H, ($C_1$–$C_4$)-alkyl or ($C_1$–$C_4$)-perfluoroalkyl;

or

R(2) is ($C_1$–$C_9$)-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

or

R(2) is SR(18), —OR(18), —NR(18)R(19) or —CR(18)R(19)R(20);

R(18) is —$C_aH_{2a}$—($C_1$–$C_9$)-heteroaryl, which is unsubstituted or substituted by 1–3 substituents selected from the group consisting of F, Cl, $CF_3$, $CH_3$, methoxy, hydroxyl, amino, methylamino, dimethylamino;

a is zero, 1 or 2;

R(19) and R(20) independently of one another are defined as R(18) or are hydrogen, ($C_1$–$C_4$)-alkyl or ($C_1$–$C_4$)-perfluoroalkyl;

or

R(2) is R(21)—$SO_m$ or R(22)R(23)N—$SO_2$—;

m is 1 or 2;

R(21) is ($C_1$–$C_8$)-alkyl, ($C_1$–$C_8$)-perfluoroalkyl, ($C_3$–$C_8$)-alkenyl or —$C_nH_{2n}$—R(24);

n is zero, 1, 2, 3 or 4;

R(24) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);

R(27) and R(28) are H, ($C_1$–$C_4$)-alkyl or ($C_1$–$C_4$)-perfluoroalkyl;

R(22) is H, ($C_1$–$C_8$)-alkyl, ($C_1$–$C_8$)-perfluoroalkyl, ($C_3$–$C_8$)-alkenyl or —$C_nH_{2n}$— R(29);

n is zero, 1, 2, 3 or 4;

R(29) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);

R(30) and R(31) are H, ($C_1$–$C_4$)-alkyl or ($C_1$–$C_4$)-perfluoroalkyl;

R(23) is hydrogen, ($C_1$–$C_4$)-alkyl or ($C_1$–$C_4$)-perfluoroalkyl;

or

R(22) and R(23) together are 4 or 5 methylene groups, of which one $CH_2$ group can be replaced by oxygen, S, NH, N—$CH_3$ or N-benzyl;

or

R(2) is R(33)X—;

X is oxygen, S, NR(34), (D=O)A— or NR(34)C=MN(*)R(35)—;

M is oxygen or S;

A is oxygen or NR(34);

D is C or SO;

R(33) is $(C_1-C_8)$-alkyl, $(C_3-C_8)$-alkenyl, $(CH_2)_bC_dF_{2d+1}$ or —$C_nH_{2n}$—R(36);

b is zero or 1;

d is 1, 2, 3, 4, 5, 6 or 7;

n is zero, 1, 2, 3, or 4;

R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);

R(37) and R(38) are H, $(C_1-C_4)$-alkyl or $(C_1-C_4)$-perfluoroalkyl;

R(34) is hydrogen, $(C_1-C_4)$-alkyl or $(C_1-C_4)$-perfluoroalkyl;

R(35) is defined as R(33);

or

R(33) and R(34) together are 4 or 5 methylene groups, of which one $CH_2$ group can be replaced by oxygen, S, NH, $N-CH_3$ or N-benzyl;

where A and $N^{(*)}$ are bonded to the phenyl nucleus of the benzoylguanidine parent structure;

or

R(2) is —SR(40), —OR(40), —NH R(40), —NR(40)R(41), —CH R(40)R(42), —CR(42)R(43)OH, —C=CR(45), —CR(46)=CR(45) or —[CR(47)R(48)]$_u$—CO—[C(R49)R(50)]$_v$-R(44);

R(40) and R(41) independently of one another are —$(CH_2)_p$—$(CHOH)_q$—$(CH_2)_r$—$(CHOH)_t$— R(51) or —$(CH_2)_p$—O—$(CH_2$—$CH_2O)_q$—R(51);

R(51) is hydrogen or methyl;

u is 1, 2, 3 or 4;

v is zero, 1, 2, 3 or 4;

p, q and r independently of one another are zero, 1, 2, 3 or 4;

t is 1,2,3or 4;

R(42) and R(43) independently of one another are hydrogen or $(C_1-C_6)$-alkyl;

or

R(42) and R(43) together with the carbon atom carrying them are a $(C_3-C_8)$-cycloalkyl;

R(44) is hydrogen, $(C_1-C_6)$-alkyl, $(C_3-C_8)$-cycloalkyl, —$C_eH_{2e}$-R(45);

e is zero, 1, 2, 3 or 4;

R(45) is phenyl, which is unsubstituted or substituted by 1–3 substituents selected from the group consisting of F, Cl, $CF_3$, methyl, methoxy and NR(52)R(53);

R(52) and R(53) are H or $(C_1-C_4)$-alkyl;

or

R(45) is $(C_1-C_9)$-heteroaryl, which is unsubstituted or substituted as phenyl;

or

R(45) is $(C_1-C_6)$-alkyl, which is unsubstituted or substituted by 1–3 OH;

R(46), R(47), R(48), R(49) and R(50) independently of one another are hydrogen or methyl;

or

R(2) is R(55)—NH—$SO_2$—;

R(55) is R(56)R(57)N—(C=Y)—;

Y is oxygen, S or N-R(58);

R(56) and R(57) independently of one another are hydrogen, $(C_1-C_8)$-alkyl, $(C_3-C_6)$-alkenyl or —$C_fH_{2f}$-R(59);

f is zero, 1, 2, 3 or 4;

R(59) is $(C_5-C_7)$-cycloalkyl, phenyl, which is unsubstituted or substituted by 1–3 substituents selected from the group consisting of F, Cl, $CF_3$, methoxy and $(C_1-C_4)$-alkyl;

or

R(56) and R(57) together are 4 or 5 methylene groups, of which one $CH_2$ group can be replaced by oxygen, S, NH, $N-CH_3$ or N-benzyl;

R(58) is defined as R(56) or is amidine;

R(3), R(4) and R(5) are independently of one another defined as R(1) or R(2), but where at least one of the substituents R(2), R(3), R(4) and R(5) must be OH; or a pharmaceutically tolerable salt thereof;

ag) a benzoylguanidine of the formula

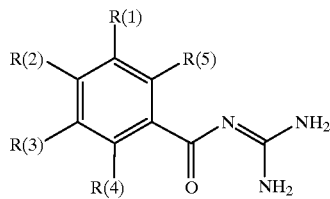

I in which:

one of the three substituents R(1), R(2) and R(3) is R(6)-A-B-D-;

R(6) is a basic protonatable radical, i.e. an amino group —NR(7)R(8), an amidino group R(7)R(8)N-C[=N-R(9)]- or a guanidino group

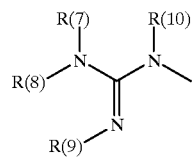

R(7), R(8), R(9) and R(10) independently of one another are hydrogen or alkyl having 1, 2, 3 or 4 carbon atoms;

or

R(7) and R(8) together are $C_aH_{2a}$;

a is 4,5,6or7;

where if a=5, 6 or 7 a methylene group of the group $C_aH_{2a}$ can be replaced by a heteroatom group O, $SO_m$ or NR(11), or R(8) and R(9) or R(9) and R(10) or R(7) and R(10) are a group $C_aH_{2a}$;

a is 2, 3, 4 or 5;

where if a=3, 4 or 5 a methylene group of the group $C_aH_{2a}$ can be replaced by a heteroatom group O, $SO_m$ or NR(11);

m is zero, 1 or 2;

R(11) is hydrogen or methyl;
or
R(6) is a basic heteroaromatic ring system having 1–9 carbon atoms;

A is $C_bH_{2b}$;
b is 1, 2, 3, 4, 5, 6, 7, 8, 9 or 10; where in the group $C_bH_{2b}$, one or two methylene groups can be replaced by one of the groupings selected from the group consisting of —O—, —CO—, —CH[OR(20)]—, —SO$_m$—, —NR(20)—, —NR(20)—CO—, —NR(20)—CO—NH—, —NR(20)—CO—NH—SO$_2$—

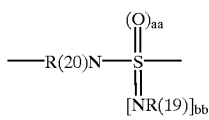

and —SO$_{aa}$[NR(19)]$_{bb}$—;
and where in the group $C_bH_{2b}$ a methylene group can be replaced by —CH—R(99), where R(99) together with R(7) forms a pyrrolidine or piperidine ring;
aa is 1 or 2;
bb is 0 or 1;
aa+bb=2;
R(19) is hydrogen or alkyl having 1, 2, 3 or 4 carbon atoms;
R(20) is hydrogen or methyl;
B is a phenylene or naphthylene radical

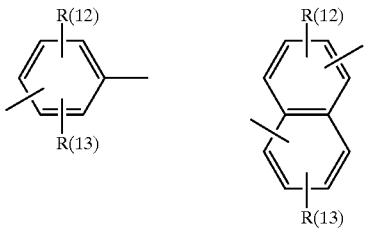

R(12) and R(13) independently of one another are hydrogen, methyl, F, Cl, Br, I, CF$_3$ or —SO$_w$-R(14);
R(14) is methyl or NR(15)R(16);
R(15) and R(16) independently of one another are hydrogen or alkyl having 1, 2, 3 or 4 carbon atoms;
w is zero, 1 or 2;
D is —C$_d$H$_{2d}$—X$_f$—;
d is zero, 1, 2, 3 or 4;
X is —O—, —CO—, —CH[OR(21)]—, —SO$_m$— or —NR(21)—;
f is zero or 1;
R(21) is hydrogen or methyl;
m is zero, 1 or 2;
and the other substituents R(1) and R(2) and R(3) in each case independently of one another are hydrogen, F, Cl, Br, I, —CN, —(C$_1$-C$_8$)— alkyl, —(C$_2$-C$_8$)-alkenyl, —NR(35)R(36) or R(1$^7$)—C$_g$H$_{2g}$—Z$_h$—;
g is zero, 1, 2, 3 or 4;
h is zero or 1;
R(35) and R(36) independently of one another are hydrogen or alkyl having 1, 2, 3, 4, 5 or 6 carbon atoms;
or
R(35) and R(36) together are 4–7 methylene groups, of which one CH$_2$ group can be replaced by oxygen, —S—, —NH—, —NCH$_3$ or —N—benzyl;

Z is —O—, —CO—, —SO$_v$, —NR(18)—, —NR(18)—CO—, —NR(18)—CO—NH— or —NR(18)—SO$_2$—;
R(18) is hydrogen or methyl;
v is zero, 1 or 2;
R(17) is hydrogen, cycloalkyl having 3, 5 or 6 carbon atoms or $C_kF_{2k+1}$—;
k is 1, 2 or 3,
or
R(17) is pyrrol-1-yl, pyrrol-2-yl or pyrrol-3-yl, which is not substituted or is substituted by 1–4 substituents selected from the group consisting of F, Cl, Br, I, —CN, (C$_2$-C$_8$)-alkanoyl, (C$_2$-C$_8$)-alkoxycarbonyl, formyl, carboxyl, —CF$_3$, methyl and methoxy;
or
R(17) -is (C$_3$-C$_8$)-cycloalkyl or phenyl, which is not substituted or is substituted by 1–3 substituents selected from the group consisting of F and Cl, —CF$_3$, methyl, hydroxyl, methoxy, —NR(37)R(38), CH$_3$SO$_2$— and H$_2$NO$_2$S—; R(37) and R(38) are hydrogen or —CH$_3$;
R(4) and R(5) independently of one another are hydrogen, alkyl having 1, 2, 3 or 4 carbon atoms, F, Cl, —OR(32), —NR(33)R(34) or —C$_r$F$_{2r+1}$;
R(32), R(33) and R(34) independently of one another are hydrogen or alkyl having 1, 2 or 3 carbon atoms;
r is 1, 2, 3 or 4;
or a pharmacologically tolerable salt thereof;
ah) an indenoylguanidine of the formula

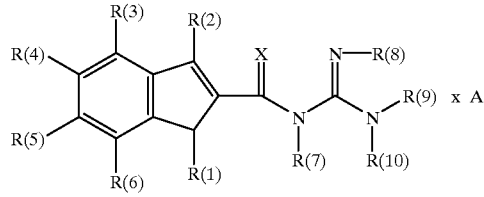

I in which:
R(1) and R(2) independently of one another are hydrogen, alkyl having 1, 2, 3, 4, 5, 6, 7, 8, 9 or 10 carbon atoms, cycloalkyl having 3, 4, 5 or 6 carbon atoms, O-alkyl having 1, 2, 3 or 4 carbon atoms, O-C(=O)-alkyl having 1, 2, 3 or 4 carbon atoms or $C_mH_{2m}$-NR(12)R(13);
R(12) and R(13) independently of one another are hydrogen or alkyl having 1, 2, 3 or 4 carbon atoms;
m is zero, 1, 2, 3 or 4;
NH-C(=O)-NH$_2$, C(=O)—O—alkyl having 1, 2, 3 or 4 carbon atoms, C(=O— NH$_2$, C(=O)-NH-alkyl having 1, 2, 3 or 4 carbon atoms, C(=O)-N(alkyl)$_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenylaryl having 2, 3, 4, 5, 6, 7, 8, 9 or 10 carbon atoms in the alkenyl group, alkynylaryl having 2, 3, 4, 5, 6, 7, 8, 9 or 10 carbon atoms in the alkynyl group, C$_1$-C$_4$-alkyl-substituted aryl, C$_1$-C$_4$-alkylheteroaryl, C$_1$-C$_4$-alkenylheteroaryl, aminoalkylaryl having 1, 2, 3 or 4 carbon atoms in the alkyl group, substituted aryl, heteroaryl and substituted heteroaryl;
R(3), R(4), R(5) and R(6) independently of one another are hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogen, (such as F, Cl, Br, I), OH, aryl, substituted aryl, heteroaryl, substituted heteroaryl, 0-lower alkyl, 0-aryl, 0-lower alkylaryl, O-substituted aryl, O-lower alkyl-substituted aryl, O—C(=O)—$C_1$-$C_4$-alkylaryl, O—C(=O)—NH—$C_1$-$C_4$-alkyl, O—C(=O)—N($C_1$-$C_4$-alkyl)$_2$, $NO_2$, CN, $CF_3$, $NH_2$, NH-C(=O)—$C_1$-$C_4$-alkyl, NH-C(=O)-$NH_2$, COOH, C(=O)—O—$C_1$-$C_4$-alkyl, C(=O)—$NH_2$, C(=O)—NH—$C_1$-$C_4$-alkyl, C(=O)-N($C_1$-$C_4$-alkyl)$_2$, $C_1$-$C_4$—COOH, $C_1$-$C_4$-alkyl-C(=O)—O—$C_1$-$C_4$-alkyl, $SO_3H$, $SO_2$-alkyl, $SO_2$-alkylaryl, $SO_2$—N—(alkyl)$_2$$SO_2$-N(alkyl)(alkylaryl), C(=O)-R(11), $C_1$-$C_{10}$-alkyl-C(=O)-R(11), $C_2$-$C_{10}$-alkenyl-C(=O)-R(11), $C_2$-$C_{10}$-alkynyl-C(=O)-R(11), NH-C(=O)-$C_1$-$C_{10}$—alkyl-C(=O)-R(11), O—$C_1$-$C_{,1}$-alkyl-C(=O)-R(11);

R(11) is $C_1$-$C_4$-alkyl, $C_1$-$C_4$-alkynyl, aryl, substituted aryl, $NH_2$, NH-$C_1$-$C_4$-alkyl, N-($C_1$-$C_4$-alkyl)$_2$, $SO_3H$, $SO_2$-alkyl, $SO_2$-alkylaryl, $SO_2$-N-(alkyl)$_2$, $SO_2$-N(alkyl)(alkylaryl);

X is O,S or NH;

R(7), R(8), R(9) and R(10) independently of one another are hydrogen, alkyl, cycloalkyl, aryl, alkylaryl;

or

R(8) and R(9) together are part of a 5-, 6- or 7-membered heterocyclic ring;

A is absent or is a nontoxic organic or inorganic acid;

ai) a benzyloxycarbonylguanidine of the formula

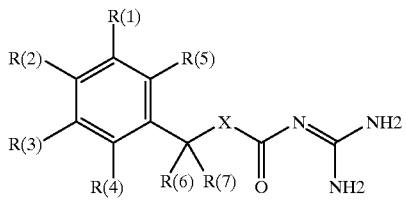

I in which:

R(1), R(2) and R(3) independently of one another are —Y—[4-R(8)-phenylen], —Y—[3-R(8)-phenylen] or —Y—[2-R(8)-phenylen], where the phenyl is in each case unsubstituted or substituted by 1–2 substituents from the group consisting of F, Cl, —$CF_3$, methyl, hydroxyl, methoxy and —NR(96)R(97);

R(96) and R(97) independently of one another are hydrogen or —$CH_3$;

Y is a bond, $CH_2$, oxygen, —S— or —NR(9);

R(9) is hydrogen or alkyl having 1, 2, 3 or 4 carbon atoms;

R(8) is $SO_a$[NR(98)]$_b$NR(99)R(10);

a is 1 or 2;

b is 0 or 1;

a+b=2;

R(98), R(99) and R(10) independently of one another are hydrogen, —($C_1$-$C_8$)-alkyl, benzyl, —($C_2$-$C_8$)-alkylene-NR(11)R(12), ($C_2$-$C_8$)-alkylene-NR(13)-($C_2$-$C_8$)-alkylene-NR(37)R(38) or ($C_0$-$C_8$)-alkylene-CR(39)R(40)CR(41)R(42)($C_0$-$C_8$)-alkylene-N R(43)R(44);

R(11), R(12), R(13), R(37), R(38), R(43) and R(44) independently of one another are hydrogen, —($C_1$-$C_8$)-alkyl or benzyl;

R(39), R(40), R(41) and R(42) independently of one another are hydrogen, —(C1–C8)-alkyl or —($C_0$-$C_3$)-alkylenephenyl, where the phenyl is not substituted or is substituted by 1–3 substituents selected from the group consisting of F, Cl, —$CF_3$, methyl and methoxy;

or

R(99) and R(10) together are 4–6 methylene groups, of which one $CH_2$ group can be replaced by oxygen, —S—, —NH—, —N—$CH_3$ or —N-benzyl;

or

R(8) is $SO_a$[NR(98)]$_b$NR(95)—[=N—R(94)]—NR(93)R(92);

R(92), R(93), R(94) and R(95) independently of one another are hydrogen or alkyl having 1, 2, 3 or 4 carbon atoms;

or

R(1), R(2) and R(3) independently of one another are pyrrol-1-yl, pyrrol-2-yl or pyrrol-3-yl, which is not substituted or is substituted by 1–4 substituents selected from the group consisting of F, Cl, Br, I, —CN, ($C_2$-$C_8$)-alkanoyl, alkanoyl, ($C_2$-$C_8$)-alkoxycarbonyl, formyl, carboxyl, —$CF_3$, methyl, methoxy;

or

R(1), R(2) and R(3) independently of one another are hydrogen, —($C_1$-$C_8$)-alkyl, —($C_2$-$C_8$)-alkenyl or —($CH_2$)$_m$R(14);

m is zero, 1 or 2;

R(14) is —($C_3$-$C_8$)-cycloalkyl or phenyl, which is not substituted or is substituted by 1–3 substituents selected from the group consisting of F and Cl, —$CF_3$, methyl, methoxy and —NR(15)R(16);

R(15) and R(16) are hydrogen or —$CH_3$;

or

R(1), R(2) and R(3) independently of one another are —Q-4-[($CH_2$)$_k$-CHR(17)-(C=O)R(20)]-phenyl, —Q—3—[($CH_2$)$_k$—CHR(17)-(C=O)R(20)]-phenyl or —Q—2-[($CH_2$)$_k$—CHR(17)-(C=O)R(20)]-phenyl, where the phenyl in each case is unsubstituted or substituted by 1–2 substituents from the group F, Cl, —$CF_3$, methyl, hydroxyl, methoxy and —NR(35)R(36);

R(35) and R(36) independently of one another are hydrogen or —$CH_3$;

Q is a bond, oxygen, —S— or —NR(18);

R(18) is hydrogen or —($C_1$-$C_4$)-alkyl;

R(17) is —OR(21) or —NR(21)R(22);

R(21) and R(22) independently of one another are hydrogen, —($C_1$-$C_8$)-alkyl, —($C_1$-$C_8$)-alkanoyl, —($C_1$-$C_8$)-alkoxycarbonyl, benzyl, benzyloxycarbonyl;

or

R(21) is trityl;

R(20) is —OR(23) or —NR(23)R(24);

R(23), R(24) independently of one another are hydrogen, —($C_1$-$C_8$)-alkyl or benzyl;

k is zero, 1, 2, 3 or 4;

or

R(1), R(2) and R(3) independently of one another are ($C_1$-$C_9$)-heteroaryl, which is linked via C or N and which is unsubstituted or substituted by 1–3 substituents from the group F, Cl, $CF_3$, $CH_3$, methoxy, hydroxyl, amino, methylamino and dimethylamino;

or

R(1), R(2) and R(3) are —SR(25), —OR(25), —NR(25)R(26), —CR(25)R(26)R(27);

R(25) is —$C_fH_{2f}$($C_1$-$C_9$)-heteroaryl, which is unsubstituted or substituted by 1–3 substituents from the group F, Cl, $CF_3$, $CH_3$, methoxy, hydroxyl, amino, methylamino and dimethylamino;

f is zero, 1 or 2;

R(26) and R(27) independently of one another are defined as R(25) or are hydrogen or ($C_1$–$C_4$)-alkyl, or R(1), R(2) and R(3) independently of one another are ($C_1$–$C_9$)-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino;

or

R(1), R(2) and R(3) independently of one another are —SR(28), —OR(28), —NR(28)R(29) or —CR(28)R(29)R(30);

R(28) is —$C_gH_{2g}$—($C_1$–$C_9$)-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;

g is zero, 1 or 2;

R(29), R(30) independently of one another are defined as R(28), hydrogen or ($C_1$–$C_4$)-alkyl;

or

R(1), R(2) and R(3) independently of one another are hydrogen, F, Cl, Br, I, —C≡N, T-($CH_2$)$_h$—($C_iF_{2i+1}$), R(31)$SO_1$—, R(32)R(33)N—CO—, R(34)—CO— or R(45)R(46)N-$SO_2$, where the perfluoroalkyl group is straight-chain or branched;

T is a bond, oxygen, —S— or —NR(47);

l is zero,1or 2;

h is zero, 1 or 2;

i is1, 2, 3, 4, 5or 6;

R(31), R(32), R(34) and R(45) independently of one another are —($C_1$–$C_8$)-alkyl, —($C_3$–$C_6$)-alkenyl, ($CH_2$)$_n$R(48) or —$CF_3$;

n is zero, 1, 2, 3 or 4;

R(47) is hydrogen or alkyl with 1, 2 or 3 carbon atoms;

R(48) is —($C_3$–$C_7$)-cycloalkyl or phenyl, which is not substituted or is substituted by 1–3 substituents selected from the group consisting of F, Cl, —$CF_3$, methyl, methoxy and —NR(49)R(50);

R(49) and R(50) are hydrogen or alkyl having 1, 2, 3 or 4 carbon atoms;

or

R(32), R(34) and R(45) are hydrogen;

R(33) and R(46) independently of one another are hydrogen or alkyl having 1, 2, 3 or 4 carbon atoms;

or

R(32) and R(33), and R(45) and R(46) together are 5 or 6 methylene groups, of which one $CH_2$ group can be replaced by oxygen, —S—, —NH—, —$NCH_3$ or —N—benzyl;

or

R(1), R(2) and R(3) independently of one another are R(51)-A-G-D-;

R(51) is a basic protonatable radical, i.e. an amino group —NR(52)R(53), an amidino group R(52)R(53)N—C[=N—R(54)]— or a guanidino group R(52)R(53)N—C[=N—R(54)]—NR(55)—;

R(52), R(53), R(54) and R(55) independently of one another are hydrogen or alkyl having 1, 2, 3 or 4 carbon atoms;

or

R(52) and R(53) are a group $C_aH_{2a}$;

α is4, 5, 6or 7;

where if α=5, 6 or 7 a carbon atom of the group $C_aH_{2a}$ can be replaced by a heteroatom group O, $SO_d$ or NR(56), or R(53) and R(54) or R(54) and R(55) or R(52) and R(55) are a group $C_yH_{2y}$;

y is2, 3, 4or 5;

where if y=3, 4 or 5 a carbon atom of the group $C_yH2y$ can be replaced by a heteroatom group O, $SO_d$ or NR(56);

d is zero, 1 or 2;

R(56) is hydrogen or methyl;

or

R(51) is a basic heteroaromatic ring system having 1–9 carbon atoms;

A is a group $C_eH_{2e}$;

e is zero, 1, 2, 3, 4, 5, 6, 7, 8, 9 or 10; where in the group $C_eH_{2e}$ a carbon atom can be replaced by one of the groupings —O—, —CO—, —CH[OR(57)]—, —$SO_r$—, —NR(57)—, —NR(57)—CO—, —NR(57)—CO—NH—, —NR(57)—CO—NH—$SO_2$— or —NR(57)—$SO_2$—;

r is zero, 1 or 2;

G is a phenylene radical

R(58) and R(59) independently of one another are hydrogen, methyl, methoxy, F, Cl, Br, I, $CF_3$ or —$SO_s$—R(60);

R(60) is methyl or NR(61)R(62);

R(61) and R(62) independently of one another are hydrogen or alkyl having 1, 2, 3 or 4 carbon atoms;

D is —$C_vH_{2v}$—$E_w$—;

v is zero, 1, 2, 3 or 4;

E is —O—, —CO—, —CH[OR(63)]—, —$SO_{aa}$— or —N R(63)—;

w is zero or 1;

aa is zero, 1 or 2

R(63) is hydrogen or methyl, or

R(1), R(2) and R(3) independently of one another are —$CF_2$R(64), —CF[R(65)][R(66)], —CF[($CF_2$)$_q$—$CF_3$)][R(65)], —C[($CF_2$)$_p$—$CF_3$]=CR(65) R(66);

R(64) is alkyl having 1, 2, 3 or 4 carbon atoms or cycloalkyl having 3, 4, 5, 6 or 7 carbon atoms;

R(65) and R(66) independently of one another are hydrogen or alkyl having 1, 2, 3 or4 carbon atoms;

q is zero, 1 or 2;

p is zero, 1 or 2;

or

R(1), R(2) and R(3) independently of one another are —OR(67) or —NR(67)R(68);

R(67) and R(68) independently of one another are hydrogen or alkyl having 1, 2, 3, 4, 5 or 6 carbon atoms;

or

R(67) and R(68) together are 4, 5, 6 or 7 methylene groups, of which one $CH_2$ group can be replaced by oxygen, —S—, $SO_2$, —NH—, —$NCH_3$ or —N—benzyl;

R(4) and R(5) independently of one another are hydrogen, alkyl having 1, 2, 3 or 4 carbon atoms, F, Cl, —OR(69), —NR(70)R(71) or —C$_2$F$_{2z+1}$;

R(69), R(70) and R(71) independently of one another are hydrogen or alkyl having 1, 2 or 3 carbon atoms;

z is 1, 2, 3 or 4;

R(6) and R(7) independently of one another are hydrogen or alkyl having 1, 2, 3 or 4 carbon atoms;

X is oxygen or NR(72);

R(72) is hydrogen or alkyl having 1, 2, 3 or 4 carbon atoms;

or a pharmaceutically tolerable salt thereof;

ak) an alkenylcarboxylic acid guanidide, carrying fluorophenyl groups, of the formula

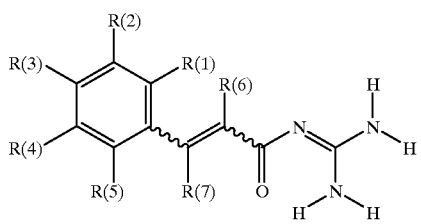

in which:

R(6) is hydrogen, (C$_1$–C$_8$)-alkyl, (C$_3$–C$_8$)-cycloalkyl or phenyl, where the phenyl group is not substituted or is substituted by 1–3 substituents selected from the group consisting of F, Cl, CF$_3$, methyl, methoxy and NR(9)R(10);

R(9) and R(10) are hydrogen, (C$_1$–C$_4$)-alkyl or (C$_1$–C$_4$)-perfluoroalkyl;

R(7) independently is defined as R(6);

R(1), R(2), R(3), R(4) and R(5) independently of one another are hydrogen or F;

where, however, at least one of the radicals R(1), R(2), R(3), R(4) and R(5) must be fluorine;

or a pharmaceutically tolerable salt thereof;

al) a benzoylguanidine of the formula

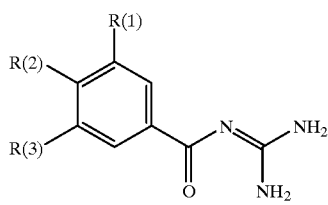

in which:

R(1) is R(4)-SO$_m$ or R(5)R(6)N—SO$_2$—;

m is 1 or 2;

R(4) and R(5) independently of one another are alkyl having 1, 2, 3, 4, 5, 6, 7 or 8 carbon atoms, alkenyl having 3, 4, 5 or 6 carbon atoms, CF$_3$ or —C$_n$H$_{2n}$-R(7);

n is zero, 1, 2, 3 or 4;

R(6) is H or alkyl having 1, 2, 3 or 4 carbon atoms;

R(7) is cycloalkyl having 3, 4, 5, 6, 7 or 8 carbon atoms or phenyl, which is not substituted or is substituted by 1–3 substituents selected from the group consisting of F, Cl, CF$_3$, methyl, methoxy and NR(8)R(9);

R(8) and R(9) are H or alkyl having 1, 2, 3 or 4 carbon atoms;

or

R(5) is also hydrogen;

or

R(5) and R(6) together are 4 or 5 methylene groups, of which a CH$_2$ group can be replaced by oxygen, S, NH, N—CH$_3$ or N-benzyl;

or

R(1) is —O$_p$—(CH$_2$)$_q$—(CF$_2$)$_r$—CF$_3$;

p is zero or 1;

q is zero, 1 or 2;

r is zero, 1, 2 or 3;

or

R(1) is —SR(10), —OR(10) or —CR(10)R(11)R(12);

R(10), R(11) and R(12) independently of one another are hydrogen, alkyl having 1, 2, 3, 4, 5, 6, 7 or 8 carbon atoms, —C$_s$H$_{2s}$—(C$_3$–C$_8$)-cycloalkyl or an aromatic system selected from the group consisting of pyridyl, pyrrolyl, quinolyl, isoquinolyl, imidazolyl or phenyl;

s is zero, 1 or 2;

where the aromatic systems pyridyl, pyrrolyl, quinolyl, isoquinolyl, imidazolyl and phenyl are unsubstituted or substituted by 1–3 substituents selected from the group consisting of F, Cl, CF$_3$, CH$_3$, methoxy, hydroxyl, amino, methylamino and dimethylamino;

R(2) is —(CH$_2$)$_u$—(CF$_2$)$_t$—CF$_3$;

t is zero, 1, 2 or 3;

is zero or 1;

R(3) is hydrogen or independently is defined as R(1);

or a pharmaceutically tolerable salt thereof;

am) a substituted cinnamic acid guanidide of the formula

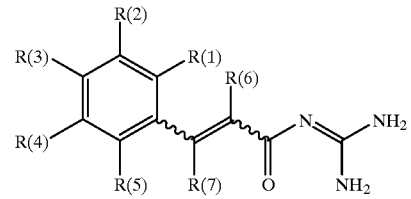

in which:

at least one of the substituents R(1), R(2), R(3), R(4) and R(5) is

—X$_a$—Y$_b$—L$_n$—U;

X is CR(16)R(17), O, S or NR(18);

R(16), R(17) and R(18) independently of one another are H, alkyl having 1, 2, 3 or 4 carbon atoms or perfluoroalkyl having 1, 2, 3 or 4 carbon atoms;

a is zero or 1;

Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;

T is NR(20), O, S or phenylene, where the phenylene is not substituted or is substituted by 1–3 substituents selected from the group consisting of F, Cl, CF$_3$, methyl, methoxy and NR(21)R(22);

R(20), R(21) and R(22) independently of one another are H, alkyl having 1, 2, 3 or 4 carbon atoms or perfluoroalkyl having 1, 2, 3 or 4 carbon atoms;

b is zero or 1;

L is O, S, NR(23) or $C_kH_{2k}$;

k is 1, 2, 3, 4, 5, 6, 7 or 8;

n is zero or 1;

U is NR(24)R(25) or an N-containing heterocycle having 1, 2, 3, 4, 5, 6, 7, 8 or 9 carbon atoms;

R(24) and R(25) independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms;

or

R(24) and R(25) together are 4 or 5 methylene groups, of which one $CH_2$ group can be replaced by oxygen, S, NH, N—$CH_3$ or N-benzyl;

where the N-containing heterocycles are N- or C-bridged and are not substituted or are substituted by 1–3 substituents selected from the group consisting of F, Cl, $CF_3$, methyl, methoxy and NR(27)R(28);

R(23), R(27) and R(28) independently of one another are H, alkyl having 1, 2, 3 or 4 carbon atoms or perfluoroalkyl having 1, 2, 3 or 4 carbon atoms;

and the other substituents R(1), R(2), R(3), R(4) and R(5) in each case independently of one another are H, F, Cl, Br, I, CN, —$O_n$—$C_mH_{2m+1}$, —$O_p$—$(CH_2)_s$—$C_qF_{2q+1}$ or —$C_rH_{2r}R(10)$;

n is zero or 1;

m is zero, 1, 2, 3, 4, 5, 6, 7 or 8;

p is zero or 1;

q is 1, 2, 3, 4, 5, 6, 7 or 8;

s is zero, 1, 2, 3 or 4;

r is zero, 1, 2, 3 or 4;

R(10) is cycloalkyl having 3, 4, 5, 6, 7 or 8 carbon atoms, or phenyl, where the phenyl is not substituted or is substituted by 1–3 substituents selected from the group consisting of F, Cl, $CF_3$, methyl, methoxy and NR(11)R(12);

R(11) and R(12) independently of one another are H, alkyl having 1, 2, 3 or 4 carbon atoms or perfluoroalkyl having 1, 2, 3 or 4 carbon atoms;

R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms; cycloalkyl having 3, 4, 5, 6, 7 or 8 carbon atoms or phenyl, which is not substituted or is substituted by 1–3 substituents selected from the group consisting of F, Cl, $CF_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

or a pharmaceutically tolerable salt thereof;

an) a benzoylguanidine of the formula

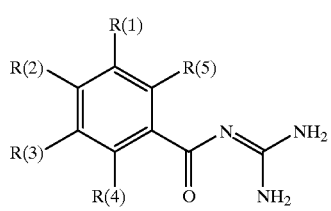

I in which:

at least one of the substituents R(1), R(2) and R(3) is R(6)—C(OH)$_2$—;

R(6) is perfluoroalkyl having 1, 2 or 3 carbon atoms, which is straight-chain or branched;

and the other substituents R(1), R(2) and R(3) independently of one another are hydrogen, OH, F, Cl, Br, I, alkyl having 1, 2, 3, 4, 5 or 6 carbon atoms, cycloalkyl having 3, 4, 5 or 6 carbon atoms, alkoxy having 1, 2, 3 or 4 carbon atoms, or phenoxy, which is unsubstituted or is substituted by 1–3 substituents selected from the group consisting of F, Cl, methyl and methoxy;

or the other substituents R(1), R(2) and R(3) independently of one another are alkyl-SO$_x$, —CR(7)=CR(8)R(9) or —C=CR(9);

x is zero, 1 or 2;

R(7) is hydrogen or methyl;

R(8) and R(9) independently of one another are hydrogen, alkyl having 1, 2, 3 or 4 carbon atoms, cycloalkyl having 3, 4, 5, 6, 7 or 8 carbon atoms, or phenyl, which is unsubstituted or is substituted by 1–3 substituents selected from the group consisting of F, Cl, $CF_3$, methyl and methoxy;

or the other substituents R(1), R(2) and R(3)

independently of one another are phenyl, $C_6H_5$-$(C_1-C_4)$-alkyl, naphthyl, biphenylyl, quinolinyl, isoquinolinyl or imidazolyl, where quinolinyl, isoquinolinyl or imidazolyl are bonded via C or N and where phenyl, $C_6H_5$-$(C_1-C_4)$-alkyl, naphthyl, biphenylyl, quinolinyl, isoquinolinyl and imidazolyl are unsubstituted or are substituted by 1–3 substituents selected from the group consisting of F, Cl, $CF_3$, $CH_3$, methoxy, hydroxyl, amino, methylamino and dimethylamino;

or the other substituents R(1), R(2) and R(3) independently of one another are SR(10), —OR(10), —CR(10)R(11)R(12);

R(10) is —$C_fH_{2f}$-$(C_3-C_8)$-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents selected from the group consisting of F, Cl, $CF_3$, $CH_3$, methoxy, hydroxyl, amino, methylamino and dimethylamino;

f is zero, 1 or 2;

R(11) and R(12) independently of one another are defined as R(10), hydrogen or alkyl having 1, 2, 3 or 4 carbon atoms;

R(4) and R(5) independently of one another are hydrogen, alkyl having 1, 2 or 3 carbon atoms, F, Cl, Br, I, CN, OR(13), NR(14)R(15), —$(CH_2)_n$-$(CF_2)_o$-$CF_3$;

R(13), R(14) and R(15) independently of one another are hydrogen or alkyl having 1, 2, 3 or 4 carbon atoms;

n is zero or 1;

o is zero, 1 or 2;

or a pharmacologically acceptable salt thereof;

ao) a sulfonimidamide of the formula

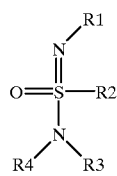

in which:
at least one of the three substituents R(1), R(2) and R(3) is a benzoylguanidine,

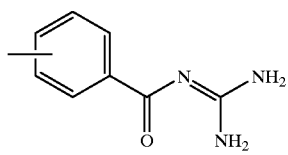

which is unsubstituted or substituted in the phenyl moiety by 1–4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$-R(14), F, Cl, Br, I, —C≡N, CF$_3$, R(22)SO$_2$—, R(23)R(24)N—CO—, R(25)—CO—, R(26)R(27)N-SO$_2$, —OR(35), —SR(35) or —NR(35)R(36);

m is zero, 1 or 2;

R(14)
is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$;

R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —CF$_3$;

n is zero, 1, 2, 3 or 4;

R(29) is —(C$_3$–C$_7$)-cycloalkyl or phenyl, which is not substituted or is substituted by 1–3 substituents selected from the group consisting of F, Cl, —CF$_3$, methyl, methoxy and —NR(30)R(31); R(30) and R(31) are hydrogen or alkyl having 1, 2, 3 or 4 carbon atoms;

or

R(23), R(25) and R(26) are hydrogen;

R(24) and R(27) independently of one another are hydrogen or alkyl having 1, 2, 3 or 4 carbon atoms;

or

R(23) and R(24), and also R(26) and R(27) together are 5 or 6 methylene groups, of which one CH$_2$ group can be replaced by oxygen, —S—, —NH—, —NCH$_3$ or —N—benzyl;

R(35) and R(36) independently of one another are hydrogen or alkyl having 1, 2, 3, 4, 5 or 6 carbon atoms;

or

R(35) and R(36) together are 4–7 methylene groups, of which one CH$_2$ group can be replaced by oxygen, —S—, —NH—, —NCH$_3$ or —N-benzyl;

or

R(35) is phenyl, which is not substituted or is substituted by 1–3 substituents selected from the group consisting of F, Cl, —CF$_3$, methyl, methoxy, SO$_2$R(5), SO$_2$NR(6)R(7) and —NR(32)R(33);

R(5) is alkyl having 1, 2, 3, 4, 5 or 6 carbon atoms;

R(6) and R(7) independently of one another are hydrogen or alkyl having 1, 2, 3 or 4 carbon atoms;

R(32) and R(33) independently of one another are hydrogen or alkyl having 1, 2, 3 or 4 carbon atoms;

or

R(35) is C$_1$–C$_9$-heteroaryl, which is unsubstituted or substituted by 1–3 substituents selected from the group consisting of F, Cl, CF$_3$, CH$_3$, methoxy, hydroxyl, amino, methylamino and dimethylamino;

and the other substituents R(1), R(2) and R(3) in each case independently of one another are alkyl having 1, 2, 3, 4, 5, 6, 7 or 8 carbon atoms, (CH$_2$)$_p$R(10);

p is zero, 1, 2, 3 or 4;

R(10) is phenyl, which is not substituted or is substituted by 1–3 substituents selected from the group consisting of F, Cl, —CF$_3$, methyl, methoxy, —SO$_2$NR(17)R(8) and —SO$_2$R(9);

R(17) and R(8) independently of one another are hydrogen or alkyl having 1, 2, 3 or 4 carbon atoms;

R(9) is alkyl having 1, 2, 3 or 4 carbon atoms;

or the other radical R(1) or R(3) in each case is hydrogen,

R(4) is hydrogen or alkyl having 1, 2, 3 or 4 carbon atoms;

or a pharmaceutically tolerable salt thereof;

ap) a benzoylguanidine of the formula

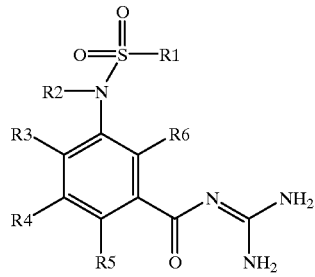

in which:
R(1) is alkyl having 1, 2, 3, 4, 5, 6, 7 or 8 carbon atoms or NR(7)R(8);

R(7) and R(8) independently of one another are hydrogen or alkyl having 1, 2, 3, 4, 5, 6, 7 or 8 carbon atoms;

R(2) is hydrogen, alkyl having 1, 2, 3, 4, 5, 6, 7 or 8 carbon atoms or —SO$_2$R(9);

R(9) independently is defined as R(1);

R(3) is hydrogen, —SR(25), —OR(25), —NR(25)R(26) or —CR(25)R(26)R(27);

R(25) is hydrogen, alkyl having 1, 2, 3, 4, 5, 6, 7 or 8 carbon atoms, or phenyl,
which is unsubstituted or substituted by 1–3 substituents selected from the group consisting of F, Cl, CF$_3$, CH$_3$, methoxy, hydroxyl, amino, methylamino and dimethylamino;

or

R(25) is —(C$_1$–Cg)-heteroaryl,
which is unsubstituted or substituted by 1–3 substituents selected from the group consisting of F, Cl, CF$_3$, $CH_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is hydrogen, F, Cl, Br, I, OH, —C≡N, $CF_3$, alkyl having 1, 2, 3, 4, 5, 6, 7 or 8 carbon atoms, alkenyl having 2, 3, 4, 5, 6, 7 or 8 carbon atoms or —$(CH_2)_m$R(14);

m is zero, 1 or 2;

R(14) is —($C_3$–$C_8$)-cycloalkyl or phenyl, which is not substituted or is substituted by 1–3 substituents selected from the group consisting of F and Cl, —$CF_3$, methyl, methoxy and —NR(15)R(16);

R(15) and R(16) independently of one another are hydrogen or —$CH_3$;

R(5) and R(6) independently of one another are hydrogen, alkyl having 1, 2, 3 or 4 carbon atoms, F, Cl, —OR(32), —NR(33)R(34) or $CF_3$;

R(32), R(33) and R(34) independently of one another are hydrogen or alkyl having 1, 2, 3 or 4 carbon atoms;

or a pharmaceutically tolerable salt thereof;

aq) a benzenedicarboxylic acid diguanidide of the formula

I in which:

one of the radicals R(1), R(2), R(3) and R(4) is —CO—N=C(NH_2)_2;

and of the other radicals R(1), R(2), R(3) and R(4) in each case:

R(1) is hydrogen, alkyl having 1, 2, 3 or 4 carbon atoms, F, Cl, Br, I, —OR(32), —NR(33)R(34) or $CF_3$;

R(32), R(33) and R(34) independently of one another are hydrogen or alkyl having 1, 2, 3 or 4 carbon atoms;

R(2) and R(4) independently of one another are hydrogen, F, Cl, Br, I, OH, —CN, $CF_3$, —CO—N=C(NH_2)_2, alkyl having 1, 2, 3, 4, 5, 6, 7 or 8 carbon atoms, alkenyl having 2, 3, 4, 5, 6, 7 or 8 carbon atoms or —$(CH_2)_m$R(14);

m is zero, 1 or 2;

R(14) is —($C_3$–$C_8$)-cycloalkyl or phenyl, which is not substituted or is substituted by 1–3 substituents selected from the group consisting of F and Cl, —$CF_3$, methyl, methoxy and —NR(15)R(16);

R(15) and R(16) are hydrogen or —$CH_3$;

or

R(2) and R(4) independently of one another are pyrrol-1-yl, pyrrol-2-yl or pyrrol-3-yl, which is not substituted or is substituted by 1–4 substituents selected from the group consisting of F, Cl, Br, I, —CN, ($C_2$–$C_8$)-alkanoyl, ($C_2$–$C_8$)-alkoxycarbonyl, formyl, carboxyl, —$CF_3$, methyl, methoxy;

or

R(2) and R(4) independently of one another are R(22)—$SO_2$—, R(23)R(24)N—CO—, R(28)—CO— or R(29)R(30)N—$SO_2$;

R(22) and R(28) independently of one another are methyl or —$CF_3$;

R(23), R(24), R(29) and R(30) independently of one another are hydrogen or methyl;

or

R(2) and R(4) independently of one another are —OR(35) or —NR(35)R(36);

R(35) and R(36) independently of one another are hydrogen or alkyl having 1, 2, 3, 4, 5 or 6 carbon atoms;

or

R(35) and R(36) together are 4–7 methylene groups, of which one $CH_2$ group can be replaced by oxygen, —S—, —NH—, —$NCH_3$ or —N—benzyl;

R(3) is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms or phenyl, which is unsubstituted or substituted by 1–3 substituents selected from the group consisting of F, Cl, $CF_3$, $CH_3$, methoxy, hydroxyl, amino, methylamino and dimethylamino;

or

R(25) is —($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(5) is alkyl having 1, 2, 3 or 4 carbon atoms, F, Cl, Br, I, X-$(CH_2)_y$—$CF_3$ or phenyl, which is not substituted or is substituted by 1–3 substituents selected from the group consisting of F and Cl, —$CF_3$, methyl, methoxy and —NR(6)R(7);

R(6) and R(7) independently of one another are hydrogen or —$CH_3$;

X is a bond or oxygen;

y is zero, 1 or 2;

or a pharmaceutically tolerable salt thereof;

ar) a benzenedicarboxylic acid diguanidide of the formula

I in which:

one of the radicals R(1), R(2), R(3) and R(5) is —CO—N=C(NH_2)_2;

and of the other radicals R(1), R(2), R(3) and R(5) in each case:

R(1) and R(5) independently of one another are hydrogen, alkyl having 1, 2, 3 or 4 carbon atoms, F, Cl, —OR(32), —NR(33)R(34) or $CF_3$;

R(32), R(33) and R(34) independently of one another are hydrogen or alkyl having 1, 2, 3 or 4 carbon atoms;

R(2) is hydrogen, F, Cl, Br, I, OH, —CN, $CF_3$, —CO—N=C(NH_2)_2, alkyl having 1, 2, 3, 4, 5, 6, 7 or 8 carbon atoms, alkenyl having 2, 3, 4, 5, 6, 7 or 8 carbon atoms or —$(CH_2)_m$R(14);

m is zero, 1 or 2;

R(14) is —($C_3$–$C_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$;

or

R(2) is R(22)—SO$_2$—, R(23)R(24)N—CO—, R(28)—CO— or R(29)R(30)N—SO$_2$;

R(22) and R(28) independently of one another are methyl or —CF$_3$;

R(23), R(24), R(29) and R(30) independently of one another are hydrogen or methyl;

or

R(2) is —OR(35) or —NR(35)R(36);

R(35) and R(36) independently of one another are hydrogen or alkyl having 1, 2, 3, 4, 5 or 6 carbon atoms;

or

R(35) and R(36) together are 4–7 methylene groups, of which one CH$_2$ group can be replaced by oxygen, —S—, —NH—, —NCH$_3$ or-N-benzyl;

R(3) is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino;

or

R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is CF$_3$, alkyl having 1, 2, 3, 4, 5, 6, 7 or 8 carbon atoms, alkenyl having 2, 3, 4, 5, 6, 7 or 8 carbon atoms, —(C$_3$–C$_8$)-cycloalkyl or —(CH$_2$)$_m$R(14);

m is 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$;

or

R(4) is phenyl, which is substituted by 2, 3, 4 or five substituents selected from the group consisting of F, Cl, CF$_3$, methyl, methoxy and —NR(15)R(16);

R(15) and R(16) independently of one another are hydrogen or CH$_3$;

or a pharmaceutically tolerable salt thereof;

as) a diaryldicarboxylic acid diguanidide of the formula

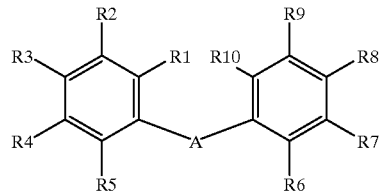

I in which:

one of the radicals R(1), R(2), R(3), R(4) and R(5) is —CO—N=C(NH$_2$)$_2$;

the other radicals R(1) and R(5) in each case independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;

the other radicals R(2) and R(4) in each case independently of one another are hydrogen, F, Cl, Br, I, OH, —CN, CF$_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) are hydrogen or —CH$_3$;

or the other radicals R(2) and R(4) in each case independently of one another are pyrrol-1-yl, pyrrol-2-yl or pyrrol-3-yl, which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy;

or the other radicals R(2) and R(4) in each case are R(22)—SO$_2$—, R(23)R(24)N—CO—, R(28)—CO— or R(29)R(30)N—SO$_2$;

R(22) and R(28) independently of one another are methyl or —CF$_3$;

R(23), R(24), R(29) and R(30) independently of one another are hydrogen or methyl;

or the other radicals R(2) and R(4) in each case independently of one another are —OR(35) or —NR(35)R(36);

R(35) and R(36) independently of one another are hydrogen or alkyl having 1, 2, 3, 4, 5 or 6 carbon atoms;

or

R(35) and R(36) together are 4–7 methylene groups, of which one CH$_2$ group can be replaced by oxygen, —S—, —NH—, —NCH$_3$ or —N—benzyl;

the other radical R(3) in each case is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino;

or
R(25) is —(C$_1$–C$_9$)-heteroaryl,
which is unsubstituted or substituted by 1–3 substituents selected from the group consisting of F, Cl, CF$_3$, CH$_3$, methoxy, hydroxyl, amino, methylamino and dimethylamino;
R(26) and R(27) independently of one another are defined as R(25) or are hydrogen or alkyl having 1, 2, 3, 4, 5, 6, 7 or 8 carbon atoms;
one of the radicals R(6), R(7), R(8), R(9) and R(10) is —CO—N=C(NH$_2$)$_2$;
the other radicals R(6) and R(10) in each case independently of one another are hydrogen, alkyl having 1, 2, 3 or 4 carbon atoms, F, Cl, —OR(132), —NR(133)R(134) or CF$_3$;
R(132), R(133) and R(134) independently of one another are hydrogen or alkyl having 1, 2, 3 or 4 carbon atoms;
the other radicals R(7) and R(9) in each case independently of one another are hydrogen, F, Cl, Br, I, OH, —CN, CF$_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_{mm}$R(114);
mm is zero, 1 or 2;
R(114) is —(C$_3$–C$_8$)-cycloalkyl or phenyl,
which is not substituted or is substituted by 1–3 substituents selected from the group consisting of F and Cl, —CF$_3$, methyl, methoxy and —NR(115)R(116);
R(115) and R(116) are hydrogen or —CH$_3$;
or
the other radicals R(7) and R(9) in each case independently of one another are pyrrol-1-yl, pyrrol-2-yl or pyrrol-3-yl, which is not substituted or is substituted by 1–4 substituents selected from the group consisting of F, Cl, Br, I, —CN, (C$_2$–C8)-alkanoyl, (C$_2$–C$_8$)-alkoxycarbonyl, formyl, carboxyl, —CF$_3$, methyl and methoxy;
or
the other radicals R(7) and R(9) in each case are R(122)—SO$_2$—, R(123)R(124)N—CO—, R(128)—CO— or R(129)R(130)N—SO$_2$;
R(122) and R(128) independently of one another are methyl or —CF$_3$;
R(123), R(124), R(129) and R(130) independently of one another are hydrogen or methyl;
or
the other radicals R(7) and R(9) in each case independently of one another are —OR(135) or —NR(135)R(136);
R(135) and R(136) independently of one another are hydrogen or alkyl having 1, 2, 3, 4, 5 or 6 carbon atoms;
or
R(135) and R(136) together are 4–7 methylene groups, of which one CH$_2$ group can be replaced by oxygen, —S—, —NH—, —NCH$_3$ or —N—benzyl;
the other radical R(8) in each case is hydrogen, —SR(125), —OR(125), —NR(125)R(126) or —CR(125)R(126)R(127);
R(125) is hydrogen, alkyl having 1, 2, 3, 4, 5, 6, 7 or 8 carbon atoms or phenyl,
which is unsubstituted or substituted by 1–3 substituents selected from the group consisting of F, Cl, CF$_3$, CH$_3$, methoxy, hydroxyl, amino, methylamino and dimethylamino;
or
R(125) is —(C$_1$–C$_9$)-heteroaryl,
which is unsubstituted or substituted by 1–3 substituents selected from the group consisting of F, Cl, CF$_3$, CH$_3$, methoxy, hydroxyl, amino, methylamino and dimethylamino;
R(126) and R(127) independently of one another are defined as R(125) or are hydrogen or alkyl having 1, 2, 3, 4, 5, 6, 7 or 8 carbon atoms;
A is absent or is —NR(11)—CO—, —NR(12)—CO—NR(13)—, —NR(17)—CO—NR(18)—SO$_2$—, —NR(19)—SO$_2$—, —SO$_2$—N R(19)—SO$_2$—, —SO$_2$—NR(19)—CO—, —O—CO—NR(19)—SO$_2$— or —CR(20)=CR(21)—;
R(11), R(12), R(13), R(17), R(18), R(19), R(20) and R(21) independently of one another are hydrogen or alkyl having 1, 2, 3, 4, 5, 6, 7 or 8 carbon atoms
or a pharmaceutically tolerable salt thereof;
at) a substituted thiophenylalkenylcarboxylic acid guanidide of the formula

I

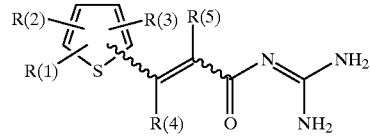

in which:
at least one of the substituents R(1), R(2) and R(3) is —O$_p$—(CH$_2$)$_s$—C$_q$F$_{2q+1}$, R(40)CO— or R(31)SO$_k$—;
p is zero or 1;
s is zero, 1, 2, 3 or 4;
q is 1, 2, 3, 4, 5, 6, 7 or 8;
k is zero, 1 or 2;
R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
which is not substituted or is substituted by 1–3 substituents selected from the group consisting of F, Cl, CF$_3$, methyl and methoxy;
R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl,
which is not substituted or is substituted by 1–3 substituents selected from the group consisting of F, Cl, CF$_3$, methyl or methoxy;
or
R(31) is NR(41)R(42);
R(41) and R(42)
independently of one another are hydrogen, alkyl having 1, 2, 3 or 4 carbon atoms, perfluoroalkyl having 1, 2, 3 or 4 carbon atoms,
or
R(41) and R(42) together are 4 or 5 methylene groups, of which one CH$_2$ group can be replaced by oxygen, S, NH, N-CH$_3$ or N-benzyl;
and the other substituents R(1), R(2) and R(3) in each case independently of one another are H, F, Cl, Br, I, CN, —O$_{na}$—C$_{ma}$H$_{2ma+1}$ or —O$_{ga}$C$_{ra}$H$_{2ra}$R(10);
na is zero or 1;
ma is zero, 1,2,3,4,5,6,7or8;
ga is zero or 1;
ra is zero, 1, 2, 3 or 4;
R(1 0) is cycloalkyl having 3, 4, 5, 6, 7 or 8 carbon atoms or phenyl, where the phenyl is not substituted or is substituted by 1–3 substituents selected from the group consisting of F, Cl, CF$_3$, methyl and methoxy;
R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl,
which is not substituted or is substituted by 1–3 substituents selected from the group consisting of F, Cl, CF$_3$, methyl, methoxy and NR(14)R(15);
R(14) and R(15) independently of one another are H, alkyl having 1, 2, 3 or 4 carbon atoms or perfluoroalkyl having 1, 2, 3 or 4 carbon atoms;
or a pharmaceutically tolerable salt thereof;
au) an ortho-substituted benzoylguanidine of the formula

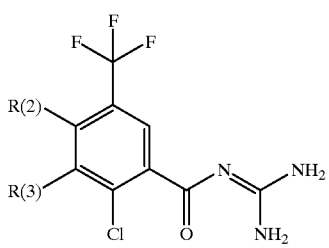

in which:
R(2) and R(3) independently of one another are hydrogen, Cl, Br, I, (C$_1$–C$_8$)-alkyl, (C$_3$–C$_8$)-cycloalkyl or —OR(5);
R(5) is (C$_1$–C8)-alkyl or —C$_d$H$_{2d}$-(C$_3$–C$_8$)-cycloalkyl;
d is zero, 1 or 2;
where one of the two substituents R(2) and R(3) is always hydrogen but both substituents R(2) and R(3) are not simultaneously hydrogen, or a pharmaceutically tolerable salt thereof;
av) a benzoylguanidine of the formula

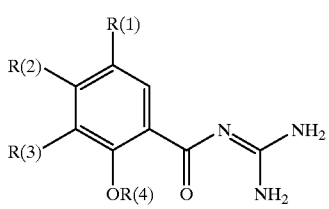

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
x is oxygen, S, NR(5),
a is zero or 1;
b is zero, 1 or 2;
c is zero, 1,2 or 3;
R(5) is H, alkyl having 1, 2, 3 or 4 carbon atoms or —C$_d$H$_{2d}$R(6);
d is zero, 1, 2, 3 or 4;
R(6) is cycloalkyl having 3, 4, 5, 6, 7 or 8 carbon atoms, phenyl, biphenylyl or naphthyl,
where the aromatics phenyl, biphenylyl or naphthyl are not substituted or are substituted by 1–3 substituents selected from the group consisting of F, Cl, CF$_3$, methyl, methoxy and NR(7)R(8);
R(7) and R(8) independently are H or alkyl having 1, 2, 3 or 4 carbon atoms;
or
R(1) is —SR(10), —OR(10) or —CR(10)R(11)R(12);
R(10) is —C$_f$H$_{2}$f-cycloalkyl having 3, 4, 5, 6, 7 or 8 carbon atoms in the cycloalkyl ring, or phenyl,
where phenyl is unsubstituted or substituted by 1–3 substituents selected from the group consisting of F, Cl, CF$_3$, CH$_3$, methoxy, hydroxyl, amino, methylamino and dimethylamino;
f is zero, 1 or 2;
R(11) and R(12) independently of one another are defined as R(10) or are hydrogen or alkyl having 1, 2, 3 or 4 carbon atoms;
or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring,
which are in each case unsubstituted or substituted by 1–3 substituents selected from the group consisting of F, Cl, CF$_3$, CH$_3$, methoxy, hydroxyl, amino, methylamino and dimethylamino,
or
R(1) is —SR(13), —OR(13), —NHR(13), —NR(13)R(14), —CHR(13)R(15), —C[R(15)R(16)OH], —C=CR(18), —C[R(19)]=CHR(18), —C[R(20)R(21)]$_k$—(CO)-[CR(22)R(23)]$_1$-R(24),
k is zero, 1, 2, 3 or 4;
l is zero, 1, 2, 3 or 4;
R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);
R(17) is hydrogen or methyl,
g,h and i identically or differently are zero, 1, 2, 3 or 4;
j is 1, 2, 3 or 4;
R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
R(18)
is phenyl,
which is unsubstituted or substituted by 1–3 substituents selected from the group consisting of F, Cl, CF$_3$, methyl, methoxy and NR(25)R(26);
R(25) and R(26) are H or alkyl having 1, 2, 3 or 4 carbon atoms;
or
R(18) is heteroaryl having 1, 2, 3, 4, 5, 6, 7, 8 or 9 carbon atoms, which is unsubstituted or substituted as phenyl;
or
R(18) is alkyl having 1, 2, 3, 4, 5 or 6 carbon atoms, which is unsubstituted or substituted by 1–3 OH;
or
R(18) is cycloalkyl having 3, 4, 5, 6, 7 or 8 carbon atoms;
R(19), R(20), R(21), R(22) and R(23) identically or differently are hydrogen or methyl;
R(24) is H, alkyl having 1, 2, 3, 4, 5 or 6 carbon atoms, cycloalkyl having 3, 4, 5, 6, 7 or 8 carbon atoms or —C$_m$H$_2$m—R(18);
m is 1, 2, 3 or 4;
R(2) and R(3) are defined as R(1);
R(4) is alkyl having 1, 2, 3 or 4 carbon atoms;
or a pharmaceutically tolerable salt thereof;

aw) an ortho-substituted benzoylguanidine of the formula

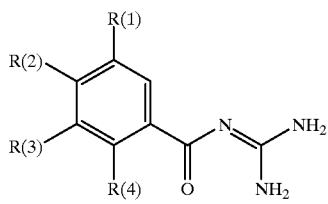

in which:
R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;
X is oxygen, S, NR(5),
a is zero or 1;
b is zero, 1 or 2;
c is zero, 1,2 or 3;
    R(5) is H, alkyl having 1, 2, 3 or 4 carbon atoms or —$C_dH_{2d}R(^6)$;
    d is zero, 1, 2, 3 or 4;
    R(6) is cycloalkyl having 3, 4, 5, 6, 7 or 8 carbon atoms, phenyl, biphenylyl or naphthyl,
      where the aromatics phenyl, biphenylyl or naphthyl are not substituted or are substituted by 1–3 substituents selected from the group consisting of F, Cl, $CF_3$, methyl, methoxy and NR(7)R(8);
    R(7) and R(8) independently are H or alkyl having 1, 2, 3 or 4 carbon atoms;
or
R(1) is —SR(10), —OR(10) or —CR(10)R(11)R(12);
    R(10) is —$C_fH_{2f}$-cycloalkyl having 3, 4, 5, 6, 7 or 8 carbon atoms in the cycloalkyl ring, or phenyl,
      where phenyl is unsubstituted or substituted by 1–3 substituents selected from the group consisting of F, Cl, $CF_3$, $CH_3$, methoxy, hydroxyl, amino, methylamino and dimethylamino;
    f is zero, 1 or 2;
    R(11) and R(12) independently of one another are defined as R(10), or are hydrogen or alkyl having 1, 2, 3 or 4 carbon atoms;
or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, $CF_3$, $CH_3$, methoxy, hydroxyl, amino, methylamino and dimethylamino,
or
R(1) is —SR(13), —OR(13), —NHR(13), —NR(13)R(14), —CHR(13)R(15), —C[R(15)R(16)OH], —C=CR(18), —C[R(19)]=CHR(18), —C[R(20)R(21)]$_k$—(CO)-[CR(22)R(23)]$_l$-R(24),
    k is zero, 1, 2, 3 or 4;
    l is zero, 1, 2, 3 or 4;
    R(13) and R(14) identically or differently are —$(CH_2)_g$—$(CHOH)_h$—$(CH_2)_i$-$(CHOH)_j$—R(17) or —$(CH_2)_g$—O—$(CH_2$-$CH_2O)_n$—R(24);

R(17) is hydrogen or methyl, g, h and i
identically or differently are zero, 1, 2, 3 or 4;
j is 1, 2, 3 or 4;
R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
R(1 8) is phenyl,
    which is unsubstituted or substituted by 1–3 substituents selected from the group consisting of F, Cl, $CF_3$, methyl, methoxy and NR(25)R(26);
    R(25) and R(26) are H or alkyl having 1, 2, 3 or 4 carbon atoms;
or
R(18) is heteroaryl having 1, 2, 3, 4, 5, 6, 7, 8 or 9 carbon atoms,
    which is unsubstituted or substituted as phenyl;
or
R(18) is alkyl having 1, 2, 3, 4, 5 or 6 carbon atoms, which is unsubstituted or substituted by 1–3 OH;
or
R(18) is cycloalkyl having 3, 4, 5, 6, 7 or 8 carbon atoms;
R(19), R(20), R(21), R(22) and R(23) identically or differently are hydrogen or methyl;
R(24) is H, alkyl having 1, 2, 3, 4, 5 or 6 carbon atoms, cycloalkyl having 3, 4, 5, 6, 7 or 8 carbon atoms or —$C_mH_{2m}$-R(18);
m is 1, 2, 3 or 4;
one of the two substituents R(2) and R(3)
    is hydroxyl;
and
the other of the substituents R(2) and R(3) in each case
    is defined as R(1);
R(4) is alkyl having 1, 2, 3 or 4 carbon atoms; alkoxy having 1, 2, 3 or 4 carbon atoms, F, Cl, Br, I or —$(CH_2)_n$—$(CF_2)_o$—$CF_3$;
n is zero or 1;
o is zero or 1;
or a pharmaceutically tolerable salt thereof;
ax) a bis-ortho-substituted benzoylguanidine of the formula

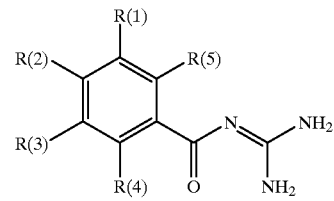

in which:
R(1), R(2) and R(3) independently of one another are R(10)—$SO_a$— or R(14)R(15)N—$SO_2$—;
a is zero, 1 or 2,
    R(10), R(14) and R(15) independently of one another are alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5 or 6 carbon atoms or —$C_{ab}H_{2ab}$-R(16);
    ab is zero, 1, 2, 3 or 4;
    R(16) is cycloalkyl having 3, 4, 5, 6 or 7 carbon atoms, or phenyl, which is not substituted or is substituted by 1–3 substituents selected from the group consisting of F, Cl, $CF_3$, methyl, methoxy and NR(17)R(18);

R(17) and R(18) independently of one another are hydrogen, $CF_3$ or alkyl having 1, 2, 3 or 4 carbon atoms;

or

R(14) and R(15) together are 4 or 5 methylene groups, of which one $CH_2$ group can be replaced by oxygen, sulfur, NH, N—$CH_3$ or N-benzyl;

or

R(14) and R(15) are hydrogen;

or

R(1), R(2) and R(3) independently of one another are SR(21), —OR(22), —NR(23)R(24) or —CR(25)R(26)R(27);

R(21), R(22), R(23) and R(25) independently of one another are —$C_bH_{2b}$-($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

b is zero, 1 or 2;

R(24), R(26) and R(27) independently of one another are hydrogen, alkyl having 1, 2, 3 or 4 carbon atoms or perfluoroalkyl having 1, 2, 3 or 4 carbon atoms;

or

R(1), R(2) and R(3) independently of one another are hydrogen, F, Cl, Br, I, CN, —$(Xa)_{dg}$—$C_{da}H_{2da+1}$, —$(Xb)_{dh}$—$(CH_2)_{db}$—$C_{de}F_{2de+1}$, alkenyl having 3, 4, 5, 6, 7 or 8 carbon atoms or —$C_{df}H_{2df}$R(30);

(Xa) is oxygen, sulfur or NR(33);

R(33) is hydrogen, alkyl having 1, 2, 3 or 4 carbon atoms or perfluoroalkyl having 1, 2, 3 or 4 carbon atoms;

dg is zero or 1;

(Xb) is oxygen, sulfur or NR(34);

R(34) is hydrogen, alkyl having 1, 2, 3 or 4 carbon atoms or perfluoroalkyl having 1, 2, 3 or 4 carbon atoms;

dh is zero or 1;

da is zero, 1, 2, 3, 4, 5, 6, 7 or 8;

db is zero, 1, 2, 3 or 4;

de is zero, 1, 2, 3, 4, 5, 6 or 7;

df is zero, 1, 2, 3 or 4;

R(30) is cycloalkyl having 3, 4, 5, 6, 7 or 8 carbon atoms, phenyl, biphenylyl or naphthyl, where the aromatics phenyl, biphenylyl and naphthyl are not substituted or are substituted by 1–3 substituents selected from the group consisting of F, Cl, $CF_3$, methyl, methoxy and NR(31)R(32);

R(31) and R(32) are hydrogen, alkyl having 1, 2, 3 or 4 carbon atoms or perfluoroalkyl having 1, 2, 3 or 4 carbon atoms;

or

R(1), R(2) and R(3) independently of one another are NR(40)R(41) or —$(Xe)$—$(CH_2)_{eb}$R(45);

R(40) and R(41) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms or $(CH_2)_e$—R(42);

e is zero, 1, 2, 3 or 4;

R(42) is cycloalkyl having 3, 4, 5, 6 or 7 carbon atoms or phenyl, which is not substituted or is substituted by 1–3 substituents selected from the group consisting of F, Cl, $CF_3$, methyl, methoxy and NR(43)R(44);

R(43) and R(44) independently of one another are hydrogen, $CF_3$ or alkyl having 1, 2, 3 or 4 carbon atoms;

or

R(40) and R(41) together are 4 or 5 methylene groups, of which one $CH_2$ group can be replaced by oxygen, sulfur, NH, N-$CH_3$ or N-benzyl;

(Xe) is oxygen, sulfur or NR(47);

R(47) is hydrogen, alkyl having 1, 2, 3 or 4 carbon atoms or perfluoroalkyl having 1, 2, 3 or 4 carbon atoms;

eb is zero, 1, 2, 3 or 4;

R(45) is cycloalkyl having 3, 4, 5, 6 or 7 carbon atoms, or phenyl, which is not substituted or is substituted by 1–3 substituents selected from the group consisting of F, Cl, $CF_3$, methyl, methoxy, NR(50)R(51) and —$(Xfa)$—$(CH_2)_{ed}$—$(Xfb)$R(46);

Xfa is $CH_2$, oxygen, sulfur or NR(48);

Xfb is oxygen, sulfur or NR(49);

R(48), R(49), R(50) and R(51) independently of one another are hydrogen, alkyl having 1, 2, 3 or 4 carbon atoms or perfluoroalkyl having 1, 2, 3 or 4 carbon atoms;

ed is 1, 2, 3 or 4;

R(46) is hydrogen, alkyl having 1, 2, 3 or 4 carbon atoms or perfluoroalkyl having 1, 2, 3 or 4 carbon atoms;

or

R(1), R(2) and R(3) independently of one another are —CHR(52)R(53);

R(52) is —$(CH_2)_g$—$(CHOH)_h$—$(CH)_i$—$(CHOH)_k$—R(54) or —$(CH_2)_g$—O—$(CH_2$—$CH_2O)_h$—R(54);

R(54) is hydrogen or methyl;

g, h, i identically or differently are zero, 1, 2, 3 or 4;

k is 1, 2, 3 or 4;

R(53) is hydrogen or alkyl having 1, 2, 3 or 4 carbon atoms;

or

R(1), R(2) and R(3) independently of one another are —C(OH)R(55)R(56);

R(55) and R(56) identically or differently are hydrogen or alkyl having 1, 2, 3 or 4 carbon atoms;

or

R(55) and R(56) together are cycloalkyl having 3, 4, 5 or 6 carbon atoms;

or

R(55) is —$CH_2OH$;

and

R(4) and R(5) independently of one another are alkyl having 1, 2, 3 or 4 carbon atoms, alkoxy having 1, 2, 3 or 4 carbon atoms, OH, F, Cl, Br, I, CN, —$O_n$—$(CH_2)_o$—$(CF_2)_p$—$CF_3$;

n is zero or 1;

o is zero, 1 or 2;

p is zero, 1 or 2;

or a pharmaceutically tolerable salt thereof;

ay) a substituted 1-naphthoylguanidine of the formula

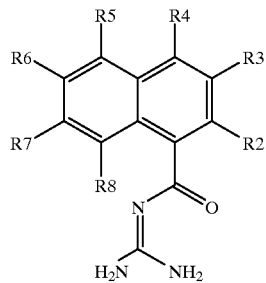

in which:

R2, R3, R4, R5, R6, R7 and R8 independently of one another are H, F, Cl, Br, I, CN, $NO_2$, $CF_3$, $C_2F_5$ or $X_aY_bZ$;

X is O, S, NR(10), CR(11)R(12), C=O, C(=O)NR(10), C(=O)O, SO, $SO_2$, $SO_2$NR(10), OC=O, NR(10)C=O or NR(10)$SO_2$,
where the linkage with the naphthalene ring in each case takes place via the left atom;
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

a is zero or 1;

Y is alkylene having 1, 2, 3, 4, 5, 6, 7 or 8 $CH_2$ groups, where one of these $CH_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

b is zero or 1;

Z is H, alkyl having 1, 2, 3, 4, 5, 6 or 7 carbon atoms, cycloalkyl having 3, 4, 5, 6 or 7 carbon atoms, C(=O)R(15), $SO_2$R(15), NR(16)R(17) or phenyl,
which is not substituted or is substituted by 1–3 substituents selected from the group consisting of F, Cl, Br, $CF_3$, methyl, methoxy and NR(21)R(22);
R(21) and R(22)
independently of one another are H or alkyl having 1, 2, 3 or 4 carbon atoms or perfluoroalkyl having 1, 2, 3 or 4 carbon atoms;
R(15) is N=C(NH$_2$)$_2$, NR(18)R(19), N(CH$_2$)$_c$NR(18)R(19) or OR(20);
c is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups, of which one $CH_2$ group can be replaced by oxygen, S, NH, N—$CH_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms;

or
R(16) and R(17) together are 4 or 5 methylene groups, of which one $CH_2$ group can be replaced by oxygen, S, NH, N—$CH_3$, N-benzyl or N-(p-chlorophenyl);
or
Z is an N-containing heterocycle having 1, 2, 3, 4, 5, 6, 7, 8 or 9 carbon atoms,
where the N-containing heterocycle is linked via N or C and is not substituted or is substituted by 1–3 substituents selected from the group consisting of F, Cl, Br, $CF_3$, methyl, methoxy and NR(21)R(22);
but where, in the case where R(4) is an alkoxy radical, at least one of the substituents R(2), R(3), R(5), R(6), R(7) and R(8) is not hydrogen;
or a pharmaceutically tolerable salt thereof;

az) a substituted 2-naphthoylguanidine of the formula

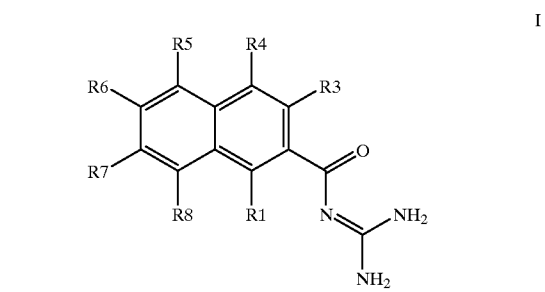

in which:

at least one of the substituents R1, R3, R4, R5, R6, R7 and R8 is
$XY_aWZ$ or $X'Y'_aWZ'$;
X is O, S, NR(10) or CR(11)R(12);
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Y is alkylene having 1, 2, 3, 4, 5, 6, 7 or 8 $CH_2$ groups, where one of these $CH_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
a is zero or 1;
W is $CH_2$, $SO_2$, S(=O)(=NH) or—if W does not immediately follow a heteroatom of the group $XY_a$— alternatively O or NR(14); R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
Z is C(=O)R(15), $SO_2$R(15) or—if W is not O or NR(14)—alternatively NR(16)R(17);
R(15) is N=C(NH$_2$)$_2$, NR(18)R(19), N(CH$_2$)bNR(18)R(19) or OR(20);
b is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups, of which one $CH_2$ group can be replaced by oxygen, S, NH, N—$CH_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

R(16) and R(17) independently of one another are H, alkyl having 1, 2, 3, 4, 5, 6, 7 or 8 carbon atoms or perfluoroalkyl having 1, 2, 3 or 4 carbon atoms;
or,
R(16) and R(17) together are 4 or 5 methylene groups, of which one $CH_2$ group can be replaced by oxygen, S, NH, N-$CH_3$, N-benzyl or N-(p-chlorophenyl);
X' is C=O, C(=O)NR(30), C(=O)O, SO, $SO_2$, $SO_2$NR(30), OC=O, NR(30)C=O or NR(30)$SO_2$,
where the linkage with the naphthalene ring in each case takes place via the left atom;
R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Z' is C(=O)R(15), $SO_2$R(15), an N-containing heterocycle having 1, 2, 3, 4, 5, 6, 7, 8 or 9 carbon atoms,
where the N-containing heterocycle is linked via N or C and is not substituted or is substituted by 1–3 substituents selected from the group consisting of F, Cl, Br, $CF_3$, methyl, methoxy and NR(21)R(22);
R(21) and R(22) independently of one another are H, alkyl having 1, 2, 3 or 4 carbon atoms or perfluoroalkyl having 1, 2, 3 or 4 carbon atoms;
R(15) is N=C($NH_2$)$_2$, NR(18)R(19), N($CH_2$)$_b$NR(18)R(19) or OR(20);
R(18) and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups, of which one $CH_2$ group can be replaced by oxygen, S, NH, N-$CH_3$, N-benzyl or N-(p-chlorophenyl);
b is 2 or 3;
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
or
Z' —if W is not O or NR(14)—is NR(16)R(17);
R(16) and R(17) independently of one another are H, alkyl having 1, 2, 3, 4, 5, 6, 7 or 8 carbon atoms or perfluoroalkyl having 1, 2, 3 or 4 carbon atoms;
or
R(16) and R(17) together are 4 or 5 methylene groups, of which one $CH_2$ group can be replaced by oxygen, S, NH, N-$CH_3$, N-benzyl or N-(p-chlorophenyl);
and the other substituents R1, R3, R4, R5, R6, R7 and R8 in each case, which are still not allocated by the definitions given above, independently of one another are H, F, Cl, Br, I, CN, $NO_2$, $CF_3$, $C_2F_5$ or $V_pQ_qU$;
V is O, S, SO, $SO_2$, NR(60), OC=O, C=O, C(=O)NR(60), C(=O)O or CR(66)R(67);
R(60), R(66) and R(67) independently of one another are H, alkyl having 1, 2, 3, 4 or 5 carbon atoms, perfluoroalkyl having 1, 2, 3 or 4 carbon atoms or cycloalkyl having 3, 4, 5, 6 or 7 carbon atoms;
p is zero or 1;
Q is alkylene having 1, 2, 3, 4, 5, 6, 7 or 8 $CH_2$ groups, where one of these $CH_2$ groups can be replaced by O, S, NR(68) or o-, p- or m-phenylene;
R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
q is zero or 1;
U is H, alkyl having 1, 2, 3, 4, 5, 6 or 7 carbon atoms, cycloalkyl having 3, 4, 5, 6 or 7 carbon atoms, C(=O)R(65), $SO_2$R(65), NR(61)R(62) or phenyl,
which is not substituted or is substituted by 1–3 substituents selected from the group consisting of F, Cl, Br, $CF_3$, methyl, methoxy and NR(63)R(64);
R(63) and R(64) independently of one another are H, alkyl having 1, 2, 3 or 4 carbon atoms or perfluoroalkyl having 1, 2, 3 or 4 carbon atoms;
R(65) is N=C($NH_2$)$_2$, NR(61)R(62) or OR(60);
R(61) and R(62) independently of one another are H, alkyl having 1, 2, 3, 4, 5, 6, 7 or 8 carbon atoms or perfluoroalkyl having 1, 2, 3 or 4 carbon atoms;
or
R(61) and R(62) together are 4 or 5 methylene groups, of which one $CH_2$ group can be replaced by oxygen, S, NH, N-$CH_3$, N-benzyl or N-(p-chlorophenyl);
or
U is an N-containing heterocycle having 1, 2, 3, 4, 5, 6, 7, 8 or 9 carbon atoms,
where the N-containing heterocycle is linked via N or C and is not substituted or is substituted by 1–3 substituents selected from the group consisting of F, Cl, Br, $CF_3$, methyl, methoxy and NR(63)R(64);
but where at least one of the substituents R5, R6, R7 and R8 is not hydrogen; or a pharmaceutically tolerable salt thereof;
ba) an ortho-substituted benzoylguanidine of the formula

I in which:
R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;
X is oxygen, sulfur or NR(9);
a is zero or 1;
b is zero, 1 or 2;
c is zero, 1, 2 or 3;
R(9) is H, alkyl having 1, 2, 3 or 4 carbon atoms or —$C_dH_{2d}$R(6);
d is zero, 1, 2, 3 or 4;
R(6) is cycloalkyl having 3, 4, 5, 6, 7 or 8 carbon atoms, phenyl, biphenylyl or naphthyl,
where the aromatics phenyl, biphenylyl or naphthyl are not substituted or are substituted by 1–3 substituents selected from the group consisting of F, Cl, $CF_3$, methyl, methoxy and NR(7)R(8);
R(7) and R(8) are independently, H or alkyl having 1, 2, 3 or 4 carbon atoms;
or
R(1) is —SR(10), —OR(10) or —CR(10)R(11)R(12);
R(10) is —$C_fH_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl,
where heteroaryl and phenyl are unsubstituted or are substituted by 1–3 substituents selected from the group consisting of F, Cl, $CF_3$, $CH_3$, methoxy, hydroxyl, amino, methylamino and dimethylamino;

f is zero, 1 or 2;

R(11) and (R12), independently of each other, are defined as R(10) or are hydrogen or alkyl having 1, 2, 3 or 4 carbon atoms;

or

R(1) is phenyl, naphthyl, biphenylyl or heteroaryl having 1, 2, 3, 4, 5, 6, 7, 8, or 9 carbon atoms, the latter linked via a carbon or nitrogen atom of the ring, each of which is unsubstituted or is substituted by 1–3 substituents selected from the group consisting of F, Cl, $CF_3$, $CH_3$, methoxy, hydroxyl, amino, methylamino and dimethylamino, or (R1) is —SR(13), —OR(13), —NHR(13), —NR(13)R(14), —CHR(13)R(15), —C[R(15)R(16)OH], —C=CR(18), —C[R(19)]=CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14), identically or differently, are

—$(CH_2)_g$—$(CHOH)_h$—$(CH_2)_i$—$(CHOH)_{kk}$—R(17) or —$(CH_2)_g$—O—$(CH_2-CH_2O)_n$—R(24);

R(17) is hydrogen or methyl, g, h and i, identically or differently, are zero, 1, 2, 3 or 4;

kk is 1, 2, 3 or 4;

R(15) and R(16), identically or differently, are hydrogen, alkyl having 1, 2, 3, 4, 5 or 6 carbon atoms, or, together with the carbon atom carrying them, cycloalkyl having 3, 4, 5, 6, 7 or 8 carbon atoms;

R(1 8)

is phenyl, which is unsubstituted or is substituted by 1–3 substituents selected from the group consisting of F, Cl, $CF_3$, methyl, methoxy and NR(25)R(26);

R(25) and R(26) are H or alkyl having 1, 2, 3 or 4 carbon atoms;

or

R(18) is heteroaryl having 1, 2, 3, 4, 5, 6, 7, 8 or 9 carbon atoms, which is unsubstituted or is substituted as phenyl;

or

R(18) is alkyl having 1, 2, 3, 4, 5 or 6 carbon atoms, which is unsubstituted or is substituted by 1–3 OH;

or

R(18) is cycloalkyl having 3, 4, 5, 6, 7 or 8 carbon atoms;

R(19), R(20), R(21), R(22) and R(23), identically or differently, are hydrogen or methyl;

R(24) is H, alkyl having 1, 2, 3, 4, 5 or 6 carbon atoms, cycloalkyl having 3, 4, 5, 6, 7 or 8 carbon atoms or —$C_mH_{2m}$—R(18);

m is 1, 2, 3 or 4;

one of the two substituents R(2) and R(3) is —O—CO—R(27);

R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl, where phenyl, biphenylyl, naphthyl, pyridyl or quinolyl are unsubstituted or substituted by 1–3 substituents selected from the group consisting of F, Cl, $CF_3$, methyl, methoxy and NR(7)R(8);

R(7) and R(8) independently of one another are hydrogen or alkyl having 1, 2, 3 or 4 carbon atoms;

where one of the substituents R(2) and R(3) is always defined as R(1);

R(4) and R(5) independently of one another are hydrogen, alkyl having 1, 2, 3 or 4 carbon atoms, alkoxy having 1, 2, 3 or 4 carbon atoms, F, Cl, Br, I, CN or —$(CH_2)_n$—$(CF_2)_o$—$CF_3$, n is zero or 1, o is zero or 1, or a pharmaceutically tolerable salt thereof;

bb) a benzoylguanidine of the formula in which:

R(1) is R(13)-$SO_m$ or R(14)R(15)N-$SO_2$—;

m is 1 or 2;

R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(16), n is zero, 1, 2, 3 or 4;

R(16) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, $CF_3$, methyl, methoxy and NR(25)R(26);

R(25) and R(26) are, independently of each other, hydrogen, alkyl having 1, 2, 3 or 4 carbon atoms or perfluoroalkyl having 1, 2, 3 or 4 carbon atoms;

R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$-R(27), n is zero, 1, 2, 3 or 4;

R(27) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, $CF_3$, methyl, methoxy and NR(28)R(29);

R(28) and R(29) are, independently of each other, hydrogen, alkyl having 1, 2, 3 or 4 carbon atoms or perfluoroalkyl having 1, 2, 3 or 4 carbon atoms;

R(15) is hydrogen, alkyl having 1, 2, 3 or 4 carbon atoms or perfluoroalkyl having 1, 2, 3 or 4 carbon atoms;

or

R(14) and R(15) are, together, 4 or 5 methylene groups of which one $CH_2$ group can be replaced by oxygen, S, NH, N-$CH_3$ or N-benzyl;

one of the substituents R(2) and R(3) is hydrogen;

and the other of the substituents R(2) and R(3) in each case is —CHR(30)R(31);

R(30) is

—$(CH_2)_g$—$(CHOH)_h$—$(CH_2)_i$—$(CHOH)_k$—R(32) or —$(CH_2)_g$—O—$(CH_2-CH_2O)_n$—R(24);

R(24) and R(32) are, independently of each other, hydrogen or methyl;

g, h and i are, identically or differently, zero, 1, 2, 3 or 4;

k is 1, 2, 3 or 4;

or the other of the substituents R(2) and R(3) in each case is —C(OH)R(33)R(34);

R(31), R(33) and R(34) are, identically or differently, hydrogen or alkyl having 1, 2, 3 or 4 carbon atoms, or R(33) and R(34) are, together, cycloalkyl having 3, 4, 5 or 6 carbon atoms;

or

R(33) is —CH$_2$OH;

R(4) is alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$;

n is zero or 1;

o is zero, 1 or 2;

or a pharmaceutically tolerable salt thereof;

bc) an indanylidineacetylguanidine of the formula

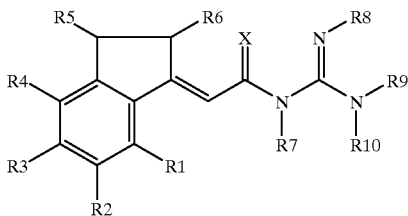

I in which:

R1, R2, R3, R4, R5 and R6 independently of one another are H, C$_1$–C$_{10}$-alkyl; haloalkyl having 1–6 carbon atoms, O—C$_1$–C$_{10}$-alkyl, haloalkoxy having 1–6 carbon atoms, F, Cl, Br, I, aryl, substituted aryl, heteroaryl, substituted heteroaryl, OH, O-lower alkyl, O-aryl, O-lower alkylaryl, O-substituted aryl, O-lower alkyl-substituted aryl, O-C(=O)-C$_1$–C$_4$-alkylaryl, O-C(=O)—NH—C$_1$–C$_4$-alkyl, O-C(=O)-N(C$_1$–C$_4$-alkyl)$_2$, NO$_2$, CN, CF$_3$, NH$_2$, NH—C(=O)—C$_1$–C$_4$-alkyl, NH-C(=O)-NH$_2$, COOH, C(=O)-O-C$_1$–C$_4$-alkyl, C(=O)-NH$_2$, C(=O)—NH—C$_1$–C$_4$-alkyl, C(=O)-N(C$_1$–C$_4$-alkyl)$_2$, C$_1$–C$_4$-COOH, C$_1$–C$_4$-alkyl-C(=O)—O—C$_1$–C$_4$-alkyl, SO$_3$H, SO$_2$-alkyl; SO$_2$-alkylaryl, SO$_2$-N-(alkyl)$_2$, SO$_2$-N(alkyl)(alkylaryl), C(=O)-R11, C$_1$–C$_{10}$-alkyl-C(=O)-R11, C$_2$–C$_{10}$-alkenyl-C(=O)-R11, C$_2$–C$_{10}$-alkynyl-C(=O)-R11, NH—C(=O)—C$_1$–C$_{10}$-alkyl-C(=O)-R11 or O-C$_1$–C$_{11}$-alkyl-C(=O)-R11;

R11 is C$_1$–C$_4$-alkyl, C$_1$–C$_4$-alkynyl, aryl, substituted aryl, NH$_2$, NH-C$_1$–C$_4$-alkyl, N-(C$_1$–C$_4$-alkyl)$_2$, SO$_3$H, SO$_2$-alkyl, SO$_2$-alkylaryl, SO$_2$-N-(alkyl)$_2$ or SO$_2$-N(alkyl)(alkylaryl);

X is O, S or NH;

R7, R8, R9 and R10 independently of one another are H, alkyl, cycloalkyl, aryl, alkylaryl, or R8 and R9 together are part of a 5-, 6- or 7-membered heterocyclic ring;

or their pharmaceutically acceptable salts;

bd) a phenyl-substituted alkenylcarboxylic acid guanidide of the formula I

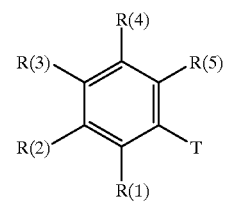

I in which:

T is

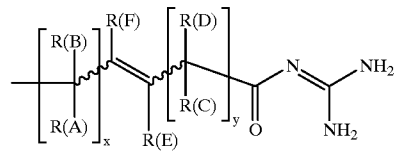

R(A) is hydrogen, F, Cl, Br, I, CN, OH, OR(6), (C$_1$–C$_4$)-alkyl, Or$_r$(CH$_2$)$_a$C$_b$F$_{2b+1}$, (C$_3$–C$_8$)-cycloalkyl oder NR(7)R(8)

r is zero or 1;

a is zero, 1, 2, 3 or 4;

b is 1, 2, 3 or 4;

R(6) is (C$_1$–C$_4$)-alkyl, (C$_1$–C$_4$)-perfluoroalkyl, (C$_3$–C$_6$)-alkenyl, (C$_3$–C$_8$)-cycloalkyl, phenyl or benzyl, the phenyl nucleus not being substituted or being substituted by 1–3 substituents selected from the group consisting of F, Cl, CF$_3$, methyl, methoxy and NR(9)R(10);

R(9) and R(10) are H, (C$_1$–C$_4$)-alkyl or (C$_1$–C$_4$)-perfluoro-alkyl;

R(7) and R(8) independently of one another are defined as R(6);

or

R(7) and R(8) together are 4 or 5 methylene groups, of which one CH$_2$ group can be replaced by oxygen, sulfur, NH, N-CH$_3$ or N-benzyl;

R(B), R(C) and R(D) independently are defined as R(A);

x is zero, 1 or 2;

y is zero, 1 or 2;

R(F) is hydrogen, F, Cl, Br, I, CN, OR(12), (C$_1$–C$_8$)-alkyl, OP(CH$_2$)$_f$C$_g$F$_{2g+1}$, (C$_3$–C$_8$)-cycloalkyl or (C$_1$–C$_9$)-heteroaryl;

p is zero or 1;

f is zero, 1, 2, 3 or 4;

g is 1, 2, 3, 4, 5, 6, 7 or 8;

R(12) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl, the phenyl nucleus not being substituted or being substituted by 1–3 substituents selected from the group consisting of F, Cl, CF$_3$, methyl, methoxy and NR(13)R(14);

R(13) and R(14) are H, (C$_1$–C$_4$)-alkyl or (C$_1$–C$_4$)-perfluoroalkyl;

R(E) is defined independently as R(F);

R(1) is defined independently as T;

or

R(1) is hydrogen, —O$_k$C$_m$H$_{2m+1}$, —O$_n$(CH$_2$)$_p$C$_q$F$_{2q+1}$, F, Cl, Br, I, CN, —(C=O)—N=C(NH$_2$)$_2$, —So$_r$R(17), —So$_{r2}$NR(31)R(32), —O$_u$(CH$_2$)$_v$C$_6$H$_5$, —O$_{u2}$—(C$_1$–C$_9$)-heteroaryl or —S$_{u2}$-(C$_1$–C$_9$)-heteroaryl;

k is zero or 1;
m is zero, 1, 2, 3, 4, 5, 6, 7 or 8;
n is zero or 1;
p is zero, 1, 2, 3 or 4;
q is 1, 2, 3, 4, 5, 6, 7 or 8;
r is zero, 1 or 2;
r2 is zero, 1 or 2;
R(31) and R(32) independently of one another are hydrogen, $(C_1-C_8)$-alkyl or $(C_1-C_8)$-perfluoroalkyl;
or
R(31) and R(32) are, together, 4 or 5 methylene groups of which one $CH_2$ group can be replaced by oxygen, S, NH, N-$CH_3$ or N-benzyl;
R(17) is $(C_1-C_8)$-alkyl;
u is zero or 1;
u2 is zero or 1;
v is zero, 1, 2, 3 or 4;
  where the phenyl nucleus is not substituted or is substituted by 1–3 substituents selected from the group consisting of F, Cl, $CF_3$, methyl, methoxy, —$(CH_2)_w$NR(21)R(22), NR(18)R(19) and $(C_1-C_9)$-heteroaryl;
R(18), R(19), R(21) and R(22) independently of one another are $(C_1-C_4)$-alkyl or $(C_1-C_4)$-perfluoroalkyl;
w is 1, 2, 3 or 4;
  where the heterocycle of the $(C_1-C_9)$-heteroaryl is unsubstituted or substituted by 1–3 substituents selected from the group consisting of F, Cl, $CF_3$, methyl or methoxy;
R(2), R(3), R(4) and R(5) independently of one another are defined as R(1),
or
R(1) and R(2) or R(2) and R(3) in each case together are —CH—CH=CH—CH—,
  which is not substituted or is substituted by 1–3 substituents selected from the group consisting of F, Cl, $CF_3$, methyl, methoxy, —$(CH_2)_{w2}$NR(24)R(25) and NR(26)R(27);
R(24), R(25), R(26) and R(27) are H, $(C_1-C_4)$-alkyl or $(C_1-C_4)$-perfluoroalkyl;
w2 is 1, 2, 3 or 4;
the radical T being present in the molecule at least twice, but only three times at most;
or a pharmaceutically tolerable salt thereof;
be) a benzoylguanidine of the formula

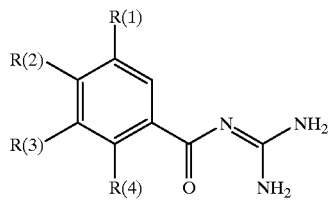

I in which:
R(1) is $CF_3$;
one of the substituents R(2) and R(3) is hydrogen;
and the other substituent R(2) or R(3) in each case is —C(OH)($CH_3$)—$CH_2$OH, —CH($CH_3$)—$CH_2$OH or —C(OH)($CH_3$)$_2$;
R(4) is methyl, methoxy, Cl or $CF_3$;
or a pharmaceutically tolerable salt thereof;

II. a compound of the formula

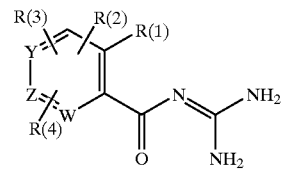

in which:
W, Y and Z
  are a nitrogen atom or a carbon atom substituted by R(2) or R(3) or R(4);
R(1) is hydrogen, A, Hal, —$CF_3$, —$CH_2F$, —$CHF_2$, —$CH_2CF_3$, —$C_2F_5$, —CN, —$NO_2$, —ethynyl, or an X—R';
A is alkyl having 1 to 6 carbon atoms;
Hal is F, Cl, Br or I;
X is oxygen, S or NR";
  R" is hydrogen, A or a cyclic methylene chain having 3 to 7 carbon atoms;
R' is H, A, HO—A—, HOOC—A—, $(C_3-C_7)$-cycloalkyl, $(C_6-C_8)$-cycloalkylalkyl, $CF_3$, $CH_2F$, $CHF_2$, $CH_2-CF_3$, Ph, —$CH_2$-Ph or Het;
  Ph is phenyl, naphthyl or biphenylyl which is unsubstituted or mono-, di- or trisubstituted by A, OA, NR'R", Hal, $CF_3$;
  Het is a mono- or binuclear saturated, unsaturated or aromatic heterocycle having 1 to 4 nitrogen, oxygen and/or sulfur atoms,
    which is unsubstituted or mono-, di- or trisubstituted by Hal, $CF_3$, A, OH, OA, —X—R', —CN, —$NO_2$, and/or carbonyl oxygen,
    where Het is bonded via N or an alkylene chain $C_mH_{2m}$ where m=zero to 6;
or
R' and R"
  together are alkylene having 4–5 carbon atoms, in which one $CH_2$ group can also be replaced by oxygen, S, NH, N—A, N—Ph and N—$CH_2$—Ph;
R(2) and R(3) independently of one another are hydrogen, Hal, A, HO—A—, X—R', —C(=N—OH)—A, A—O—CO—$(C_1-C_4)$-alkyl—, CN, $NO_2$, COOH, halogen-substituted A, in particular $CF_3$, $CH_2F$, $CHF_2$, $C_2F_5$, $CH_2CF_3$, or $S(O)_nR'''$;
R''' is A, Ph or —Het;
n is zero, 1 or 2;
or
R(2) and R(3)
  independently of one another are $SO_2NR'R"$, Ph or —O—Ph, —O—$CH_2$—Ph, —CO—A, —CHO, —COOA, —CSNR'R", CONR'R", —CH=CH—COOH, —CH=CH—COOA, indenyl, indanyl, decahydronaphthyl, cyclopentenyl, dihydrothienyl, dihydrofuryl, heterobicyclyl, alkylthienyl, halothienyl, haloalkylthienyl, acylthienyl, halofuryl, haloalkylfuryl or pyrrolyl;
or
R(2) and R(3)
  independently of one another are R(5)—O—;
  R(5) is hydrogen, A, $(C_1-C_6)$-alkenyl or $(C_3-C_7)$-cycloalkyl;

R(4) is Ph, Het, —O—Het; CF$_3$, S(O)$_n$R'", —SO$_2$NR'R",
alk;

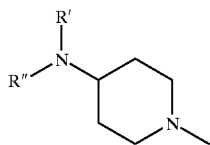

or two of the substituents R(1) to R(4) together are a group
—O—CR(6)R(7)—CO—NR(8)—,

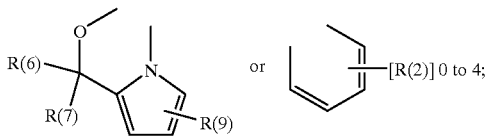

where R(2) has the meaning indicated;
R(6), R(7), R(8) and R(9) independently of one another
are H or A;
or
R(8) is (C$_5$–C$_7$)-cycloalkyl;
or
R(9) is cyano;
alk is straight-chain or branched (C$_1$–C$_8$)-alkyl or (C$_3$–C$_8$)-
cycloalkyl,
which is unsubstituted or mono-, di- or trisubstituted by
A;
or
alk is an ethenyl or ethynyl radical which is substituted by
H, A, Ph or Het;
III. an indoloylguanidine derivative of the formula

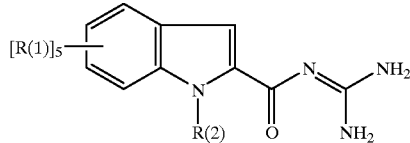

in which
R(2) is hydrogen, unsubstituted or substituted (C$_1$–C$_8$)-
alkyl, (C$_3$–C$_7$)-cycloalkyl, OH, (C$_1$–C$_6$)-alkyl—O—, an
aromatic radical or a group —CH$_2$—R(20);
R(20) is (C$_2$–C$_6$)-alkenyl or (C$_2$–C$_6$)-alkynyl;
R(1) is 1 to 5 identical or different substituents, which are:
hydrogen, unsubstituted or substituted (C$_1$–C$_8$)-alkyl,
(C$_2$–C$_6$)-alkenyl, (C$_2$–C$_6$)-alkynyl, (C$_3$–C$_7$)-cycloalkyl,
halogen, —NO$_2$, (C$_2$–C$_8$)-alkanoyl, arylalkanoyl having
up to 10 carbon atoms, aroyl having up to 11 carbon
atoms, —COOH, (C$_2$–C$_6$)-alkoxycarbonyl, an aromatic
group or one of the following mentioned groups: —OR
(3), —NR(6)R(7) or —S(O)$_n$R(40);
R(3) is hydrogen, (C$_1$–C$_8$)-alkyl, substituted (C$_1$–C$_8$)-
alkyl, (C$_3$–C$_7$)-cycloalkyl, an aromatic radical or a
group —CH$_2$—R(30);
R(30) is alkenyl or alkynyl;
R(6) and R(7) independently of one another are hydrogen,
unsubstituted or substituted (C$_1$–C$_8$)-alkyl, (C$_3$–C$_7$)-
cycloalkyl, (C$_2$–C$_8$)-alkanoyl, an arylalkanoyl group
having up to 10 carbon atoms, an aroyl group having up
to 11 carbon atoms, an aromatic group or —CH$_2$—R
(60);

R(60) is (C$_2$–C$_6$)-alkenyl or (C$_2$–C$_6$)-alkynyl;
or
R(6) and R(7) together with the nitrogen atom are a
5–7-membered cyclic amine, which can additionally
contain further heteroatoms in the ring;
n is zero, 1 or 2;
R(40) is unsubstituted or substituted (C$_1$–C$_8$)-alkyl, or an
aromatic group, or a group

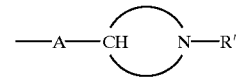

A is oxygen, —S(O)$_n$— or —N(R50)—;
R(50) is hydrogen or (C$_1$–C$_8$)-alkyl;
R' is hydrogen, unsubstituted or substituted (C$_1$–C$_8$)-
alkyl, in which the ring represents a saturated 3–8-
membered heterocycle having a nitrogen atom,
said substituted alkyl carries one or more groups selected
from the group consisting of halogen, —OH, (C$_1$–C$_6$)-
alkoxy, —CN, —COOH, (C$_2$–C$_6$)-alkoxycarbonyl,
(C$_2$–C$_8$)-alkanoyl, arylalkanoyl having up to 10 carbon
atoms, aroyl having up to 11 carbon atoms, an aromatic
group, —CONR(4)(R5),
R(4) and R(5)
identically or differently are hydrogen or (C$_1$–C$_8$)-
alkyl;
or
R(4) and R(5) are connected to one another and together
form a 5–7-membered cyclic amine which can addi-
tionally contain further heteroatoms in the ring,
or said substituted alkyl carries a group

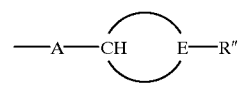

in which:
E is a nitrogen atom or a CH group;
R" is hydrogen, (C$_1$–C$_8$)-alkyl which is unsubstituted or
substituted by OH or substituted (C$_1$–C$_8$)-alkyl,
(C$_1$–C$_6$)-alkoxy, —CN, —COOH, (C$_2$–C$_6$)-
alkoxycarbonyl, (C$_2$–C$_8$)-alkanoyl, aralkanoyl having
up to 10 carbon atoms, aroyl having up to 11 carbon
atoms, an aromatic group, —NR(6)R(7), —CONR(4)
R(5);
R(4) and R(5)
independently of one another are hydrogen or (C$_1$–C$_8$)-
alkyl;
where the cyclic system of the formula

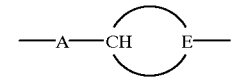

is a 3–8-mebered saturated aliphatic or heterocyclic ring
system having a nitrogen atom,
and where the aromatic groups mentioned are an aryl radical
having up to 10 carbon atoms, a 5- or 6-membered het-
eroaryl radical having 1–4 nitrogen atoms, a 5- or
6-membered heteroaryl group containing 1 or 2 nitrogen
atoms and a heteroatom which is oxygen or sulfur, or furyl, and where the aryl radicals mentioned can be unsubstituted or substituted by unsubstituted ($C_1$–$C_8$)-alkyl or substituted ($C_1$–$C_8$)-alkyl, halogen, —$NO_2$, ($C_2$–$C_6$)-alkoxycarbonyl, COOH, —OR(3), NR(6)R(7), —CONR(4)R(5), —$SO_2$NR(6)R(7) or $S(O)_n$R(40), where R(1) and the guanidinocarbonyl radical can be in any desired position of the 5- or 6-membered ring of the indole system, or an appropriate pharmaceutically tolerable salt thereof;

IV. a heterocyclic guanidine derivative of the formula

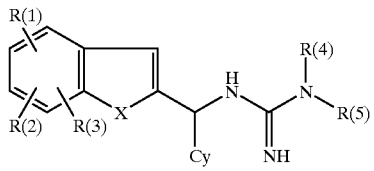

in which:

X is —O—, —S—, —NH—, —N[($C_1$–$C_4$)-alkyl]— or —N(phenyl)—;

R(1), R(2) and R(3) are hydrogen, halogen, ($C_1$–$C_4$)-alkyl, ($C_1$–$C_4$)-alkyl—O—, phenyl, benzyl;

or two of the substituents R(1), R(2) and R(3)
together with one side of the benzo system are a 4–6-membered carbocyclic ring;

R(4) and R(5) independently of one another are hydrogen, ($C_1$–$C_{12}$)-alkyl, benzhydryl, aralkyl,
which is unsubstituted or substituted by one or more substituents from the groups halogen, ($C_1$–$C_4$)-alkyl, ($C_1$–$C_4$)-alkyl—O— or —$CF_3$, —$(CH_2)_m$—$CH_2$—T, m is zero to 3;

T is —CO—O—T(1);
T(1) is hydrogen or ($C_1$–$C_4$)-alkyl;

Cy is a benzo-fused unsaturated or dihydro-5-membered ring heterocycle

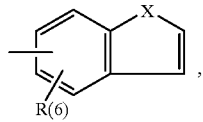, a pyrazole or imidazole ring of the formula

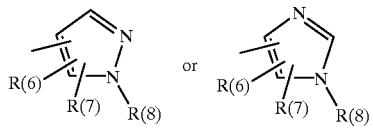

a naphthyl radical or a dihydro- or tetrahydronaphthyl radical

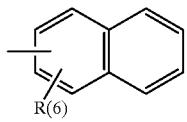

a 2-, 3- or 4-pyridyl radical

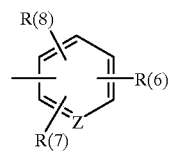

Z is N— or CH;

a thienyl radical

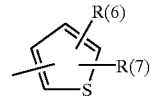

R(6) is hydrogen, halogen, hydroxyl, ($C_1$–$C_{10}$)-alkyl, ($C_1$–$C_{10}$)-alkyl—O—, phenoxy, ($C_1$–$C_{10}$)-alkyloxymethyloxy- or —$(O)_n$S—R(9);

R(9) is ($C_1$–$C_{10}$)-alkyl, thienyl, pyridyl, thiazolyl, thiadiazolyl, imidazolyl, pyrazolyl or phenyl,
each of which is unsubstituted or mono- or disubstituted by halogen, ($C_1$–$C_4$)-alkyl or ($C_1$–$C_4$)-alkyl—O—;

R(7) and R(8) are hydrogen, halogen, hydroxyl, ($C_1$–$C_{10}$)-alkyl, ($C_1$–$C_{10}$)-alkyl—O—, phenyl, phenoxy or ($C_1$–$C_{10}$)-alkoxymethyloxy;

or

Cy is phenyl,
which is unsubstituted or is mono- or disubstituted by halogen, ($C_1$–$C_4$)-alkyl or ($C_1$–$C_4$)-alkyl—O—;

or

Cy is —Gr—Am;
Gr is —R(13)—R(12)—$(CH_2)_q$—C[W][W(1)]—$(CH_2)_{q'}$—; R(13)R(14)— or —R(15)—;

R(12) is a single bond, —O—, —$(O)_n$S—, —CO— or —CONH—;

R(13) is a single bond, phenyl, thienyl, pyridyl, thiazolyl, thiadiazolyl, imidazolyl or pyrazolyl;

R(14) is a single bond or $SO_2$—;

R(15) is ($C_2$–$C_{10}$)-alkenyl or ($C_2$–$C_{10}$)-alkynyl;

W and W(1) independently of one another are hydrogen, ($C_1$–$C_4$)-alkyl;

or

W and W(1)
cyclically connected to one another are a ($C_3$–$C_8$)-hydrocarbon ring;

q and q' are zero to 9;

Am is —NR(10)R(11);

R(10) is hydrogen, ($C_1$–$C_4$)-alkyl or benzyl,

R(11) is ($C_1$–$C_4$)-alkyl, phenyl or benzyl;

or

R(10) and R(11) together are a ($C_3$–$C_{10}$)-alkylene group, which is unsubstituted or substituted by —COOH, ($C_1$–$C_5$)-alkoxycarbonyl, ($C_2$–$C_4$)-hydroxylalkylene or benzyl;

or

Am is pyrrolyl, pyridyl, pyrazolyl, morpholinyl, dihydropyridyl, tetrahydropyridyl, quinuclidinyl, imidazolyl, 3-azabicyclo[3.2.1]octyl, which is unsubstituted or substituted by $(C_1-C_4)$-alkyl, or Am is azabicyclo[3.2.2]nonyl;

or

Am is a piperazine group of the formula

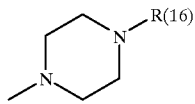

R(16) is hydrogen, $(C_1-C_4)$-alkyl, $(C_3-C_6)$-cycloalkyl, phenyl, tolyl, methoxyphenyl, halophenyl, diphenylmethylene, benzyl or pyridyl;

or

Am is an azido group $-(O)_t-(CH2)_q-C[W][W(1)]-(CH2)_{q'}-N_3$;

t is zero or 1;

where W and W(1) have the previously indicated meaning;

or an optical enantiomer or a pharmacologically tolerable salt thereof; and

V. a guanidine compound of the formula

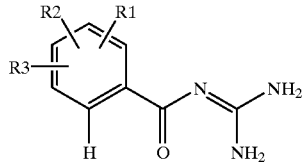

where R1=R2 is H, halo, alkyl, CN, $NO_2$, perfluoroalkyl, $SO_nCF_3$; R3 is $CH=CH_2$, $CH_2-CH=CH_2$, $CH_2-CH_2-CH=CH_2$, cycloalkenyl, cycloalkenylalkyl; R4 is alkyl, (substituted) phenyl.

* * * * *

UNITED STATES PATENT AND TRADEMARK OFFICE
CERTIFICATE OF CORRECTION

PATENT NO.  : 6,114,393
DATED       : September 5, 2000
INVENTOR(S) : Lang et al.

It is certified that error appears in the above-identified patent and that said Letters Patent is hereby corrected as shown below:

Column 96, claim 1,
Line 11, insert "a" before -- benzoylguanidine --.

Column 97, claim 1,
Line 61, "und" should read -- and --.

Column 98, claim 1,
Line 17, insert -- O -- after "Y is".
Line 38, "x" should read -- X --.
Line 49, delete period after "4" and insert semicolon therefor; insert text from Claim 14, Col. 112, line 5, beginning "R(8) is" through Col. 194, line 20.

Column 112, claim 1,
Line 66, insert space between "or" and "3".

Column 113, claim 1,
Line 35, delete space between "1" and "2".
Line 38, delete space between "1" and "5".

Column 115, claim 1,
Line 44, "C6" should read -- $C_6$ --.

Column 117, claim 1,
Line 30, insert space between "or" and "4".

Column 119, claim 1,
Line 2, insert spaces between "2" "or" and "3".

Column 120, claim 1,
Line 21, "O" should read -- o --.
Line 62, "R($^{15}$)" should read -- R(15) --.

Column 121, claim 1,
Line 36, "H2n" should read -- $H_{2n}$ --.
Line 49, insert space between "$CH_3$" and "or".

Column 122, claim 1,
Line 45, "x" should read -- X --.

UNITED STATES PATENT AND TRADEMARK OFFICE
CERTIFICATE OF CORRECTION

PATENT NO. : 6,114,393
DATED : September 5, 2000
INVENTOR(S) : Lang et al.

It is certified that error appears in the above-identified patent and that said Letters Patent is hereby corrected as shown below:

Column 125, claim 1,
Line 64, "S(O)S" should read -- $S(O)_s$ --.

Column 126, claim 1,
Line 17, "z" should read -- Z --.
Line 40, "x" should read -- X --.

Column 127, claim 1,
Line 36, "(C1-C$_4$)" should read -- $(C_1-C_4)$ --.

Column 128, claim 1,
Line 19, "$(CH_2)_{z1}$" should read -- $(CH_2)_{zl}$ --.

Column 130, claim 1,
Lines 10, 23 and 27, "R(1110b)" should read -- R(110b) --.
Line 34, "$C_{za1}H_{2za1}$" should read -- $C_{zal} H_{2zal}$ --.
Line 36, "za1" should read -- zal --.

Column 131, claim 1,
Line 48, "R(1 46)" should read -- R(146) --.

Column 132, claim 1,
Line 47, "R(1 76)" should read -- R(176) --.

Column 134, claim 1,
Line 5, "(24)]," should read -- $(24)]_l$ --.
Line 12, insert "j" before -- is --.

Column 136, claim 1,
Line 14, "$R(^8)$" should read -- R(8) --.
Line 43, "$C_{al}H_{2al}$" should read -- $C_{al}H_{2al}$ --.
Line 44, "a1" should read -- al --.

Column 137, claim 1,
Line 29, "$C_9$" should read -- $C_g$ --.

Column 138, claim 1,
Line 9, delete "15" before -- R(3) --.
Line 14, "S" should read -- s --.

UNITED STATES PATENT AND TRADEMARK OFFICE
CERTIFICATE OF CORRECTION

PATENT NO. : 6,114,393
DATED : September 5, 2000
INVENTOR(S) : Lang et al.

It is certified that error appears in the above-identified patent and that said Letters Patent is hereby corrected as shown below:

Column 139, claim 1,
Line 15, "V" should read -- v --.
Line 65, "CH3" should read -- $CH_3$ --.

Column 140, claim 1,
Line 18, "thai" should read -- than --.
Line 37, "$(C_1-C3)$" should read -- $(C_1-C_3)$ --.
Line 63, "$C_{al}$" should read -- $C_{al}$ --.
Line 65, "a1" should read -- al --.

Column 142, claim 1,
Line 53, insert space between "$CH_3$" and "or".
Line 59, delete space between "CH" and "R".

Column 145, claim 1,
Line 11, insert space between "or" and "2".

Column 151, claim 1,
Line 30, "$F_{2r+}1$" should read -- $F_{2r+1}$ --.

Column 152, claim 1,
Line 39, insert space between "1" and "or".
Line 66, insert space between "$CH_2$" and "group".

Column 153, claim 1,
Line 45, "1,2,3or 4" should read -- 1, 2, 3 or 4 --.

Column 154, claim 1,
Line 56, "is4,5,6or7" should read -- is 4, 5, 6 or 7 --.
Line 63, insert space after "is".

Column 155, claim 1,
Line 59, "$R(1^7)$" should read -- R(17) --.

Column 159, claim 1,
Line 26, "$SO_1$" should read -- $SO_I$ --.
Line 30, "1 is" should read -- I is --.
Line 30, "zero, 1or 2" should read -- zero, 1 or 2 --.

UNITED STATES PATENT AND TRADEMARK OFFICE
CERTIFICATE OF CORRECTION

PATENT NO. : 6,114,393
DATED : September 5, 2000
INVENTOR(S) : Lang et al.

It is certified that error appears in the above-identified patent and that said Letters Patent is hereby corrected as shown below:

<u>Column 160, claim 1,</u>
Line 7, "y" should read -- Y --.
Line 7, insert a space after "is" and a space after "4".

<u>Column 161, claim 1,</u>
Line 3, "$C_2$" should read -- Cz --.
Line 6, "3or4" should read -- 3 or 4 --.

<u>Column 173, claim 1,</u>
Line 31, "$(C_1-C8)$" should read -- $(C_1-C_8)$ --.
Line 54, "x" should read -- X --.

<u>Column 174, claim 1,</u>
Line 28, "$(23)]_1$" should read -- $(23)]_I$ --.
Line 31, "1 is" should read -- I is --.

<u>Column 175, claim 1,</u>
Line 61, "$(23)]_1$," should read -- $(23)]_I$ --.
Line 63, "1 is" should read -- I is --.

<u>Column 183, claim 1,</u>
Line 19, "R(23)]," should read -- $R(23)]_I$ --.
Line 21, "1 is" should read -- I is --.

<u>Column 186, claim 1,</u>
Line 24, "Or" should read -- $O_r$ --.
Line 25, "oder" should read -- or --.
Line 48, "OP" should read -- $O_p$ --.

<u>Column 100, claim 13,</u>
Line 36, "x" should read -- X --.
Line 52, "x" should read -- X --.
Line 60, "und" should read -- and --.

<u>Column 101, claim 13,</u>
Line 65, "R(1)" should read -- R(4) -- (in formula).

<u>Column 102, claim 13,</u>
Line 45, insert space after "m)".

UNITED STATES PATENT AND TRADEMARK OFFICE
CERTIFICATE OF CORRECTION

PATENT NO. : 6,114,393  
DATED : September 5, 2000  
INVENTOR(S) : Lang et al.

Page 5 of 6

It is certified that error appears in the above-identified patent and that said Letters Patent is hereby corrected as shown below:

Column 103, claim 13,
Line 45, "x" should read -- X --.

Column 104, claim 13,
Line 25, insert space between "," and "and".

Column 105, claim 13,
Line 61, "13(6)" should read -- R(6) --.
Line 67, delete period after "or".

Column 106, claim 13,
Line 8, "1 to 4" should read -- 1 to 4 --.
Line 48, "in dependently" should read -- independently --.
Line 52, "$C_aH2a$" should read -- $C_aH_{2a}$ --.
Line 60, "CaH2a" should read -- $C_aH_{2a}$ --.
Line 66, "R(1 1)" should read -- R(11) --.

Column 107, claim 13,
Line 3, "H2b" should read -- $H_{2b}$ --.
Line 49, insert space between "1," and "2,".

Column 108, claim 13,
Line 1, "z" should read -- Z --.

Column 109, claim 13,
Line 33, "hiving" should read -- having --.

UNITED STATES PATENT AND TRADEMARK OFFICE
CERTIFICATE OF CORRECTION

PATENT NO. : 6,114,393
DATED : September 5, 2000
INVENTOR(S) : Lang et al.

It is certified that error appears in the above-identified patent and that said Letters Patent is hereby corrected as shown below:

<u>Column 110, claim 13,</u>
Line 47, "corisisting" should read -- consisting --.

<u>Column 111, claim 13,</u>
Line 34, delete space between "w" and "2"; add semicolon after "4".

Signed and Sealed this

Ninth Day of April, 2002

JAMES E. ROGAN
*Director of the United States Patent and Trademark Office*

*Attest:*

*Attesting Officer*